(12) United States Patent
Kong et al.

(10) Patent No.: US 11,472,874 B2
(45) Date of Patent: Oct. 18, 2022

(54) ANTI-MS4A4A ANTIBODIES AND METHODS OF USE THEREOF

(71) Applicant: Alector LLC, South San Francisco, CA (US)

(72) Inventors: Philip Kong, San Francisco, CA (US); Herve Rhinn, San Francisco, CA (US); Tina Schwabe, San Francisco, CA (US); Angie Yee, San Francisco, CA (US); Ilaria Tassi, San Francisco, CA (US); Muhammad Abbas Alhawagri, San Francisco, CA (US); Arnon Rosenthal, Woodside, CA (US)

(73) Assignee: Alector LLC, South San Francisco, CA (US)

( * ) Notice: Subject to any disclaimer, the term of this patent is extended or adjusted under 35 U.S.C. 154(b) by 0 days.

(21) Appl. No.: 16/965,676

(22) PCT Filed: Jan. 31, 2019

(86) PCT No.: PCT/US2019/016156
§ 371 (c)(1),
(2) Date: Jul. 29, 2020

(87) PCT Pub. No.: WO2019/152715
PCT Pub. Date: Aug. 8, 2019

(65) Prior Publication Data
US 2021/0040200 A1 Feb. 11, 2021

Related U.S. Application Data

(60) Provisional application No. 62/783,096, filed on Dec. 20, 2018, provisional application No. 62/624,600, filed on Jan. 31, 2018.

(51) Int. Cl.
*C07K 16/28* (2006.01)

(52) U.S. Cl.
CPC .......... *C07K 16/28* (2013.01); *C07K 2317/24* (2013.01); *C07K 2317/31* (2013.01); *C07K 2317/71* (2013.01)

(58) Field of Classification Search
None
See application file for complete search history.

(56) References Cited

U.S. PATENT DOCUMENTS

| 9,969,799 B2 | 5/2018 | Wang et al. |
| 2009/0011409 A1 | 1/2009 | Sharma et al. |

(Continued)

FOREIGN PATENT DOCUMENTS

| CN | 105759057 A | 7/2016 |
| WO | WO-02062946 A2 | 8/2002 |

(Continued)

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

(Continued)

*Primary Examiner* — Aurora M Fontainhas
(74) *Attorney, Agent, or Firm* — Sterne, Kessler, Goldstein & Fox P.L.L.C.

(57) ABSTRACT

The present disclosure is generally directed to compositions that include antibodies, e.g., monoclonal, antibodies, antibody fragments, etc., that specifically bind a MS4A4A polypeptide, e.g., a mammalian MS4A4A or human MS4A4A, and use of such compositions in preventing, reducing risk, or treating an individual in need thereof.

29 Claims, 25 Drawing Sheets

Specification includes a Sequence Listing.

(56) References Cited

U.S. PATENT DOCUMENTS

| | | |
|---|---|---|
| 2016/0376359 A1 | 12/2016 | Wang et al. |
| 2017/0355756 A1 | 12/2017 | Julien et al. |
| 2021/0079074 A1 | 3/2021 | Kong et al. |
| 2021/0122817 A1 | 4/2021 | Kong et al. |

FOREIGN PATENT DOCUMENTS

| | | |
|---|---|---|
| WO | WO-2008068048 A2 | 6/2008 |
| WO | WO-2011147851 A1 | 12/2011 |
| WO | WO-2017143036 A1 | 8/2017 |
| WO | WO-2019152706 A1 | 8/2019 |
| WO | WO-2019152715 A1 | 8/2019 |
| WO | WO-2021022083 A2 | 2/2021 |

OTHER PUBLICATIONS

Chen, C., et al., "Enhancement and destruction of antibody function by somatic mutation: unequal occurrence is controlled by V gene combinatorial associations," EMBO Journal 14(12):2784-2794, Oxford University Press, United Kingdom (1995).

International Search Report and Written Opinion dated Jan. 28, 2021 in Application No. PCT/US2020/044335, EPO, Netherlands, 15 pages.

Kussie, P.H., et al., "A Single Engineered Amino Acid Substitution Changes Antibody Fine Specificity," Journal of Immunology 152(1):146-152, American Association of Immunology, United States (1994).

Office Action dated Oct. 18, 2021 in U.S. Appl. No. 16/943,123, inventor Sun, J., et al., filed Jul. 30, 2020, 15 pages.

Reitz, C., "Toward Precision medicine in Alzheimer's Disease," Ann. Transl. Med 4(6):107, 7 pages, AME Publishing Corp, United States (2016).

Stanford Health Now, "Alzheimer's Prevention, Treatment and Research—A Q&A with Dr. Frank Longo," retrieved from: stanfordhealthcare.org/Stanford-health-now/2016/alzheimers-prevention-treatment-research-qa-longo.html, accessed on May 3, 2016, 2 pages.

Proitsi, P., et al., "Alzheimer's disease susceptibility variants in the MS4A6A gene are associated with altered levels of MS4A6A expression in blood," Neurobiol Aging 35(2):279-290, Elseiver, Netherlands (2013).

International Search Report and Written Opinion dated Jan. 28, 2021 in Application No. PCT/US2019/016141, KIPO, Korea, 11 pages.

Puri, M., et al., "The Evaluation of MS4A4A and MS4A8B Expression in Hematopoietic Cells," retrieved from: https://prism.ucalgary.ca/bitstream/handle/11023/1791/ucalgary2014purmandip.pdf;jsessionid=cda23b615634fb7f5836e43810707090?sequence=2, retrieved Oct. 21, 2020, 160 pages (2014).

Al-Shawi, R., et al., "Neurotoxic and Neurotrophic Roles of ProNGF and the Receptor Sortilin in the Adult and Ageing Nervous System," European Journal of Neuroscience 28(9):2103-2114, Wiley-Blackwell Publishing Ltd., United Kingdom (Dec. 2008).

Allen, M., et al., "Novel late-onset Alzheimer disease loci variants associate with brain gene expression," Neurology 79(3):221-228, Lippincott Williams and Wilkins Ltd., United States (Jul. 2012).

Antúnez, C., et al., "The membrane-spanning 4-domains, subfamily A (MS4A) gene cluster contains a common variant associated with Alzheimer's disease," Genome Medicine 3:33, 8 pages, BioMed Central Ltd., United Kingdom (May 2011).

Arnett, M.J., et al., "Pro-NGF, Sortilin, and p75$^{NTR}$: Potential Mediators of Injury-induced Apoptosis in the Mouse Dorsal Root Ganglion," Brain Research 1183:32-42, Elsevier, Netherlands (Dec. 2007).

Barber, R.C., "The Genetics of Alzheimer's Disease," Scientifica (Cairo) 2072:246210, 14 pages, Hindawi Publishing Corporation, Egypt (Dec. 2012).

Beattie, M.S., et al., "ProNGF Induces p75-mediated Death of Oligodendrocytes Following Spinal Cord Injury," Neuron 36(3):375-386, Cell Press, United States (Oct. 2002).

Bubien, J.K., et al., "Transfection of the CD20 Cell Surface Molecule Into Ectopic Cell Types Generates a $Ca^{2+}$ Conductance Found Constitutively in B Lymphocytes," The Journal of Cell Biology 121(5):1121-1132, Rockefeller University Press, United States (Jun. 1993).

Cruse, G., et al., "The CD20 Homologue MS4A4 Directs Trafficking of KIT Toward Clathrin-independent Endocytosis Pathways and Thus Regulates Receptor Signaling and Recycling," Molecular Biology of the Cell 26(9):1711-1727, American Society for Cell Biology, United States (May 2015).

Deming, Y., et al., "The MS4A gene cluster is a key regulator of soluble TREM2 and Alzheimer disease risk," Science Translational Medicine 11(505):eaau2291, 18 pages, American Association for the Advancement of Science, United States (Aug. 2019).

Denardo, D.G., et al., "Leukocyte Complexity Predicts Breast Cancer Survival and Functionally Regulates Response to Chemotherapy," Cancer Discovery 1(1):54-67, American Association for Cancer Research, United States (Jun. 2011).

Drake, A.W., and Klakamp, S.L., "A Rigorous Multiple Independent Binding Site Model for Determining Cell-based Equilibrium Dissociation Constants," Journal of Immunological Methods 318(1-2):147-152, Elsevier, Netherlands (Jan. 2007).

Efthymiou, A.G., and Goate, A.M., "Late Onset Alzheimer's Disease Genetics Implicates Microglial Pathways in Disease Risk," Molecular Neurodegeneration 12:43, BioMed Central Ltd., United Kingdom (May 2017).

Elias-Sonnenschein, L.S., et al., "Genetic loci associated with Alzheimer's disease and cerebrospinal fluid biomarkers in a Finnish case-control cohort," PLoS One 8(4):e59676, 9 pages, Public Library of Science, United States (Apr. 2013).

Engle, S.J., et al., "Best Practices For Translational Disease Modeling Using Human iPSC-derived Neurons," Neuron 100(4):783-797, Cell Press, United States (Nov. 2018).

Fahnestock, M., et al., "The Precursor Pro-nerve Growth Factor is the Predominant Form of Nerve Growth Factor in Brain and is Increased in Alzheimer's Disease," Molecular and Cellular Neuroscience 18(2):210-220, Academic Press, United States (Aug. 2001).

Fan, Y.J., et al., "Differential Effects of Pro-BDNF on Sensory Neurons After Sciatic Nerve Transection in Neonatal Rats," European Journal of Neuroscience 27(9):2380-2390, Wiley-Blackwell, France (May 2008).

Greer, P.L., et al., "A Family of Non-GPCR Chemosensors Defines an Alternative Logic for Mammalian Olfaction," Cell 165(1):1734-1748, Cell Press, United States (Jun. 2016).

Harrington, A.W., et al., "Secreted ProNGF is a Pathophysiological Death-inducing Ligand After Adult CNS Injury," Proceedings of the National Academy of Sciences of the United States of America 101(16):6226-6230, National Academy of Sciences, United States (Apr. 2004).

Hollingworth, P., et al., "Common Variants at ABCA7, MS4A6A/MS4A4E, EPHA1, CD33 and CD2AP Are Associated With Alzheimer's Disease," Nature Genetics 43(5):429-435, Nature Publishing Group, United Kingdom (May 2011).

Idusogie, E.E., et al., "Mapping of the C1q Binding Site on Rituxan, A Chimeric Antibody with a Human IgG1 Fc," The Journal of Immunology 164(8):4178-4184, American Association of Immunologists, United States (2000).

Ishibashi, K., et al., "Identification of a New Multigene Four-transmembrane Family (MS4A) Related to CD20, HTm4 and β Subunit of the High-affinity IgE Receptor," Gene 264(1):87-93, Elsevier, Netherlands (Feb. 2001).

International Search Report and Written Opinion for Application No. PCT/US2019/016156, European Patent Office, Netherlands, dated Apr. 23, 2019, 13 pages.

Jansen, P., et al., "Roles for the Pro-neurotrophin Receptor Sortilin in Neuronal Development, Aging and Brain Injury," Nature Neuroscience 10(11):1449-1457, Nature Publishing Group, United Kingdom (Nov. 2007).

Karch, C.M., et al., "Expression of novel Alzheimer's disease risk genes in control and Alzheimer's disease brains," PLoS One 7(11):e50976, 9 pages, Public Library of Science, United States (Nov. 2012).

(56) References Cited

OTHER PUBLICATIONS

Karch, C.M., et al., "Alzheimer's disease risk genes and mechanisms of disease pathogenesis," *Biol Psychiatry* 77(1):43-51, Elsevier Inc., Netherlands (Jan. 2015).

Kay, B.K., et al., "The Importance of Being Proline: the Interaction of Proline-rich Motifs in Signaling Proteins With Their Cognate Domains," *FASEB* 74(2):231-241, The Federation of American Societies for Experimental Biology, United States (Feb. 2000).

Koslowski, M., et al., "MS4A12 is a Colon-selective Store-operated Calcium Channel Promoting Malignant Cell Processes," *Cancer Research* 68(9):3458-3466, American Association for Cancer Research, United States (May 2008).

Kuek, L.E., et al., "The MS4A family: counting past 1, 2 and 3," *Immunology and Cell Biology* 94:11-23, American Society for Immunology Inc., United States (Apr. 2015).

Lambert, J.C., et al., "Meta-analysis of 74,046 Individuals Identifies 11 New Susceptibility Loci for Alzheimer's Disease," *Nature Genetics* 45(12):1452-1458, Nature Publishing Group, United Kingdom (Dec. 2013).

Liang, Y., and Tedder, T.F., "Identification of a CD20-, FcεRIβ-, and HTm4-related Gene Family: Sixteen New MS4A Family Members Expressed in Human and Mouse," *Genomics* 72(2):119-127, Academic Press, United States (Mar. 2001).

Liang, C.C., et al., "In Vitro Scratch Assay: a Convenient and Inexpensive Method for Analysis of Cell Migration in Vitro" *Nature Protocols* 2(2):329-333, Nature Publishing Group, United Kingdom (2007).

Ma, J., et al., "MS4A6A genotypes are associated with the atrophy rates of Alzheimer's disease related brain structures," *Oncotarget* 7(37):58779-58788, Impact Journals LLC, United States (Sep. 2016).

Murthy, M.N., et al., "Increased Brain Expression of GPNMB Is Associated with Genome Wide Significant Risk for Parkinson's Disease on Chromosome 7p15.3," *Neurogenetics* 18(3):121-133, Springer-Verlag, Germany (Jul. 2017).

Naj, A.C., et al., "Common Variants at MS4A4/MS4A6E, CD2AP, CD33 and EPHA1 Are Associated With Late-onset Alzheimer's Disease," *Nature Genetics* 43(5):436-441, Nature Publishing Group, United Kingdom (May 2011).

Nakamura, K., et al., "Intracellular Sortilin Expression Pattern Regulates ProNGF-induced Naturally Occurring Cell Death During Development," *Cell Death and Differentiation* 14(8):1552-1554, Nature Publishing Group, United Kingdom (Aug. 2007).

Nykjaer, A., et al., "Sortilin is Essential for ProNGF-induced Neuronal Cell Death," *Nature* 427(6977):843-848, Nature Publishing Group, United Kingdom (Feb. 2004).

Nykjaer, A., et al., "$P75^{NTR}$—Live or Let Die," *Current Opinion in Neurobiology* 15(1):49-57, Elsevier Ltd., Netherlands (Feb. 2005).

Peng, X., et al., "Preclinical Evaluation of 3D185, a Novel Potent Inhibitor of FGFR1/2/3 and CSF-1R, in FGFR-Dependent and Macrophage-Dominant Cancer models," *Journal of Experimental & Clinical Cancer Research* 38(1):372, BioMed Central, United Kingdom (Aug. 2019).

Piccio, L., et al., "Cerebrospinal Fluid Soluble TREM2 is Higher in Alzheimer Disease and Associated With Mutation Status," *Acta Neuropathologica* 131(6):925-933, Springer Verlag, Germany (Jun. 2016).

Pocock, J.M., et al., "Modelling Microglial Function With Induced Pluripotent Stem Cells: An Update," *Nature Reviews Neuroscience* 19(8):445-452, Nature Publishing Group, United Kingdom (Aug. 2018).

Provenzano, M.J., et al., "P75NTR and Sortilin Increase After Facial Nerve Injury," *Laryngoscope* 118(1):87-93, Wiley-Blackwell, United States (Jan. 2008).

Salimi, A., et al., "Comparison Of Different Protocols For Neural Differentiation Of Human Induced Pluripotent Stem Cells," *Molecular Biology Reports* 41(3):1713-1721, Springer, Netherlands (Mar. 2014).

Sanyal, R., et al., "MS4A4A: a novel cell surface marker for M2 macrophages and plasma cells," *Immunology and Cell Biology* 95(7):611-619, American Society for Immunology Inc., United States (Apr. 2017).

Shang, L., et al., "Selective Antibody Intervention of Toll-like Receptor 4 Activation through Fc γ Receptor Tethering," *The Journal of Biological Chemistry* 289(22):15309-15318, American Society for Biochemistry and Molecular Biology, United States (May 2014).

Tcw, J., et al., "An Efficient Platform For Astrocyte Differentiation From Human Induced Pluripotent Stem Cells," *Stem Cell Reports* 9(2):600-614, Cell Press, United States (Aug. 2017).

Teng, H.K., et al., "ProBDNF Induces Neuronal Apoptosis via Activation of a Receptor Complex of $P75^{NTR}$ and Sortilin," *The Journal of Neuroscience* 25(22):5455-5463, Society for Neuroscience, United States (Jun. 2005).

Thornton, P., et al., "TREM2 shedding by cleavage at the H157-S158 bond is accelerated for the Alzheimer's disease-associated H157Y variant," *EMBO Mol Med* 9:1366-1378, Wiley-Blackwell, United Kingdom (Oct. 2017).

Tomay, F., "Regulation and function of the tetraspanin-like molecule MS4A4A in alternatively activated and tumor-associated macrophages," XP055578452, Retrieved from the Internet: https://air.unimi.it/retrieve/handle/2434/248877/338927/phd_unimi_R09505.pdf, Feb. 10, 2015, pp. 1-160.

Volosin, M., et al., "Interaction of Survival and Death Signaling in Basal Forebrain Neurons: Roles of Neurotrophins and Proneurotrophins," *The Journal of Neuroscience* 26(29):7756-7766, Society for Neuroscience, United States (Jul. 2006).

Volosin, M., et al., "Induction of Proneurotrophins and Activation of $P75^{NTR}$-mediated Apoptosis via Neurotrophin Receptor-interacting Factor in Hippocampal Neurons After Seizures," *The Journal of Neuroscience* 28(39):9870-9879, Society for Neuroscience, United States (Sep. 2008).

Wei, Y., et al., "Enhanced Protein Expressions of Sortilin and $P75^{NTR}$ in Retina of Rat Following Elevated Intraocular Pressure-induced Retinal Ischemia," *Neuroscience Letters* 429(2-3):169-174, Elsevier, Ireland (Dec. 2007).

Yano, H., et al., "Proneurotrophin-3 Is a Neuronal Apoptotic Ligand: Evidence for Retrograde-Directed Cell Killing," *The Journal of Neuroscience* 29(47):14790-14802, Society for Neuroscience, United States (Nov. 2009).

\* cited by examiner

| | | | | |
|---|---|---|---|---|
| 4A-1 | 4A-7 | 4A-13 | 4A-19 | 5C12 |
| 4A-2 | 4A-8 | 4A-14 | 4A-20 | 3F2 |
| 4A-3 | 4A-9 | 4A-15 | 4A-21 | msIgG1 Isotype Ctrl |
| 4A-4 | 4A-10 | 4A-16 | 4A-22 | msIgG2a Isotype Ctrl |
| 4A-5 | 4A-11 | 4A-17 | 4A-23 | msIgG2b Isotype Ctrl |
| 4A-6 | 4A-12 | 4A-18 | 4A-24 | No Primary Ctrl |

4A-1

| PLATE NAME | Sample Name | Mean : APC-A |
|---|---|---|
| Plate E | Specimen_001_D2_D02_032.fcs | 5349 |
| Plate D | Specimen_001_D2_D02_032.fcs | 17820 |
| Plate C | Specimen_001_D2_D02_032.fcs | 117 |

4A-7

| PLATE NAME | Sample Name | Mean : APC-A |
|---|---|---|
| Plate E | Specimen_001_C2_C02_022.fcs | 2171 |
| Plate D | Specimen_001_C2_C02_022.fcs | 3893 |
| Plate C | Specimen_001_C2_C02_022.fcs | 111 |

4A-13

| PLATE NAME | Sample Name | Mean : APC-A |
|---|---|---|
| Plate E | Specimen_001_B3_B03_013.fcs | 5712 |
| Plate D | Specimen_001_B3_B03_013.fcs | 32635 |
| Plate C | Specimen_001_B3_B03_013.fcs | 112 |

| PLATE NAME | Sample Name | Mean : APC-A |
|---|---|---|
| Plate E | Specimen_001_C4_C04_024.fcs | 261 |
| Plate D | Specimen_001_C4_C04_024.fcs | 532 |
| Plate C | Specimen_001_C4_C04_024.fcs | 114 |

4A-19

| PLATE NAME | Sample Name | Mean : APC-A |
|---|---|---|
| Plate E | Specimen_001_F3_F03_053.fcs | 129 |
| Plate D | Specimen_001_F3_F03_053.fcs | 19464 |
| Plate C | Specimen_001_F3_F03_053.fcs | 110 |

5C12

| PLATE NAME | Sample Name | Mean : APC-A |
|---|---|---|
| Plate E | Specimen_001_B1_B01_011.fcs | 5841 |
| Plate D | Specimen_001_B1_B01_011.fcs | 20596 |
| Plate C | Specimen_001_B1_B01_011.fcs | 113 |

4A-2

| | PLATE NAME | Sample Name | Mean : APC-A |
|---|---|---|---|
| | Plate E | Specimen_001_E2_E02_042.fcs | 874 |
| | Plate D | Specimen_001_E2_E02_042.fcs | 1498 |
| | Plate C | Specimen_001_E2_E02_042.fcs | 113 |

| | PLATE NAME | Sample Name | Mean : APC-A |
|---|---|---|---|
| | Plate E | Specimen_001_C3_C03_023.fcs | 168 |
| | Plate D | Specimen_001_C3_C03_023.fcs | 252 |
| | Plate C | Specimen_001_C3_C03_023.fcs | 111 |

| | PLATE NAME | Sample Name | Mean : APC-A |
|---|---|---|---|
| | Plate E | Specimen_001_D4_D04_034.fcs | 317 |
| | Plate D | Specimen_001_D4_D04_034.fcs | 652 |
| | Plate C | Specimen_001_D4_D04_034.fcs | 116 |

3F2

| PLATE NAME | Sample Name | Mean : APC-A |
|---|---|---|
| Plate E | Specimen_001_G3_G03_063.fcs | 128 |
| Plate D | Specimen_001_G3_G03_063.fcs | 21060 |
| Plate C | Specimen_001_G3_G03_063.fcs | 110 |

4A-3

| PLATE NAME | Sample Name | Mean : APC-A |
|---|---|---|
| Plate E | Specimen_001_C1_C01_021.fcs | 4623 |
| Plate D | Specimen_001_C1_C01_021.fcs | 17447 |
| Plate C | Specimen_001_C1_C01_021.fcs | 119 |

4A-9

| PLATE NAME | Sample Name | Mean : APC-A |
|---|---|---|
| Plate E | Specimen_001_F2_F02_052.fcs | 1821 |
| Plate D | Specimen_001_F2_F02_052.fcs | 3463 |
| Plate C | Specimen_001_F2_F02_052.fcs | 111 |

4A-15

| | PLATE NAME | Sample Name | Mean : APC-A |
|---|---|---|---|
| | Plate E | Specimen_001_D3_D03_033.fcs | 604 |
| | Plate D | Specimen_001_D3_D03_033.fcs | 594 |
| | Plate C | Specimen_001_D3_D03_033.fcs | 112 |

4A-21

| | PLATE NAME | Sample Name | Mean : APC-A |
|---|---|---|---|
| | Plate E | Specimen_001_E4_E04_044.fcs | 2294 |
| | Plate D | Specimen_001_E4_E04_044.fcs | 3605 |
| | Plate C | Specimen_001_E4_E04_044.fcs | 122 | msIgG1 Isotype Ctrl

| | PLATE NAME | Sample Name | Mean : APC-A |
|---|---|---|---|
| | Plate E | Specimen_001_H3_H03_073.fcs | 116 |
| | Plate D | Specimen_001_H3_H03_073.fcs | 181 |
| | Plate C | Specimen_001_H3_H03_073.fcs | 111 |

| PLATE NAME | Sample Name | Mean : APC-A |
|---|---|---|
| Plate E | Specimen_001_A5_A05_005.fcs | 491 |
| Plate D | Specimen_001_A5_A05_005.fcs | 905 |
| Plate C | Specimen_001_A5_A05_005.fcs | 114 |

| PLATE NAME | Sample Name | Mean : APC-A |
|---|---|---|
| Plate E | Specimen_001_G5_G05_065.fcs | 109 |
| Plate D | Specimen_001_G5_G05_065.fcs | 155 |
| Plate C | Specimen_001_G5_G05_065.fcs | 106 |

| PLATE NAME | Sample Name | Mean : APC-A |
|---|---|---|
| Plate E | Specimen_001_A2_A02_002.fcs | 6401 |
| Plate D | Specimen_001_A2_A02_002.fcs | 25702 |
| Plate C | Specimen_001_A2_A02_002.fcs | 107 |

| PLATE NAME | Sample Name | Mean : APC-A |
|---|---|---|
| Plate E | Specimen_001_H2_H02_072.fcs | 538 |
| Plate D | Specimen_001_H2_H02_072.fcs | 1161 |
| Plate C | Specimen_001_H2_H02_072.fcs | 105 |

| PLATE NAME | Sample Name | Mean : APC-A |
|---|---|---|
| Plate E | Specimen_001_A4_A04_004.fcs | 5293 |
| Plate D | Specimen_001_A4_A04_004.fcs | 16862 |
| Plate C | Specimen_001_A4_A04_004.fcs | 111 |

| PLATE NAME | Sample Name | Mean : APC-A |
|---|---|---|
| Plate E | Specimen_001_C5_C05_025.fcs | 178 |
| Plate D | Specimen_001_C5_C05_025.fcs | 314 |
| Plate C | Specimen_001_C5_C05_025.fcs | 117 |

| PLATE NAME | Sample Name | Mean : APC-A |
|---|---|---|
| Plate E | Specimen_001_H5_H05_075.fcs | 107 |
| Plate D | Specimen_001_H5_H05_075.fcs | 155 |
| Plate C | Specimen_001_H5_H05_075.fcs | 111 |

| PLATE NAME | Sample Name | Mean : APC-A |
|---|---|---|
| Plate E | Specimen_001_B2_B02_012.fcs | 5422 |
| Plate D | Specimen_001_B2_B02_012.fcs | 39586 |
| Plate C | Specimen_001_B2_B02_012.fcs | 113 |

| PLATE NAME | Sample Name | Mean : APC-A |
|---|---|---|
| Plate E | Specimen_001_A3_A03_003.fcs | 3740 |
| Plate D | Specimen_001_A3_A03_003.fcs | 9880 |
| Plate C | Specimen_001_A3_A03_003.fcs | 111 |

| | PLATE NAME | Sample Name | Mean : APC-A |
|---|---|---|---|
| ☐ | Plate E | Specimen_001_B4_B04_014.fcs | 2405 |
| ☐ | Plate D | Specimen_001_B4_B04_014.fcs | 27705 |
| ☒ | Plate C | Specimen_001_B4_B04_014.fcs | 131 |

| | PLATE NAME | Sample Name | Mean : APC-A |
|---|---|---|---|
| ☐ | Plate E | Specimen_001_F6_F06_056.fcs | 242 |
| ☐ | Plate D | Specimen_001_F6_F06_056.fcs | 568 |
| ☒ | Plate C | Specimen_001_F6_F06_056.fcs | 111 |

| | PLATE NAME | Sample Name | Mean : APC-A |
|---|---|---|---|
| ☐ | Plate E | Specimen_001_H10_H10_080.fcs | 122 |
| ☐ | Plate D | Specimen_001_H10_H10_080.fcs | 177 |
| ☒ | Plate C | Specimen_001_H10_H10_080.fcs | 109 |

| | | | | |
|---|---|---|---|---|
| 4A-1 | 4A-7 | 4A-13 | 4A-19 | 5C12 |
| 4A-2 | 4A-8 | 4A-14 | 4A-20 | 3F2 |
| 4A-3 | 4A-9 | 4A-15 | 4A-21 | msIgG1 Isotype Ctrl |
| 4A-4 | 4A-10 | 4A-16 | 4A-22 | msIgG2a Isotype Ctrl |
| 4A-5 | 4A-11 | 4A-17 | 4A-23 | msIgG2b Isotype Ctrl |
| 4A-6 | 4A-12 | 4A-18 | 4A-24 | No Primary Ctrl |

SEQUENCE LISTING

<160> NUMBER OF SEQ ID NOS: 355

<210> SEQ ID NO 1

```
<211> LENGTH: 239
<212> TYPE: PRT
<213> ORGANISM: Homo sapiens

<400> SEQUENCE: 1

Met His Gln Thr Tyr Ser Arg His Cys Arg Pro Glu Ser Thr Phe
1               5                   10                  15

Ser Ala Ala Met Thr Thr Met Gln Gly Met Glu Gln Ala Met Pro Gly
                20                  25                  30

Ala Gly Pro Gly Val Pro Gln Leu Gly Asn Met Ala Val Ile His Ser
                35                  40                  45

His Leu Trp Lys Gly Leu Gln Glu Lys Phe Leu Lys Gly Glu Pro Lys
            50                  55                  60

Val Leu Gly Val Val Gln Ile Leu Thr Ala Leu Met Ser Leu Ser Met
65                  70                  75                  80

Gly Ile Thr Met Met Cys Met Ala Ser Asn Thr Tyr Gly Ser Asn Pro
                85                  90                  95

Ile Ser Val Tyr Ile Gly Tyr Thr Ile Trp Gly Ser Val Met Phe Ile
                100                 105                 110

Ile Ser Gly Ser Leu Ser Ile Ala Ala Gly Ile Arg Thr Thr Lys Gly
                115                 120                 125

Leu Val Arg Gly Ser Leu Gly Met Asn Ile Thr Ser Ser Val Leu Ala
            130                 135                 140

Ala Ser Gly Ile Leu Ile Asn Thr Phe Ser Leu Ala Phe Tyr Ser Phe
145                 150                 155                 160

His His Pro Tyr Cys Asn Tyr Tyr Gly Asn Ser Asn Asn Cys His Gly
                165                 170                 175

Thr Met Ser Ile Leu Met Gly Leu Asp Gly Met Val Leu Leu Leu Ser
            180                 185                 190

Val Leu Glu Phe Cys Ile Ala Val Ser Leu Ser Ala Phe Gly Cys Lys
                195                 200                 205

Val Leu Cys Cys Thr Pro Gly Gly Val Val Leu Ile Leu Pro Ser His
            210                 215                 220

Ser His Met Ala Glu Thr Ala Ser Pro Thr Pro Leu Asn Glu Val
225                 230                 235

<210> SEQ ID NO 2
<211> LENGTH: 236
<212> TYPE: PRT
<213> ORGANISM: Mus musculus

<400> SEQUENCE: 2

Met Leu Val Ile Gln Gly Thr Glu Gln Ser Ala Leu Glu Ala Gly Tyr
1               5                   10                  15

Gly Ala Gln Gln Asn Gly Gln Pro Leu Tyr Val Asn Ser His Ser Trp
                20                  25                  30

Lys Arg Met Thr Glu Lys Phe Leu Lys Gly Glu Pro Lys Ile Leu Gly
                35                  40                  45

Ile Val Gln Ile Val Ile Ala Ile Met Asn Leu Ser Ile Gly Ile Met
            50                  55                  60

Met Ile Ile Ala Thr Val Ser Thr Gly Glu Ile Pro Pro Ser Ser Val
65                  70                  75                  80

Tyr Ile Gly Tyr Pro Ile Trp Gly Ser Leu Met Phe Ile Ile Ser Gly
                85                  90                  95

Ser Phe Ser Ile Val Ala Gly Arg Arg Thr Thr Lys Gly Leu Val Arg
                100                 105                 110
```

```
Ser Ser Leu Gly Leu Asn Ile Thr Ser Ser Val Phe Ala Phe Ser Gly
        115                 120                 125

Ile Val Ile Ser Ser Leu Ser Pro Gly Ile Tyr Ser Phe His Val Tyr
130                 135                 140

Tyr Cys Thr Tyr Arg Gly Ser Ser Glu Gly Cys His Met Thr Leu Ser
145                 150                 155                 160

Ile Leu Met Gly Leu Asp Ile Val Val Val Leu Ser Val Leu Glu
                165                 170                 175

Phe Cys Ile Gly Val Ser Leu Ser Ala Phe Gly Cys Arg Val Met Cys
                180                 185                 190

Cys Asn Pro Gly Gly Val Met Ile Ile Met Pro Ser Asn Pro Thr Lys
                195                 200                 205

Ala Glu Thr Ala Asn Pro Val Thr Leu Gln Ser Gly Leu Met Pro Pro
210                 215                 220

Glu His Gln Glu Arg Asn Val Pro Glu Asn Met His
225                 230                 235
```

<210> SEQ ID NO 3
<211> LENGTH: 238
<212> TYPE: PRT
<213> ORGANISM: Macaca fascicularis

<400> SEQUENCE: 3

```
His Gln Thr Tyr Arg Arg His Cys Arg Pro Glu Glu Ser Thr Phe Ser
1               5                   10                  15

Ala Ala Met Thr Thr Met Gln Gly Met Glu Gln Ala Thr Pro Gly Ala
                20                  25                  30

Gly Pro Gly Val Pro Gln Leu Gly Asn Met Ala Val Val His Ser His
            35                  40                  45

Leu Trp Lys Gly Leu Gln Glu Lys Phe Leu Lys Gly Glu Pro Lys Val
50                  55                  60

Leu Gly Val Val Gln Ile Leu Ile Ala Leu Met Ser Leu Ser Met Gly
65                  70                  75                  80

Ile Thr Met Met Cys Val Ala Phe Ser Ala Tyr Gly His Tyr Pro Ile
                85                  90                  95

Ser Val Tyr Ile Gly Tyr Thr Ile Trp Gly Ser Val Met Phe Ile Ile
            100                 105                 110

Ser Gly Ser Leu Ser Ile Ala Ala Gly Ile Arg Thr Thr Lys Gly Leu
        115                 120                 125

Val Arg Gly Ser Leu Gly Met Asn Ile Thr Ser Ser Val Leu Ala Val
    130                 135                 140

Ser Ala Ile Leu Ile Asn Thr Ile Ser Leu Thr Ile Tyr Ser Phe Tyr
145                 150                 155                 160

His Arg Tyr Cys Asn Tyr Tyr Gly Asn Pro Asn Asn Cys His Gly Thr
                165                 170                 175

Val Ser Ile Leu Met Gly Met Asp Gly Met Val Leu Leu Leu Ser Val
            180                 185                 190

Leu Glu Phe Cys Ile Ala Val Ser Leu Ser Ala Phe Gly Cys Lys Ala
        195                 200                 205

Ile Cys Cys Thr Pro Gly Gly Val Val Leu Ile Ile Pro Ser Asn Ser
    210                 215                 220

His Met Ala Glu Ala Ala Pro Leu Thr Pro Leu Asn Glu Val
225                 230                 235
```

-continued

```
<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Asp Tyr Glu Met Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Lys Tyr Gly Met Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Asp Tyr Val Leu Val
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Asp Ala Trp Met Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asp Tyr Val Met Ile
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Asp Tyr Tyr Met Tyr
1               5

<210> SEQ ID NO 10
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Ser Gly Tyr Tyr Trp Asn
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Ser Tyr Trp Met Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Asp Ala Trp Leu Asp
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Asp Tyr Val Ile Leu
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Gly Tyr Trp Ile Glu
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Ser Tyr Trp Ile His
1               5

<210> SEQ ID NO 16
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 16

Asp Tyr Gly Ile Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Asp Tyr Asn Met Asp
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Ser Tyr Gly Leu Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Asp Tyr Asn Ile His
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Trp Ile Asn Thr Tyr Thr Gly Glu Pro Thr Tyr Ala Asp Asp Phe Gln
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Trp Ile Asn Thr Tyr Thr Ala Glu Pro Thr Tyr Gly Asp Asp Phe Lys
1               5                   10                  15

Gly
```

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Asn Ile Asn Pro Tyr Tyr Gly Asn Ser Asp Tyr Asn Leu Lys Phe Glu
1               5                   10                  15

Gly

<210> SEQ ID NO 23
<211> LENGTH: 19
<212> TYPE: PRT
<213> ORGANISM: Artificial Sequence
<220> FEATURE:
<223> OTHER INFORMATION: Synthetic Construct

<400> SEQUENCE: 23

Glu Ile Arg Ser Lys Thr Asn Ser His Ala Thr Tyr Tyr Ala Glu Ser
1               5                   10                  15

Val Lys Gly

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Asn Ile Asn Pro Tyr Tyr Gly Ser Thr Ser Tyr Asn Leu Lys Phe Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Tyr Ile Asn Asn Gly Gly Gly Ser Thr Tyr Tyr Pro Asp Thr Val Lys
1               5                   10                  15

Gly

<210> SEQ ID NO 26
<211> LENGTH: 16
<212> TYPE: PRT
<213> ORGANISM: Artificial Sequence
<220> FEATURE:
<223> OTHER INFORMATION: Synthetic Construct

<400> SEQUENCE: 26

Tyr Ile Ser Tyr Asp Gly Asn Asn Lys Tyr Asn Pro Ser Leu Lys Asn
1               5                   10                  15

<210> SEQ ID NO 27
<211> LENGTH: 19
<212> TYPE: PRT
<213> ORGANISM: Artificial Sequence
<220> FEATURE:

<223> OTHER INFORMATION: Synthetic Construct

<400> SEQUENCE: 27

Glu Ile Arg Ser Lys Ala Asn Asp His Ala Thr Tyr Tyr Ala Glu Ser
1               5                   10                  15

Val Lys Gly

<210> SEQ ID NO 28
<211> LENGTH: 19
<212> TYPE: PRT
<213> ORGANISM: Artificial Sequence
<220> FEATURE:
<223> OTHER INFORMATION: Synthetic Construct

<400> SEQUENCE: 28

Glu Ile Arg Ser Lys Thr Asp Asn His Ala Thr Tyr Phe Ala Glu Ser
1               5                   10                  15

Val Lys Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Tyr Ile Asn Pro Gly Thr Gly Tyr Thr Glu Tyr Asn Gln Lys Phe Lys
1               5                   10                  15

Asp

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

His Ile Asn Pro Tyr Tyr Ala Asn Ser Asp Tyr Asn Val Asn Phe Arg
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Glu Ile Leu Pro Gly Ile Gly Asn Thr Lys Tyr Ser Glu Lys Phe Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

Asn Ile Asn Pro Thr Asn Gly Gly Thr Asn Tyr Asn Glu Arg Phe Lys
1               5                   10                  15

Ser

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Glu Ile Tyr Pro Arg Ser Gly Asn Thr Tyr Tyr Asn Glu Lys Phe Lys
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Asp Ile Asn Pro Asn Asn Gly Tyr Thr Ile Tyr Asn Gln Lys Phe Lys
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic Construct

<400> SEQUENCE: 35

Trp Ile Asn Thr Tyr Ser Gly Val Pro Thr Tyr Ala Asn Asp Phe Lys
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Synthetic Construct

<400> SEQUENCE: 36

Tyr Ile Asn Pro Asn Asn Asp Asp Thr Thr Phe Asn Gln Lys Phe Lys
1               5                   10                  15

Gly

<210> SEQ ID NO 37
<211> LENGTH: 19
<212> TYPE: PRT
<213> ORGANISM: Artificial Sequence
<220> FEATURE:
<223> OTHER INFORMATION: Synthetic Construct

<400> SEQUENCE: 37

Glu Ile Arg Asp Asn Ala Asp Asn His Pro Thr Tyr Tyr Ala Glu Ser
1               5                   10                  15

Val Lys Gly

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Asn Tyr Tyr Tyr Gly Asn Gly Asp Val Met Asp Tyr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Construct

<400> SEQUENCE: 39

Ser Ala Glu Leu Val Arg His Tyr Tyr Ala Leu Asp Tyr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Tyr Gly Leu Tyr Ala Met Asp Phe
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Asp Tyr Tyr Gly Ile Phe
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Tyr Gly Tyr Asp Ala Leu Asp Asn
1               5

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43

Gln Gly Asn Leu Ile Tyr Tyr Ser Gly Ser Ser Leu Phe Ala Tyr
1               5                   10                  15

```
<210> SEQ ID NO 44
<211> LENGTH: 3
<212> TYPE: PRT
<213> ORGANISM: Artificial Sequence
<220> FEATURE:
<223> OTHER INFORMATION: Synthetic Construct

<400> SEQUENCE: 44

Arg Asp Tyr
1

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Asp Tyr Tyr Gly Phe Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Construct

<400> SEQUENCE: 46

Ser Thr Phe Ala Ser
1               5

<210> SEQ ID NO 47
<211> LENGTH: 13
<212> TYPE: PRT
<213> ORGANISM: Artificial Sequence
<220> FEATURE:
<223> OTHER INFORMATION: Synthetic Construct

<400> SEQUENCE: 47

Phe Tyr Tyr Gly Ser Pro Tyr Tyr Tyr Ala Met Asp Tyr
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Tyr Gly Ser Gly Met Asp Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Ser Leu Leu Arg Ala Met Asp Tyr
1               5
```

```
<210> SEQ ID NO 50
<211> LENGTH: 11
<212> TYPE: PRT
<213> ORGANISM: Artificial Sequence
<220> FEATURE:
<223> OTHER INFORMATION: Synthetic Construct

<400> SEQUENCE: 50

Ala Tyr Tyr Tyr Gly Ser Ser Leu Phe Ala Tyr
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Lys Gly Leu Leu Arg Asp Phe Asp Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Ser Thr Gly Pro Tyr Phe Asp Tyr
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Construct

<400> SEQUENCE: 53

Ser Leu Val Asp Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Ser Pro Tyr Cys Tyr Phe Asp Val
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Asp Tyr Tyr Gly Ser His
1               5

<210> SEQ ID NO 56
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Ser Ala Ser Ser Ser Val Ser Tyr Ile His
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Synthetic Construct

<400> SEQUENCE: 57

Arg Ser Ser Gln Ser Leu Val His Ser Asn Gly Asn Ile Tyr Leu Glu
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic Construct

<400> SEQUENCE: 58

Arg Ser Ser Gln Thr Ile Val His Ser Asn Gly Asn Ser Tyr Leu Glu
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic Construct

<400> SEQUENCE: 59

Lys Ser Thr Gln Ser Leu Leu Asp Ser Asp Gly Lys Thr Phe Leu Asn
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic Construct

<400> SEQUENCE: 60

Arg Ser Ser Gln Ser Ile Val His Ser Asn Gly Asn Thr Tyr Leu Asp
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic Construct

<400> SEQUENCE: 61

Arg Ser Ser Gln Ser Ile Val His Ser Asn Arg Asn Thr Tyr Leu Glu
1               5                   10                  15

<210> SEQ ID NO 62
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 62

Arg Ser Ser Gln Asn Ile Val His Ser Asn Gly Ile Thr Tyr Leu Glu
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic Construct

<400> SEQUENCE: 63

Lys Ser Ser Gln Ser Leu Leu Asp Arg Asp Gly Lys Thr Phe Leu Asn
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic Construct

<400> SEQUENCE: 64

Lys Ser Ser Gln Ser Leu Leu Asp Ser Asp Gly Lys Thr Tyr Leu Asn
1               5                   10                  15

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Lys Ala Ser Gln Ser Val Asp Thr Asp Val Ala
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Synthetic Construct

<400> SEQUENCE: 66

Lys Ser Ser Gln Ser Leu Leu Asp Arg Asp Gly Lys Thr Tyr Leu Asn
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic Construct

<400> SEQUENCE: 67

Arg Ser Ser Gln Ser Ile Val His Ser Asp Gly Asn Thr Tyr Leu Glu
1               5                   10                  15

<210> SEQ ID NO 68
<211> LENGTH: 10
<212> TYPE: PRT
```

<213> ORGANISM: Artificial Sequence
<220> FEATURE:
<223> OTHER INFORMATION: Synthetic Construct

<400> SEQUENCE: 68

Ser Ala Ile Ser Ser Ile Ser Tyr Met His
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic Construct

<400> SEQUENCE: 69

Lys Ala Ser Gln Asn Val Gly Thr Ala Val Ala
1               5                   10

<210> SEQ ID NO 70
<211> LENGTH: 16
<212> TYPE: PRT
<213> ORGANISM: Artificial Sequence
<220> FEATURE:
<223> OTHER INFORMATION: Synthetic Construct

<400> SEQUENCE: 70

Lys Ser Ser Gln Ser Leu Leu Glu Ser Asp Gly Lys Thr Tyr Leu Asn
1               5                   10                  15

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Arg Ala Ser Glu Asn Ile Tyr Ser Tyr Leu Ala
1               5                   10

<210> SEQ ID NO 72
<211> LENGTH: 16
<212> TYPE: PRT
<213> ORGANISM: Artificial Sequence
<220> FEATURE:
<223> OTHER INFORMATION: Synthetic Construct

<400> SEQUENCE: 72

Lys Ser Ser Gln Ser Leu Leu Tyr Ser Asp Gly Lys Thr Tyr Leu Ser
1               5                   10                  15

<210> SEQ ID NO 73
<211> LENGTH: 11
<212> TYPE: PRT
<213> ORGANISM: Artificial Sequence
<220> FEATURE:
<223> OTHER INFORMATION: Synthetic Construct

<400> SEQUENCE: 73

Lys Ala Ser Gln Asp Ile Asn Lys Tyr Ile Val
1               5                   10

<210> SEQ ID NO 74
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 74

Lys Ala Ser Gln Ser Leu Leu Asp Ser Asp Gly Lys Thr Tyr Leu Asn
1               5                   10                  15

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct

<400> SEQUENCE: 75

Ser Thr Ser Asn Leu Ala Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

Lys Val Ser Asn Arg Phe Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Construct

<400> SEQUENCE: 77

Leu Val Ser Lys Leu Asp Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct

<400> SEQUENCE: 78

Arg Val Ser Asn Arg Phe Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Construct

<400> SEQUENCE: 79

Lys Ile Ser Asn Arg Phe Ser
1               5

<210> SEQ ID NO 80
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 80

Ser Ala Ser Asn Arg Tyr Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic Construct

<400> SEQUENCE: 81

Asp Thr Ser Lys Leu Ala Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Ser Ala Ser Tyr Arg His Thr
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Asn Gly Lys Thr Leu Ala Glu
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Tyr Thr Ser Thr Leu Gln Pro
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

Leu Val Ser Lys Met Asp Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 86

Gln Gln Arg Thr Gly Phe Pro Leu Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Construct

<400> SEQUENCE: 87

Ser Gln Gly Ser His Val Pro Pro Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Phe Gln Ser Ser His Val Pro Leu Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Trp Gln Gly Thr His Phe Pro Gln Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Phe Gln Gly Ser His Val Pro Leu Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Construct

<400> SEQUENCE: 91

Phe Gln Gly Ser His Val Pro Trp Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 92

Phe Gln Gly Ser His Val Pro Tyr Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Construct

<400> SEQUENCE: 93

His Gln Tyr Asn Ser Tyr Pro Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Construct

<400> SEQUENCE: 94

Phe Gln Gly Ser His Phe Pro Leu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Construct

<400> SEQUENCE: 95

His Gln Arg Ser Ser Tyr Pro Tyr Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct

<400> SEQUENCE: 96

Gln Gln Tyr Ser Thr Tyr Pro Trp Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct

<400> SEQUENCE: 97

Trp Gln Gly Thr His Phe Pro His Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Construct

<400> SEQUENCE: 98
```

Gln His His Tyr Gly Ile Pro Arg Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Construct

<400> SEQUENCE: 99

Trp Gln Gly Ile Asp Phe His Gln Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Leu Gln Tyr Asp Asn Leu Trp Thr
1               5

<210> SEQ ID NO 101
<211> LENGTH: 121
<212> TYPE: PRT
<213> ORGANISM: Artificial Sequence
<220> FEATURE:
<223> OTHER INFORMATION: Synthetic Construct

<400> SEQUENCE: 101

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Val Asp Tyr
                20                  25                  30

Glu Met Asn Trp Val Lys Gln Ala Pro Gly Lys Gly Leu Glu Trp Leu
            35                  40                  45

Gly Trp Ile Asn Thr Tyr Thr Gly Glu Pro Thr Tyr Ala Asp Asp Phe
    50                  55                  60

Gln Gly Arg Phe Ala Phe Ser Leu Val Thr Ser Val Ser Thr Ala Tyr
65                  70                  75                  80

Leu Gln Ile Asn Asn Leu Lys His Glu Asp Met Ala Thr Tyr Leu Cys
                85                  90                  95

Thr Arg Asn Tyr Tyr Gly Asn Gly Asp Val Met Asp Tyr Trp Gly
                100                 105                 110

Gln Gly Thr Ser Val Thr Val Ser Ser
        115                 120

<210> SEQ ID NO 102
<211> LENGTH: 122
<212> TYPE: PRT
<213> ORGANISM: Artificial Sequence
<220> FEATURE:
<223> OTHER INFORMATION: Synthetic Construct

<400> SEQUENCE: 102

Gln Ile Gln Leu Val Gln Ser Gly Pro Glu Leu Lys Thr Pro Gly Glu
1               5                   10                  15

Thr Val Lys Ile Ser Cys Lys Ser Gly Tyr Thr Phe Thr Lys Tyr
                20                  25                  30

Gly Met Asn Trp Val Lys Gln Ala Pro Gly Lys Gly Leu Lys Trp Met
            35                  40                  45

Ala Trp Ile Asn Thr Tyr Thr Ala Glu Pro Thr Tyr Gly Asp Asp Phe
 50                  55                  60

Lys Gly Arg Phe Ala Leu Ser Leu Glu Thr Ser Ala Asn Thr Ala Tyr
 65                  70                  75                  80

Leu Gln Ile Asn Asn Leu Lys Asn Glu Asp Thr Ala Thr Tyr Phe Cys
                85                  90                  95

Ala Arg Ser Ala Glu Leu Val Arg His Tyr Tyr Ala Leu Asp Tyr Trp
                100                 105                 110

Gly Gln Gly Thr Ser Val Thr Val Ser Ser
            115                 120

<210> SEQ ID NO 103
<211> LENGTH: 117
<212> TYPE: PRT
<213> ORGANISM: Artificial Sequence
<220> FEATURE:
<223> OTHER INFORMATION: Synthetic Construct

<400> SEQUENCE: 103

Glu Ile Gln Leu Gln Gln Thr Gly Pro Asp Leu Val Lys Pro Gly Thr
 1               5                  10                  15

Ser Val Lys Ile Ser Cys Lys Ala Ser Gly Tyr Ser Phe Thr Asp Tyr
                20                  25                  30

Val Leu Val Trp Val Lys Gln Ser His Gly Lys Ser Leu Glu Trp Ile
            35                  40                  45

Gly Asn Ile Asn Pro Tyr Tyr Gly Asn Ser Asp Tyr Asn Leu Lys Phe
 50                  55                  60

Glu Gly Lys Ala Arg Leu Thr Val Asp Arg Ser Ser Thr Ala Tyr
 65                  70                  75                  80

Met Gln Leu Asn Ser Leu Thr Ser Glu Asp Ser Ala Val Tyr Tyr Cys
                85                  90                  95

Ala Arg Tyr Gly Leu Tyr Ala Met Asp Phe Trp Gly Gln Gly Thr Ser
                100                 105                 110

Val Thr Val Ser Ser
            115

<210> SEQ ID NO 104
<211> LENGTH: 117
<212> TYPE: PRT
<213> ORGANISM: Artificial Sequence
<220> FEATURE:
<223> OTHER INFORMATION: Synthetic Construct

<400> SEQUENCE: 104

Glu Val Lys Val Glu Glu Ser Gly Gly Gly Leu Val Gln Pro Gly Gly
 1               5                  10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Thr Asn Ser His Ala Thr Tyr Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr

```
                    85                  90                  95
Tyr Cys Thr Val Asp Tyr Tyr Gly Ile Phe Trp Gly Gln Gly Thr Leu
                100                 105                 110
Val Thr Val Ser Ser
        115

<210> SEQ ID NO 105
<211> LENGTH: 117
<212> TYPE: PRT
<213> ORGANISM: Artificial Sequence
<220> FEATURE:
<223> OTHER INFORMATION: Synthetic Construct

<400> SEQUENCE: 105

Glu Ile Gln Leu Gln Gln Thr Gly Pro Glu Leu Val Lys Pro Gly Ala
1               5                   10                  15
Ser Val Lys Ile Ser Cys Lys Ala Ser Gly Tyr Ser Phe Thr Asp Tyr
                20                  25                  30
Val Met Ile Trp Val Lys Gln Ser His Gly Lys Ser Leu Glu Trp Ile
            35                  40                  45
Gly Asn Ile Asn Pro Tyr Tyr Gly Ser Thr Ser Tyr Asn Leu Lys Phe
        50                  55                  60
Lys Gly Lys Ala Thr Leu Thr Val Asp Lys Ser Ser Ser Thr Ala Tyr
65                  70                  75                  80
Met Gln Leu Lys Ser Leu Thr Ser Glu Asp Ser Ala Val Tyr Tyr Cys
                85                  90                  95
Ala Arg Tyr Gly Tyr Asp Ala Leu Asp Asn Trp Gly Gln Gly Thr Ser
                100                 105                 110
Val Thr Val Ser Ser
        115

<210> SEQ ID NO 106
<211> LENGTH: 124
<212> TYPE: PRT
<213> ORGANISM: Artificial Sequence
<220> FEATURE:
<223> OTHER INFORMATION: Synthetic Construct

<400> SEQUENCE: 106

Glu Val Lys Leu Val Glu Ser Gly Gly Gly Leu Val Gln Pro Gly Gly
1               5                   10                  15
Ser Leu Lys Leu Ser Cys Ala Thr Ser Gly Phe Thr Phe Ser Asp Tyr
                20                  25                  30
Tyr Met Tyr Trp Val Arg Gln Thr Pro Glu Lys Arg Leu Glu Trp Val
            35                  40                  45
Ala Tyr Ile Asn Asn Gly Gly Gly Ser Thr Tyr Tyr Pro Asp Thr Val
        50                  55                  60
Lys Gly Arg Phe Thr Ile Ser Arg Asp Asn Ala Lys Asn Thr Leu Tyr
65                  70                  75                  80
Leu Gln Met Ser Arg Leu Lys Ser Glu Asp Thr Ala Met Tyr Tyr Cys
                85                  90                  95
Ala Arg Gln Gly Asn Leu Ile Tyr Tyr Ser Gly Ser Ser Leu Phe Ala
                100                 105                 110
Tyr Trp Gly Gln Gly Thr Met Val Thr Val Ser Ser
        115                 120

<210> SEQ ID NO 107
<211> LENGTH: 112
```

```
<212> TYPE: PRT
<213> ORGANISM: Artificial Sequence
<220> FEATURE:
<223> OTHER INFORMATION: Synthetic Construct

<400> SEQUENCE: 107

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Asn Asn Lys Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asn Arg Asp Tyr Trp Gly Gln Gly Thr Thr Leu Thr Val Ser Ser
            100                 105                 110

<210> SEQ ID NO 108
<211> LENGTH: 117
<212> TYPE: PRT
<213> ORGANISM: Artificial Sequence
<220> FEATURE:
<223> OTHER INFORMATION: Synthetic Construct

<400> SEQUENCE: 108

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asp His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Ser Val Asp Tyr Tyr Gly Phe Phe Trp Gly Gln Gly Thr Leu
            100                 105                 110

Val Thr Val Ser Ala
        115

<210> SEQ ID NO 109
<211> LENGTH: 116
<212> TYPE: PRT
<213> ORGANISM: Artificial Sequence
<220> FEATURE:
<223> OTHER INFORMATION: Synthetic Construct

<400> SEQUENCE: 109

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
```

```
                35                  40                  45
Ala Glu Ile Arg Ser Lys Thr Asp Asn His Ala Thr Tyr Phe Ala Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Gly Asp Thr Gly Ile Tyr
                85                  90                  95

Tyr Cys Tyr Gly Ser Thr Phe Ala Ser Trp Gly Gln Gly Thr Leu Val
            100                 105                 110

Thr Val Ser Ser
            115

<210> SEQ ID NO 110
<211> LENGTH: 122
<212> TYPE: PRT
<213> ORGANISM: Artificial Sequence
<220> FEATURE:
<223> OTHER INFORMATION: Synthetic Construct

<400> SEQUENCE: 110

Gln Val Gln Leu Gln Gln Ser Gly Ala Glu Leu Ala Gln Pro Gly Ala
1               5                   10                  15

Ser Val Lys Met Ser Cys Lys Ala Ser Gly Tyr Thr Phe Ser Ser Tyr
            20                  25                  30

Trp Met Tyr Trp Val Lys Gln Gly Pro Gly Gln Gly Leu Glu Trp Ile
        35                  40                  45

Gly Tyr Ile Asn Pro Gly Thr Gly Tyr Thr Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Phe Tyr Tyr Gly Ser Pro Tyr Tyr Tyr Ala Met Asp Tyr Trp
            100                 105                 110

Gly Gln Gly Thr Ser Val Thr Val Ser Ser
        115                 120

<210> SEQ ID NO 111
<211> LENGTH: 117
<212> TYPE: PRT
<213> ORGANISM: Artificial Sequence
<220> FEATURE:
<223> OTHER INFORMATION: Synthetic Construct

<400> SEQUENCE: 111

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Leu Asp Trp Val Arg Gln Ser Pro Glu Lys Gly Leu Glu Trp Val
        35                  40                  45

Ala Glu Ile Arg Ser Lys Ala Asn Asp His Ala Thr Tyr Tyr Ala Glu
        50                  55                  60

Ser Val Lys Gly Arg Phe Thr Ile Ser Arg Asp Asp Ser Lys Ser Arg
65                  70                  75                  80

Phe Tyr Leu Gln Met Asn Ser Leu Arg Ala Glu Asp Thr Gly Ile Tyr
                85                  90                  95
```

```
Tyr Cys Ser Val Asp Tyr Gly Phe Phe Trp Gly Gln Gly Thr Leu
            100                 105                 110

Val Thr Val Ser Ala
        115

<210> SEQ ID NO 112
<211> LENGTH: 116
<212> TYPE: PRT
<213> ORGANISM: Artificial Sequence
<220> FEATURE:
<223> OTHER INFORMATION: Synthetic Construct

<400> SEQUENCE: 112

Glu Ile Gln Leu Gln Gln Thr Gly Pro Asp Leu Val Lys Pro Gly Ala
1               5                   10                  15

Ser Val Lys Ile Ser Cys Lys Ala Ser Gly Tyr Ser Phe Thr Asp Tyr
            20                  25                  30

Val Ile Leu Trp Val Lys Gln Ser His Gly Lys Thr Leu Glu Trp Ile
        35                  40                  45

Gly His Ile Asn Pro Tyr Tyr Ala Asn Ser Asp Tyr Asn Val Asn Phe
    50                  55                  60

Arg Gly Lys Ala Thr Leu Thr Val Asp Lys Ser Ser Thr Ala His
65                  70                  75                  80

Met Gln Leu Asn Ser Leu Thr Ser Glu Asp Ser Ala Val Tyr Tyr Cys
                85                  90                  95

Val Arg Tyr Gly Ser Gly Met Asp Tyr Trp Gly Gln Gly Thr Ser Val
            100                 105                 110

Thr Val Ser Ser
        115

<210> SEQ ID NO 113
<211> LENGTH: 117
<212> TYPE: PRT
<213> ORGANISM: Artificial Sequence
<220> FEATURE:
<223> OTHER INFORMATION: Synthetic Construct

<400> SEQUENCE: 113

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asp His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Ser Val Asp Tyr Tyr Gly Phe Phe Trp Gly Gln Gly Thr Met
            100                 105                 110

Val Thr Val Ser Ala
        115

<210> SEQ ID NO 114
<211> LENGTH: 117
<212> TYPE: PRT
<213> ORGANISM: Artificial Sequence
```

```
<220> FEATURE:
<223> OTHER INFORMATION: Synthetic Construct

<400> SEQUENCE: 114

Gln Val Gln Leu Gln Gln Ser Ala Ala Glu Leu Met Lys Pro Gly Ala
1               5                   10                  15

Ser Val Lys Leu Ser Cys Lys Ala Thr Gly Tyr Thr Phe Thr Gly Tyr
                20                  25                  30

Trp Ile Glu Trp Leu Lys Gln Arg Pro Gly His Gly Leu Glu Trp Ile
            35                  40                  45

Gly Glu Ile Leu Pro Gly Ile Gly Asn Thr Lys Tyr Ser Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Ser Leu Leu Arg Ala Met Asp Tyr Trp Gly Gln Gly Thr Ser
            100                 105                 110

Val Thr Val Ser Ser
        115

<210> SEQ ID NO 115
<211> LENGTH: 120
<212> TYPE: PRT
<213> ORGANISM: Artificial Sequence
<220> FEATURE:
<223> OTHER INFORMATION: Synthetic Construct

<400> SEQUENCE: 115

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Ile His Trp Val Lys Gln Arg Pro Gly Gln Gly Leu Glu Trp Ile
            35                  40                  45

Gly Asn Ile Asn Pro Thr Asn Gly Gly Thr Asn Tyr Asn Glu Arg Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ala
        115                 120

<210> SEQ ID NO 116
<211> LENGTH: 118
<212> TYPE: PRT
<213> ORGANISM: Artificial Sequence
<220> FEATURE:
<223> OTHER INFORMATION: Synthetic Construct

<400> SEQUENCE: 116

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ser Phe Ile Asp Tyr
                20                  25                  30
```

Gly Ile Ser Trp Val Lys Gln Arg Thr Gly Gln Gly Leu Glu Trp Ile
                35                  40                  45

Gly Glu Ile Tyr Pro Arg Ser Gly Asn Thr Tyr Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Lys Gly Leu Leu Arg Asp Phe Asp Tyr Trp Gly Gln Gly Thr
                100                 105                 110

Thr Leu Thr Val Ser Ser
            115

<210> SEQ ID NO 117
<211> LENGTH: 117
<212> TYPE: PRT
<213> ORGANISM: Artificial Sequence
<220> FEATURE:
<223> OTHER INFORMATION: Synthetic Construct

<400> SEQUENCE: 117

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Asp Trp Ile
                35                  40                  45

Gly Asp Ile Asn Pro Asn Asn Gly Tyr Thr Ile Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Arg Leu Thr Ser Glu Asp Thr Ala Val Tyr Tyr Cys
                85                  90                  95

Ala Arg Ser Thr Gly Pro Tyr Phe Asp Tyr Trp Gly Gln Gly Thr Thr
                100                 105                 110

Leu Thr Val Ser Ser
            115

<210> SEQ ID NO 118
<211> LENGTH: 114
<212> TYPE: PRT
<213> ORGANISM: Artificial Sequence
<220> FEATURE:
<223> OTHER INFORMATION: Synthetic Construct

<400> SEQUENCE: 118

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Ser Tyr
                20                  25                  30

Gly Leu Ser Trp Val Lys Gln Thr Pro Gly Lys Gly Leu Lys Trp Met
                35                  40                  45

Gly Trp Ile Asn Thr Tyr Ser Gly Val Pro Tyr Ala Asn Asp Phe
        50                  55                  60

Lys Gly Arg Phe Ala Phe Ser Leu Glu Thr Ser Ala Ser Thr Thr Tyr
65                  70                  75                  80

Leu Arg Ile Asn Asn Leu Lys Asn Asp Asp Thr Ala Thr Tyr Phe Cys
                85                  90                  95

Ala Arg Ser Leu Val Asp Tyr Trp Gly Gln Gly Thr Pro Leu Thr Val
            100                 105                 110

Ser Ser

<210> SEQ ID NO 119
<211> LENGTH: 117
<212> TYPE: PRT
<213> ORGANISM: Artificial Sequence
<220> FEATURE:
<223> OTHER INFORMATION: Synthetic Construct

<400> SEQUENCE: 119

Glu Val Gln Leu Gln Gln Ser Gly Pro Glu Leu Val Lys Pro Gly Ala
1               5                   10                  15

Ser Val Lys Met Ser Cys Gln Ala Ser Gly Tyr Thr Phe Thr Asp Tyr
            20                  25                  30

Asn Ile His Trp Val Lys Gln Ser His Gly Lys Ser Leu Lys Trp Ile
        35                  40                  45

Gly Tyr Ile Asn Pro Asn Asn Asp Thr Thr Phe Asn Gln Lys Phe
    50                  55                  60

Lys Gly Lys Ala Thr Leu Thr Val Asn Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Pro Tyr Cys Tyr Phe Asp Val Trp Gly Thr Gly Thr Thr
            100                 105                 110

Val Thr Val Ser Ser
        115

<210> SEQ ID NO 120
<211> LENGTH: 117
<212> TYPE: PRT
<213> ORGANISM: Artificial Sequence
<220> FEATURE:
<223> OTHER INFORMATION: Synthetic Construct

<400> SEQUENCE: 120

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asp Asn Ala Asp Asn His Pro Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Ser Asp Tyr Tyr Gly Ser His Trp Gly Gln Gly Thr Thr
            100                 105                 110

Leu Thr Val Ser Ser
        115

<210> SEQ ID NO 121
<211> LENGTH: 106
<212> TYPE: PRT
<213> ORGANISM: Artificial Sequence

```
<220> FEATURE:
<223> OTHER INFORMATION: Synthetic Construct

<400> SEQUENCE: 121

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Ile
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Thr Gly Phe Pro Leu Thr
                85                  90                  95

Phe Gly Gly Gly Thr Gln Leu Glu Ile Lys
            100                 105

<210> SEQ ID NO 122
<211> LENGTH: 112
<212> TYPE: PRT
<213> ORGANISM: Artificial Sequence
<220> FEATURE:
<223> OTHER INFORMATION: Synthetic Construct

<400> SEQUENCE: 122

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Ile Tyr Leu Glu Trp Phe Leu Gln Lys Pro Gly Gln Ser
        35                  40                  45

Leu Lys Ile Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Ser Gln Gly
                85                  90                  95

Ser His Val Pro Pro Thr Phe Gly Ala Gly Thr Lys Leu Glu Leu Arg
            100                 105                 110

<210> SEQ ID NO 123
<211> LENGTH: 112
<212> TYPE: PRT
<213> ORGANISM: Artificial Sequence
<220> FEATURE:
<223> OTHER INFORMATION: Synthetic Construct

<400> SEQUENCE: 123

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Ser Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Val Phe Thr Leu Lys Ile
65                  70                  75                  80

Ser Arg Val Glu Ala Glu Asp Leu Gly Val Tyr Phe Cys Phe Gln Ser
            85                  90                  95

Ser His Val Pro Leu Thr Phe Gly Val Gly Thr Lys Leu Glu Leu Lys
            100                 105                 110

<210> SEQ ID NO 124
<211> LENGTH: 112
<212> TYPE: PRT
<213> ORGANISM: Artificial Sequence
<220> FEATURE:
<223> OTHER INFORMATION: Synthetic Construct

<400> SEQUENCE: 124

Asp Val Val Met Thr Gln Thr Pro Leu Thr Leu Ser Val Thr Ile Gly
1               5                   10                  15

Gln Pro Ala Ser Ile Ser Cys Lys Ser Thr Gln Ser Leu Leu Asp Ser
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Phe Cys Trp Gln Gly
            85                  90                  95

Thr His Phe Pro Gln Thr Phe Gly Gly Gly Thr Lys Leu Glu Ile Lys
            100                 105                 110

<210> SEQ ID NO 125
<211> LENGTH: 112
<212> TYPE: PRT
<213> ORGANISM: Artificial Sequence
<220> FEATURE:
<223> OTHER INFORMATION: Synthetic Construct

<400> SEQUENCE: 125

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Asp Trp Ser Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Leu Thr Phe Gly Ala Gly Thr Lys Leu Glu Leu Lys
            100                 105                 110

<210> SEQ ID NO 126
<211> LENGTH: 112
<212> TYPE: PRT
<213> ORGANISM: Artificial Sequence
<220> FEATURE:
<223> OTHER INFORMATION: Synthetic Construct

<400> SEQUENCE: 126

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Arg Asn Thr Tyr Leu Glu Trp Tyr Val Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

<210> SEQ ID NO 127
<211> LENGTH: 112
<212> TYPE: PRT
<213> ORGANISM: Artificial Sequence
<220> FEATURE:
<223> OTHER INFORMATION: Synthetic Construct

<400> SEQUENCE: 127

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Ile Thr Tyr Leu Glu Trp Phe Leu Gln Lys Pro Gly Gln Ser
        35                  40                  45

Pro Thr Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Asp Ile Lys
                100                 105                 110

<210> SEQ ID NO 128
<211> LENGTH: 112
<212> TYPE: PRT
<213> ORGANISM: Artificial Sequence
<220> FEATURE:
<223> OTHER INFORMATION: Synthetic Construct

<400> SEQUENCE: 128

Asp Val Val Met Thr Gln Thr Pro Leu Thr Leu Ser Val Thr Ile Gly
1               5                   10                  15

Gln Thr Ala Ser Ile Ser Cys Lys Ser Ser Gln Ser Leu Leu Asp Arg
            20                  25                  30

Asp Gly Lys Thr Phe Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

-continued

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 129
<211> LENGTH: 112
<212> TYPE: PRT
<213> ORGANISM: Artificial Sequence
<220> FEATURE:
<223> OTHER INFORMATION: Synthetic Construct

<400> SEQUENCE: 129

Asp Val Val Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Asn Leu Glu Ile Lys
            100                 105                 110

<210> SEQ ID NO 130
<211> LENGTH: 107
<212> TYPE: PRT
<213> ORGANISM: Artificial Sequence
<220> FEATURE:
<223> OTHER INFORMATION: Synthetic Construct

<400> SEQUENCE: 130

Asp Ile Val Met Thr Gln Ser Gln Lys Phe Met Ser Thr Ser Val Gly
1               5                   10                  15

Asp Arg Val Thr Phe Thr Cys Lys Ala Ser Gln Ser Val Asp Thr Asp
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys His Gln Tyr Asn Ser Tyr Pro Leu
                85                  90                  95

Thr Phe Gly Ala Gly Thr Lys Leu Glu Leu Lys
            100                 105

<210> SEQ ID NO 131
<211> LENGTH: 112
<212> TYPE: PRT
<213> ORGANISM: Artificial Sequence
<220> FEATURE:
<223> OTHER INFORMATION: Synthetic Construct

<400> SEQUENCE: 131

Ala Val Val Met Thr Gln Thr Pro Leu Thr Leu Ser Val Thr Ile Gly

```
1               5                   10                  15
Gln Pro Ala Ser Ile Ser Cys Lys Ser Ser Gln Ser Leu Leu Asp Arg
            20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65              70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110
```

<210> SEQ ID NO 132
<211> LENGTH: 112
<212> TYPE: PRT
<213> ORGANISM: Artificial Sequence
<220> FEATURE:
<223> OTHER INFORMATION: Synthetic Construct

<400> SEQUENCE: 132

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser His Phe Pro Leu Thr Phe Gly Ala Gly Thr Lys Leu Glu Leu Lys
            100                 105                 110
```

<210> SEQ ID NO 133
<211> LENGTH: 106
<212> TYPE: PRT
<213> ORGANISM: Artificial Sequence
<220> FEATURE:
<223> OTHER INFORMATION: Synthetic Construct

<400> SEQUENCE: 133

```
Gln Ile Val Leu Thr Gln Ser Pro Ala Ile Met Ser Ala Ser Pro Gly
1               5                   10                  15

Glu Lys Val Thr Met Thr Cys Ser Ala Ile Ser Ser Ile Ser Tyr Met
            20                  25                  30

His Trp Tyr Gln Leu Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65              70                  75                  80

Asp Ala Ala Thr Tyr Tyr Cys His Gln Arg Ser Ser Tyr Pro Tyr Thr
                85                  90                  95
```

```
Phe Gly Gly Gly Thr Lys Leu Glu Ile Lys
            100                 105
```

<210> SEQ ID NO 134
<211> LENGTH: 107
<212> TYPE: PRT
<213> ORGANISM: Artificial Sequence
<220> FEATURE:
<223> OTHER INFORMATION: Synthetic Construct

<400> SEQUENCE: 134

```
Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Ser Gln Gln Lys Pro Gly Gln Ser Pro Lys Leu Leu Ile
        35                  40                  45

Tyr Ser Ala Ser Tyr Arg His Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Thr Tyr Pro Trp
                85                  90                  95

Thr Phe Gly Gly Gly Thr Lys Leu Glu Ile Lys
            100                 105
```

<210> SEQ ID NO 135
<211> LENGTH: 112
<212> TYPE: PRT
<213> ORGANISM: Artificial Sequence
<220> FEATURE:
<223> OTHER INFORMATION: Synthetic Construct

<400> SEQUENCE: 135

```
Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Gly Gly Thr Lys Leu Glu Ile Lys
            100                 105                 110
```

<210> SEQ ID NO 136
<211> LENGTH: 107
<212> TYPE: PRT
<213> ORGANISM: Artificial Sequence
<220> FEATURE:
<223> OTHER INFORMATION: Synthetic Construct

<400> SEQUENCE: 136

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
```

```
                20                  25                  30

Leu Ala Trp Tyr Gln Gln Lys Gln Gly Lys Ser Pro Gln Phe Leu Val
            35                  40                  45

Tyr Asn Gly Lys Thr Leu Ala Glu Gly Val Pro Ser Arg Phe Ser Gly
        50                  55                  60

Cys Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Ile Pro Arg
                85                  90                  95

Thr Phe Gly Gly Gly Thr Lys Leu Glu Ile Lys
            100                 105

<210> SEQ ID NO 137
<211> LENGTH: 112
<212> TYPE: PRT
<213> ORGANISM: Artificial Sequence
<220> FEATURE:
<223> OTHER INFORMATION: Synthetic Construct

<400> SEQUENCE: 137

Asp Val Val Met Thr Gln Thr Pro Phe Thr Leu Ser Val Thr Ile Gly
1               5                   10                  15

Gln Ser Ala Ser Ile Ser Cys Lys Ser Ser Gln Ser Leu Leu Tyr Ser
                20                  25                  30

Asp Gly Lys Thr Tyr Leu Ser Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ile Asp Phe His Gln Thr Phe Gly Gly Gly Thr Lys Leu Glu Ile Lys
            100                 105                 110

<210> SEQ ID NO 138
<211> LENGTH: 106
<212> TYPE: PRT
<213> ORGANISM: Artificial Sequence
<220> FEATURE:
<223> OTHER INFORMATION: Synthetic Construct

<400> SEQUENCE: 138

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
                20                  25                  30

Ile Val Trp Tyr Gln His Lys Pro Gly Lys Gly Pro Arg Leu Leu Ile
            35                  40                  45

Asn Tyr Thr Ser Thr Leu Gln Pro Gly Ile Pro Ser Arg Phe Ser Gly
        50                  55                  60

Gly Gly Ser Gly Gly Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys
            100                 105
```

<210> SEQ ID NO 139
<211> LENGTH: 112
<212> TYPE: PRT
<213> ORGANISM: Artificial Sequence
<220> FEATURE:
<223> OTHER INFORMATION: Synthetic Construct

<400> SEQUENCE: 139

Asp Val Val Met Thr Gln Thr Pro Phe Thr Leu Ser Val Thr Ile Gly
1               5                   10                  15

Gln Pro Ala Ser Ile Ser Cys Lys Ala Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Met Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 140
<211> LENGTH: 19
<212> TYPE: DNA
<213> ORGANISM: Artificial Sequence
<220> FEATURE:
<223> OTHER INFORMATION: Synthetic Construct

<400> SEQUENCE: 140
agctgggaag gtgtgcaca                                            19

<210> SEQ ID NO 141
<211> LENGTH: 21
<212> TYPE: DNA
<213> ORGANISM: Artificial Sequence
<220> FEATURE:
<223> OTHER INFORMATION: Synthetic Construct

<400> SEQUENCE: 141
ccattttgtc gttcactgcc a                                         21

<210> SEQ ID NO 142
<211> LENGTH: 5
<212> TYPE: PRT
<213> ORGANISM: Artificial Sequence
<220> FEATURE:
<223> OTHER INFORMATION: Synthetic Construct

<400> SEQUENCE: 142

Ser Phe Gly Val Thr
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic Construct

<400> SEQUENCE: 143

Asn Tyr Trp Met Gln

```
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic Construct

<400> SEQUENCE: 144

Ser Phe Tyr Met Ser
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic Construct

<400> SEQUENCE: 145

His Tyr Gly Met Ser
1               5

<210> SEQ ID NO 146
<211> LENGTH: 5
<212> TYPE: PRT
<213> ORGANISM: Artificial Sequence
<220> FEATURE:
<223> OTHER INFORMATION: Synthetic Construct

<400> SEQUENCE: 146

Ser Tyr Thr Met Ser
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic Construct

<400> SEQUENCE: 147

Asn Tyr Trp Met Asn
1               5

<210> SEQ ID NO 148
<211> LENGTH: 5
<212> TYPE: PRT
<213> ORGANISM: Artificial Sequence
<220> FEATURE:
<223> OTHER INFORMATION: Synthetic Construct

<400> SEQUENCE: 148

Asp Thr Tyr Ile His
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic Construct

<400> SEQUENCE: 149

Arg Tyr Trp Met Ser
1               5
```

```
<210> SEQ ID NO 150
<211> LENGTH: 5
<212> TYPE: PRT
<213> ORGANISM: Artificial Sequence
<220> FEATURE:
<223> OTHER INFORMATION: Synthetic Construct

<400> SEQUENCE: 150

Thr Tyr Thr Met Ser
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic Construct

<400> SEQUENCE: 151

Ser Tyr Gly Val His
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic Construct

<400> SEQUENCE: 152

Asn Tyr Trp Leu Gly
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic Construct

<400> SEQUENCE: 153

Ser Tyr Gly Met Ser
1               5

<210> SEQ ID NO 154
<211> LENGTH: 16
<212> TYPE: PRT
<213> ORGANISM: Artificial Sequence
<220> FEATURE:
<223> OTHER INFORMATION: Synthetic Construct

<400> SEQUENCE: 154

Ile Ile Trp Gly Asp Gly Ser Thr Asn Tyr His Ser Ala Leu Ile Ser
1               5                   10                  15

<210> SEQ ID NO 155
<211> LENGTH: 17
<212> TYPE: PRT
<213> ORGANISM: Artificial Sequence
<220> FEATURE:
<223> OTHER INFORMATION: Synthetic Construct

<400> SEQUENCE: 155

Ala Thr His Pro Gly His Gly Asp Thr Arg Tyr Thr Gln Lys Phe Lys
1               5                   10                  15
```

<210> SEQ ID NO 156
<211> LENGTH: 17
<212> TYPE: PRT
<213> ORGANISM: Artificial Sequence
<220> FEATURE:
<223> OTHER INFORMATION: Synthetic Construct

<400> SEQUENCE: 156

Ala Ile Asn Ser Asn Gly Gly Ser Thr Tyr Tyr Pro Asp Thr Val Lys
1               5                   10                  15
Gly

<210> SEQ ID NO 157
<211> LENGTH: 17
<212> TYPE: PRT
<213> ORGANISM: Artificial Sequence
<220> FEATURE:
<223> OTHER INFORMATION: Synthetic Construct

<400> SEQUENCE: 157

Ala Ile Asn Ser Asn Gly Gly Ser Thr Tyr Tyr Pro Asp Ser Val Lys
1               5                   10                  15
Gly

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

Thr Ile Gly Arg Asp Gly Ile His Thr Asp Tyr Arg Asp Ser Val Lys
1               5                   10                  15
Gly

<210> SEQ ID NO 159
<211> LENGTH: 16
<212> TYPE: PRT
<213> ORGANISM: Artificial Sequence
<220> FEATURE:
<223> OTHER INFORMATION: Synthetic Construct

<400> SEQUENCE: 159

Ser Leu Ser Ser Gly Gly Ser Thr Tyr Tyr Pro Asp Ser Val Lys Gly
1               5                   10                  15

<210> SEQ ID NO 160
<211> LENGTH: 19
<212> TYPE: PRT
<213> ORGANISM: Artificial Sequence
<220> FEATURE:
<223> OTHER INFORMATION: Synthetic Construct

<400> SEQUENCE: 160

Glu Ile Arg Leu Lys Ser Asn Asn Tyr Ala Thr His Tyr Ala Glu Ser
1               5                   10                  15
Val Lys Gly

<210> SEQ ID NO 161
<211> LENGTH: 17
<212> TYPE: PRT

```
<213> ORGANISM: Artificial Sequence
<220> FEATURE:
<223> OTHER INFORMATION: Synthetic Construct

<400> SEQUENCE: 161

Arg Ile Asp Pro Ala Asn Asp Asn Thr Lys Tyr Asp Pro Lys Phe Gln
1               5                   10                  15

Gly

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Glu Ile Lys Ser Asp Ser Ser Thr Ile Asn Tyr Thr Pro Ser Leu Lys
1               5                   10                  15

Asp

<210> SEQ ID NO 163
<211> LENGTH: 17
<212> TYPE: PRT
<213> ORGANISM: Artificial Sequence
<220> FEATURE:
<223> OTHER INFORMATION: Synthetic Construct

<400> SEQUENCE: 163

Thr Ile Ser Ser Gly Gly Ser Tyr Thr Phe Tyr Pro Asp Ser Val Lys
1               5                   10                  15

Gly

<210> SEQ ID NO 164
<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Val Ile Trp Val Gly Gly Ser Thr Asn Tyr Asn Ser Ala Leu Met Ser
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Asp Ile Phe Pro Gly Gly Asn Tyr Leu Lys Asn Asn Glu Lys Phe Lys
1               5                   10                  15

Gly

<210> SEQ ID NO 166
<211> LENGTH: 17
<212> TYPE: PRT
<213> ORGANISM: Artificial Sequence
<220> FEATURE:
<223> OTHER INFORMATION: Synthetic Construct

<400> SEQUENCE: 166
```

```
His Ile Ser Gly Gly Thr Phe Thr His Tyr Pro Asp Ser Val Lys
1               5                   10                  15
Gly
```

<210> SEQ ID NO 167
<211> LENGTH: 16
<212> TYPE: PRT
<213> ORGANISM: Artificial Sequence
<220> FEATURE:
<223> OTHER INFORMATION: Synthetic Construct

<400> SEQUENCE: 167

```
Val Ile Trp Ser Gly Gly Ser Thr Asp Tyr Asn Ala Ala Phe Ile Ser
1               5                   10                  15
```

<210> SEQ ID NO 168
<211> LENGTH: 12
<212> TYPE: PRT
<213> ORGANISM: Artificial Sequence
<220> FEATURE:
<223> OTHER INFORMATION: Synthetic Construct

<400> SEQUENCE: 168

```
Arg Asp Tyr Asp Gly Arg Glu Asp Val Met Gly Tyr
1               5                   10
```

<210> SEQ ID NO 169
<211> LENGTH: 15
<212> TYPE: PRT
<213> ORGANISM: Artificial Sequence
<220> FEATURE:
<223> OTHER INFORMATION: Synthetic Construct

<400> SEQUENCE: 169

```
Glu Glu Val Tyr Tyr Gly Phe Arg Ser Tyr Trp Tyr Phe Asp Val
1               5                   10                  15
```

<210> SEQ ID NO 170
<211> LENGTH: 14
<212> TYPE: PRT
<213> ORGANISM: Artificial Sequence
<220> FEATURE:
<223> OTHER INFORMATION: Synthetic Construct

<400> SEQUENCE: 170

```
Gln Asn Tyr Tyr Gly Ser Ser Ser Tyr Trp Tyr Phe Asp Val
1               5                   10
```

<210> SEQ ID NO 171
<211> LENGTH: 12
<212> TYPE: PRT
<213> ORGANISM: Artificial Sequence
<220> FEATURE:
<223> OTHER INFORMATION: Synthetic Construct

<400> SEQUENCE: 171

```
His Leu Tyr Tyr Gly Leu Tyr Tyr Ala Met Asp Tyr
1               5                   10
```

<210> SEQ ID NO 172
<211> LENGTH: 12
<212> TYPE: PRT
<213> ORGANISM: Artificial Sequence
<220> FEATURE:
<223> OTHER INFORMATION: Synthetic Construct

<400> SEQUENCE: 172

```
His Leu Tyr Tyr Gly Leu Tyr Tyr Ser Met Asp Tyr
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Synthetic Construct

<400> SEQUENCE: 173

Asp Tyr Tyr Val Ser Ser Tyr Arg Trp Tyr Phe Asp Val
1               5                   10

<210> SEQ ID NO 174
<211> LENGTH: 6
<212> TYPE: PRT
<213> ORGANISM: Artificial Sequence
<220> FEATURE:
<223> OTHER INFORMATION: Synthetic Construct

<400> SEQUENCE: 174

Asp Pro Pro Met Asp Tyr
1               5

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct

<400> SEQUENCE: 175

Ile Ala Tyr Gly Ser Trp Ala Leu Asp Tyr
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Synthetic Construct

<400> SEQUENCE: 176

Arg Gly Phe Tyr Asp Tyr Asp Ala Trp Phe Ala Tyr
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Synthetic Construct

<400> SEQUENCE: 177

Asp Asn Thr Thr Gly Asp Arg Gly Trp Tyr Phe Asp Val
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Synthetic Construct

<400> SEQUENCE: 178
```

Ala Val Tyr Tyr Tyr Gly Ser Ser Tyr Tyr Phe Asp Tyr
1               5                   10

<210> SEQ ID NO 179
<211> LENGTH: 6
<212> TYPE: PRT
<213> ORGANISM: Artificial Sequence
<220> FEATURE:
<223> OTHER INFORMATION: Synthetic Construct

<400> SEQUENCE: 179

Met Ile Ile Val Asp Tyr
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Construct

<400> SEQUENCE: 180

Ser Ser Ala Asn Phe Pro Phe Thr Tyr
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic Construct

<400> SEQUENCE: 181

Glu Gly Ala Gly Thr Arg Phe Ala Tyr
1               5

<210> SEQ ID NO 182
<211> LENGTH: 10
<212> TYPE: PRT
<213> ORGANISM: Artificial Sequence
<220> FEATURE:
<223> OTHER INFORMATION: Synthetic Construct

<400> SEQUENCE: 182

Leu Tyr Tyr Gly Tyr Asp Gly Phe Ala Tyr
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Synthetic Construct

<400> SEQUENCE: 183

Lys Ala Thr Gln Asn Val Arg Thr Ala Val Ala
1               5                   10

<210> SEQ ID NO 184
<211> LENGTH: 15
<212> TYPE: PRT
<213> ORGANISM: Artificial Sequence
<220> FEATURE:
<223> OTHER INFORMATION: Synthetic Construct

<400> SEQUENCE: 184

Arg Ala Ser Glu Ser Val Asp Asn Tyr Gly Val Ser Phe Met Asn

```
1               5                  10                 15
```

<210> SEQ ID NO 185
<211> LENGTH: 12
<212> TYPE: PRT
<213> ORGANISM: Artificial Sequence
<220> FEATURE:
<223> OTHER INFORMATION: Synthetic Construct

<400> SEQUENCE: 185

```
Ser Val Ser Ser Ser Ile Ser Ser Ser Asn Leu His
1               5                  10
```

<210> SEQ ID NO 186
<211> LENGTH: 10
<212> TYPE: PRT
<213> ORGANISM: Artificial Sequence
<220> FEATURE:
<223> OTHER INFORMATION: Synthetic Construct

<400> SEQUENCE: 186

```
Ser Ala Ser Ser Ser Val Ser Phe Met Tyr
1               5                  10
```

<210> SEQ ID NO 187
<211> LENGTH: 11
<212> TYPE: PRT
<213> ORGANISM: Artificial Sequence
<220> FEATURE:
<223> OTHER INFORMATION: Synthetic Construct

<400> SEQUENCE: 187

```
Arg Ala Ser Gln Asp Ile Ser Asn Tyr Leu Asn
1               5                  10
```

<210> SEQ ID NO 188
<211> LENGTH: 10
<212> TYPE: PRT
<213> ORGANISM: Artificial Sequence
<220> FEATURE:
<223> OTHER INFORMATION: Synthetic Construct

<400> SEQUENCE: 188

```
Ser Ala Ser Ser Ser Val Ser Tyr Met His
1               5                  10
```

<210> SEQ ID NO 189
<211> LENGTH: 11
<212> TYPE: PRT
<213> ORGANISM: Artificial Sequence
<220> FEATURE:
<223> OTHER INFORMATION: Synthetic Construct

<400> SEQUENCE: 189

```
Lys Ala Ser Gln Asn Val Asp Thr Asn Val Ala
1               5                  10
```

<210> SEQ ID NO 190
<211> LENGTH: 10
<212> TYPE: PRT
<213> ORGANISM: Artificial Sequence
<220> FEATURE:
<223> OTHER INFORMATION: Synthetic Construct

<400> SEQUENCE: 190

```
Ser Ala Ser Ser Ser Val Thr Tyr Met Tyr
1               5                  10
```

<210> SEQ ID NO 191
<211> LENGTH: 15
<212> TYPE: PRT
<213> ORGANISM: Artificial Sequence
<220> FEATURE:
<223> OTHER INFORMATION: Synthetic Construct

<400> SEQUENCE: 191

Gln Ala Ser Glu Ser Val Ser Phe Ala Gly Lys Ser Leu Met His
1               5                   10                  15

<210> SEQ ID NO 192
<211> LENGTH: 11
<212> TYPE: PRT
<213> ORGANISM: Artificial Sequence
<220> FEATURE:
<223> OTHER INFORMATION: Synthetic Construct

<400> SEQUENCE: 192

Arg Ala Ser Gln Ser Ile Gly Thr Ser Ile His
1               5                   10

<210> SEQ ID NO 193
<211> LENGTH: 15
<212> TYPE: PRT
<213> ORGANISM: Artificial Sequence
<220> FEATURE:
<223> OTHER INFORMATION: Synthetic Construct

<400> SEQUENCE: 193

Arg Ala Ser Gln Ser Val Ser Ser Ser Thr Tyr Ser Tyr Leu His
1               5                   10                  15

<210> SEQ ID NO 194
<211> LENGTH: 10
<212> TYPE: PRT
<213> ORGANISM: Artificial Sequence
<220> FEATURE:
<223> OTHER INFORMATION: Synthetic Construct

<400> SEQUENCE: 194

Thr Ala Ser Ser Ser Leu Ser Tyr Met Tyr
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Synthetic Construct

<400> SEQUENCE: 195

Arg Pro Ser Gln Asp Ile Ser Asn Ser Leu Asn
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic Construct

<400> SEQUENCE: 196

Lys Ala Ser Gln Asp Val Ser Thr Ala Val Ala
1               5                   10

```
<210> SEQ ID NO 197
<211> LENGTH: 7
<212> TYPE: PRT
<213> ORGANISM: Artificial Sequence
<220> FEATURE:
<223> OTHER INFORMATION: Synthetic Construct

<400> SEQUENCE: 197

Leu Ala Ser Asn Arg His Thr
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic Construct

<400> SEQUENCE: 198

Gly Ala Ser Asn Gln Gly Ser
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic Construct

<400> SEQUENCE: 199

Gly Thr Ser Asn Leu Ala Ser
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic Construct

<400> SEQUENCE: 200

Tyr Thr Ser Asn Leu His Ser
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic Construct

<400> SEQUENCE: 201

Ser Thr Ser Asn Leu Val Ser
1               5

<210> SEQ ID NO 202
<211> LENGTH: 7
<212> TYPE: PRT
<213> ORGANISM: Artificial Sequence
<220> FEATURE:
<223> OTHER INFORMATION: Synthetic Construct

<400> SEQUENCE: 202

Ser Ala Ser Phe Arg Tyr Ser
1               5
```

```
<210> SEQ ID NO 203
<211> LENGTH: 7
<212> TYPE: PRT
<213> ORGANISM: Artificial Sequence
<220> FEATURE:
<223> OTHER INFORMATION: Synthetic Construct

<400> SEQUENCE: 203

Leu Thr Ser Asn Arg Ala Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic Construct

<400> SEQUENCE: 204

Arg Ala Ser Asn Leu Glu Ser
1               5

<210> SEQ ID NO 205
<211> LENGTH: 7
<212> TYPE: PRT
<213> ORGANISM: Artificial Sequence
<220> FEATURE:
<223> OTHER INFORMATION: Synthetic Construct

<400> SEQUENCE: 205

Tyr Ala Ser Glu Ser Ile Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic Construct

<400> SEQUENCE: 206

Tyr Ala Ser Asn Leu Glu Ser
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic Construct

<400> SEQUENCE: 207

Leu Thr Ser Asn Leu Ala Ser
1               5

<210> SEQ ID NO 208
<211> LENGTH: 7
<212> TYPE: PRT
<213> ORGANISM: Artificial Sequence
<220> FEATURE:
<223> OTHER INFORMATION: Synthetic Construct

<400> SEQUENCE: 208

Ser Thr Ser Lys Leu His Ser
1               5

<210> SEQ ID NO 209
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 209

Ser Ala Ser Tyr Arg Tyr Thr
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic Construct

<400> SEQUENCE: 210

Leu Gln His Trp Ser Tyr Pro Leu Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic Construct

<400> SEQUENCE: 211

Gln Gln Ser Lys Glu Val Pro Pro Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic Construct

<400> SEQUENCE: 212

Gln Gln Trp Ser Arg Tyr Pro Leu Thr
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic Construct

<400> SEQUENCE: 213

Phe Gln Gly Ser Gly Phe Pro Leu Thr
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Construct

<400> SEQUENCE: 214

Phe Gln Gly Ser Gly Tyr Pro Leu Thr
1               5

<210> SEQ ID NO 215
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 215

Gln Gln Gly Lys Ser Phe Pro Trp Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Synthetic Construct

<400> SEQUENCE: 216

His Gln Arg Thr Ser Tyr Pro Trp Thr
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic Construct

<400> SEQUENCE: 217

Gln Gln Tyr Asn Ser Tyr Pro Trp Thr
1               5

<210> SEQ ID NO 218
<211> LENGTH: 9
<212> TYPE: PRT
<213> ORGANISM: Artificial Sequence
<220> FEATURE:
<223> OTHER INFORMATION: Synthetic Construct

<400> SEQUENCE: 218

Gln Gln Trp Ser Ser Asn Pro Pro Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic Construct

<400> SEQUENCE: 219

Met Gln Ser Met Glu Asp Pro Arg Thr
1               5

<210> SEQ ID NO 220
<211> LENGTH: 9
<212> TYPE: PRT
<213> ORGANISM: Artificial Sequence
<220> FEATURE:
<223> OTHER INFORMATION: Synthetic Construct

<400> SEQUENCE: 220

Gln Gln Ser Asn Ser Trp Pro Thr Thr
1               5

<210> SEQ ID NO 221
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 221

Gln His Ser Trp Glu Ile Pro Leu Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Construct

<400> SEQUENCE: 222

Gln Gln Trp Ser Ser Asn Pro Leu Thr
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic Construct

<400> SEQUENCE: 223

Gln Gln Asp Tyr Thr Leu Pro Trp Thr
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224

Gln Gln His Tyr Ser Thr Pro Leu Thr
1               5

<210> SEQ ID NO 225
<211> LENGTH: 120
<212> TYPE: PRT
<213> ORGANISM: Artificial Sequence
<220> FEATURE:
<223> OTHER INFORMATION: Synthetic Construct

<400> SEQUENCE: 225

Gln Val Gln Leu Arg Glu Ser Gly Pro Gly Leu Val Ala Pro Ser Gln
1               5                   10                  15

Ser Leu Ser Ile Thr Cys Thr Val Ser Gly Phe Ser Leu Ser Ser Phe
                20                  25                  30

Gly Val Thr Trp Val Arg Gln Pro Pro Gly Lys Gly Leu Glu Trp Leu
            35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Arg Leu Gln Thr Asp Asp Thr Ala Thr Tyr Tyr Cys Ala
                85                  90                  95

Lys Arg Asp Tyr Asp Gly Arg Glu Asp Val Met Gly Tyr Trp Gly Gln
                100                 105                 110

Gly Thr Ser Val Thr Val Ser Ser
        115                 120

<210> SEQ ID NO 226
<211> LENGTH: 124
<212> TYPE: PRT
<213> ORGANISM: Artificial Sequence
<220> FEATURE:
<223> OTHER INFORMATION: Synthetic Construct

<400> SEQUENCE: 226

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Lys Gln Arg Pro Gly Gln Gly Leu Glu Trp Ile
        35                  40                  45

Gly Ala Thr His Pro Gly His Gly Asp Thr Arg Tyr Thr Gln Lys Phe
    50                  55                  60

Lys Gly Lys Ala Thr Leu Ser Ala Asp Lys Ser Ser Ser Thr Ala Tyr
65                  70                  75                  80

Met Gln Leu Ser Asn Leu Ala Ser Glu Asp Ser Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Ala Gly Thr Thr Val Thr Val Ser Ser
        115                 120

<210> SEQ ID NO 227
<211> LENGTH: 123
<212> TYPE: PRT
<213> ORGANISM: Artificial Sequence
<220> FEATURE:
<223> OTHER INFORMATION: Synthetic Construct

<400> SEQUENCE: 227

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Phe
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Gln Asn Tyr Tyr Gly Ser Ser Ser Tyr Trp Tyr Phe Asp Val
            100                 105                 110

Trp Gly Ala Gly Thr Thr Val Thr Val Ser Ser
    115                 120

<210> SEQ ID NO 228
<211> LENGTH: 121
<212> TYPE: PRT
<213> ORGANISM: Artificial Sequence
<220> FEATURE:
<223> OTHER INFORMATION: Synthetic Construct

<400> SEQUENCE: 228

Asp Val Lys Leu Val Glu Ser Gly Gly Gly Leu Ala Lys Leu Gly Gly
1               5                   10                  15

Ser Leu Lys Leu Ser Cys Ala Ala Ser Gly Phe Thr Phe Ser Ser Phe
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Leu Tyr Tyr Gly Leu Tyr Tyr Ala Met Asp Tyr Trp Gly
            100                 105                 110

Gln Gly Thr Ser Val Thr Val Ser Ser
        115                 120

<210> SEQ ID NO 229
<211> LENGTH: 121
<212> TYPE: PRT
<213> ORGANISM: Artificial Sequence
<220> FEATURE:
<223> OTHER INFORMATION: Synthetic Construct

<400> SEQUENCE: 229

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser His Tyr
            20                  25                  30

Gly Met Ser Trp Val Arg Gln Thr Pro Asp Lys Arg Leu Asp Trp Val
        35                  40                  45

Ala Thr Ile Gly Arg Asp Gly Ile His Thr Asp Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Gly Ser Leu Lys Ser Glu Asp Ser Ala Ile Phe Tyr Cys
                85                  90                  95

Ala Arg His Leu Tyr Tyr Gly Leu Tyr Tyr Ser Met Asp Tyr Trp Gly
            100                 105                 110

Gln Gly Thr Ser Val Thr Val Ser Ser
        115                 120

<210> SEQ ID NO 230
<211> LENGTH: 121
<212> TYPE: PRT
<213> ORGANISM: Artificial Sequence
<220> FEATURE:
<223> OTHER INFORMATION: Synthetic Construct

<400> SEQUENCE: 230

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Ser Leu Ser Ser Gly Gly Ser Thr Tyr Tyr Pro Asp Ser Val Lys
        50                  55                  60

Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Lys Asp Tyr Tyr Val Ser Ser Tyr Arg Trp Tyr Phe Asp Val Trp Gly
                100                 105                 110

Ala Gly Thr Thr Val Thr Val Ser Ser
        115                 120

<210> SEQ ID NO 231
<211> LENGTH: 117
<212> TYPE: PRT
<213> ORGANISM: Artificial Sequence
<220> FEATURE:
<223> OTHER INFORMATION: Synthetic Construct

<400> SEQUENCE: 231

Glu Val Asn Leu Glu Glu Ser Gly Gly Gly Leu Val Gln Pro Gly Gly
 1               5                  10                  15

Ser Met Lys Leu Ser Cys Val Ala Ser Gly Phe Thr Phe Asn Asn Tyr
                20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Pro Glu Asp Thr Ala Ile Tyr
                 85                  90                  95

Tyr Cys Thr Thr Asp Pro Pro Met Asp Tyr Ser Gly Gln Gly Thr Pro
                100                 105                 110

Val Thr Val Ser Ser
        115

<210> SEQ ID NO 232
<211> LENGTH: 119
<212> TYPE: PRT
<213> ORGANISM: Artificial Sequence
<220> FEATURE:
<223> OTHER INFORMATION: Synthetic Construct

<400> SEQUENCE: 232

Glu Val His Leu Gln Gln Ser Gly Ala Glu Val Val Lys Pro Gly Ala
 1               5                  10                  15

Ser Val Lys Leu Ser Cys Thr Ala Ser Gly Phe Asn Ile Lys Asp Thr
                20                  25                  30

Tyr Ile His Trp Val Met Gln Arg Pro Glu Gln Gly Leu Glu Trp Ile
            35                  40                  45

Gly Arg Ile Asp Pro Ala Asn Asp Asn Thr Lys Tyr Asp Pro Lys Phe
        50                  55                  60

Gln Gly Lys Ala Thr Ile Thr Ser Asp Thr Ser Ser Asn Thr Ala Tyr
 65                  70                  75                  80

Leu His Leu Ser Ser Leu Thr Ser Glu Asp Thr Ala Val Tyr Tyr Cys
                 85                  90                  95

Ala Arg Ile Ala Tyr Gly Ser Trp Ala Leu Asp Tyr Trp Gly Gln Gly
                100                 105                 110

Thr Ser Val Thr Val Ser Ser
        115

<210> SEQ ID NO 233
<211> LENGTH: 121
<212> TYPE: PRT
<213> ORGANISM: Artificial Sequence
<220> FEATURE:
<223> OTHER INFORMATION: Synthetic Construct

<400> SEQUENCE: 233

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Lys Ser Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Arg Gly Phe Tyr Asp Tyr Asp Ala Trp Phe Ala Tyr Trp Gly
            100                 105                 110

Gln Gly Thr Leu Val Thr Val Ser Ser
        115                 120

<210> SEQ ID NO 234
<211> LENGTH: 122
<212> TYPE: PRT
<213> ORGANISM: Artificial Sequence
<220> FEATURE:
<223> OTHER INFORMATION: Synthetic Construct

<400> SEQUENCE: 234

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Gly Thr Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Tyr Thr Phe Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Asp Asn Thr Thr Gly Asp Arg Gly Trp Tyr Phe Asp Val Trp
            100                 105                 110

Gly Ala Gly Thr Thr Val Thr Val Ser Ser
        115                 120

<210> SEQ ID NO 235
<211> LENGTH: 121
<212> TYPE: PRT
<213> ORGANISM: Artificial Sequence
<220> FEATURE:
<223> OTHER INFORMATION: Synthetic Construct

<400> SEQUENCE: 235

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Val Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Ala Val Tyr Tyr Tyr Gly Ser Ser Tyr Tyr Phe Asp Tyr Trp Gly
            100                 105                 110

Gln Gly Thr Thr Val Thr Val Ser Ser
        115                 120
```

<210> SEQ ID NO 236
<211> LENGTH: 117
<212> TYPE: PRT
<213> ORGANISM: Artificial Sequence
<220> FEATURE:
<223> OTHER INFORMATION: Synthetic Construct

<400> SEQUENCE: 236

```
Glu Val Lys Leu Glu Glu Ser Gly Gly Gly Leu Val Gln Pro Gly Arg
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ser Ser Met Ile Ile Val Asp Tyr Trp Gly Gln Gly Thr Thr
            100                 105                 110

Val Thr Val Ser Ser
        115
```

<210> SEQ ID NO 237
<211> LENGTH: 118
<212> TYPE: PRT
<213> ORGANISM: Artificial Sequence
<220> FEATURE:
<223> OTHER INFORMATION: Synthetic Construct

<400> SEQUENCE: 237

```
Gln Val His Leu Gln Gln Ser Gly Thr Glu Leu Val Arg Pro Gly Thr
1               5                   10                  15

Ser Val Arg Ile Ser Cys Lys Ala Ser Gly Tyr Thr Phe Thr Asn Tyr
            20                  25                  30

Trp Leu Gly Trp Val Lys Glu Arg Thr Gly His Gly Leu Glu Trp Ile
        35                  40                  45
```

Gly Asp Ile Phe Pro Gly Gly Asn Tyr Leu Lys Asn Glu Lys Phe
            50                  55                  60

Lys Gly Lys Ala Thr Leu Thr Ala Asp Thr Ser Ser Thr Ala Tyr
 65                  70                  75                  80

Met Gln Leu Asn Gly Leu Thr Ser Glu Asp Ser Ala Val Tyr Phe Cys
                 85                  90                  95

Ala Arg Ser Ser Ala Asn Phe Pro Phe Thr Tyr Trp Gly Gln Gly Thr
                100                 105                 110

Leu Val Thr Val Ser Ser
        115

<210> SEQ ID NO 238
<211> LENGTH: 118
<212> TYPE: PRT
<213> ORGANISM: Artificial Sequence
<220> FEATURE:
<223> OTHER INFORMATION: Synthetic Construct

<400> SEQUENCE: 238

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
                 20                  25                  30

Gly Met Ser Trp Val Arg Gln Thr Pro Glu Lys Arg Leu Glu Trp Val
             35                  40                  45

Ala His Ile Ser Gly Gly Gly Thr Phe Thr His Tyr Pro Asp Ser Val
         50                  55                  60

Lys Gly Arg Phe Thr Ile Ser Arg Asp Asn Ala Lys Asn Asn Leu Tyr
 65                  70                  75                  80

Leu Gln Met Ser Ser Leu Arg Ser Glu Asp Thr Ala Leu Tyr Tyr Cys
                 85                  90                  95

Ala Arg Glu Gly Ala Gly Thr Arg Phe Ala Tyr Trp Gly Gln Gly Thr
                100                 105                 110

Leu Val Thr Val Ser Ser
        115

<210> SEQ ID NO 239
<211> LENGTH: 118
<212> TYPE: PRT
<213> ORGANISM: Artificial Sequence
<220> FEATURE:
<223> OTHER INFORMATION: Synthetic Construct

<400> SEQUENCE: 239

Gln Val Gln Met Lys Gln Ser Gly Pro Gly Leu Val Gln Pro Ser Gln
 1               5                  10                  15

Ser Leu Ser Ile Thr Cys Thr Val Ser Gly Phe Ser Leu Thr Ser Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Ser Thr Asp Tyr Asn Ala Ala Phe Ile
         50                  55                  60

Ser Arg Leu Ser Ile Ser Lys Asp Asn Ser Lys Ser Gln Val Phe Phe
 65                  70                  75                  80

Lys Met Asn Ser Leu Gln Ala Asp Asp Thr Ala Ile Tyr Tyr Cys Val
                 85                  90                  95

Arg Leu Tyr Tyr Gly Tyr Asp Gly Phe Ala Tyr Trp Gly Gln Gly Thr

-continued

```
                100                 105                 110

Leu Val Thr Val Ser Ser
            115

<210> SEQ ID NO 240
<211> LENGTH: 107
<212> TYPE: PRT
<213> ORGANISM: Artificial Sequence
<220> FEATURE:
<223> OTHER INFORMATION: Synthetic Construct

<400> SEQUENCE: 240

Asp Ile Val Met Thr Gln Ser Gln Lys Phe Met Ser Thr Ser Val Gly
1               5                   10                  15

Asp Arg Val Ser Ile Thr Cys Lys Ala Thr Gln Asn Val Arg Thr Ala
            20                  25                  30

Val Ala Trp Tyr Gln Gln Lys Pro Gly Gln Ser Pro Lys Pro Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Leu Gln His Trp Ser Tyr Pro Leu
                85                  90                  95

Thr Phe Gly Ala Gly Thr Lys Leu Glu Met Lys
            100                 105

<210> SEQ ID NO 241
<211> LENGTH: 111
<212> TYPE: PRT
<213> ORGANISM: Artificial Sequence
<220> FEATURE:
<223> OTHER INFORMATION: Synthetic Construct

<400> SEQUENCE: 241

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Val Ser Phe Met Asn Trp Phe Gln Gln Lys Pro Gly Gln Pro Pro
        35                  40                  45

Lys Leu Leu Ile Tyr Gly Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
            100                 105                 110

<210> SEQ ID NO 242
<211> LENGTH: 108
<212> TYPE: PRT
<213> ORGANISM: Artificial Sequence
<220> FEATURE:
<223> OTHER INFORMATION: Synthetic Construct

<400> SEQUENCE: 242

Glu Ile Val Leu Thr Gln Ser Pro Ala Leu Met Ala Ala Ser Pro Gly
1               5                   10                  15
```

```
Glu Lys Val Thr Ile Thr Cys Ser Val Ser Ser Ile Ser Ser
            20                  25                  30

Asn Leu His Trp Tyr Arg Gln Lys Ser Glu Thr Ser Pro Lys Pro Trp
        35                  40                  45

Ile Tyr Gly Thr Ser Asn Leu Ala Ser Gly Val Pro Val Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Arg Tyr Pro
                 85                  90                  95

Leu Thr Phe Gly Ala Gly Thr Lys Leu Glu Leu Lys
            100                 105
```

<210> SEQ ID NO 243
<211> LENGTH: 106
<212> TYPE: PRT
<213> ORGANISM: Artificial Sequence
<220> FEATURE:
<223> OTHER INFORMATION: Synthetic Construct

<400> SEQUENCE: 243

```
Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Val Ser Phe Met
            20                  25                  30

Tyr Trp Tyr Gln Glu Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Met Gly Ala Glu
 65                  70                  75                  80

Asp Val Ala Thr Tyr Tyr Cys Phe Gln Gly Ser Gly Phe Pro Leu Thr
                 85                  90                  95

Phe Gly Ser Gly Thr Lys Leu Glu Ile Lys
            100                 105
```

<210> SEQ ID NO 244
<211> LENGTH: 106
<212> TYPE: PRT
<213> ORGANISM: Artificial Sequence
<220> FEATURE:
<223> OTHER INFORMATION: Synthetic Construct

<400> SEQUENCE: 244

```
Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Val Ser Phe Met
            20                  25                  30

Tyr Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Leu Thr
                 85                  90                  95

Phe Gly Ser Gly Thr Lys Leu Glu Ile Lys
```

<210> SEQ ID NO 245
<211> LENGTH: 107
<212> TYPE: PRT
<213> ORGANISM: Artificial Sequence
<220> FEATURE:
<223> OTHER INFORMATION: Synthetic Construct

<400> SEQUENCE: 245

Asp Ile Gln Met Thr Gln Ile Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Ser Phe Pro Trp
                85                  90                  95

Thr Phe Gly Gly Gly Thr Lys Leu Glu Ile Lys
            100                 105

<210> SEQ ID NO 246
<211> LENGTH: 106
<212> TYPE: PRT
<213> ORGANISM: Artificial Sequence
<220> FEATURE:
<223> OTHER INFORMATION: Synthetic Construct

<400> SEQUENCE: 246

Gln Ile Val Leu Thr Gln Ser Pro Ala Phe Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Val Ser Gly Val Pro Asp Arg Phe Ser Gly Ser
    50                  55                  60

Gly Ser Gly Thr Ser Tyr Ser Leu Thr Ile Ser Arg Met Glu Ala Glu
65                  70                  75                  80

Tyr Ala Ala Thr Tyr Tyr Cys His Gln Arg Thr Ser Tyr Pro Trp Thr
                85                  90                  95

Phe Gly Gly Gly Thr Lys Leu Glu Ile Lys
            100                 105

<210> SEQ ID NO 247
<211> LENGTH: 107
<212> TYPE: PRT
<213> ORGANISM: Artificial Sequence
<220> FEATURE:
<223> OTHER INFORMATION: Synthetic Construct

<400> SEQUENCE: 247

Asp Ile Val Met Thr Gln Ser Gln Lys Phe Met Ser Thr Ser Val Gly
1               5                   10                  15

Asp Arg Val Ile Val Thr Cys Lys Ala Ser Gln Asn Val Asp Thr Asn
            20                  25                  30

Val Ala Trp Tyr Gln Gln Lys Pro Gly Gln Ser Pro Lys Thr Leu Ile
            35                  40                  45

Tyr Ser Ala Ser Phe Arg Tyr Ser Gly Val Pro Asp Arg Phe Thr Gly
         50                  55                  60

Ser Gly Ser Gly Thr Asp Phe Thr Leu Ser Ile Ser Asn Val Gln Ser
65                  70                  75                  80

Glu Asp Leu Ala Glu Tyr Phe Cys Gln Gln Tyr Asn Ser Tyr Pro Trp
                85                  90                  95

Thr Phe Gly Gly Gly Thr Lys Leu Glu Ile Lys
            100                 105

<210> SEQ ID NO 248
<211> LENGTH: 106
<212> TYPE: PRT
<213> ORGANISM: Artificial Sequence
<220> FEATURE:
<223> OTHER INFORMATION: Synthetic Construct

<400> SEQUENCE: 248

Gln Ile Val Leu Thr Gln Ser Pro Thr Leu Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Arg Ala Ser Gly Val Pro Thr Arg Phe Ser Gly Ser
    50                  55                  60

Gly Ser Gly Thr Ser His Ser Leu Thr Ile Ser Tyr Met Glu Ala Glu
65                  70                  75                  80

Asp Ala Ala Thr Tyr Tyr Cys Gln Gln Trp Ser Asn Pro Pro Thr
                85                  90                  95

Phe Gly Ala Gly Thr Lys Leu Glu Leu Arg
            100                 105

<210> SEQ ID NO 249
<211> LENGTH: 111
<212> TYPE: PRT
<213> ORGANISM: Artificial Sequence
<220> FEATURE:
<223> OTHER INFORMATION: Synthetic Construct

<400> SEQUENCE: 249

Asp Ile Val Leu Thr Gln Ser Pro Val Ser Leu Ala Val Ser Leu Gly
1               5                   10                  15

Gln Arg Ala Thr Ile Ser Cys Gln Ala Ser Glu Ser Val Ser Phe Ala
            20                  25                  30

Gly Lys Ser Leu Met His Trp Phe Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Glu Ser Asp Phe Thr Leu Thr Ile Asp
65                  70                  75                  80

Pro Val Glu Glu Asp Asp Ala Thr Met Tyr Tyr Cys Met Gln Ser Met
                85                  90                  95

Glu Asp Pro Arg Thr Phe Gly Gly Gly Thr Lys Leu Glu Ile Lys
            100                 105                 110

-continued

<210> SEQ ID NO 250
<211> LENGTH: 107
<212> TYPE: PRT
<213> ORGANISM: Artificial Sequence
<220> FEATURE:
<223> OTHER INFORMATION: Synthetic Construct

<400> SEQUENCE: 250

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Thr
                85                  90                  95

Thr Phe Gly Gly Gly Thr Lys Leu Glu Ile Lys
            100                 105
```

<210> SEQ ID NO 251
<211> LENGTH: 111
<212> TYPE: PRT
<213> ORGANISM: Artificial Sequence
<220> FEATURE:
<223> OTHER INFORMATION: Synthetic Construct

<400> SEQUENCE: 251

```
Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Ser Ser
            20                  25                  30

Thr Tyr Ser Tyr Leu His Trp Tyr Gln Gln Arg Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Val Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Met Lys
            100                 105                 110
```

<210> SEQ ID NO 252
<211> LENGTH: 106
<212> TYPE: PRT
<213> ORGANISM: Artificial Sequence
<220> FEATURE:
<223> OTHER INFORMATION: Synthetic Construct

<400> SEQUENCE: 252

```
Gln Ile Val Leu Thr Gln Ser Pro Ala Leu Met Ser Ala Ser Pro Gly
1               5                   10                  15

Glu Lys Val Thr Met Thr Cys Thr Ala Ser Ser Ser Leu Ser Tyr Met
            20                  25                  30

Tyr Trp Tyr Gln Gln Arg Pro Arg Ser Ser Pro Lys Pro Trp Ile Tyr
        35                  40                  45
```

```
Leu Thr Ser Asn Leu Ala Ser Gly Val Pro Thr Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Met Lys
            100                 105

<210> SEQ ID NO 253
<211> LENGTH: 107
<212> TYPE: PRT
<213> ORGANISM: Artificial Sequence
<220> FEATURE:
<223> OTHER INFORMATION: Synthetic Construct

<400> SEQUENCE: 253

Asp Ile Gln Met Thr Gln Thr Thr Ser Ser Leu Ser Ala Ser Leu Gly
 1               5                  10                  15

Asp Arg Val Thr Ile Ser Cys Arg Pro Ser Gln Asp Ile Ser Asn Ser
             20                  25                  30

Leu Asn Trp Tyr Gln Gln Lys Pro Asp Gly Thr Val Lys Leu Leu Ile
         35                  40                  45

Tyr Ser Thr Ser Lys Leu His Ser Gly Val Pro Ser Arg Phe Ser Gly
 50                  55                  60

Ser Gly Ser Gly Ile Asp Tyr Ser Leu Thr Ile Ser Asn Leu Glu Gln
 65                  70                  75                  80

Glu Asp Ile Ala Thr Tyr Phe Cys Gln Gln Asp Tyr Leu Pro Trp
                 85                  90                  95

Thr Phe Gly Gly Gly Thr Lys Leu Asp Val Lys
            100                 105

<210> SEQ ID NO 254
<211> LENGTH: 107
<212> TYPE: PRT
<213> ORGANISM: Artificial Sequence
<220> FEATURE:
<223> OTHER INFORMATION: Synthetic Construct

<400> SEQUENCE: 254

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Tyr Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Leu
                 85                  90                  95

Thr Phe Gly Ala Gly Thr Lys Leu Glu Leu Lys
            100                 105

<210> SEQ ID NO 255
<211> LENGTH: 13
<212> TYPE: PRT
```

```
<213> ORGANISM: Artificial Sequence
<220> FEATURE:
<223> OTHER INFORMATION: Synthetic Construct

<400> SEQUENCE: 255

Ser Met Ala Ser Asn Thr Tyr Gly Ser Asn Pro Ile Ser
1               5                   10

<210> SEQ ID NO 256
<211> LENGTH: 13
<212> TYPE: PRT
<213> ORGANISM: Artificial Sequence
<220> FEATURE:
<223> OTHER INFORMATION: Synthetic Construct

<400> SEQUENCE: 256

Cys Ala Ala Ser Asn Thr Tyr Gly Ser Asn Pro Ile Ser
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Synthetic Construct

<400> SEQUENCE: 257

Cys Met Ser Ser Asn Thr Tyr Gly Ser Asn Pro Ile Ser
1               5                   10

<210> SEQ ID NO 258
<211> LENGTH: 13
<212> TYPE: PRT
<213> ORGANISM: Artificial Sequence
<220> FEATURE:
<223> OTHER INFORMATION: Synthetic Construct

<400> SEQUENCE: 258

Cys Met Ala Ala Asn Thr Tyr Gly Ser Asn Pro Ile Ser
1               5                   10

<210> SEQ ID NO 259
<211> LENGTH: 13
<212> TYPE: PRT
<213> ORGANISM: Artificial Sequence
<220> FEATURE:
<223> OTHER INFORMATION: Synthetic Construct

<400> SEQUENCE: 259

Cys Met Ala Ser Ala Thr Tyr Gly Ser Asn Pro Ile Ser
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Synthetic Construct

<400> SEQUENCE: 260

Cys Met Ala Ser Asn Ala Tyr Gly Ser Asn Pro Ile Ser
1               5                   10

<210> SEQ ID NO 261
<211> LENGTH: 13
<212> TYPE: PRT
<213> ORGANISM: Artificial Sequence
```

<220> FEATURE:
<223> OTHER INFORMATION: Synthetic Construct

<400> SEQUENCE: 261

Cys Met Ala Ser Asn Thr Ala Gly Ser Asn Pro Ile Ser
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Synthetic Construct

<400> SEQUENCE: 262

Cys Met Ala Ser Asn Thr Tyr Ala Ser Asn Pro Ile Ser
1               5                   10

<210> SEQ ID NO 263
<211> LENGTH: 13
<212> TYPE: PRT
<213> ORGANISM: Artificial Sequence
<220> FEATURE:
<223> OTHER INFORMATION: Synthetic Construct

<400> SEQUENCE: 263

Cys Met Ala Ser Asn Thr Tyr Gly Ala Asn Pro Ile Ser
1               5                   10

<210> SEQ ID NO 264
<211> LENGTH: 13
<212> TYPE: PRT
<213> ORGANISM: Artificial Sequence
<220> FEATURE:
<223> OTHER INFORMATION: Synthetic Construct

<400> SEQUENCE: 264

Cys Met Ala Ser Asn Thr Tyr Gly Ser Ala Pro Ile Ser
1               5                   10

<210> SEQ ID NO 265
<211> LENGTH: 13
<212> TYPE: PRT
<213> ORGANISM: Artificial Sequence
<220> FEATURE:
<223> OTHER INFORMATION: Synthetic Construct

<400> SEQUENCE: 265

Cys Met Ala Ser Asn Thr Tyr Gly Ser Asn Ala Ile Ser
1               5                   10

<210> SEQ ID NO 266
<211> LENGTH: 13
<212> TYPE: PRT
<213> ORGANISM: Artificial Sequence
<220> FEATURE:
<223> OTHER INFORMATION: Synthetic Construct

<400> SEQUENCE: 266

Cys Met Ala Ser Asn Thr Tyr Gly Ser Asn Pro Ala Ser
1               5                   10

<210> SEQ ID NO 267
<211> LENGTH: 13
<212> TYPE: PRT
<213> ORGANISM: Artificial Sequence
<220> FEATURE:

<223> OTHER INFORMATION: Synthetic Construct

<400> SEQUENCE: 267

Cys Met Ala Ser Asn Thr Tyr Gly Ser Asn Pro Ile Ala
1               5                   10

<210> SEQ ID NO 268
<211> LENGTH: 21
<212> TYPE: PRT
<213> ORGANISM: Artificial Sequence
<220> FEATURE:
<223> OTHER INFORMATION: Synthetic Construct

<400> SEQUENCE: 268

Ala Phe His His Pro Tyr Cys Asn Tyr Tyr Gly Asn Ser Asn Asn Cys
1               5                   10                  15

His Gly Thr Met Ser
            20

<210> SEQ ID NO 269
<211> LENGTH: 21
<212> TYPE: PRT
<213> ORGANISM: Artificial Sequence
<220> FEATURE:
<223> OTHER INFORMATION: Synthetic Construct

<400> SEQUENCE: 269

Ser Ala His His Pro Tyr Cys Asn Tyr Tyr Gly Asn Ser Asn Asn Cys
1               5                   10                  15

His Gly Thr Met Ser
            20

<210> SEQ ID NO 270
<211> LENGTH: 21
<212> TYPE: PRT
<213> ORGANISM: Artificial Sequence
<220> FEATURE:
<223> OTHER INFORMATION: Synthetic Construct

<400> SEQUENCE: 270

Ser Phe Ala His Pro Tyr Cys Asn Tyr Tyr Gly Asn Ser Asn Asn Cys
1               5                   10                  15

His Gly Thr Met Ser
            20

<210> SEQ ID NO 271
<211> LENGTH: 21
<212> TYPE: PRT
<213> ORGANISM: Artificial Sequence
<220> FEATURE:
<223> OTHER INFORMATION: Synthetic Construct

<400> SEQUENCE: 271

Ser Phe His Ala Pro Tyr Cys Asn Tyr Tyr Gly Asn Ser Asn Asn Cys
1               5                   10                  15

His Gly Thr Met Ser
            20

<210> SEQ ID NO 272
<211> LENGTH: 21
<212> TYPE: PRT
<213> ORGANISM: Artificial Sequence
<220> FEATURE:
<223> OTHER INFORMATION: Synthetic Construct

<400> SEQUENCE: 272

Ser Phe His His Pro Ala Cys Asn Tyr Tyr Gly Asn Ser Asn Cys
1               5                   10                  15

His Gly Thr Met Ser
            20

<210> SEQ ID NO 273
<211> LENGTH: 21
<212> TYPE: PRT
<213> ORGANISM: Artificial Sequence
<220> FEATURE:
<223> OTHER INFORMATION: Synthetic Construct

<400> SEQUENCE: 273

Ser Phe His His Pro Tyr Ser Asn Tyr Tyr Gly Asn Ser Asn Cys
1               5                   10                  15

His Gly Thr Met Ser
            20

<210> SEQ ID NO 274
<211> LENGTH: 21
<212> TYPE: PRT
<213> ORGANISM: Artificial Sequence
<220> FEATURE:
<223> OTHER INFORMATION: Synthetic Construct

<400> SEQUENCE: 274

Ser Phe His His Pro Tyr Cys Ala Tyr Tyr Gly Asn Ser Asn Cys
1               5                   10                  15

His Gly Thr Met Ser
            20

<210> SEQ ID NO 275
<211> LENGTH: 21
<212> TYPE: PRT
<213> ORGANISM: Artificial Sequence
<220> FEATURE:
<223> OTHER INFORMATION: Synthetic Construct

<400> SEQUENCE: 275

Ser Phe His His Pro Tyr Cys Asn Ala Tyr Gly Asn Ser Asn Cys
1               5                   10                  15

His Gly Thr Met Ser
            20

<210> SEQ ID NO 276
<211> LENGTH: 21
<212> TYPE: PRT
<213> ORGANISM: Artificial Sequence
<220> FEATURE:
<223> OTHER INFORMATION: Synthetic Construct

<400> SEQUENCE: 276

Ser Phe His His Pro Tyr Cys Asn Tyr Ala Gly Asn Ser Asn Cys
1               5                   10                  15

His Gly Thr Met Ser
            20

<210> SEQ ID NO 277
<211> LENGTH: 21
<212> TYPE: PRT
<213> ORGANISM: Artificial Sequence
<220> FEATURE:
<223> OTHER INFORMATION: Synthetic Construct

```
<400> SEQUENCE: 277

Ser Phe His His Pro Tyr Cys Asn Tyr Tyr Ala Asn Ser Asn Asn Cys
1               5                   10                  15

His Gly Thr Met Ser
            20

<210> SEQ ID NO 278
<211> LENGTH: 21
<212> TYPE: PRT
<213> ORGANISM: Artificial Sequence
<220> FEATURE:
<223> OTHER INFORMATION: Synthetic Construct

<400> SEQUENCE: 278

Ser Phe His His Pro Tyr Cys Asn Tyr Tyr Gly Ala Ser Asn Asn Cys
1               5                   10                  15

His Gly Thr Met Ser
            20

<210> SEQ ID NO 279
<211> LENGTH: 21
<212> TYPE: PRT
<213> ORGANISM: Artificial Sequence
<220> FEATURE:
<223> OTHER INFORMATION: Synthetic Construct

<400> SEQUENCE: 279

Ser Phe His His Pro Tyr Cys Asn Tyr Tyr Gly Asn Ala Asn Asn Cys
1               5                   10                  15

His Gly Thr Met Ser
            20

<210> SEQ ID NO 280
<211> LENGTH: 21
<212> TYPE: PRT
<213> ORGANISM: Artificial Sequence
<220> FEATURE:
<223> OTHER INFORMATION: Synthetic Construct

<400> SEQUENCE: 280

Ser Phe His His Pro Tyr Cys Asn Tyr Tyr Gly Asn Ser Asn Ala Cys
1               5                   10                  15

His Gly Thr Met Ser
            20

<210> SEQ ID NO 281
<211> LENGTH: 21
<212> TYPE: PRT
<213> ORGANISM: Artificial Sequence
<220> FEATURE:
<223> OTHER INFORMATION: Synthetic Construct

<400> SEQUENCE: 281

Ser Phe His His Pro Tyr Cys Asn Tyr Tyr Gly Asn Ser Asn Asn Ser
1               5                   10                  15

His Gly Thr Met Ser
            20

<210> SEQ ID NO 282
<211> LENGTH: 21
<212> TYPE: PRT
<213> ORGANISM: Artificial Sequence
<220> FEATURE:
```

<223> OTHER INFORMATION: Synthetic Construct

<400> SEQUENCE: 282

Ser Phe His His Pro Tyr Cys Asn Tyr Tyr Gly Asn Ser Asn Asn Cys
1               5                   10                  15

Ala Gly Thr Met Ser
            20

<210> SEQ ID NO 283
<211> LENGTH: 21
<212> TYPE: PRT
<213> ORGANISM: Artificial Sequence
<220> FEATURE:
<223> OTHER INFORMATION: Synthetic Construct

<400> SEQUENCE: 283

Ser Phe His His Pro Tyr Cys Asn Tyr Tyr Gly Asn Ser Asn Asn Cys
1               5                   10                  15

His Ala Thr Met Ser
            20

<210> SEQ ID NO 284
<211> LENGTH: 21
<212> TYPE: PRT
<213> ORGANISM: Artificial Sequence
<220> FEATURE:
<223> OTHER INFORMATION: Synthetic Construct

<400> SEQUENCE: 284

Ser Phe His His Pro Tyr Cys Asn Tyr Tyr Gly Asn Ser Asn Asn Cys
1               5                   10                  15

His Gly Ala Met Ser
            20

<210> SEQ ID NO 285
<211> LENGTH: 21
<212> TYPE: PRT
<213> ORGANISM: Artificial Sequence
<220> FEATURE:
<223> OTHER INFORMATION: Synthetic Construct

<400> SEQUENCE: 285

Ser Phe His His Pro Tyr Cys Asn Tyr Tyr Gly Asn Ser Asn Asn Cys
1               5                   10                  15

His Gly Thr Ala Ser
            20

<210> SEQ ID NO 286
<211> LENGTH: 21
<212> TYPE: PRT
<213> ORGANISM: Artificial Sequence
<220> FEATURE:
<223> OTHER INFORMATION: Synthetic Construct

<400> SEQUENCE: 286

Ser Phe His His Pro Tyr Cys Asn Tyr Tyr Gly Asn Ser Asn Asn Cys
1               5                   10                  15

His Gly Thr Met Ala
            20

<210> SEQ ID NO 287
<211> LENGTH: 18
<212> TYPE: PRT
<213> ORGANISM: Artificial Sequence

```
<220> FEATURE:
<223> OTHER INFORMATION: Synthetic Construct

<400> SEQUENCE: 287

Ser Phe His His Pro Tyr Cys Asn Tyr Tyr Asn Asn Cys His Gly Thr
1               5                   10                  15

Met Ser

<210> SEQ ID NO 288
<211> LENGTH: 16
<212> TYPE: PRT
<213> ORGANISM: Artificial Sequence
<220> FEATURE:
<223> OTHER INFORMATION: Synthetic Construct

<400> SEQUENCE: 288

Ser Phe His His Pro Tyr Cys Asn Asn Asn Cys His Gly Thr Met Ser
1               5                   10                  15

<210> SEQ ID NO 289
<211> LENGTH: 13
<212> TYPE: PRT
<213> ORGANISM: Artificial Sequence
<220> FEATURE:
<223> OTHER INFORMATION: Synthetic Construct

<400> SEQUENCE: 289

Cys Met Ala Ser Asn Thr Tyr Gly Ser Asn Pro Ile Ser
1               5                   10

<210> SEQ ID NO 290
<211> LENGTH: 21
<212> TYPE: PRT
<213> ORGANISM: Artificial Sequence
<220> FEATURE:
<223> OTHER INFORMATION: Synthetic Construct

<400> SEQUENCE: 290

Ser Phe His His Pro Tyr Cys Asn Tyr Tyr Gly Asn Ser Asn Asn Cys
1               5                   10                  15

His Gly Thr Met Ser
            20

<210> SEQ ID NO 291
<211> LENGTH: 248
<212> TYPE: PRT
<213> ORGANISM: Homo sapiens

<400> SEQUENCE: 291

Met Thr Ser Gln Pro Val Pro Asn Glu Thr Ile Ile Val Leu Pro Ser
1               5                   10                  15

Asn Val Ile Asn Phe Ser Gln Ala Glu Lys Pro Glu Pro Thr Asn Gln
                20                  25                  30

Gly Gln Asp Ser Leu Lys Lys His Leu His Ala Glu Ile Lys Val Ile
            35                  40                  45

Gly Thr Ile Gln Ile Leu Cys Gly Met Met Val Leu Ser Leu Gly Ile
        50                  55                  60

Ile Leu Ala Ser Ala Ser Phe Ser Pro Asn Phe Thr Gln Val Thr Ser
65                  70                  75                  80

Thr Leu Leu Asn Ser Ala Tyr Pro Phe Ile Gly Pro Phe Phe Phe Ile
                85                  90                  95

Ile Ser Gly Ser Leu Ser Ile Ala Thr Glu Lys Arg Leu Thr Lys Leu
```

```
                100             105             110
Leu Val His Ser Ser Leu Val Gly Ser Ile Leu Ser Ala Leu Ser Ala
            115                 120                 125
Leu Val Gly Phe Ile Ile Leu Ser Val Lys Gln Ala Thr Leu Asn Pro
        130                 135                 140
Ala Ser Leu Gln Cys Glu Leu Asp Lys Asn Asn Ile Pro Thr Arg Ser
145                 150                 155                 160
Tyr Val Ser Tyr Phe Tyr His Asp Ser Leu Tyr Thr Thr Asp Cys Tyr
                165                 170                 175
Thr Ala Lys Ala Ser Leu Ala Gly Thr Leu Ser Leu Met Leu Ile Cys
            180                 185                 190
Thr Leu Leu Glu Phe Cys Leu Ala Val Leu Thr Ala Val Leu Arg Trp
        195                 200                 205
Lys Gln Ala Tyr Ser Asp Phe Pro Gly Ser Val Leu Phe Leu Pro His
    210                 215                 220
Ser Tyr Ile Gly Asn Ser Gly Met Ser Ser Lys Met Thr His Asp Cys
225                 230                 235                 240
Gly Tyr Glu Glu Leu Leu Thr Ser
                245
```

<210> SEQ ID NO 292
<211> LENGTH: 15
<212> TYPE: PRT
<213> ORGANISM: Homo sapiens

<400> SEQUENCE: 292

```
Ile Thr Met Met Cys Met Ala Ser Asn Thr Tyr Gly Ser Asn Pro
1               5                   10                  15
```

<210> SEQ ID NO 293
<211> LENGTH: 15
<212> TYPE: PRT
<213> ORGANISM: Homo sapiens

<400> SEQUENCE: 293

```
Met Met Cys Met Ala Ser Asn Thr Tyr Gly Ser Asn Pro Ile Ser
1               5                   10                  15
```

<210> SEQ ID NO 294
<211> LENGTH: 15
<212> TYPE: PRT
<213> ORGANISM: Homo sapiens

<400> SEQUENCE: 294

```
Cys Met Ala Ser Asn Thr Tyr Gly Ser Asn Pro Ile Ser Val Tyr
1               5                   10                  15
```

<210> SEQ ID NO 295
<211> LENGTH: 15
<212> TYPE: PRT
<213> ORGANISM: Homo sapiens

<400> SEQUENCE: 295

```
Ala Ser Asn Thr Tyr Gly Ser Asn Pro Ile Ser Val Tyr Ile Gly
1               5                   10                  15
```

<210> SEQ ID NO 296
<211> LENGTH: 15
<212> TYPE: PRT
<213> ORGANISM: Homo sapiens

<400> SEQUENCE: 296

Leu Ala Phe Tyr Ser Phe His His Pro Tyr Cys Asn Tyr Tyr Gly
1               5                   10                  15

<210> SEQ ID NO 297
<211> LENGTH: 15
<212> TYPE: PRT
<213> ORGANISM: Homo sapiens

<400> SEQUENCE: 297

Phe Tyr Ser Phe His His Pro Tyr Cys Asn Tyr Tyr Gly Asn Ser
1               5                   10                  15

<210> SEQ ID NO 298
<211> LENGTH: 15
<212> TYPE: PRT
<213> ORGANISM: Homo sapiens

<400> SEQUENCE: 298

Ser Phe His His Pro Tyr Cys Asn Tyr Tyr Gly Asn Ser Asn Asn
1               5                   10                  15

<210> SEQ ID NO 299
<211> LENGTH: 15
<212> TYPE: PRT
<213> ORGANISM: Homo sapiens

<400> SEQUENCE: 299

His His Pro Tyr Cys Asn Tyr Tyr Gly Asn Ser Asn Asn Cys His
1               5                   10                  15

<210> SEQ ID NO 300
<211> LENGTH: 15
<212> TYPE: PRT
<213> ORGANISM: Homo sapiens

<400> SEQUENCE: 300

Pro Tyr Cys Asn Tyr Tyr Gly Asn Ser Asn Asn Cys His Gly Thr
1               5                   10                  15

<210> SEQ ID NO 301
<211> LENGTH: 15
<212> TYPE: PRT
<213> ORGANISM: Homo sapiens

<400> SEQUENCE: 301

Cys Asn Tyr Tyr Gly Asn Ser Asn Asn Cys His Gly Thr Met Ser
1               5                   10                  15

<210> SEQ ID NO 302
<211> LENGTH: 15
<212> TYPE: PRT
<213> ORGANISM: Homo sapiens

<400> SEQUENCE: 302

Tyr Tyr Gly Asn Ser Asn Asn Cys His Gly Thr Met Ser Ile Leu
1               5                   10                  15

<210> SEQ ID NO 303
<211> LENGTH: 15
<212> TYPE: PRT
<213> ORGANISM: Homo sapiens

<400> SEQUENCE: 303

```
Gly Asn Ser Asn Asn Cys His Gly Thr Met Ser Ile Leu Met Gly
1               5                  10                  15
```

<210> SEQ ID NO 304
<211> LENGTH: 7
<212> TYPE: PRT
<213> ORGANISM: Artificial Sequence
<220> FEATURE:
<223> OTHER INFORMATION: Synthetic Construct

<400> SEQUENCE: 304

```
Thr Ser Asp Met Gly Val Gly
1               5
```

<210> SEQ ID NO 305
<211> LENGTH: 7
<212> TYPE: PRT
<213> ORGANISM: Artificial Sequence
<220> FEATURE:
<223> OTHER INFORMATION: Synthetic Construct

<400> SEQUENCE: 305

```
Thr Ser Asp Met Gly Val Gly
1               5
```

<210> SEQ ID NO 306
<211> LENGTH: 5
<212> TYPE: PRT
<213> ORGANISM: Artificial Sequence
<220> FEATURE:
<223> OTHER INFORMATION: Synthetic Construct

<400> SEQUENCE: 306

```
His Tyr Gly Met Ser
1               5
```

<210> SEQ ID NO 307
<211> LENGTH: 5
<212> TYPE: PRT
<213> ORGANISM: Artificial Sequence
<220> FEATURE:
<223> OTHER INFORMATION: Synthetic Construct

<400> SEQUENCE: 307

```
Ser Phe Gly Val Asn
1               5
```

<210> SEQ ID NO 308
<211> LENGTH: 5
<212> TYPE: PRT
<213> ORGANISM: Artificial Sequence
<220> FEATURE:
<223> OTHER INFORMATION: Synthetic Construct

<400> SEQUENCE: 308

```
Asn Tyr Trp Met Asn
1               5
```

<210> SEQ ID NO 309
<211> LENGTH: 5
<212> TYPE: PRT
<213> ORGANISM: Artificial Sequence
<220> FEATURE:
<223> OTHER INFORMATION: Synthetic Construct

<400> SEQUENCE: 309

Gly Tyr Phe Met Asn

```
1               5

<210> SEQ ID NO 310
<211> LENGTH: 16
<212> TYPE: PRT
<213> ORGANISM: Artificial Sequence
<220> FEATURE:
<223> OTHER INFORMATION: Synthetic Construct

<400> SEQUENCE: 310

Asp Ile Trp Trp Asp Asp Asn Lys Tyr Tyr Asn Pro Ser Leu Lys Ser
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Synthetic Construct

<400> SEQUENCE: 311

Asp Ile Trp Trp Asp Asp Asn Lys Tyr Tyr Asn Pro Ser Leu Lys Ser
1               5                   10                  15

<210> SEQ ID NO 312
<211> LENGTH: 17
<212> TYPE: PRT
<213> ORGANISM: Artificial Sequence
<220> FEATURE:
<223> OTHER INFORMATION: Synthetic Construct

<400> SEQUENCE: 312

Thr Ile Ser Ser Gly Gly Ser Ser Thr Tyr Tyr Pro Asp Ser Val Lys
1               5                   10                  15

Gly

<210> SEQ ID NO 313
<211> LENGTH: 16
<212> TYPE: PRT
<213> ORGANISM: Artificial Sequence
<220> FEATURE:
<223> OTHER INFORMATION: Synthetic Construct

<400> SEQUENCE: 313

Ile Ile Trp Gly Asp Gly Ser Thr Asn Phe His Ser Ala Leu Met Ser
1               5                   10                  15

<210> SEQ ID NO 314
<211> LENGTH: 19
<212> TYPE: PRT
<213> ORGANISM: Artificial Sequence
<220> FEATURE:
<223> OTHER INFORMATION: Synthetic Construct

<400> SEQUENCE: 314

Glu Ile Arg Leu Lys Ser Asn Asn Tyr Ala Thr His Tyr Ala Glu Ser
1               5                   10                  15

Val Lys Gly

<210> SEQ ID NO 315
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 315

Arg Ile Asn Pro Tyr Asn Gly Asp Thr Leu Tyr Asn Gln Lys Phe Lys
1               5                   10                  15
Gly

<210> SEQ ID NO 316
<211> LENGTH: 10
<212> TYPE: PRT
<213> ORGANISM: Artificial Sequence
<220> FEATURE:
<223> OTHER INFORMATION: Synthetic Construct

<400> SEQUENCE: 316

Arg Ala Asn Tyr Gly Asn Leu Phe Asp Tyr
1               5                   10

<210> SEQ ID NO 317
<211> LENGTH: 10
<212> TYPE: PRT
<213> ORGANISM: Artificial Sequence
<220> FEATURE:
<223> OTHER INFORMATION: Synthetic Construct

<400> SEQUENCE: 317

Arg Ala Asn Tyr Gly Asn Leu Phe Asp Tyr
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Synthetic Construct

<400> SEQUENCE: 318

His Leu Tyr Tyr Gly Leu Tyr Tyr Ala Met Asp Tyr
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Synthetic Construct

<400> SEQUENCE: 319

Arg Asp Tyr Asp Gly Arg Asp Asp Val Met Gly Tyr
1               5                   10

<210> SEQ ID NO 320
<211> LENGTH: 6
<212> TYPE: PRT
<213> ORGANISM: Artificial Sequence
<220> FEATURE:
<223> OTHER INFORMATION: Synthetic Construct

<400> SEQUENCE: 320

Met Ile Ile Val Asp Tyr
1               5

<210> SEQ ID NO 321
<211> LENGTH: 12
<212> TYPE: PRT
<213> ORGANISM: Artificial Sequence
<220> FEATURE:
<223> OTHER INFORMATION: Synthetic Construct
```

<400> SEQUENCE: 321

Val Lys Gly Tyr Asp Tyr Asp Gly Ala Met Asp Tyr
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthetic Construct

<400> SEQUENCE: 322

Lys Ala Ser Gln Asn Val Arg Ser Ala Val Ala
1               5                   10

<210> SEQ ID NO 323
<211> LENGTH: 15
<212> TYPE: PRT
<213> ORGANISM: Artificial Sequence
<220> FEATURE:
<223> OTHER INFORMATION: Synthetic Construct

<400> SEQUENCE: 323

Lys Ala Ser Gln Ser Val Asp Tyr Asp Gly Asp Ser Tyr Met Asn
1               5                   10                  15

<210> SEQ ID NO 324
<211> LENGTH: 10
<212> TYPE: PRT
<213> ORGANISM: Artificial Sequence
<220> FEATURE:
<223> OTHER INFORMATION: Synthetic Construct

<400> SEQUENCE: 324

Ser Ala Ser Ser Ser Val Ser Phe Met Tyr
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic Construct

<400> SEQUENCE: 325

Lys Ala Ser Gln Thr Val Arg Thr Ala Val Ala
1               5                   10

<210> SEQ ID NO 326
<211> LENGTH: 15
<212> TYPE: PRT
<213> ORGANISM: Artificial Sequence
<220> FEATURE:
<223> OTHER INFORMATION: Synthetic Construct

<400> SEQUENCE: 326

Arg Ala Ser Gln Ser Val Ser Ser Thr Tyr Ser Tyr Leu His
1               5                   10                  15

<210> SEQ ID NO 327
<211> LENGTH: 17
<212> TYPE: PRT
<213> ORGANISM: Artificial Sequence
<220> FEATURE:
<223> OTHER INFORMATION: Synthetic Construct

```
<400> SEQUENCE: 327

Arg Ser Ser Gln Ser Leu Leu Gln Ser Gly Asn Gln Lys Ser Ser Leu
1               5                   10                  15
Ala

<210> SEQ ID NO 328
<211> LENGTH: 7
<212> TYPE: PRT
<213> ORGANISM: Artificial Sequence
<220> FEATURE:
<223> OTHER INFORMATION: Synthetic Construct

<400> SEQUENCE: 328

Trp Ala Ser Asn Arg His Thr
1               5

<210> SEQ ID NO 329
<211> LENGTH: 7
<212> TYPE: PRT
<213> ORGANISM: Artificial Sequence
<220> FEATURE:
<223> OTHER INFORMATION: Synthetic Construct

<400> SEQUENCE: 329

Ala Ala Ser Asn Leu Glu Ser
1               5

<210> SEQ ID NO 330
<211> LENGTH: 7
<212> TYPE: PRT
<213> ORGANISM: Artificial Sequence
<220> FEATURE:
<223> OTHER INFORMATION: Synthetic Construct

<400> SEQUENCE: 330

Asp Thr Ser Lys Leu Ala Ser
1               5

<210> SEQ ID NO 331
<211> LENGTH: 7
<212> TYPE: PRT
<213> ORGANISM: Artificial Sequence
<220> FEATURE:
<223> OTHER INFORMATION: Synthetic Construct

<400> SEQUENCE: 331

Leu Ala Ser Asn Arg His Thr
1               5

<210> SEQ ID NO 332
<211> LENGTH: 7
<212> TYPE: PRT
<213> ORGANISM: Artificial Sequence
<220> FEATURE:
<223> OTHER INFORMATION: Synthetic Construct

<400> SEQUENCE: 332

Tyr Ala Ser Asn Leu Glu Ser
1               5

<210> SEQ ID NO 333
<211> LENGTH: 7
<212> TYPE: PRT
<213> ORGANISM: Artificial Sequence
<220> FEATURE:
<223> OTHER INFORMATION: Synthetic Construct
```

<400> SEQUENCE: 333

Trp Ala Arg Thr Arg Gln Ser
1               5

<210> SEQ ID NO 334
<211> LENGTH: 8
<212> TYPE: PRT
<213> ORGANISM: Artificial Sequence
<220> FEATURE:
<223> OTHER INFORMATION: Synthetic Construct

<400> SEQUENCE: 334

Leu Gln His Trp Asn Tyr Leu Thr
1               5

<210> SEQ ID NO 335
<211> LENGTH: 9
<212> TYPE: PRT
<213> ORGANISM: Artificial Sequence
<220> FEATURE:
<223> OTHER INFORMATION: Synthetic Construct

<400> SEQUENCE: 335

Gln Gln Ser Asn Glu Asp Pro Arg Thr
1               5

<210> SEQ ID NO 336
<211> LENGTH: 9
<212> TYPE: PRT
<213> ORGANISM: Artificial Sequence
<220> FEATURE:
<223> OTHER INFORMATION: Synthetic Construct

<400> SEQUENCE: 336

Phe Gln Gly Ser Gly Phe Pro Leu Thr
1               5

<210> SEQ ID NO 337
<211> LENGTH: 9
<212> TYPE: PRT
<213> ORGANISM: Artificial Sequence
<220> FEATURE:
<223> OTHER INFORMATION: Synthetic Construct

<400> SEQUENCE: 337

Leu Gln His Trp Ser Tyr Pro Leu Thr
1               5

<210> SEQ ID NO 338
<211> LENGTH: 9
<212> TYPE: PRT
<213> ORGANISM: Artificial Sequence
<220> FEATURE:
<223> OTHER INFORMATION: Synthetic Construct

<400> SEQUENCE: 338

Gln His Ser Trp Glu Ile Pro Leu Thr
1               5

<210> SEQ ID NO 339
<211> LENGTH: 9
<212> TYPE: PRT
<213> ORGANISM: Artificial Sequence
<220> FEATURE:
<223> OTHER INFORMATION: Synthetic Construct

<400> SEQUENCE: 339

Gln Gln Tyr Ser Asp Thr Pro Phe Thr
1               5

<210> SEQ ID NO 340
<211> LENGTH: 120
<212> TYPE: PRT
<213> ORGANISM: Artificial Sequence
<220> FEATURE:
<223> OTHER INFORMATION: Synthetic Construct

<400> SEQUENCE: 340

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Asp Met Gly Val Gly Trp Val Arg Gln Pro Ser Gly Glu Gly Leu Glu
        35                  40                  45

Trp Leu Ala Asp Ile Trp Trp Asp Asp Asn Lys Tyr Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Asn Tyr Gly Asn Leu Phe Asp Tyr Trp Gly Gln
            100                 105                 110

Gly Thr Ala Val Thr Val Ser Ser
        115                 120

<210> SEQ ID NO 341
<211> LENGTH: 120
<212> TYPE: PRT
<213> ORGANISM: Artificial Sequence
<220> FEATURE:
<223> OTHER INFORMATION: Synthetic Construct

<400> SEQUENCE: 341

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Asp Met Gly Val Gly Trp Val Arg Gln Pro Ser Gly Glu Gly Leu Glu
        35                  40                  45

Trp Leu Ala Asp Ile Trp Trp Asp Asp Asn Lys Tyr Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Asn Tyr Gly Asn Leu Phe Asp Tyr Trp Gly Gln
            100                 105                 110

Gly Thr Ala Val Thr Val Ser Ser
        115                 120

<210> SEQ ID NO 342
<211> LENGTH: 121
<212> TYPE: PRT
<213> ORGANISM: Artificial Sequence
<220> FEATURE:

<223> OTHER INFORMATION: Synthetic Construct

<400> SEQUENCE: 342

Glu Val Gln Val Val Glu Ser Gly Gly Asp Leu Val Lys Pro Gly Gly
1               5                   10                  15

Ser Leu Lys Leu Ser Cys Thr Ala Ser Gly Phe Thr Phe Ser His Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Thr Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Leu Tyr Tyr Gly Leu Tyr Tyr Ala Met Asp Tyr Trp Gly
            100                 105                 110

Gln Gly Thr Ser Val Thr Val Ser Ser
        115                 120

<210> SEQ ID NO 343
<211> LENGTH: 120
<212> TYPE: PRT
<213> ORGANISM: Artificial Sequence
<220> FEATURE:
<223> OTHER INFORMATION: Synthetic Construct

<400> SEQUENCE: 343

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Phe
            20                  25                  30

Gly Val Asn Trp Phe Arg Gln Pro Pro Gly Lys Gly Leu Glu Trp Leu
        35                  40                  45

Gly Ile Ile Trp Gly Asp Gly Ser Thr Asn Phe His Ser Ala Leu Met
    50                  55                  60

Ser Arg Leu Ser Ile Ser Lys Asp Asn Ser Lys Ser Gln Val Phe Leu
65                  70                  75                  80

Lys Leu Asn Arg Leu Gln Thr Asp Asp Thr Ala Thr Tyr Tyr Cys Ala
                85                  90                  95

Lys Arg Asp Tyr Asp Gly Arg Asp Asp Val Met Gly Tyr Trp Gly Gln
            100                 105                 110

Gly Thr Ser Val Thr Val Ser Ser
        115                 120

<210> SEQ ID NO 344
<211> LENGTH: 117
<212> TYPE: PRT
<213> ORGANISM: Artificial Sequence
<220> FEATURE:
<223> OTHER INFORMATION: Synthetic Construct

<400> SEQUENCE: 344

Glu Val Lys Leu Glu Glu Ser Gly Gly Gly Leu Val Gln Pro Gly Arg
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val

```
                35                  40                  45
Ala Glu Ile Arg Leu Lys Ser Asn Asn Tyr Ala Thr His Tyr Ala Glu
            50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ser Ser Met Ile Ile Val Asp Tyr Trp Gly Gln Gly Thr Thr
            100                 105                 110

Val Thr Val Ser Ser
        115

<210> SEQ ID NO 345
<211> LENGTH: 121
<212> TYPE: PRT
<213> ORGANISM: Artificial Sequence
<220> FEATURE:
<223> OTHER INFORMATION: Synthetic Construct

<400> SEQUENCE: 345

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Asn Gly Tyr
            20                  25                  30

Phe Met Asn Trp Val Met Gln Ser His Gly Glu Ser Leu Glu Trp Ile
                35                  40                  45

Gly Arg Ile Asn Pro Tyr Asn Gly Asp Thr Leu Tyr Asn Gln Lys Phe
            50                  55                  60

Lys Gly Lys Ala Thr Leu Thr Val Asp Lys Ser Ser Ser Thr Gly His
65                  70                  75                  80

Met Glu Leu Arg Ser Leu Ala Ser Glu Asp Ser Ala Val Tyr Tyr Cys
                85                  90                  95

Ala Arg Val Lys Gly Tyr Asp Tyr Asp Gly Ala Met Asp Tyr Trp Gly
            100                 105                 110

Gln Gly Thr Ser Val Thr Val Ser Ser
        115                 120

<210> SEQ ID NO 346
<211> LENGTH: 106
<212> TYPE: PRT
<213> ORGANISM: Artificial Sequence
<220> FEATURE:
<223> OTHER INFORMATION: Synthetic Construct

<400> SEQUENCE: 346

Asp Ile Val Met Thr Gln Ser Leu Lys Phe Met Ser Thr Ser Val Gly
1               5                   10                  15

Asp Arg Val Ser Ile Thr Cys Lys Ala Ser Gln Asn Val Arg Ser Ala
            20                  25                  30

Val Ala Trp Tyr Gln Gln Lys Pro Gly Gln Ser Pro Lys Val Leu Ile
                35                  40                  45

Tyr Trp Ala Ser Asn Arg His Thr Gly Val Pro Asp Arg Phe Thr Gly
            50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Leu Thr
                85                  90                  95
```

```
Phe Gly Ser Gly Thr Lys Leu Glu Ile Lys
            100                 105

<210> SEQ ID NO 347
<211> LENGTH: 111
<212> TYPE: PRT
<213> ORGANISM: Artificial Sequence
<220> FEATURE:
<223> OTHER INFORMATION: Synthetic Construct

<400> SEQUENCE: 347

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110

<210> SEQ ID NO 348
<211> LENGTH: 106
<212> TYPE: PRT
<213> ORGANISM: Artificial Sequence
<220> FEATURE:
<223> OTHER INFORMATION: Synthetic Construct

<400> SEQUENCE: 348

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Phe Met
            20                  25                  30

Tyr Trp Tyr Gln Glu Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Gly Ala Glu
65                  70                  75                  80

Asp Val Ala Thr Tyr Tyr Cys Phe Gln Gly Ser Gly Phe Pro Leu Thr
                85                  90                  95

Phe Gly Ser Gly Thr Lys Leu Glu Ile Lys
            100                 105

<210> SEQ ID NO 349
<211> LENGTH: 107
<212> TYPE: PRT
<213> ORGANISM: Artificial Sequence
<220> FEATURE:
<223> OTHER INFORMATION: Synthetic Construct

<400> SEQUENCE: 349

Asp Ile Val Met Thr Gln Ser Gln Lys Ile Met Ser Thr Ser Val Gly
1               5                   10                  15

Asp Arg Val Ser Ile Thr Cys Lys Ala Ser Gln Thr Val Arg Thr Ala
```

```
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Ser Tyr Pro Leu
                85                  90                  95

Thr Phe Gly Ala Gly Thr Lys Leu Glu Met Lys
            100                 105

<210> SEQ ID NO 350
<211> LENGTH: 111
<212> TYPE: PRT
<213> ORGANISM: Artificial Sequence
<220> FEATURE:
<223> OTHER INFORMATION: Synthetic Construct

<400> SEQUENCE: 350

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Ser Ser
            20                  25                  30

Thr Tyr Ser Tyr Leu His Trp Tyr Gln Gln Arg Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Val Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Met Lys
            100                 105                 110

<210> SEQ ID NO 351
<211> LENGTH: 113
<212> TYPE: PRT
<213> ORGANISM: Artificial Sequence
<220> FEATURE:
<223> OTHER INFORMATION: Synthetic Construct

<400> SEQUENCE: 351

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Gln Ser
            20                  25                  30

Gly Asn Gln Lys Ser Ser Leu Ala Trp Tyr Gln Gln Lys Pro Gly Gln
        35                  40                  45

Pro Pro Lys Leu Leu Ile Phe Trp Ala Arg Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Ser Asp Thr Pro Phe Thr Phe Gly Gln Gly Thr Lys Leu Glu Ile
            100                 105                 110
```

Lys

```
<210> SEQ ID NO 352
<211> LENGTH: 6
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 1
<223> OTHER INFORMATION: Xaa = Ser, Ile, Val, Leu
<220> FEATURE:
<221> NAME/KEY: VARIANT
<222> LOCATION: 2, 4, 5
<223> OTHER INFORMATION: Xaa = Any Amino Acid
<220> FEATURE:
<221> NAME/KEY: VARIANT
<222> LOCATION: 6
<223> OTHER INFORMATION: Xaa = Ile, Val, or Leu

<400> SEQUENCE: 352

Xaa Xaa Tyr Xaa Xaa Xaa
1               5

<210> SEQ ID NO 353
<211> LENGTH: 21
<212> TYPE: PRT
<213> ORGANISM: Artificial Sequence
<220> FEATURE:
<223> OTHER INFORMATION: Synthetic Construct

<400> SEQUENCE: 353

Ser Phe His His Ala Tyr Cys Asn Tyr Tyr Gly Asn Ser Asn Asn Cys
1               5                   10                  15

His Gly Thr Met Ser
            20

<210> SEQ ID NO 354
<211> LENGTH: 21
<212> TYPE: PRT
<213> ORGANISM: Artificial Sequence
<220> FEATURE:
<223> OTHER INFORMATION: Synthetic Construct

<400> SEQUENCE: 354

Ser Phe His His Pro Tyr Cys Asn Tyr Tyr Gly Asn Ser Ala Asn Cys
1               5                   10                  15

His Gly Thr Met Ser
            20

<210> SEQ ID NO 355
<211> LENGTH: 20
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 2, 3, 5, 6, 7, 8, 9, 10, 11, 12, 13, 14, 15, 16, 18, 19
<223> OTHER INFORMATION: Xaa = Any Amino Acid and up to six can be
      present or absent
<220> FEATURE:
<221> NAME/KEY: VARIANT
<222> LOCATION: 4, 20
<223> OTHER INFORMATION: Xaa = Ile or Leu
```

```
<400> SEQUENCE: 355

Tyr Xaa Xaa Xaa Xaa Xaa Xaa Xaa Xaa Xaa Xaa Xaa Xaa Xaa Xaa
1               5                   10                  15

Tyr Xaa Xaa Xaa
            20
```

ANTI-MS4A4A ANTIBODIES AND METHODS OF USE THEREOF

CROSS-REFERENCE TO RELATED APPLICATIONS

The application is a U.S. national stage entry of PCT/US2019/016156, filed Jan. 31, 2019, which claims the benefit of U.S. Provisional Application No. 62/624,600, filed Jan. 31, 2018, and U.S. Provisional Application No. 62/783,096, filed Dec. 20, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 4503_0020002_Seqlisting _ST25.TXT, created on Jul. 21, 2020; size: 149,865 bytes).

FIELD OF THE PRESENT DISCLOSURE

The present disclosure relates to anti-MS4A4A antibodies and therapeutic uses of such antibodies.

BACKGROUND OF THE PRESENT DISCLOSURE

The membrane-spanning 4-domain subfamily A (MS4A) gene cluster is present on chromosome 11q12 and includes eighteen genes. The MS4A gene family encodes membrane proteins typically having tetra-spanning topology (Ishibashi et al, 2001, Gene, 265:87-93; Liang and Tedder, 2001, Genomics, 72:119-127; Efthymiou and Goate, 2017, Molecular Neurodegeneration, 12:43). The membrane spanning domains are interconnected by one intracellular loop and two extracellular loops with both N- and C-termini residing within the cytosol. Most MS4A proteins share amino acid sequence homology to that of MS4A1 (CD20) (20-30% similarity), with the highest degree of sequence identity occurring in the first three transmembrane domains. The highly conserved motifs within these transmembrane regions across different MS4A proteins suggest that the membrane spanning domains have an important general role in MS4A protein function. The regions of greatest variation between MS4A proteins occur within their N- and C-terminal cytoplasmic domains and the putative second extracellular loop (Ishibashi et al, 2001, Gene, 265:87-93), suggesting that these regions impart unique functional properties.

Despite this diversity, the MS4A domains possess some shared elements. For instance, one notable feature conserved in MS4A proteins (with the exception of MS4A8B and MS4A12) is the conservation of two cysteine residues in the putative second extracellular loop that may form a disulfide bridge. The N- and C-terminal domains of MS4A proteins are also rich in proline residues, although the functional significance of this remains to be elucidated (Hulett et al, 2001, Genomics, 72:119-127). Proline rich regions are, however, commonly involved in various cellular processes such as cytoskeletal rearrangement, initiation of transcription, signaling cascades, and association with SH3 domains as part of an adaptor system to facilitate protein-protein interactions (Kay et al, 2000, FASEB J, 14:231-241).

The MS4A protein family is relatively uncharacterized functionally, with some important exceptions: MS4A1 (CD20) is expressed exclusively in B lymphocytes, where the protein has a function in signaling by the B cell antigen receptor, and calcium influx. CD20 is the target of immunotherapeutic antibodies used to deplete pathogenic B cells in chronic lymphocytic leukemia, lymphomas, autoimmune diseases, and in solid organ transplantation. MS4A2 (FcεRβ) is a signaling subunit of the high affinity IgE receptor (FcεRI) and the low affinity IgG receptor (FcεRIII) on mast cells, having a key role in hypersensitivity and allergic reactions. MS4A2 is an ITAM-domain protein that amplifies signals through a 4-protein high affinity IgE receptor complex. MS4A3 (Htm4) is expressed on intracellular membranes of lymphoid and myeloid cells, and functions as an adaptor protein in cell cycle regulation.

While the majority of MS4A family members are uncharacterized, reports suggest MS4A proteins act as chemosensors and chemoreceptors for a variety of exogenous and endogenous ligands, including fatty acids, peptides, and sulfated steroids, and have been implicated in mediating calcium influx, regulating endocytosis, trafficking, and may act as adapters for signal transduction complexes (Cruse et al, 2015, Mol Biol Cell, 26:1711-1727; Greer et al, 2016, Cell, 165:1734-1748; Eon Kuek et al, 2016, Cell, 165:1734-1748; Koslowski et al, 2008, Cancer Res, 68:3458-3466; Bubien et al, 1993; J Cell Biol, 121:1121-1132).

Certain MS4A genes have been genetically linked to various disorders and diseases, in particular neurodegenerative disorders. For example, genome-wide significance association analyses have identified the MS4A gene cluster, located on chromosome 11q12, as one of the most significant Alzheimer's disease loci. One gene of particular interest identified is MS4A4A (Lambert et al, 2013, Nat Genet, 45:1452-1458; Hollingworth et al, 2011, Nat Genet, 43:429-435; Naj et al, 2011, Nat Genet, 43:436-441).

Accordingly, there is a need for therapies targeting MS4A4A, including antibodies that specifically bind to MS4A4A, and/or therapies that are capable of modulating (e.g., inhibiting or reducing; activating or enhancing) the activity of MS4A4A, such as by reducing or increasing MS4A4A protein levels or activity, in order to treat various diseases, disorders, and conditions associated with MS4A4A activity.

All references cited herein, including patent applications and publications, are hereby incorporated by reference in their entirety.

SUMMARY OF THE PRESENT DISCLOSURE

The present disclosure is generally directed to anti-MS4A4A antibodies and methods of using such antibodies. The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disease, disorder, or condition selected from the group consisting of Alzheimer's disease, late onset Alzheimer's disease, dementia, and cognitive impairment, the method comprising administering to the individual in need thereof a therapeutically effective amount of an anti-MS4A4A antibody. In some embodiments, the present disclosure provides a method for preventing, reducing risk, or treating an individual having a disease, disorder, or condition associated with increased expression or activity of MS4A4A, the method comprising administering to the individual in need thereof a therapeutically effective amount of an anti-MS4A4A antibody. In some embodiments, the present disclosure provides a method for preventing, reducing risk, or treating an individual having a disease, disorder, or condition associated with reduced expression or activity of MS4A4A, the method comprising administering to the individual in need thereof a therapeutically effective amount of an anti-MS4A4A antibody.

In certain embodiments that may be combined with any of the preceding embodiments, an anti-MS4A4A antibody of the present disclosure binds a discontinuous MS4A4A epitope. In certain embodiments that may be combined with any of the preceding embodiments, the discontinuous MS4A4A epitope comprises two or more peptides, three or more peptides, four or more peptides, five or more peptides, six or more peptides, seven or more peptides, eight or more peptides, nine or more peptides, or 10 or more peptides. In certain embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1, of the amino acid sequence of SEQ ID NO:2, or of the amino acid sequence of SEQ ID NO:3; or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian MS4A4A protein corresponding to the amino acid sequence of SEQ ID NO: 1, to the amino acid sequence of SEQ ID NO:2, or to the amino acid sequence of SEQ ID NO:3.

In certain embodiments that may be combined with any of the preceding embodiments, an anti-MS4A4A antibody of the present disclosure binds to a conformational epitope of MS4A4A. In certain embodiments that may be combined with any of the preceding embodiments, an anti-MS4A4A antibody of the present disclosure binds to a linear epitope of MS4A4A.

In some embodiments that may be combined with any of the preceding embodiments, an anti-MS4A4A antibody of the present disclosure binds to extracellular domain 1 (ECL1) of MS4A4A. In some embodiments that may be combined with any of the preceding embodiments, an anti-MS4A4A antibody of the present disclosure binds to one or more amino acids within the amino acid sequence CMASNTYGSNPIS (SEQ ID NO:289) of SEQ ID NO:1. In some embodiments that may be combined with any of the preceding embodiments, an anti-MS4A4A antibody of the present disclosure binds to extracellular domain 2 (ECL2) of MS4A4A. In some embodiments that may be combined with any of the preceding embodiments, an anti-MS4A4A antibody of the present disclosure binds to one or more amino acids within the amino acid sequence SFHHPYCNYYGNSNNCHGTMS (SEQ ID NO:290) of SEQ ID NO:1

In some embodiments that may be combined with any of the preceding embodiments, an anti-MS4A4A antibody of the present disclosure binds to a region or epitope in human MS4A4A comprising amino acid residues 155-177 of human MS4A4A of SEQ ID NO:1. In some embodiments that may be combined with any of the preceding embodiments, an anti-MS4A4A antibody of the present disclosure binds to one or more amino acids within amino acid residues 155-177 of human MS4A4A of SEQ ID NO:1. In some embodiments that may be combined with any of the preceding embodiments, an anti-MS4A4A antibody of the present disclosure binds to a region or epitope in human MS4A4A comprising the amino acid sequence LAFYSFHHPYCNYYG (SEQ ID NO:296). In some embodiments that may be combined with any of the preceding embodiments, an anti-MS4A4A antibody of the present disclosure binds to one or more amino acid residues within the amino acid sequence LAFYSFHHPYCNYYG (SEQ ID NO:296). In some embodiments that may be combined with any of the preceding embodiments, an anti-MS4A4A antibody of the present disclosure binds to a region or epitope in human MS4A4A comprising the amino acid sequence FYSFHHPYCNYYGNS (SEQ ID NO:297). In some embodiments that may be combined with any of the preceding embodiments, an anti-MS4A4A antibody of the present disclosure binds to one or more amino acid residues within the amino acid sequence FYSFHHPYCNYYGNS (SEQ ID NO:297). In some embodiments that may be combined with any of the preceding embodiments, an anti-MS4A4A antibody of the present disclosure binds to a region or epitope in human MS4A4A comprising the amino acid sequence SFHHPYCNYYGNSNN (SEQ ID NO:298). In some embodiments that may be combined with any of the preceding embodiments, an anti-MS4A4A antibody of the present disclosure binds to one or more amino acid residues within the amino acid sequence SFHHPYCNYYGNSNN (SEQ ID NO:298). In some embodiments that may be combined with any of the preceding embodiments, an anti-MS4A4A antibody of the present disclosure binds to a region or epitope in human MS4A4A comprising the amino acid sequence HHPYCNYYGNSNNCH (SEQ ID NO:299). In some embodiments that may be combined with any of the preceding embodiments, an anti-MS4A4A antibody of the present disclosure binds to one or more amino acid residues within the amino acids sequence HHPYCNYYGNSNNCH (SEQ ID NO:299). In some embodiments that may be combined with any of the preceding embodiments, an anti-MS4A4A antibody of the present disclosure binds to a region or epitope in human MS4A4A comprising the amino acid sequence PYCNYYGNSNNCHGT (SEQ ID NO:300). In some embodiments that may be combined with any of the preceding embodiments, an anti-MS4A4A antibody of the present disclosure binds to one or more amino acid residues within the amino acid sequence PYCNYYGNSNNCHGT (SEQ ID NO:300).

In some embodiments that may be combined with any of the preceding embodiments, an anti-MS4A4A antibody of the present disclosure competes with one or more reference anti-MS4A4A antibodies selected from the group consisting of 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof for binding to MS4A4A. In some embodiments, the anti-MS4A4A antibody comprises the $V_H$ an $V_L$ (e.g., as shown in Table 4B and Table 9B below) of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

In some embodiments that may be combined with any of the preceding embodiments, an anti-MS4A4A antibody of the present disclosure binds to an epitope of human MS4A4A that is the same as or overlaps with the MS4A4A epitope bound by at least one reference antibody selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof. In some embodiments, the anti-MS4A4A antibody comprises the $V_H$ an $V_L$ (e.g., as shown in Table 4B and Table 9B below) of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

In some embodiments that may be combined with any of the preceding embodiments, an anti-MS4A4A antibody of the present disclosure binds essentially the same MS4A4A epitope bound by at least one reference antibody selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof. In some embodiments, the anti-MS4A4A antibody comprises the $V_H$ an $V_L$ (e.g., as shown in Table 4B and Table 9B below) of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

In some embodiments that may be combined with any of the preceding embodiments, an anti-MS4A4A antibody of the present disclosure binds to a linear epitope on MS4A4A. In some embodiments that may be combined with any of the preceding embodiments, an anti-MS4A4A antibody of the present disclosure binds to one or more amino acids within amino acid residues 1-64 of human MS4A4A. In some embodiments that may be combined with any of the preceding embodiments, an anti-MS4A4A antibody of the present disclosure binds to one or more amino acids within amino acid residues 65-85 of human MS4A4A. In some embodiments that may be combined with any of the preceding embodiments, an anti-MS4A4A antibody of the present disclosure bind to one or more amino acids within amino acid residues 86-98 of human MS4A4A. In some embodiments that may be combined with any of the preceding embodiments, an anti-MS4A4A antibody of the present disclosure binds to one or more amino acids within amino acid residues 99-119 of human MS4A4A. In some embodiments that may be combined with any of the preceding embodiments, an anti-MS4A4A of the present disclosure binds to one or more amino acids within amino acid residues 120-137 of human MS4A4A. In some embodiments, an anti-MS4A4A of the present disclosure binds to one or more amino acids within amino acid residues 138-158 of human MS4A4A. In some embodiments that may be combined with any of the preceding embodiments, an anti-MS4A4A of the present disclosure binds to one or more amino acids within amino acid residues 159-179 of human MS4A4A. In some embodiments that may be combined with any of the preceding embodiments, an anti-MS4A4A of the present disclosure binds to one or more amino acids within amino acid residues 180-200 of human MS4A4A. In some embodiments that may be combined with any of the preceding embodiments, an anti-MS4A4A of the present disclosure binds to one or more amino acids within amino acid residues 201-239 of human MS4A4A. In some embodiments that may be combined with any of the preceding embodiments, an anti-MS4A4A antibody of the present disclosure binds to extracellular domain 1 (ECL1) of MS4A4A. In some embodiments, an anti-MS4A4A antibody of the present disclosure binds to extracellular domain 2 (ECL2) of MS4A4A. In some embodiments, an anti-MS4A4A antibody of the present disclosure binds to ECL1 domain and ECL2 domain of MS4A4A.

In some embodiments that may be combined with any of the preceding embodiments, an anti-MS4A4A of the present disclosure is an isolated antibody that binds to human MS4A4A, wherein the antibody comprises a heavy chain variable region and a light chain variable region, wherein the heavy chain variable region comprises: an HVR-H1 comprising an amino acid sequence selected from the group consisting of SEQ ID NOs:4-19; an HVR-H2 comprising an amino acid sequence selected from the group consisting of SEQ ID NOs:20-37; and an HVR-H3 comprising an amino acid sequence selected from the group consisting of SEQ ID NOs:38-55; and the light chain variable region comprises: an HVR-L1 comprising an amino acid sequence selected from the group consisting of SEQ ID NOs:56-74; an HVR-L2 comprising an amino acid sequence selected from the group consisting of SEQ ID NOs:75-85; and an HVR-L3 comprising an amino acid sequence selected from the group consisting of SEQ ID NOs:86-100.

In some embodiments that may be combined with any of the preceding embodiments, an anti-MS4A4A of the present disclosure is an isolated antibody that binds to human MS4A4A, wherein the antibody comprises a heavy chain variable region, wherein the heavy chain variable region comprises an amino acid sequence selected from the group consisting of SEQ ID NOs:101-120.

In some embodiments that may be combined with any of the preceding embodiments, an anti-MS4A4A of the present disclosure is an isolated antibody that binds to human MS4A4A, wherein the antibody comprises a light chain variable region, wherein the light chain variable region comprises an amino acid sequence selected from the group consisting of SEQ ID NOs:121-139.

In some embodiments that may be combined with any of the preceding embodiments, an anti-MS4A4A of the present disclosure is an isolated antibody that binds to human MS4A4A, wherein the antibody comprises a heavy chain variable region and a light chain variable region, wherein the heavy chain variable region comprises an amino acid sequence selected from the group consisting of SEQ ID NOs:101-120; and wherein the light chain variable region comprises an amino acid sequence selected from the group consisting of SEQ ID NOs:121-139.

In some embodiments that may be combined with any of the preceding embodiments, an anti-MS4A4A of the present disclosure is an isolated antibody that binds to human MS4A4A, wherein the antibody comprises a heavy chain variable region and a light chain variable region, wherein the heavy chain variable region comprises: an HVR-H1 comprising an amino acid sequence selected from the group consisting of SEQ ID NOs:142-153; an HVR-H2 comprising an amino acid sequence selected from the group consisting of SEQ ID NOs:154-167; and an HVR-H3 comprising an amino acid sequence selected from the group consisting of SEQ ID NOs:168-182; and the light chain variable region comprises: an HVR-L1 comprising an amino acid sequence selected from the group consisting of SEQ ID NOs:183-196; an HVR-L2 comprising an amino acid sequence selected from the group consisting of SEQ ID NOs:197-209; and an HVR-L3 comprising an amino acid sequence selected from the group consisting of SEQ ID NOs:210-224.

In some embodiments that may be combined with any of the preceding embodiments, an anti-MS4A4A of the present disclosure is an isolated antibody that binds to human MS4A4A, wherein the antibody comprises a heavy chain variable region, wherein the heavy chain variable region comprises an amino acid sequence selected from the group consisting of SEQ ID NOs:225-239.

In some embodiments that may be combined with any of the preceding embodiments, an anti-MS4A4A of the present disclosure is an isolated antibody that binds to human MS4A4A, wherein the antibody comprises a light chain variable region, wherein the light chain variable region comprises an amino acid sequence selected from the group consisting of SEQ ID NOs:240-254.

In some embodiments that may be combined with any of the preceding embodiments, an anti-MS4A4A of the present disclosure is an isolated antibody that binds to human MS4A4A, wherein the antibody comprises a heavy chain variable region and a light chain variable region, wherein the heavy chain variable region comprises an amino acid sequence selected from the group consisting of SEQ ID NOs:225-239; and wherein the light chain variable region comprises an amino acid sequence selected from the group consisting of SEQ ID NOs:240-254.

In some embodiments that may be combined with any of the preceding embodiments, an anti-MS4A4A of the present disclosure is an isolated antibody that binds to human MS4A4A, wherein the antibody comprises a heavy chain variable region and a light chain variable region, wherein the heavy chain variable region comprises: an HVR-H1 comprising an amino acid sequence selected from the group consisting of SEQ ID NOs:304-309; an HVR-H2 comprising an amino acid sequence selected from the group consisting of SEQ ID NOs:310-315; and an HVR-H3 comprising an amino acid sequence selected from the group consisting of SEQ ID NOs:316-321; and the light chain variable region comprises: an HVR-L1 comprising an amino acid sequence selected from the group consisting of SEQ ID NOs:322-327; an HVR-L2 comprising an amino acid sequence selected from the group consisting of SEQ ID NOs:328-333; and an HVR-L3 comprising an amino acid sequence selected from the group consisting of SEQ ID NOs:334-339.

In some embodiments that may be combined with any of the preceding embodiments, an anti-MS4A4A of the present disclosure is an isolated antibody that binds to human MS4A4A, wherein the antibody comprises a heavy chain variable region, wherein the heavy chain variable region comprises an amino acid sequence selected from the group consisting of SEQ ID NOs:340-345.

In some embodiments that may be combined with any of the preceding embodiments, an anti-MS4A4A of the present disclosure is an isolated antibody that binds to human MS4A4A, wherein the antibody comprises a light chain variable region, wherein the light chain variable region comprises an amino acid sequence selected from the group consisting of SEQ ID NOs:346-351.

In some embodiments that may be combined with any of the preceding embodiments, an anti-MS4A4A of the present disclosure is an isolated antibody that binds to human MS4A4A, wherein the antibody comprises a heavy chain variable region and a light chain variable region, wherein the heavy chain variable region comprises an amino acid sequence selected from the group consisting of SEQ ID NOs:340-345; and wherein the light chain variable region comprises an amino acid sequence selected from the group consisting of SEQ ID NOs:346-351.

In certain embodiments that may be combined with any of the preceding embodiments, the MS4A4A protein is a mammalian protein or a human protein. In certain embodiments that may be combined with any of the preceding embodiments, the MS4A4A protein is a wild-type protein. In certain embodiments that may be combined with any of the preceding embodiments, the MS4A4A protein is a naturally occurring variant. In certain embodiments that may be combined with any of the preceding embodiments, the antibody is an agonist antibody, wherein the antibody induces one or more MS4A4A activities. In certain embodiments that may be combined with any of the preceding embodiments, the isolated antibody induces, enhances, or retains MS4A4A clustering on a cell surface. In certain embodiments that may be combined with any of the preceding embodiments, the antibody is an antagonist antibody, wherein the antibody inhibits or reduces one or more MS4A4A activities. In certain embodiments that may be combined with any of the preceding embodiments, the isolated antibody reduces or inhibits MS4A4A clustering on a cell surface.

In some embodiments that may be combined with any of the preceding embodiments, an anti-MS4A4A antibody of the present disclosure reduces or inhibits the interaction or binding of MS4A4A and at least one MS4A4A ligand or binding partner.

In some embodiments that may be combined with any of the preceding embodiments, an anti-MS4A4A antibody of the present disclosure increases or enhances the interaction or binding of MS4A4A and at least one MS4A4A ligand or binding partner.

In some embodiments that may be combined with any of the preceding embodiments, an anti-MS4A4A antibody of the present disclosure increases soluble TREM2 levels. In some embodiments that may be combined with any of the preceding embodiments, an anti-MS4A4A antibody of the present disclosure increases membrane TREM2 levels. In some embodiments that may be combined with any of the preceding embodiments, an anti-MS4A4A antibody of the present disclosure increases soluble TREM2 levels and plasma membrane/cell surface TRME2 levels.

In some embodiments that may be combined with any of the preceding embodiments, an anti-MS4A4A antibody of the present disclosure decreases or reduces the levels of M2 cell surface markers in a myeloid cell, e.g., a macrophage. In some embodiments that may be combined with any of the preceding embodiments, an anti-MS4A4A antibody of the present disclosure decreases or reduces cell surface levels of CD200R, Dectin-1, and/or CD163 in myeloid cells, e.g., a macrophage.

In some embodiments that may be combined with any of the preceding embodiments, an anti-MS4A4A antibody of the present disclosure enhances or increases the formation of signaling complexes. In some embodiments that may be combined with any of the preceding embodiments, an anti-MS4A4A antibody of the present disclosure enhances or increases the formation of signaling complexes associated with ITAM-encoding adaptor proteins. In some embodiments that may be combined with any of the preceding embodiments, an anti-MS4A4A antibody of the present disclosure enhances or increases the formation of inhibitory signaling complexes. In some embodiments that may be combined with any of the preceding embodiments, an anti-MS4A4A antibody of the present disclosure enhances or increases the formation of inhibitory signaling complexes associated with ITIM-encoding adaptor proteins.

In some embodiments that may be combined with any of the preceding embodiments, an anti-MS4A4A antibody of the present disclosure inhibits (e.g., blocks) or reduces the formation of signaling complexes. In some embodiments that may be combined with any of the preceding embodiments, an anti-MS4A4A antibody of the present disclosure inhibits (e.g., blocks) or reduces the formation of signaling complexes associated with ITAM-encoding adaptor proteins. In some embodiments that may be combined with any of the preceding embodiments, an anti-MS4A4A antibody of the present disclosure inhibits (e.g., blocks) or reduces the formation of inhibitory signaling complexes. In some embodiments that may be combined with any of the preceding embodiments, an anti-MS4A4A antibody of the present disclosure inhibits (e.g., blocks) or reduces the formation of inhibitory signaling complexes associated with ITIM-encoding adaptor proteins.

In some embodiments that may be combined with any of the preceding embodiments, an anti-MS4A4A antibody of the present disclosure inhibits (e.g., blocks) or reduces formation of MS4A4A homo-oligomeric cell surface protein complexes by: a) reducing the effective levels of MS4A4A available for MS4A4A homo-oligomeric complex formation; b) blocking one or more of the sites on MS4A4A required for MS4A4A homo-oligomeric complex formation; c) preventing one or more posttranslational events on MS4A4A that are required for MS4A4A homo-oligomeric complex formation and/or for correct processing and/or cellular localization of MS4A4A; d) inducing degradation of MS4A4A; e) changing the conformation of MS4A4A, or any combination thereof.

In some embodiments that may be combined with any of the preceding embodiments, an anti-MS4A4A antibody of the present disclosure increases or enhances formation of MS4A4A homo-oligomeric cell surface protein complexes by: a) increasing the effective levels of MS4A4A available for MS4A4A homo-oligomeric complex formation; b) stabilizing one or more of the sites on MS4A4A required for MS4A4A homo-oligomeric complex formation; c) maintaining cell surface expression of MS4A4A to allow for homo-oligomeric complex formation and/or for correct processing and/or maintaining correct cellular localization of MS4A4A; d) reducing degradation of MS4A4A; e) changing the conformation of MS4A4A, or any combination thereof.

In some embodiments that may be combined with any of the preceding embodiments, an anti-MS4A4A antibody of the present disclosure inhibits (e.g., blocks) or reduces MS4A4A hetero-oligomeric cell surface protein complex formation with one or more signal transduction adaptor proteins by: a) reducing the effective levels of MS4A4A available for MS4A4A hetero-oligomeric complex formation; b); blocking one or more of the sites on MS4A4A required for MS4A4A hetero-oligomeric complex formation; c) preventing one or more posttranslational events on MS4A4A that are required for MS4A4A hetero-oligomeric complex formation and/or for correct processing and/or cellular localization of MS4A4A; d) inducing degradation of MS4A4A; e) changing the conformation of MS4A4A, or any combination thereof.

In some embodiments that may be combined with any of the preceding embodiments, an anti-MS4A4A antibody of the present disclosure increases or enhances MS4A4A hetero-oligomeric cell surface protein complex formation with one or more signal transduction adaptor proteins by: a) increasing the effective levels of MS4A4A available for MS4A4A hetero-oligomeric complex formation; b) stabilizing one or more of the sites on MS4A4A required for MS4A4A hetero-oligomeric complex formation; c) maintaining cell surface expression of MS4A4A to allow for MS4A4A hetero-oligomeric complex formation and/or for correct processing and/or maintaining correct cellular localization of MS4A4A; d) reducing degradation of MS4A4A; e) changing the conformation of MS4A4A, or any combination thereof.

In certain embodiments that may be combined with any of the preceding embodiments, the anti-MS4A4A antibody is a human antibody, a humanized antibody, a bispecific antibody, a monoclonal antibody, a multivalent antibody, a conjugated antibody, or a chimeric antibody.

In certain embodiments that may be combined with any of the preceding embodiments, the anti-MS4A4A antibody is a bispecific antibody recognizing a first antigen and a second antigen. In certain embodiments that may be combined with any of the preceding embodiments, the first antigen is MS4A4A and the second antigen is an antigen facilitating transport across the blood-brain-barrier. In certain embodiments that may be combined with any of the preceding embodiments, the second antigen is selected from the group consisting of MS4A4A, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, and CD98hc, and ANG1005.

In some embodiments that may be combined with any of the preceding embodiments, the antibody is a monoclonal antibody. In some embodiments that may be combined with any of the preceding embodiments, the antibody is a human antibody. In some embodiments that may be combined with any of the preceding embodiments, the antibody is a humanized antibody. In some embodiments that may be combined with any of the preceding embodiments, the antibody is a bispecific antibody. In some embodiments that may be combined with any of the preceding embodiments, the antibody is a multivalent antibody. In some embodiments that may be combined with any of the preceding embodiments, the antibody is a chimeric antibody. In some embodiments that may be combined with any of the preceding embodiments, the antibody is of the IgG class, the IgM class, or the IgA class. In some embodiments, the antibody is of the IgG class and has an IgG1, IgG2, or IgG4 isotype. In certain embodiments that may be combined with any of the preceding embodiments, the anti-MS4A4A antibody is an antibody fragment that binds to an epitope comprising amino acid residues on human MS4A4A or a mammalian MS4A4A protein. In certain embodiments that may be combined with any of the preceding embodiments, the fragment is an Fab, Fab', Fab'-SH, F(ab')2, Fv, or scFv fragment.

Other aspects of the present disclosure relate to an isolated (e.g., monoclonal) anti-MS4A4A antibody, wherein the anti-MS4A4A antibody comprises at least one, two, three, four, five, or six HVRs of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220. In some embodiments, the anti-MS4A4A antibody comprises the six HVRs (e.g., as shown in Table 4A and Table 9A below) of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220. In some embodiments, the anti-MS4A4A antibody comprises the $V_H$ and/or $V_L$ of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220. In some embodiments, the anti-MS4A4A antibody comprises the $V_H$ an $V_L$ (e.g., as shown in Table 4B and Table 9B below) of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

Other aspects of the present disclosure relate to an isolated nucleic acid comprising a nucleic acid sequence encoding the anti-MS4A4A antibody of any of the preceding embodiments. Other aspects of the present disclosure relate to a vector comprising the nucleic acid of any of the preceding embodiments. Other aspects of the present disclosure relate to an isolated host cell comprising the vector of any of the preceding embodiments. Other aspects of the present disclosure relate to a method of producing an anti-MS4A4A antibody, comprising culturing the host cell of any of the preceding embodiments so that the anti-MS4A4A antibody is produced. In certain embodiments, the method further comprises recovering the anti-MS4A4A antibody produced by the host cell. Other aspects of the present disclosure relate to an isolated anti-MS4A4A antibody produced by the method of any of the preceding embodiments. Other aspects of the present disclosure relate to a pharmaceutical composition comprising the anti-MS4A4A antibody of any of the preceding embodiments, and a pharmaceutically acceptable carrier.

In certain embodiments that may be combined with any of the preceding embodiments, the anti-MS4A4A antibody binds specifically to human MS4A4A, mouse MS4A4A, cyno MS4A4A, or a combination thereof.

Some aspects of the present disclosure provide an isolated antibody that binds to human MS4A4A, wherein the antibody increases soluble TREM2 levels, increases plasma-membrane or cell surface TREM2 levels, or increases soluble TREM2 and increases plasma-membrane or cell surface TREM2 levels in myeloid cells. In some embodiments, the antibody increases soluble TREM2 levels by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by at least 100% compared to a control antibody of the same isotype. In some embodiments, the antibody increases plasma-membrane or cell surface TREM2 levels by at least 65%, by at least 70%, by at least 75%, by at least 80%, by at least 85%, by at least 90%, by at least 95%, by at least 100%, by at least 105%, by at least 110%, by at least 115%, by at least 120%, by at least 125%, by at least 130%, by at least 135%, by at least 140%, by at least 145%, or by at least 150% compared to a control antibody of the same isotype. In some embodiments, the antibody reduces expression of M2 cell surface receptors/markers on myeloid cells.

Other aspects of the present disclosure provide an isolated antibody that binds to human MS4A4A, wherein the antibody reduces expression of M2 cell surface receptors/markers on myeloid cells. In some embodiments, the antibody reduces expression of one or more of CD200R, Dectin-1, CD163, CD14, and SIRPα on myeloid cells.

In some embodiments of any of the above aspects and embodiments of the present disclosure, the antibody increases the viability of macrophages.

Other aspects of the present disclosure provide an isolated anti-MS4A4A antibody, wherein the anti-MS4A4A antibody comprises at least one, two, three, four, five, or six HVRs of an antibody selected from the group consisting of: 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

Other aspects of the present disclosure provide an isolated antibody that binds to human MS4A4A, wherein the antibody comprises a heavy chain variable region and a light chain variable region, wherein the heavy chain variable region comprises: (a) an HVR-H1 comprising an amino acid sequence selected from the group consisting of SEQ ID NOs: 4-19 or an amino acid sequence with at least about 95% homology to SEQ ID NOs: 4-19, an amino acid sequence selected from the group consisting of SEQ ID NOs:142-153 or an amino acid sequence with at least about 95% homology to SEQ ID NOs: 142-153, or an amino acid sequence selected from the group consisting of SEQ ID NOs:304-309 or an amino acid sequence with at least about 95% homology to SEQ ID NOs:304-309; (b) an HVR-H2 comprising an amino acid sequence selected from the group consisting of SEQ ID NOs: 20-37 or an amino acid sequence with at least about 95% homology to SEQ ID NOs:20-37, an amino acid sequence selected from the group consisting of SEQ ID NOs:154-167 or an amino acid sequence with at least about 95% homology to SEQ ID NOs:154-167, or an amino acid sequence selected from the group consisting of SEQ ID NOs:310-315 or an amino acid sequence with at least about 95% homology to SEQ ID NOs:310-315; and (c) an HVR-H3 comprising an amino acid sequence selected from the group consisting of SEQ ID NOs: 38-55 or an amino acid sequence with at least about 95% homology to SEQ ID NOs:38-55, an amino acid sequence selected from the group consisting of SEQ ID NOs: 168-182 or an amino acid sequence with at least about 95% homology to SEQ ID NOs:168-182, or an amino acid sequence selected from the group consisting of SEQ ID NOs:316-321 or an amino acid sequence with at least about 95% homology to SEQ ID NOs:316-321; and wherein the light chain variable region comprises: (d) an HVR-L1 comprising an amino acid sequence selected from the group consisting of SEQ ID NOs: 56-74 or an amino acid sequence with at least about 95% homology to SEQ ID NOs:56-74, an amino acid sequence selected from the group consisting of SEQ ID NOs: 183-196 or an amino acid sequence with at least about 95% homology to SEQ ID NOs:183-196, or an amino acid sequence selected from the group consisting of SEQ ID NOs:322-327 or an amino acid sequence with at least about 95% homology to SEQ ID NOs:322-327; (e) an HVR-L2 comprising an amino acid sequence selected from the group consisting of SEQ ID NOs:75-85 or an amino acid sequence with at least about 95% homology to SEQ ID NOs:75-85, an amino acid sequence selected from the group consisting of SEQ ID NOs:197-209 or an amino acid sequence with at least about 95% homology to SEQ ID NOs:197-209, or an amino acid sequence selected from the group consisting of SEQ ID NOs:328-333 or an amino acid sequence with at least about 95% homology to SEQ ID NOs:328-333; and (f) an HVR-L3 comprising an amino acid sequence selected from the group consisting of SEQ ID NOs: 86-100 or an amino acid sequence with at least about 95% homology to SEQ ID NOs:86-100, an amino acid sequence selected from the group consisting of SEQ ID NOs: 210-224 or an amino acid sequence with at least about 95% homology to SEQ ID NOs:210-224, or an amino acid sequence selected from the group consisting of SEQ ID NOs:334-339 or an amino acid sequence with at least about 95% homology to SEQ ID NOs:334-339.

In some embodiments of any of the above aspects and embodiments of the present disclosure, the heavy chain variable region comprises an amino acid sequence selected from the group consisting of SEQ ID NOs:101-120 or an amino acid sequence having at least 90% identity to SEQ ID NOs:101-120, an amino acid sequence selected from the group consisting of SEQ ID NOs: 225-239 or an amino acid sequence having at least 90% identity to SEQ ID NOs:225-239, or an amino acid sequence selected from the group consisting of SEQ ID NOs: 340-345 or an amino acid sequence having at least 90% identity to SEQ ID NOs:340-345. In some embodiments of any of the above aspects and embodiments of the present disclosure, the light chain variable region comprises an amino acid sequence selected from the group consisting of SEQ ID NOs:121-139 or an amino acid sequence having at least 90% identity to SEQ ID NOs:121-139, an amino acid sequence selected from the group consisting of SEQ ID NOs: 240-254 or an amino acid sequence having at least 90% identity to SEQ ID NOs:240-254, or an amino acid sequence selected from the group consisting of SEQ ID NOs: 346-351 or an amino acid sequence having at least 90% identity to SEQ ID NOs:346-351.

Some aspects of the present disclosure provide an isolated antibody that binds to human MS4A4A, wherein the antibody comprises a heavy chain variable region and a light chain variable region, wherein: (a) the heavy chain variable region comprises an HVR-H1 comprising the amino acid sequence of SEQ ID NO: 15 or an amino acid sequence with at least about 95% homology to SEQ ID NO: 15, an HVR-H2 comprising the amino acid sequence of SEQ ID NO: 32 or an amino acid sequence with at least about 95% homology to SEQ ID NO: 32, and HVR-H3 comprising the amino acid sequence of SEQ ID NO: 50 or an amino acid sequence with at least about 95% homology to SEQ ID NO: 50, and the light chain variable region comprises an HVR-L1 comprising the amino acid sequence of SEQ ID NO: 69 or an amino acid sequence with at least about 95% homology to SEQ ID NO: 69, an HVR-L2 comprising the amino acid sequence of SEQ ID NO: 82 or an amino acid sequence with at least about 95% homology to SEQ ID NO: 82, and HVR-L3 comprising the amino acid sequence of SEQ ID NO: 96 or an amino acid sequence with at least about 95% homology to SEQ ID NO: 96; (b) the heavy chain variable region comprises an HVR-H1 comprising the amino acid sequence of SEQ ID NO: 18 or an amino acid sequence with at least about 95% homology to SEQ ID NO: 18, an HVR-H2 comprising the amino acid sequence of SEQ ID NO: 35 or an amino acid sequence with at least about 95% homology to SEQ ID NO: 35, and HVR-H3 comprising the amino acid sequence of SEQ ID NO: 53 or an amino acid sequence with at least about 95% homology to SEQ ID NO: 53, and the light chain variable region comprises an HVR-L1 comprising the amino acid sequence of SEQ ID NO: 72 or an amino acid sequence with at least about 95% homology to SEQ ID NO: 72, an HVR-L2 comprising the amino acid sequence of SEQ ID NO: 77 or an amino acid sequence with at least about 95% homology to SEQ ID NO: 77, and HVR-L3 comprising the amino acid sequence of SEQ ID NO: 99 or an amino acid sequence with at least about 95% homology to SEQ ID NO: 99; or (c) the heavy chain variable region comprises an HVR-H1 comprising the amino acid sequence of SEQ ID NO: 143 or an amino acid sequence with at least about 95% homology to SEQ ID NO: 143, an HVR-H2 comprising the amino acid sequence of SEQ ID NO: 155 or an amino acid sequence with at least about 95% homology to SEQ ID NO: 155, and HVR-H3 comprising the amino acid sequence of SEQ ID NO: 169 or an amino acid sequence with at least about 95% homology to SEQ ID NO: 169, and the light chain variable region comprises an HVR-L1 comprising the amino acid sequence of SEQ ID NO: 184 or an amino acid sequence with at least about 95% homology to SEQ ID NO: 184, an HVR-L2 comprising the amino acid sequence of SEQ ID NO: 198 or an amino acid sequence with at least about 95% homology to SEQ ID NO: 198, and HVR-L3 comprising the amino acid sequence of SEQ ID NO: 211 or an amino acid sequence with at least about 95% homology to SEQ ID NO: 211.

In some embodiments of any of the above aspects and embodiments of the present disclosure, the antibody binds to cynomolgus MS4A4A.

In some aspects of the present disclosure, the antibody competes with one or more of the antibodies of any one of the above embodiments for binding to human MS4A4A. In some aspects, the antibody binds essentially the same or overlapping MS4A4A epitope as the antibody of any one of above embodiments.

In some embodiments of any of the above aspects and embodiments of the present disclosure, the antibody binds to extracellular domain 1 of human MS4A4A. In some embodiments, the antibody binds to extracellular domain 2 of human MS4A4A. In some embodiments, the antibody binds to one or more amino acids within amino acid residues 155-177 of human MS4A4A of SEQ ID NO:1. In some embodiments, the antibody binds to one or more amino acid residues selected from the group consisting of Y92, H161, Y164, N166, N170, T177, and M178 of SEQ ID NO: 1, or one or more amino acid residues on a mammalian MS4A4A protein corresponding to an amino acid residue selected from the group consisting of Y92, H161, Y164, N166, N170, T177, and M178 of SEQ ID NO: 1. In some embodiments, the antibody reduces or inhibits the interaction or binding of MS4A4A and at least one MS4A4A ligand or binding partner. In some embodiments, the antibody increases or enhances the interaction or binding of MS4A4A and at least one MS4A4A ligand or binding partner. In some embodiments, the antibody reduces decline in cognitive and behavioral function and improves cognitive and behavioral function.

In some embodiments of any of the above aspects and embodiments of the present disclosure, the antibody is a murine antibody, a human antibody, a humanized antibody, a bispecific antibody, a monoclonal antibody, a multivalent antibody, a conjugated antibody, or a chimeric antibody. In some embodiments, the antibody is of the IgG class, the IgM class, or the IgA class. In some embodiments, the antibody is of the IgG class and has an IgG1, IgG2, or IgG4 isotype. In some embodiments, the antibody is an antibody fragment. In some embodiments, the fragment is a Fab, Fab', Fab'-SH, F(ab')2, Fv or scFv fragment. In some embodiments, the antibody further comprises: (a) an antigen facilitating transport across the blood-brain-barrier; (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005; (c) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72) c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (e) a protein, lipid, polysaccharide, or glycolipid expressed on one or more tumor cells.

Other aspects of the present disclosure relate to an isolated nucleic acid comprising a nucleic acid sequence encoding the antibody of any one of the above embodiments. Other aspects of the present disclosure relate to a vector comprising the nucleic acids of the present disclosure. Other aspects of the present disclosure relate to an isolated host cell comprising the vector of the present disclosure. Other aspects of the present disclosure relate to a method of producing an antibody that binds to human MS4A4A, comprising culturing a cell of the present disclosure so that the antibody is produced. In some embodiments, the method further comprising recovering the antibody produced by the cell. Other aspects of the present disclosure relate to a pharmaceutical composition comprising an antibody of the present disclosure and a pharmaceutically acceptable carrier.

Other aspects of the present disclosure relate to a method of preventing, reducing risk, or treating an individual having a disease, disorder, or injury selected from the group consisting of Alzheimer's disease, late onset Alzheimer's disease, and cognitive impairment, the method comprising administering to an individual in need thereof a therapeutically effective amount of an antibody of the present disclosure. Other aspects of the present disclosure relate to A method of preventing, reducing risk, or treating an individual having a disease, disorder, condition, or injury caused by or associated with over expression or increased activity of MS4A4A, the method comprising administering to an individual in need thereof a therapeutically effective amount of an antibody of the present disclosure.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 3A shows a table indicating anti-MS4A4A antibody of the present disclosure. FIGS. 3B-3K show FACS plots and correspond to each anti-MS4A4A antibody of the present disclosure as indicated in FIG. 3A.

FIGS. 4A-4K show FACS analyses of anti-MS4A4A antibodies of the present disclosure binding to untransfected U937 cells (shading) or binding to U937 cells transfected with human MS4A4A (clear trace). FIG. 4A shows a table indicating anti-MS4A4A antibody of the present disclosure. FIGS. 4B-4K show FACS plots and correspond to each anti-MS4A4A antibody of the present disclosure as indicated in FIG. 4A.

DETAILED DESCRIPTION OF THE PRESENT DISCLOSURE

Figure 1A:
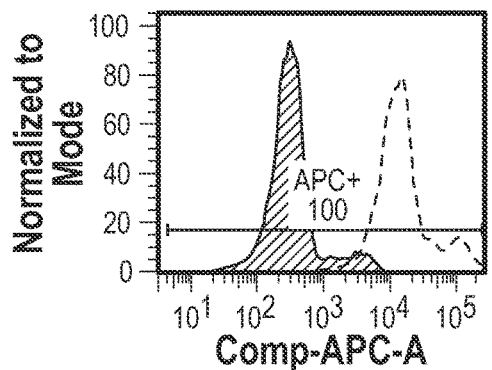
FIG. 1A shows representative FACS plots of HEK293 cells transiently transfected with human MS4A4A (clear trace) and non-transfected cells (shaded trace) stained with hybridoma supernatant containing anti-MS4A4A antibody of the present disclosure.

The present disclosure relates to anti-MS4A4A antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "MS4A4A" or "MS4A4A polypeptide" are used interchangeably herein refer herein to any native MS4A4A from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed MS4A4A as well as any form of MS4A4A that results from processing in the cell. In some embodiments, the MS4A4A is human MS4A4A. In some embodiments, the amino acid sequence of an exemplary MS4A4A is Uniprot Accession No. Q96JQ5 as of Dec. 1, 2001. In some embodiments, the amino acid sequence of an exemplary human MS4A4A is SEQ ID NO: 1.

The terms "anti-MS4A4A antibody," an "antibody that binds to MS4A4A," and "antibody that specifically binds MS4A4A" refer to an antibody that is capable of binding MS4A4A with sufficient affinity such that the antibody is useful as a diagnostic and/or therapeutic agent in targeting MS4A4A. In one embodiment, the extent of binding of an anti-MS4A4A antibody to an unrelated, non-MS4A4A polypeptide is less than about 10% of the binding of the antibody to MS4A4A as measured, e.g., by a radioimmunoassay (RIA). In certain embodiments, an antibody that binds to MS4A4A has a dissociation constant (KD) of <1 µM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$M to $10^{-13}$ M). In certain embodiments, an anti-MS4A4A antibody binds to an epitope of MS4A4A that is conserved among MS4A4A from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$M or lower, $10^{-9}$ M or lower, $10^{-10}$ M or lower, $10^{-11}$ M or lower, $10^{-12}$ M or lower or a KD in the range of $10^{-4}$ M to $10^{-6}$M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., Basic and Clinical Immunology, 8th Ed., Daniel P. Stites, Abba I. Ten and Tristram G. Parslow (eds.), Appleton & Lange, Norwalk, Conn., 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("µ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, 4$^{th}$ ed. (W.B. Saunders Co., 2000).

The "variable region" or "variable domain" of an antibody, such as an anti-MS4A4A antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-MS4A4A antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-MS4A4A antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-MS4A4A antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10):1057-1062 (1995)); single-chain antibody molecules and multispecific antibodies formed from antibody fragments.

Papain digestion of antibodies, such as anti-MS4A4A antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-MS4A4A antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-MS4A4A antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-MS4A4A antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-MS4A4A antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-MS4A4A antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-MS4A4A antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-MS4A4A antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. Bio/Technology 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155: 1994-2004 (1995); Jackson et al. *J. Immunol.* 154(7):3310-9 (1995); and Hawkins et al, *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., MS4A4A or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a MS4A4A polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-MS4A4A antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-MS4A4A antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

I. Anti-MS4A4A Antibodies

Provided herein are anti-MS4A4A antibodies. Antibodies provided herein are useful, e.g., for the diagnosis or treatment of MS4A4A-associated disorders.

In one aspect, the present disclosure provides isolated (e.g., monoclonal) antibodies that bind to an epitope within a MS4A4A protein of the present disclosure. MS4A4A proteins of the present disclosure include, without limitation, a mammalian MS4A4A protein, human MS4A4A protein, mouse MS4A4A protein, and cyno MS4A4A protein. MS4A4A proteins of the present disclosure include naturally-occurring variants of MS4A4A.

Human MS4A4A is a 239-amino acid protein that encodes a membrane glycoprotein. The amino acid sequence of human MS4A4A is set forth in SEQ ID NO:1:

MHQTYSRHCRPEESTFSAAMTTMQGMEQAMPGAGPGVPQLGNMAVIHSHL

WKGLQEKFLKGEPKVLGVVQILTALMSLSMGITMMCMASNTYGSNPISVY

IGYTIWGSVMFIISGSLSIAAGIRTTKGLVRGSLGMNITSSVLAASGILI

NTFSLAFYSFHHPYCNYYGNSNNCHGTMSILMGLDGMVLLLSVLEFCIAV

SLSAFGCKVLCCTPGGVVLILPSHSHMAETASPTPLNEV

Additionally, the amino acid sequence of mouse MS4A4A is set forth in SEQ ID NO:2:

MLVIQGTEQSALEAGYGAQQNGQPLYVNSHSWKRMTEKFLKGEPKILGIV

QIVIAIMNLSIGIMMIIATVSTGEIPPSSVYIGYPIWGSLMFIISGSFSI

VAGRRTTKGLVRSSLGLNITSSVFAFSGIVISSLSPGIYSFHVYYCTYRG

SSEGCHMTLSILMGLDIVVVVLSVLEFCIGVSLSAFGCRVMCCNPGGVMI

IMPSNPTKAETANPVTLQSGLMPPEHQERNVPENMH

Additionally, the amino acid sequence of cynomolgus (cyno) MS4A4A is set forth in SEQ ID NO:3:

HQTYRRHCRPEESTFSAAMTTMQGMEQATPGAGPGVPQLGNMAVVHSHLW

KGLQEKFLKGEPKVLGVVQILIALMSLSMGITMMCVAFSAYGHYPISVYI

GYTIWGSVMFIISGSLSIAAGIRTTKGLVRGSLGMNITSSVLAVSAILIN

TISLTIYSFYHRYCNYYGNPNNCHGTVSILMGMDGMVLLLSVLEFCIAVS

LSAFGCKAICCTPGGVVLIIPSNSHMAEAAPLTPLNEV

Additionally, the amino acid sequence of human MS4A6A is set forth in SEQ ID NO:291:

MTSQPVPNETIIVLPSNVINFSQAEKPEPTNQGQDSLKKHLHAEIKVIGT

IQILCGMMVLSLGIILASASFSPNFTQVTSTLLNSAYPFIGPFFFIISGS

LSIATEKRLTKLLVHSSLVGSILSALSALVGFIILSVKQATLNPASLQCE

LDKNNIPTRSYVSYFYHDSLYTTDCYTAKASLAGTLSLMLICTLLEFCLA

VLTAVLRWKQAYSDFPGSVLFLPHSYIGNSGMSSKMTHDCGYEELLTS

In some embodiments, MS4A4A is expressed in a cell. In some embodiments, MS4A4A is expressed in myeloid cells. In some embodiments, MS4A4A is expressed in brain cells. In some embodiments, MS4A4A is expressed in astrocytes, including without limitation mature astrocytes. In some embodiments, MS4A4A is expressed in oligodendrocytes. In some embodiments, MS4A4A is expressed in microglial cells. In some embodiments, MS4A4A is expressed in immune cells, including without limitation, macrophages, eosinophils, mast cells, dendritic cells, natural killer cells, neutrophils, and T cells. In some embodiment, MS4A4A is expressed in olfactory cells. In some embodiments, MS4A4A is expressed on the cell surface.

MS4A4A proteins of the present disclosure include several domains, including without limitation, a cytoplasmic domain (amino acid residues 1-64 of human MS4A4A; see SEQ ID NO:1); a transmembrane domain (amino acid residues 65-85 of human MS4A4A); an extracellular domain (extracellular domain 1; ECL1), corresponding to amino acid residues 86-98 of human MS4A4A; a transmembrane domain (amino acid residues 99-119 of human MS4A4A); a cytoplasmic domain (amino acid residues 120-137 of human MS4A4A); a transmembrane domain (amino acid residues 138-158 of human MS4A4A); an extracellular domain (extracellular domain 2; ECL2), corresponding to amino acid residues 159-179; a transmembrane domain (amino acid residues 180-200 of human MS4A4A); and a cytoplasmic domain (amino acid residues 201-239 of human MS4A4A). Additionally, MS4A4A proteins of the present disclosure are expressed in a number of tissues and cells, including without limitation, the brain, neurons, glial cells, endothelial cells, perivascular cells, pericytes, etc.

MS4A4A Binding Partners and Adaptor Molecules

Further provided herein are methods of screening for anti-MS4A4A antibodies that bind MS4A4A, and that block the interactions between MS4A4A and one or more MS4A4A ligands or binding partners. In some embodiments, a peptide library can be synthesized in which a MS4A4A protein is dissected into consecutive 15-mer and 25-mer peptides separated by one amino acid residue and subsequently spotted onto filters. Binding of a MS4A4A ligand or binding partner can then then tested for its ability to interact with the MS4A4A peptide or with peptides in the presence or absence of anti-MS4A4A antibodies by SPOT binding analysis (e.g., Frank, R and Overwin, H (1996) Methods. Mol. Biol. 66, 149-169; Reineke, U et al., (2002) J. Immunol. Methods 267, 13-26; and Andersen, O S et al., (2010) J, BIOLOGICAL CHEMISTRY 285, 12210-12222). In some embodiments, a cellulose support can be prepared as an N-modified cellulose-aminohydroxylpropyl ether membrane, and all rounds of synthesis are started with spot definition by 9-fluorenylmethoxycar-bonyalanine-pentafluoophenyl ester that creates an alanine linker between peptide and membrane. For example, an automated linear synthesis of stepwise addition of the different amino acids protected at their N-terminal by 9-fluorenyl-methoxycarbo-nyl and appropriate side-chain protection for the growing peptide chain. In some embodiments, the pattern of de-protection, activation, and coupling is continued until 16-mer peptides are produced, resulting in an equally distributed array of covalently anchored peptides to the cellulose support at their C-terminal ends with N-terminal free ends (Scharn, D et al., (2000) J. Comb. Chem. 2, 361-369). In some embodiments, removal of the side protection group can be performed in two steps. First, the membrane can be treated with 90% trifluoroacetic acid (in dichlormethane, containing 3% triisobutylsilane and 2% H2O); and secondly with, for example, 60% trifluoroacetic acid (in dichlormethane, containing 3% triisobutylsilane and 2% H2O). To remove trifluoroacetic acid salts, the membrane can be washed several times with $H_2O$, ethanol, Tris-buffered saline, and ethanol, and then dried. Finally, the membrane is blocked in blocking buffer dilated in Tris-buffered saline (pH 8.0) and supplemented with 5% sac-charose for 2 h before the predefined peptide library is ready for ligand binding analysis. In some embodiments, for binding studies of cellulose-bound peptides, membrane-bound librariescan be incubated with combined S-peptide and polyhistidine-tagged ligands in the presence or absence of anti-MS4A4A antibodies, for example, in blocking buffer overnight at 4° C., followed by a second incubation with 1 mg/ml of HRP-conjugated S-protein also in blocking buffer but for 3 h at room temperature. Subsequently, the membrane can be washed, for example, three times for 10 min with Tris-buffered saline before quantitative characterization of bound ligand may be carried out using the UptiLight chemiluminescence substrate and a LumiImager instrument, providing the spot signal intensities in Boehringer light units. Alternatively, detection of bound ligand can be performed by an immunochemical assay with an antibody against a histidine tag from and a secondary HRP-conjugated anti-mouse antibody. Incubations can be performed utilizing standard Western blotting procedures and spot detection.

Further provided herein are methods of screening for anti-MS4A4A antibodies that block interactions (e.g., binding) MS4A4A and one or more MS4A4A ligands or binding partners.

In some embodiments, the interaction between MS4A4A and MS4A4A ligands or binding partners may be characterized using surface Plasmon resonance analysis (e.g., Skeldal et al., 2012 J Biol Chem., 287:43798; and Andersen et al., 201, J Biol Chem, 285, 12210-12222). Determination of direct binding of MS4A4A ligand or binding partner to immobilized MS4A4A in the presence or absence of blocking anti-MS4A4A antibodies can be performed, for example, on a Biacore2000 instrument (Biacore, Sweden) using CaHBS as standard running buffer (10 mM HEPES, pH 7.4, 140 mM NaCl, 2 mM $CaCl_2$, 1 mM EGTA, and 0.005% Tween 20). In some embodiments, a biosensor chip from Biacore (CM5) can be activated using the NHS/EDC method followed by coating with MS4A4A to a protein density of 79 $fmol/mm^2$ and used for affinity measurements of the binding partner. Preparation of a biosensor surface with pro-MS4A4A will follow an equal procedure. Regeneration of the flow cell after each cycle of ligand binding experiment can be done by two 10-µl pulses of regeneration buffer (10 mM glycine-HCl, pH 4.0, 500 mM NaCl, 20 mM EDTA, and 0.005% Tween 20) and a single injection of 0.001% SDS. Fitting of sensorgrams for affinity estimations can be done, for example, by using BIAevaluation version 3.1. Following similar protocols, immobilization of HisS-NGFpro or HisS-BDNFpro may also done on a CM5 biosensor chip using the NHS/EDC coupling kit, giving similar surface densities of immobilized protein (~300 fmol/$mm^2$). A biosensor chip with immobilized with a MS4A4A ligand or binding partner can also be used to examine the binding of MS4A4A in the absence or presence of competing MS4A4A antibodies.

In some embodiments, the interaction between MS4A4A and MS4A4A ligands and binding partners can be characterized using a pulldown assay (e.g., Andersen et al., 2010, J Biol Chem, 285, 12210-12222). For example, expressed intracellular or extracellular domains of MS4A4A can be incubated with tagged MS4A4A ligands or binding partners in the absence or presence of MS4A4A blocking antibodies and are precipitated using 100 µl of glutathione (GSH)-Sepharose beads (Amersham Biosciences, catalog no. 17-0756-01). The amount of applied receptor domains can be determined by precipitation using Talon beads as control. Bound proteins can be separated by SDS-PAGE analysis and visualized using anti-histidine antibody by standard Western blotting analysis.

In some embodiments, the interaction between MS4A4A and MS4A4A ligands and binding partners may be characterized using cellulose-bound proteins (e.g., Andersen et al., 2010, J Biol Chem, 285, 12210-12222). For example, membrane-bound proteins can be incubated with another MS4A4A ligand or binding partner; in blocking buffer overnight at 4° C., followed by a second incubation with 1 µg/ml of HRP-conjugated S-protein also in blocking buffer but for 3 hours at room temperature. Subsequently, the membrane may be washed three times for 10 minutes with Tris-buffered saline before quantitative characterization of bound ligand is carried out using the UptiLight chemiluminescence substrate and a LumiImager instrument, providing the spot signal intensities in Boehringer light units. Alternatively, detection of bound ligand can be performed by an immunochemical assay with an antibody against the histidine tag and a secondary HRP-conjugated anti-mouse antibody. Incubations can be followed by standard Western blotting analysis and spot detection.

In some embodiments, the interaction between MS4A4A and MS4A4A ligands and binding partners may be characterized using a proximity ligation assay (e.g., Gustafsen et al., 2013 The Journal of Neuroscience, 33:64-71). For example, proximity ligation assay (PLA) (DuolinkII) on cells expressing or exposed to MS4A4A and its ligand or binding partner can be performed with the primary antibodies anti-MS4A4A, and antibodies against the binding partner, followed by incubation with secondary antibodies conjugated to oligonucleotides, which hybridize to subsequently added circle-forming oligonucleotides and prime a rolling circle amplification when the antigens are located within proximity of 40 nm. The amplified DNA can be visualized by addition of complementary fluorescent-labeled oligonucleotides.

In some embodiments, the interaction between MS4A4A and MS4A4A ligands and binding partners may be characterized using alkaline phosphatase-tagged ligands in cell binding assays (e.g., Hu et al., 2005, J. Neurosci. 25, 5298-5304; Fournier et al., 2001, Nature 409, 341-346; Lauren et al., 2009, Nature 457, 1128-1132; and Hu et al., 2010, Neuron 68, 654-667). For example, alkaline phosphatase (AP)-tagged ligands can be made to assess binding to MS4A4A on transfected cells or primary neurons. To detect AP tagged ligand binding to cells expressing MS4A4A, cultures can be washed with, for example, Hanks balanced salt solution containing 20 mM sodium HEPES, pH 7.05, and 1 mg/ml bovine serum albumin (BSA) (HBH). Then, the plates can be incubated with AP tagged ligands in the presence or absence of MS4A4A blocking antibodies, for example, in HBH for 2 h at 23° C. AP bound ligand can be detected and quantified according to methods well-known in the art.

In certain embodiments that may be combined with any of the preceding embodiments, the anti-MS4A4A antibody further inhibits interaction between MS4A4A and one or more of its ligands, signaling proteins or binding proteins by: a) reducing the effective levels of MS4A4A available for interacting with the one or more ligands or binding proteins; b) blocking one or more of the sites on MS4A4A required for interaction with the one or more ligands or binding proteins; c) preventing one or more posttranslational events on MS4A4A that are required for interaction with the one or more ligands or binding proteins and/or for correct processing and/or subcellular localization of MS4A4A; d) inducing degradation of MS4A4A; e) changing the conformation of MS4A4A, or any combination thereof. In certain embodiments that may be combined with any of the preceding embodiments, the anti-MS4A4A antibody binds specifically to human MS4A4A, mouse MS4A4A, cyno MS4A4A, or a combination thereof. In certain embodiments that may be combined with any of the preceding embodiments, the anti-MS4A4A antibody is a human antibody, a humanized antibody, a bispecific antibody, a monoclonal antibody, a multivalent antibody, a conjugated antibody, or a chimeric antibody. In certain embodiments that may be combined with any of the preceding embodiments, the anti-MS4A4A antibody is a bispecific antibody recognizing a first antigen and a second antigen. In certain embodiments that may be combined with any of the preceding embodiments, the first antigen is MS4A4A and the second antigen is an antigen facilitating transport across the blood-brain-barrier. In certain embodiments that may be combined with any of the preceding embodiments, the second antigen is selected from the group consisting of MS4A4A, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, and CD98hc, and ANG1005.

Signal transduction adaptor proteins are, without limitation, proteins that are accessory to other proteins associated with a signal transduction pathway. Adaptor proteins contain various protein-binding modules or motifs that link or protein-binding partners together and facilitate the creation of larger signaling complexes. Adaptor proteins often contain several domains within their structure that allow specific interactions with one or more other specific proteins. For example, Src homology 2 (SH2) domains recognize specific amino acid residue sequences within proteins containing phosphotyrosine residues. The interaction of adaptor proteins and other signaling proteins allows for a diversity of specific and coordinated protein-protein interactions to occur within a cell during and associated with signal transduction.

An immunoreceptor tyrosine-based activation motif (ITAM) is a conserved sequence of four amino acid residues that is repeated twice in the cytoplasmic tails of certain cell surface proteins of the immune system. The consensus motif is YxxI/Lx$_{(6-12)}$YxxI/L (SEQ ID NO: 355) in the C-terminus of certain proteins. The two repeats are typically separated by between 6 and 12 amino acid residues (YxxL/Ix$_{(6-12)}$YxxL/I (SEQ ID NO: 355)). ITAMs are important for signal transduction; the tyrosine residues within these motifs are phosphorylated following interaction of receptor molecules with their ligands and form docking sites for other proteins involved in signal transduction (Barrow and Trowsdale, 2006, Eur J Immunol, 36:1646-1653).

An immunoreceptor tyrosine-based inhibition motif (ITIM) is a conserved sequence of amino acids (S/I/V/LxYxxI/V/L (SEQ ID NO: 352)) that is found in the cytoplasmic tails of certain inhibitory receptors of the immune system. After ITIM-containing inhibitory receptors interact with their ligand, their ITIM motif becomes phosphorylated by enzymes of the Src kinase family, allowing them to recruit other enzymes (such as various phosphotyrosine phosphatases), which decrease the activation of molecules involved in signal transduction. (Barrow and Trowsdale, 2006, Eur J Immunol, 36:1646-1653).

Alternatively, some receptors have no intrinsic ITAM motif, but instead encode positively charged transmembrane amino acids, such as lysine or arginine. These positively charged amino acid residues mediate association with corresponding negatively charged transmembrane amino acid residues of ITAM-encoding adaptor proteins. Upon ligand recognition and receptor clustering, tyrosine amino acid residues are phosphorylated by Src family protein tyrosine kinase (PTK). Dual-phosphorylated ITAM motifs serve as docking sites for the tandem SH2 domains of Syk family PTK, such as ZAP-70 or Syk. Syk family PTK phosphorylate a series of intracellular substrates, leading to the formation of membrane-proximal scaffolds, resulting to recruitment of important effector molecules, such as phospholipase C-c (PLCc), leading to calcium signaling, as well as Ras activation, which results in stimulation of the ERK pathway and cellular activation.

Studies support the importance of MS4A proteins in forming signaling complexes with other cell surface membrane proteins that modulate or propagate downstream biochemical signals. Although binding partners have, in most instances, yet to be clearly determined for MS4A proteins other than MS4A1 and MS4A2, predictive protein analyses show that Src homology 2(SH2) and SH3 domain-binding sites are commonly found on the N- and C-terminal regions of MS4A proteins, which may serve as docking platforms for other signaling molecules (Dinkel et al, 2012, Nucl Acids Res, 40:DD242-D251) SH domains bind preferentially to proline-rich sequences, which are also commonly found in the cytoplasmic tails of MS4A proteins (Liang and Tedder, 2001, Genomics, 72:119-127; Kay et al, 2000, FASEB J, 14:231-241). This feature of MS4A proteins provides a strong basis for their being intimately involved in protein-protein interactions and may also associated with one another to form signaling complexes.

Accordingly, in some embodiments, an anti-MS4A4A antibody of the present disclosure enhances or increases the formation of signaling complexes. In some embodiments, an anti-MS4A4A antibody of the present disclosure enhances or increases the formation of signaling complexes associated with ITAM-encoding adaptor proteins. In some embodiments, an anti-MS4A4A antibody of the present disclosure enhances or increases the formation of inhibitory signaling complexes. In some embodiments, an anti-MS4A4A antibody of the present disclosure enhances or increases the formation of inhibitory signaling complexes associated with ITIM-encoding adaptor proteins.

In some embodiments, an anti-MS4A4A antibody of the present disclosure inhibits (e.g., blocks) or reduces the formation of signaling complexes. In some embodiments, an anti-MS4A4A antibody of the present disclosure inhibits (e.g., blocks) or reduces the formation of signaling complexes associated with ITAM-encoding adaptor proteins. In some embodiments, an anti-MS4A4A antibody of the present disclosure inhibits (e.g., blocks) or reduces the formation of inhibitory signaling complexes. In some embodiments, an anti-MS4A4A antibody of the present disclosure inhibits (e.g., blocks) or reduces the formation of inhibitory signaling complexes associated with ITIM-encoding adaptor proteins.

In some embodiments that may be combined with any of the preceding embodiments, an anti-MS4A4A antibody of the present disclosure inhibits (e.g., blocks) or reduces formation of MS4A4A homo-oligomeric cell surface protein complexes by: a) reducing the effective levels of MS4A4A available for MS4A4A homo-oligomeric complex formation; b) blocking one or more of the sites on MS4A4A required for MS4A4A homo-oligomeric complex formation; c) preventing one or more posttranslational events on MS4A4A that are required for MS4A4A homo-oligomeric complex formation and/or for correct processing and/or cellular localization of MS4A4A; d) inducing degradation of MS4A4A; e) changing the conformation of MS4A4A, or any combination thereof.

In some embodiments that may be combined with any of the preceding embodiments, an anti-MS4A4A antibody of the present disclosure increases or enhances formation of MS4A4A homo-oligomeric cell surface protein complexes by: a) increasing the effective levels of MS4A4A available for MS4A4A homo-oligomeric complex formation; b) stabilizing one or more of the sites on MS4A4A required for MS4A4A homo-oligomeric complex formation; c) maintaining cell surface expression of MS4A4A to allow for homo-oligomeric complex formation and/or for correct processing and/or maintaining correct cellular localization of MS4A4A; d) reducing degradation of MS4A4A; e) changing the conformation of MS4A4A, or any combination thereof.

In some embodiments that may be combined with any of the preceding embodiments, an anti-MS4A4A antibody of the present disclosure inhibits (e.g., blocks) or reduces MS4A4A hetero-oligomeric cell surface protein complex formation with one or more signal transduction adaptor proteins by: a) reducing the effective levels of MS4A4A available for MS4A4A hetero-oligomeric complex formation; b); blocking one or more of the sites on MS4A4A required for MS4A4A hetero-oligomeric complex formation; c) preventing one or more posttranslational events on MS4A4A that are required for MS4A4A hetero-oligomeric complex formation and/or for correct processing and/or cellular localization of MS4A4A; d) inducing degradation of MS4A4A; e) changing the conformation of MS4A4A, or any combination thereof.

In some embodiments that may be combined with any of the preceding embodiments, an anti-MS4A4A antibody of the present disclosure increases or enhances MS4A4A hetero-oligomeric cell surface protein complex formation with one or more signal transduction adaptor proteins by: a) increasing the effective levels of MS4A4A available for MS4A4A hetero-oligomeric complex formation; b) stabilizing one or more of the sites on MS4A4A required for MS4A4A hetero-oligomeric complex formation; c) maintaining cell surface expression of MS4A4A to allow for MS4A4A hetero-oligomeric complex formation and/or for correct processing and/or maintaining correct cellular localization of MS4A4A; d) reducing degradation of MS4A4A; e) changing the conformation of MS4A4A, or any combination thereof.

In some embodiments that may be combined with any of the preceding embodiments, an anti-MS4A4A antibody of the present disclosure increases or enhances MS4A4A receptor clustering. In some embodiments that may be combined with any of the preceding embodiments, an anti-MS4A4A antibody of the present disclosure inhibits or reduces MS4A4A receptor clustering. In some embodiments, the increase or enhancement of, or the inhibition or reduction of, MS4A4A receptor clustering is in a myeloid cell.

MS4A4A in Macrophage and Microglial Cell Function

Macrophages and myeloid cells of the central nervous system (CNS) are inherently plastic in their phenotype and function. Macrophages in vitro can be divided into M1 macrophages and M2 macrophages, which have differing phagocytic and inflammatory potentials, phenotypes, and activities. For example, in peripheral organs, macrophages having an M1 phenotype are considered to have pro-inflammatory and anti-microbial phenotype and function, while macrophages having an M2 phenotype are considered to be in a more homeostatic state, having an anti-inflammatory phenotype and function.

Microglia associated with healthy, homeostatic conditions express more M2 markers on their cell surface (e.g., CD200R, CD163 and CD115) compared to that of M1 markers (e.g., CD16, MHC Class II, CD86) (Ginhoux and Prinz, 2015, Cold Spring Harb Perspect Biol, 7:a020537). However, disease associated microglia (DAM) in both mouse models of Alzheimer's disease and in human Alzheimer's disease are in a proinflammatory or activated state. Disease associated microglia in proinflammatory or activated states are considered beneficial by playing an active role in reducing the pathology associated with Alzheimer's disease and other neurodegenerative disorders.

MS4A4A expression is elevated in M2 macrophages in vitro, and it has been suggested that MS4A4A is a novel cell surface marker for M2 macrophages. Additionally, MS4A4A has also been shown to regulate cell surface transport of cKit on mast cells, suggesting a role of MS4A4A in modulating mast cell degranulation and survival (Cruse et al, 2015, Molecular Biol Cell, 26:1711-1727). Taken together, these reported findings suggest that targeting MS4A4A may affect the recycling, expression, and/or degradation of various macrophage cell surface receptors associated with M1 and M2 macrophage phenotypes, thus affecting their functions and activities.

As described herein, anti-MS4A4A antibodies of the present disclosure affected the expression of M2 macrophage cell surface markers. In particular, anti-MS4A4A antibodies of the present disclosure reduced the cell surface expression of CD200R, Dectin-1, and CD163 in macrophages, suggesting that anti-MS4A4A antibodies modulate macrophage polarization, function, and/or activity by reducing expression of M2 macrophage cell surface receptors. Anti-MS4A4A antibodies of the present disclosure reduced M2 macrophage cell surface receptors, suggesting that anti-MS4A4A antibodies of the present disclosure are effective at altering the physiological state of microglial cells to that of a more protective phenotype, such as to a more proinflammatory or activated state. Accordingly, anti-MS4A4A antibodies of the present disclosure are useful in treating Alzheimer's disease and other neurodegenerative disorders, in part, by altering the phenotype of macrophages and microglia to a proinflammatory and activated state.

MS4A4A and TREM2 Expression

Neurodegenerative diseases are characterized, in part, by defective immune function in the central nervous system (CNS). For example, a decrease in viability and function in the CNS myeloid cell compartment, including but not restricted to microglia, is thought to contribute to susceptibility to neurodegenerative disorders, such as Alzheimer's disease. Pharmacological intervention that enhances viability and/or function of myeloid cells would provide effective treatment to ameliorate the onset, severity, or progression of such neurodegenerative diseases and disorders.

Triggering receptor expressed on myeloid cells-2 (TREM2) is an immunoglobulin-like receptor that is expressed primarily on myeloid cells, such as macrophages, dendritic cells, monocytes, Langerhans cells of skin, Kupffer cells, osteoclasts, and microglia. TREM2 is highly expressed on microglia and infiltrating macrophages in the CNS during experimental autoimmune encephalomyelitis and Alzheimer's disease (Piccio et al, 2007, Eur J Immunol, 37:1290-1301; Wang, 2015, Cell, 160:1061-1071). The TREM2 pathway is considered a key modulator of CNS myeloid cell viability and function.

Data from human genetics studies have suggested strong genetic links between MS4A4A and TREM2 and with susceptibility to Alzheimer's disease (Piccio et al., 2016, Acta Neuropathol, 131:925-9330). In particular, MS4A4A alleles protective for Alzheimer's disease are linked to increased sTREM2 levels in the cerebrospinal fluid in patients.

As described herein, anti-MS4A4A antibodies of the present disclosure increased cellular ATP levels in macrophages, indicating that anti-MA4A4A antibodies are effective at increasing, maintaining, or enhancing cell (e.g., macrophages, myeloid cells) viability and function. Additionally, anti-MS4A4A antibodies of the present disclosure increased sTREM2 and mTREM2 levels in macrophages, in contrast to that previously reported in which commercially-available anti-MS4A4A antibody 5C12 reduced sTREM2 levels in supernatants of cultured human macrophages (Deming et al, 2018, bioRxiv, doi: dx doi org/10.1101/352179). As increased MS4A4A protective alleles for Alzheimer's disease are linked to increased sTREM2 levels, the results provided herein indicated that anti-MS4A4A antibodies of the present disclosure mimic or replicate a protective phenotype in neurodegenerative diseases and disorders, such as Alzheimer's disease, by increasing sTREM2 and mTREM2 levels.

As described herein, anti-MS4A4A antibodies of the present disclosure increase sTREM2 levels, increase mTREM2 levels, or increase both sTREM2 and mTREM2 levels in myeloid cells. In some embodiments, the anti-MS4A4A antibody increases soluble TREM2 levels by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by at least 100% compared to a control antibody of the same isotype. In some embodiments, the anti-MS4A4A antibody increases plasma-membrane or cell surface TREM2 levels by at least 65%, by at least 70%, by at least 75%, by at least 80%, by at least 85%, by at least 90%, by at least 95%, by at least 100%, by at least 105%, by at least 110%, by at least 115%, by at least 120%, by at least 125%, by at least 130%, by at least 135%, by at least 140%, by at least 145%, or by at least 150% compared to a control antibody of the same isotype. TREM2 levels in myeloid cells can be measured by any assay known to one of skill in the art. For example, Example 41 of the present disclosure describes assays for measuring the modulation of soluble and plasma-membrane or cell surface TREM2 in human primary macrophages when treated with purified anti-MS4A4A antibodies. An exemplary method of generating purified antibodies free of endotoxins or with low levels of endotoxins is described in Example 41 herein. After incubating the macrophages with the purified anti-MS4A4A antibody, supernatants are collected and sTREM2 levels determined using a Meso Scale Discovery (MSD) assay. Alternatively, macrophages are collected after incubation and subjected to flow cytometry to determine mTREM2 levels using an anti-TREM2 antibody conjugated to allophycocyanin or similar fluorophores.

Agonist Antibodies

Anti-MS4A4A antibodies of the present disclosure generally bind to one or more MS4A4A proteins expressed in a cell. One class of antibodies is agonist antibodies. For example, the MS4A4A receptor may require clustering on the cell surface in order to transduce a signal. Thus agonist antibodies may have unique features to stimulate, for example, the MS4A4A receptor. For example, they may have the correct epitope specificity that is compatible with receptor activation, as well as the ability to induce or retain receptor clustering on the cell surface.

In vivo, antibodies may cluster receptors by multiple potential mechanisms. Some isotypes of human antibodies such as IgG2 have, due to their unique structure, an intrinsic ability to cluster receptors, or retain receptors in a clustered configuration, thereby activating receptors such as MS4A4A without binding to an Fc receptor (e.g., White et al., (2015) Cancer Cell 27, 138-148).

Other antibodies cluster receptors (e.g., MS4A4A) by binding to Fcg receptors on adjacent cells. Binding of the constant IgG Fc part of the antibody to Fcg receptors leads to aggregation of the antibodies, and the antibodies in turn aggregate the receptors to which they bind through their variable region (Chu et al (2008) Mol Immunol, 45:3926-3933; and Wilson et al., (2011) Cancer Cell 19, 101-113). Binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is often a preferred way to cluster antibodies in vivo, since binding to FcgRIIB is not associated with immune adverse effects.

Other mechanisms may also be used to cluster receptors (e.g., MS4A4A). For example, antibody fragments (e.g., Fab fragments) that are cross-linked together may be used to cluster receptors (e.g., MS4A4A) in a manner similar to antibodies with Fc regions that bind Fcg receptors, as described above. Without wishing to be bound to theory, it is thought that cross-linked antibody fragments (e.g., Fab fragments) may function as agonist antibodies if they induce receptor clustering on the cell surface and bind an appropriate epitope on the target (e.g., MS4A4A).

Therefore, in some embodiments, antibodies that bind a MS4A4A protein may include agonist antibodies that due to their epitope specificity bind MS4A4A and activate one or more MS4A4A activities. Without wishing to be bound to theory, such antibodies may bind to the ligand-binding site on the target antigen (e.g., MS4A4A) and mimic the action of a natural ligand, or stimulate the target antigen to transduce signal by binding to one or more domains that are not the ligand-binding sites. Such antibodies would not interfere with ligand binding and may act additively or synergistically with the natural ligands.

In some embodiments, an anti-MS4A4A antibody of the present disclosure is an agonist antibody that induces or increases one or more MS4A4A activities. In some embodiments the anti-MS4A4A antibody induces or increases one or more activities of MS4A4A protein that is expressed in a cell. In some embodiments, an anti-MS4A4A antibody of the present disclosure is an antagonist antibody that reduces or inhibits one of more MS4A4A activities. In some embodiments the anti-MS4A4A antibody reduces or inhibits one or more activities of MS4A4A protein that is expressed in a cell.

Inert Antibodies

Another class of antibodies of the present disclosure includes inert antibodies. As used herein, "inert" antibodies refer to antibodies that specifically bind their target antigen but do not modulate (e.g., decrease/inhibit or activate/induce) antigen function. For example, in the case of MS4A4A, inert antibodies do not modulate ligand binding and/or MS4A4A activities. Without wishing to be bound to theory, it is thought that antibodies that do not have the ability to cluster MS4A4A on the cell surface may be inert antibodies even if they have an epitope specificity that is compatible with receptor activation.

In some embodiments, antibodies that bind a MS4A4A protein may include antibodies that bind MS4A4A but, due to their epitope specificity, do not modulate protein function. Such functionally inert antibodies can be used as cargo to transport toxins as described for the CD33 antibody Gemtuzumab zogamicin, (marketed as Mylotarg) which is conjugated to the cytotoxic agent from the class of calicheamicins and is used to target and kill acute myelogenous leukemia tumors (Naito et al., (2000), Leukemia, 14, 1436-1443; Ricart (2011) Clin Cancer Res 17; 6417-6436; Hamann et al., (2002) Journal: Bioconjugate Chemistry, 13, 47-58; and Beitz et al., (2001) Clin Cancer Res 7; 1490-6.). Therefore, in some embodiments, antibodies of the present disclosure are inert antibodies that bind MS4A4A but are incapable of inducing one or more MS4A4A activities (e.g., a MS4A4A activity described herein).

Antagonist Antibodies

A third class of antibodies of the present disclosure includes antagonist antibodies. In some embodiments, antibodies that bind a MS4A4A protein may include antagonist antibodies that bind MS4A4A inhibit one or more MS4A4A activities, either by preventing interaction between MS4A4A and its ligand(s), or by preventing the transduction of signal of MS4A4A into the cell cytoplasm in the presence of ligand. In some embodiments, antagonist antibodies of the present disclosure may have the epitope specificity of an agonist antibody of the present disclosure, but have an Fc domain that is not capable of binding Fcg receptors and thus is unable to, for example, cluster MS4A4A receptor.

In some embodiments, an antibody of the present disclosure is an antagonist antibody. In some embodiments, the antagonist antibody inhibits one or more MS4A4A activities. In some embodiments, the antagonist antibody decreases activity of one or more MS4A4A-dependent genes. In some embodiments, the antagonist antibody inhibits interaction between MS4A4A and one or more MS4A4A ligands. In some embodiments, the antagonist antibody inhibits MS4A4A signal transduction. In some embodiments, the antagonist antibody inhibits interaction between MS4A4A and one or more MS4A4A ligands and inhibits MS4A4A signal transduction.

In some embodiments, antibody cross-linking is required for agonist antibody function. Antibody cross-linking can occur through binding to a secondary antibody in vitro or through binding to Fc receptors in vivo. For example, antagonistic antibodies can be converted to agonistic antibodies via biotin/streptavidin cross-linking or secondary antibody binding in vitro (see for example Gravestein et al., 1996, J. Exp. Med. 184:675-685; Gravestein et al., 1994, International Immunol, 7:551-557). Agonistic antibodies may exert their activity by mimicking the biological activity of the receptor ligand or by enhancing receptor aggregation, thereby activating receptor signaling. In some embodiments, the absence of antibody cross-linking is required for antagonistic activity. Antagonistic antibodies may exert their activity by blocking receptor-ligand interactions.

Calcium Influx

Cell lines transfected with MS4A1 showed an increased calcium conductance across the plasma membrane, suggesting that MS4A1 functions as an important channel for regulating calcium homeostasis. (Parolini et al, 2012, Int J Biochem Cell Biol, 44:2095-2105; Li et al, 2003, J Biol Chem, 278:42427-42434) MS4A proteins are thus involved in the control of intracellular free calcium concentration by regulating (e.g., increasing) calcium influx and/or by mobilizing calcium from intracellular stores (Ishibashi et al, 2001, Gene, 264:87-93). Due to the conservation in protein structure within the MS4A family, other MS4A proteins (e.g., MS4A4A and MS4A6A) may share overlapping calcium regulatory functions (Ma et al, 2015, Mol Neurobiol, 51:1240-1248). Accordingly, in some embodiments, an anti-MS4A4A antibody of the present disclosure modulates calcium levels in a cell, calcium influx, and/or calcium mobilization from intracellular stores. In some embodiments, an anti-MS44A antibody of the present disclosure increases calcium influx in a cell and/or increases calcium mobilization in a cell from intracellular stores. In some embodiments, an anti-MS4A4A antibody of the present disclosure reduces calcium influx in a cell and/or reduces calcium mobilization in a cell from intracellular stores.

Additionally, members of the MS4A protein family are chemoreceptors expressed within necklace olfactory sensory neurons. Results support a model in which MS4A receptors bind inhaled odorants and induce calcium influx into necklace olfactory sensory neurons, supporting a role of MS4A family members in regulating calcium influx in various cells (Greer et al, 2016, Cell, 165:1734-1748).

A. Exemplary Antibodies and Certain Other Antibody Embodiments

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs:4, 5, 6, 7, 8, 9, 10, 11, 12, 13, 14, 15, 16, 17, 18, and 19, or an amino acid with at least about 95% homology to an amino acid selected from the group consisting of SEQ ID NOs:4, 5, 6, 7, 8, 9, 10, 11, 12, 13, 14, 15, 16, 17, 18, and 19; (b) HVR-H2 comprising an amino acid sequence selected from the group consisting of SEQ ID NOs:20, 21, 22, 23, 24, 25, 26, 27, 28, 29, 30, 31, 32, 33, 34, 35, 36, and 37, or an amino acid with at least about 95% homology to an amino acid selected from the group consisting of SEQ ID NOs:20, 21, 22, 23, 24, 25, 26, 27, 28, 29, 30, 31, 32, 33, 34, 35, 36, and 37; (c) HVR-H3 comprising an amino acid sequence selected from the group consisting of SEQ ID NOs:38, 39, 40, 41, 42, 43, 44, 45, 46, 47, 48, 49, 50, 51, 52, 53, 54, and 55, or an amino acid with at least about 95% homology to an amino acid selected from the group consisting of SEQ ID NOs:38, 39, 40, 41, 42, 43, 44, 45, 46, 47, 48, 49, 50, 51, 52, 53, 54, and 55; (d) HVR-L1 comprising an amino acid sequence selected from the group consisting of SEQ ID NOs:56, 57, 58, 59, 60, 61, 62, 63, 64, 65, 66, 67, 68, 69, 70, 71, 72, 73, and 74, or an amino acid with at least about 95% homology to an amino acid selected from the group consisting of SEQ ID NOs:56, 57, 58, 59, 60, 61, 62, 63, 64, 65, 66, 67, 68, 69, 70, 71, 72, 73, and 74; (e) HVR-L2 comprising an amino acid sequence selected from the group consisting of SEQ ID NOs:75, 76, 77, 78, 79, 80, 81, 82, 83, 84, and 85, or an amino acid with at least about 95% homology to an amino acid selected from the group consisting of SEQ ID NOs:75, 76, 77, 78, 79, 80, 81, 82, 83, 84, and 85; and (f) HVR-L3 comprising an amino acid sequence selected from the group consisting of SEQ ID NOs:86, 87, 88, 89, 90, 91, 92, 93, 94, 95, 96, 97, 98, 99, and 100, or an amino acid with at least about 95% homology to an amino acid selected from the group consisting of SEQ ID NOs:86, 87, 88, 89, 90, 91, 92, 93, 94, 95, 96, 97, 98, 99, and 100.

In some embodiments, provided herein are anti-MS4A4A antibodies comprising at least one, two, three, four, five, or six HVRs selected from: (a) HVR-H1 comprising the amino acid sequence of SEQ ID NO:4; (b) HVR-H2 comprising the amino acid sequence of SEQ ID NO:20; (c) HVR-H3 comprising the amino acid sequence of SEQ ID NO:38; (d) HVR-L1 comprising the amino acid sequence of SEQ ID NO:56; (e) HVR-L2 comprising the amino acid sequence of SEQ ID NO:75; and (f) HVR-L3 comprising the amino acid sequence of SEQ ID NO:86; (a) HVR-H1 comprising the amino acid sequence of SEQ ID NO:5; (b) HVR-H2 comprising the amino acid sequence of SEQ ID NO:21; (c) HVR-H3 comprising the amino acid sequence of SEQ ID NO:39; (d) HVR-L1 comprising the amino acid sequence of SEQ ID NO:57; (e) HVR-L2 comprising the amino acid sequence of SEQ ID NO:76; and (f) HVR-L3 comprising the amino acid sequence of SEQ ID NO:87; (a) HVR-H1 comprising the amino acid sequence of SEQ ID NO:6; (b) HVR-H2 comprising the amino acid sequence of SEQ ID NO:22; (c) HVR-H3 comprising the amino acid sequence of SEQ ID NO:40; (d) HVR-L1 comprising the amino acid sequence of SEQ ID NO:58; (e) HVR-L2 comprising the amino acid sequence of SEQ ID NO:76; and (f) HVR-L3 comprising the amino acid sequence of SEQ ID NO:88; (a) HVR-H1 comprising the amino acid sequence of SEQ ID NO:7; (b) HVR-H2 comprising the amino acid sequence of SEQ ID NO:23; (c) HVR-H3 comprising the amino acid sequence of SEQ ID NO:41; (d) HVR-L1 comprising the amino acid sequence of SEQ ID NO:59; (e) HVR-L2 comprising the amino acid sequence of SEQ ID NO:77; and (f) HVR-L3 comprising the amino acid sequence of SEQ ID NO:89; (a) HVR-H1 comprising the amino acid sequence of SEQ ID NO:8; (b) HVR-H2 comprising the amino acid sequence of SEQ ID NO:24; (c) HVR-H3 comprising the amino acid sequence of SEQ ID NO:42; (d) HVR-L1 comprising the amino acid sequence of SEQ ID NO:60; (e) HVR-L2 comprising the amino acid sequence of SEQ ID NO:78; and (f) HVR-L3 comprising the amino acid sequence of SEQ ID NO:90; (a) HVR-H1 comprising the amino acid sequence of SEQ ID NO:9; (b) HVR-H2 comprising the amino acid sequence of SEQ ID NO:25; (c) HVR-H3 comprising the amino acid sequence of SEQ ID NO:43; (d) HVR-L1 comprising the amino acid sequence of SEQ ID NO:61; (e) HVR-L2 comprising the amino acid sequence of SEQ ID NO:76; and (f) HVR-L3 comprising the amino acid sequence of SEQ ID NO:91; (a) HVR-H1 comprising the amino acid sequence of SEQ ID NO:10; (b) HVR-H2 comprising the amino acid sequence of SEQ ID NO:26; (c) HVR-H3 comprising the amino acid sequence of SEQ ID NO:44; (d) HVR-L1 comprising the amino acid sequence of SEQ ID NO:62; (e) HVR-L2 comprising the amino acid sequence of SEQ ID NO:79; and (f) HVR-L3 comprising the amino acid sequence of SEQ ID NO:92; (a) HVR-H1 comprising the amino acid sequence of SEQ ID NO:7; (b) HVR-H2 comprising the amino acid sequence of SEQ ID NO:27; (c) HVR-H3 comprising the amino acid sequence of SEQ ID NO:45; (d) HVR-L1 comprising the amino acid sequence of SEQ ID NO:63; (e) HVR-L2 comprising the amino acid sequence of SEQ ID NO:77; and (f) HVR-L3 comprising the amino acid sequence of SEQ ID NO:89; (a) HVR-H1 comprising the amino acid sequence of SEQ ID NO:7; (b) HVR-H2 comprising the amino acid sequence of SEQ ID NO:28; (c) HVR-H3 comprising the amino acid sequence of SEQ ID NO:46; (d) HVR-L1 comprising the amino acid sequence of SEQ ID NO:64; (e) HVR-L2 comprising the amino acid sequence of SEQ ID NO:77; and (f) HVR-L3 comprising the amino acid sequence of SEQ ID NO:89; (a) HVR-H1 comprising the amino acid sequence of SEQ ID NO:11; (b) HVR-H2 comprising the amino acid sequence of SEQ ID NO:29; (c) HVR-H3 comprising the amino acid sequence of SEQ ID NO:47; (d) HVR-L1 comprising the amino acid sequence of SEQ ID NO:65; (e) HVR-L2 comprising the amino acid sequence of SEQ ID NO:80; and (f) HVR-L3 comprising the amino acid sequence of SEQ ID NO:93; (a) HVR-H1 comprising the amino acid sequence of SEQ ID NO:7; (b) HVR-H2 comprising the amino acid sequence of SEQ ID NO:27; (c) HVR-H3 comprising the amino acid sequence of SEQ ID NO:45; (d) HVR-L1 comprising the amino acid sequence of SEQ ID NO:63; (e) HVR-L2 comprising the amino acid sequence of SEQ ID NO:77; and (f) HVR-L3 comprising the amino acid sequence of SEQ ID NO:89; (a) HVR-H1 comprising the amino acid sequence of SEQ ID NO:12; (b) HVR-H2 comprising the amino acid sequence of SEQ ID NO:27; (c) HVR-H3 comprising the amino acid sequence of SEQ ID NO:45; (d) HVR-L1 comprising the amino acid sequence of SEQ ID NO:66; (e) HVR-L2 comprising the amino acid sequence of SEQ ID NO:77; and (f) HVR-L3 comprising the amino acid sequence of SEQ ID NO:89; (a) HVR-H1 comprising the amino acid sequence of SEQ ID NO:13; (b) HVR-H2 comprising the amino acid sequence of SEQ ID NO:30; (c) HVR-H3 comprising the amino acid sequence of SEQ ID NO:48; (d) HVR-L1 comprising the amino acid sequence of SEQ ID NO:67; (e) HVR-L2 comprising the amino acid sequence of SEQ ID NO:76; and (f) HVR-L3 comprising the amino acid sequence of SEQ ID NO:94; (a) HVR-H1 comprising the amino acid sequence of SEQ ID NO:7; (b) HVR-H2 comprising the amino acid sequence of SEQ ID NO:27; (c) HVR-H3 comprising the amino acid sequence of SEQ ID NO:45; (d) HVR-L1 comprising the amino acid sequence of SEQ ID NO:63; (e) HVR-L2 comprising the amino acid sequence of SEQ ID NO:77; and (f) HVR-L3 comprising the amino acid sequence of SEQ ID NO:89; (a) HVR-H1 comprising the amino acid sequence of SEQ ID NO:14; (b) HVR-H2 comprising the amino acid sequence of SEQ ID NO:31; (c) HVR-H3 comprising the amino acid sequence of SEQ ID NO:49; (d) HVR-L1 comprising the amino acid sequence of SEQ ID NO:68; (e) HVR-L2 comprising the amino acid sequence of SEQ ID NO:81; and (f) HVR-L3 comprising the amino acid sequence of SEQ ID NO:95; (a) HVR-H1 comprising the amino acid sequence of SEQ ID NO:15; (b) HVR-H2 comprising the amino acid sequence of SEQ ID NO:32; (c) HVR-H3 comprising the amino acid sequence of SEQ ID NO:50; (d) HVR-L1 comprising the amino acid sequence of SEQ ID NO:69; (e) HVR-L2 comprising the amino acid sequence of SEQ ID NO:82; and (f) HVR-L3 comprising the amino acid sequence of SEQ ID NO:96; (a) HVR-H1 comprising the amino acid sequence of SEQ ID NO:16; (b) HVR-H2 comprising the amino acid sequence of SEQ ID NO:33; (c) HVR-H3 comprising the amino acid sequence of SEQ ID NO:51; (d) HVR-L1 comprising the amino acid sequence of SEQ ID NO:70; (e) HVR-L2 comprising the amino acid sequence of SEQ ID NO:77; and (f) HVR-L3 comprising the amino acid sequence of SEQ ID NO:97; (a) HVR-H1 comprising the amino acid sequence of SEQ ID NO:17; (b) HVR-H2 comprising the amino acid sequence of SEQ ID NO:34; (c) HVR-H3 comprising the amino acid sequence of SEQ ID NO:52; (d) HVR-L1 comprising the amino acid sequence of SEQ ID NO:71; (e) HVR-L2 comprising the amino acid sequence of SEQ ID NO:83; and (f) HVR-L3 comprising the amino acid sequence of SEQ ID NO:98; (a) HVR-H1 comprising the amino acid sequence of SEQ ID NO:18; (b) HVR-H2 comprising the amino acid sequence of SEQ ID NO:35; (c) HVR-H3 comprising the amino acid sequence of SEQ ID NO:53; (d) HVR-L1 comprising the amino acid sequence of SEQ ID NO:72; (e) HVR-L2 comprising the amino acid sequence of SEQ ID NO:77; and (f) HVR-L3 comprising the amino acid sequence of SEQ ID NO:99; (a) HVR-H1 comprising the amino acid sequence of SEQ ID NO:19; (b) HVR-H2 comprising the amino acid sequence of SEQ ID NO:36; (c) HVR-H3 comprising the amino acid sequence of SEQ ID NO:54; (d) HVR-L1 comprising the amino acid sequence of SEQ ID NO:73; (e) HVR-L2 comprising the amino acid sequence of SEQ ID NO:84; and (f) HVR-L3 comprising the amino acid sequence of SEQ ID NO:100; (a) HVR-H1 comprising the amino acid sequence of SEQ ID NO:7; (b) HVR-H2 comprising the amino acid sequence of SEQ ID NO:37; (c) HVR-H3 comprising the amino acid sequence of SEQ ID NO:55; (d) HVR-L1 comprising the amino acid sequence of SEQ ID NO:74; (e) HVR-L2 comprising the amino acid sequence of SEQ ID NO:85; and (f) HVR-L3 comprising the amino acid sequence of SEQ ID NO:89.

In some embodiments, an anti-MS4A4A antibody of the present disclosure comprises an HVR-H1 comprising the amino acid sequence of SEQ ID NO:15, an HVR-H2 comprising the amino acid sequence of SEQ ID NO:32, an HVR-H3 comprising the amino acid sequence of SEQ ID NO:50, an HVR-L1 comprising the amino acid sequence of SEQ ID NO:69, an HVR-L2 comprising the amino acid sequence of SEQ ID NO:82, and an HVR-L3 comprising the amino acid sequence of SEQ ID NO:96.

In some embodiments, an anti-MS4A4A antibody of the present disclosure comprises an HVR-H1 comprising the amino acid sequence of SEQ ID NO:18, an HVR-H2 comprising the amino acid sequence of SEQ ID NO:35, an HVR-H3 comprising the amino acid sequence of SEQ ID NO:53, an HVR-L1 comprising the amino acid sequence of SEQ ID NO:72, an HVR-L2 comprising the amino acid sequence of SEQ ID NO:77, and an HVR-L3 comprising the amino acid sequence of SEQ ID NO:99.

In some embodiments, provided herein are anti-MS4A4A antibodies comprising at least one, at least two, or all three $V_H$ HVR sequences selected from (a) HVR-H1 comprising an amino acid sequence selected from the group consisting of SEQ ID NO:4, 5, 6, 7, 8, 9, 10, 11, 12, 13, 14, 15, 16, 17, 18, and 19, or an amino acid sequence with at least about 95% homology to an amino acid sequence selected from the group consisting of SEQ ID NO:4, 5, 6, 7, 8, 9, 10, 11, 12, 13, 14, 15, 16, 17, 18, and 19; (b) HVR-H2 comprising an amino acid sequence selected from the group consisting of SEQ ID NO:20, 21, 22, 23, 24, 25, 26, 27, 28, 29, 30, 31, 32, 33, 34, 35, 36, and 37, or an amino acid sequence with at least about 95% homology to an amino acid sequence selected from the group consisting of 20, 21, 22, 23, 24, 25, 26, 27, 28, 29, 30, 31, 32, 33, 34, 35, 36, and 37; and (c) HVR-H3 comprising an amino acid sequence selected from the group consisting of SEQ ID NO: 38, 39, 40, 41, 42, 43, 44, 45, 46, 47, 48, 49, 50, 51, 52, 53, 54, and 55, or an amino acid sequence with at least about 95% homology to an amino acid sequence selected from the group consisting of 38, 39, 40, 41, 42, 43, 44, 45, 46, 47, 48, 49, 50, 51, 52, 53, 54, and 55.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NO: 56, 57, 58, 59, 60, 61, 62, 63, 64, 65, 66, 67, 68, 69, 70, 71, 72, 73, and 74, or an amino acid sequence with at least about 95% homology to an amino acid sequence selected from the group consisting of SEQ ID NO: 56, 57, 58, 59, 60, 61, 62, 63, 64, 65, 66, 67, 68, 69, 70, 71, 72, 73, and 74; (e) HVR-L2 comprising an amino acid sequence selected from the group consisting of SEQ ID NOs:75, 76, 77, 78, 79, 80, 81, 82, 83, 84, and 85, or an amino acid sequence with at least about 95% homology to an amino acid sequence selected from the group consisting of SEQ ID NOs:75, 76, 77, 78, 79, 80, 81, 82, 83, 84, and 85; and (f) HVR-L3 comprising an amino acid sequence selected from the group consisting of SEQ ID NOs:86, 87, 88, 89, 90, 91, 92, 93, 94, 95, 96, 97, 98, 99, and 100, or an amino acid sequence with at least about 95% homology to an amino acid sequence selected from the group consisting of SEQ ID NOs:86, 87, 88, 89, 90, 91, 92, 93, 94, 95, 96, 97, 98, 99, and 100.

In some embodiments, provided herein are anti-MS4A4A antibodies comprising (a) a $V_H$ domain comprising at least one, at least two, or all three $V_H$ HVR sequences selected from (i) HVR-H1 comprising an amino acid sequence selected from the group consisting of SEQ ID NO:4, 5, 6, 7, 8, 9, 10, 11, 12, 13, 14, 15, 16, 17, 18, and 19, or an amino acid sequence with at least about 95% homology to an amino acid sequence selected from the group consisting of SEQ ID NO:4, 5, 6, 7, 8, 9, 10, 11, 12, 13, 14, 15, 16, 17, 18, and 19, (ii) HVR-H2 comprising an amino acid sequence selected from the group consisting of SEQ ID NO: 20, 21, 22, 23, 24, 25, 26, 27, 28, 29, 30, 31, 32, 33, 34, 35, 36, and 37, or an amino acid sequence with at least about 95% homology to an amino acid sequence selected from the group consisting of SEQ ID NO: 20, 21, 22, 23, 24, 25, 26, 27, 28, 29, 30, 31, 32, 33, 34, 35, 36, and 37, and (iii) HVR-H3 comprising an amino acid sequence selected from the group consisting of SEQ ID NO: 38, 39, 40, 41, 42, 43, 44, 45, 46, 47, 48, 49, 50, 51, 52, 53, 54, and 55, or an amino acid sequence with at least about 95% homology to an amino acid sequence selected from the group consisting of SEQ ID NO: 38, 39, 40, 41, 42, 43, 44, 45, 46, 47, 48, 49, 50, 51, 52, 53, 54, and 55, and (b) a $V_L$ domain comprising at least one, at least two, or all three $V_L$ HVR sequences selected from (i) HVR-L1 comprising an amino acid sequence selected from the group consisting of SEQ ID NO: 56, 57, 58, 59, 60, 61, 62, 63, 64, 65, 66, 67, 68, 69, 70, 71, 72, 73, and 74, or an amino acid sequence with at least about 95% homology to an amino acid sequence selected from the group consisting of SEQ ID NO: 56, 57, 58, 59, 60, 61, 62, 63, 64, 65, 66, 67, 68, 69, 70, 71, 72, 73, and 74, (ii) HVR-L2 comprising an amino acid sequence selected from the group consisting of SEQ ID NO: 75, 76, 77, 78, 79, 80, 81, 82, 83, 84, and 85, or an amino acid sequence with at least about 95% homology to an amino acid sequence selected from the group consisting of SEQ ID NO: 75, 76, 77, 78, 79, 80, 81, 82, 83, 84, and 85, and (iii) HVR-L3 comprising an amino acid sequence selected from the group consisting of SEQ ID NO: 86, 87, 88, 89, 90, 91, 92, 93, 94, 95, 96, 97, 98, 99, and 100, or an amino acid sequence with at least about 95% homology to an amino acid sequence selected from the group consisting of SEQ ID NO: 86, 87, 88, 89, 90, 91, 92, 93, 94, 95, 96, 97, 98, 99, and 100.

In some embodiments, provided herein are anti-MS4A4A antibodies comprising (a) a $V_H$ domain comprising (i) HVR-H1 comprising an amino acid sequence selected from the group consisting of SEQ ID NO:4, 5, 6, 7, 8, 9, 10, 11, 12, 13, 14, 15, 16, 17, 18, and 19, or an amino acid sequence with at least about 95% homology to an amino acid sequence selected from the group consisting of SEQ ID NO:4, 5, 6, 7, 8, 9, 10, 11, 12, 13, 14, 15, 16, 17, 18, and 19, (ii) HVR-H2 comprising an amino acid sequence selected from the group consisting of SEQ ID NO: 20, 21, 22, 23, 24, 25, 26, 27, 28, 29, 30, 31, 32, 33, 34, 35, 36, and 37, or an amino acid sequence with at least about 95% homology to an amino acid sequence selected from the group consisting of SEQ ID NO: 20, 21, 22, 23, 24, 25, 26, 27, 28, 29, 30, 31, 32, 33, 34, 35, 36, and 37, and (iii) HVR-H3 comprising an amino acid sequence selected from the group consisting of SEQ ID NO: 38, 39, 40, 41, 42, 43, 44, 45, 46, 47, 48, 49, 50, 51, 52, 53, 54, and 55, or an amino acid sequence with at least about 95% homology to an amino acid sequence selected from the group consisting of SEQ ID NO: 38, 39, 40, 41, 42, 43, 44, 45, 46, 47, 48, 49, 50, 51, 52, 53, 54, and 55, and (b) a $V_L$ domain comprising (i) HVR-L1 comprising an amino acid sequence selected from the group consisting of SEQ ID NO: 56, 57, 58, 59, 60, 61, 62, 63, 64, 65, 66, 67, 68, 69, 70, 71, 72, 73, and 74, or an amino acid sequence with at least about 95% homology to an amino acid sequence selected from the group consisting of SEQ ID NO: 56, 57, 58, 59, 60, 61, 62, 63, 64, 65, 66, 67, 68, 69, 70, 71, 72, 73, and 74, (ii) HVR-L2 comprising an amino acid sequence selected from the group consisting of SEQ ID NO: 75, 76, 77, 78, 79, 80, 81, 82, 83, 84, and 85 SEQ ID NO: 75, 76, 77, 78, 79, 80, 81, 82, 83, 84, and 85, or an amino acid sequence with at least about 95% homology to an amino acid sequence selected from the group consisting of SEQ ID NO: 75, 76, 77, 78, 79, 80, 81, 82, 83, 84, and 85, and (iii) HVR-L3 comprising an amino acid sequence selected from the group consisting of SEQ ID NO: 86, 87, 88, 89, 90, 91, 92, 93, 94, 95, 96, 97, 98, 99, and 100, or an amino acid sequence with at least about 95% homology to an amino acid sequence selected from the group consisting of SEQ ID NO: 86, 87, 88, 89, 90, 91, 92, 93, 94, 95, 96, 97, 98, 99, and 100.

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs:142, 143, 144, 145, 146, 147, 148, 149, 150, 151, 152, and 153, or an amino acid sequence with at least about 95% homology to an amino acid sequence selected from the group consisting of SEQ ID NOs:142, 143, 144, 145, 146, 147, 148, 149, 150, 151, 152, and 153; (b) HVR-H2 comprising an amino acid sequence selected from the group consisting of SEQ ID NOs:154, 155, 156, 157, 158, 159, 160, 161, 162, 163, 164, 165, 166, and 167, or an amino acid sequence with at least about 95% homology to an amino acid sequence selected from the group consisting of SEQ ID NOs:154, 155, 156, 157, 158, 159, 160, 161, 162, 163, 164, 165, 166, and 167; (c) HVR-H3 comprising an amino acid sequence selected from the group consisting of SEQ ID NOs:168, 169, 170, 171, 172, 173, 174, 175, 176, 177, 178, 179, 180, 181, and 182, or an amino acid sequence with at least about 95% homology to an amino acid sequence selected from the group consisting of SEQ ID NOs:168, 169, 170, 171, 172, 173, 174, 175, 176, 177, 178, 179, 180, 181, and 182; (d) HVR-L1 comprising an amino acid sequence selected from the group consisting of SEQ ID NOs:183, 184, 185, 186, 187, 188, 189, 190, 191, 192, 193, 194, 195, and 196, or an amino acid sequence with at least about 95% homology to an amino acid sequence selected from the group consisting of SEQ ID NOs:183, 184, 185, 186, 187, 188, 189, 190, 191, 192, 193, 194, 195, and 196; (e) HVR-L2 comprising an amino acid sequence selected from the group consisting of SEQ ID NOs:81, 197, 198, 199, 200, 201, 202, 203, 204, 205, 206, 207, 208, and 209, or an amino acid sequence with at least about 95% homology to an amino acid sequence selected from the group consisting of SEQ ID NOs:81, 197, 198, 199, 200, 201, 202, 203, 204, 205, 206, 207, 208, and 209; and (f) HVR-L3 comprising an amino acid sequence selected from the group consisting of SEQ ID NOs:210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs:210, 211, 212, 213, 214, 215, 216, 217, 218, 219, 220, 221, 222, 223, and 224.

In some embodiments, provided herein are anti-MS4A4A antibodies comprising at least one, two, three, four, five, or six HVRs selected from: (a) HVR-H1 comprising the amino acid sequence of SEQ ID NO:142; (b) HVR-H2 comprising the amino acid sequence of SEQ ID NO:154; (c) HVR-H3 comprising the amino acid sequence of SEQ ID NO:168; (d) HVR-L1 comprising the amino acid sequence of SEQ ID NO:183; (e) HVR-L2 comprising the amino acid sequence of SEQ ID NO:197; and (f) HVR-L3 comprising the amino acid sequence of SEQ ID NO:210; (a) HVR-H1 comprising the amino acid sequence of SEQ ID NO:143; (b) HVR-H2 comprising the amino acid sequence of SEQ ID NO:155; (c) HVR-H3 comprising the amino acid sequence of SEQ ID NO:169; (d) HVR-L1 comprising the amino acid sequence of SEQ ID NO:184; (e) HVR-L2 comprising the amino acid sequence of SEQ ID NO:198; and (f) HVR-L3 comprising the amino acid sequence of SEQ ID NO:211; (a) HVR-H1 comprising the amino acid sequence of SEQ ID NO:144; (b) HVR-H2 comprising the amino acid sequence of SEQ ID NO:156; (c) HVR-H3 comprising the amino acid sequence of SEQ ID NO:170; (d) HVR-L1 comprising the amino acid sequence of SEQ ID NO:185; (e) HVR-L2 comprising the amino acid sequence of SEQ ID NO:199; and (f) HVR-L3 comprising the amino acid sequence of SEQ ID NO:212; (a) HVR-H1 comprising the amino acid sequence of SEQ ID NO:144; (b) HVR-H2 comprising the amino acid sequence of SEQ ID NO:157; (c) HVR-H3 comprising the amino acid sequence of SEQ ID NO:171; (d) HVR-L1 comprising the amino acid sequence of SEQ ID NO:186; (e) HVR-L2 comprising the amino acid sequence of SEQ ID NO:81; and (f) HVR-L3 comprising the amino acid sequence of SEQ ID NO:213; (a) HVR-H1 comprising the amino acid sequence of SEQ ID NO:145; (b) HVR-H2 comprising the amino acid sequence of SEQ ID NO:158; (c) HVR-H3 comprising the amino acid sequence of SEQ ID NO:172; (d) HVR-L1 comprising the amino acid sequence of SEQ ID NO:186; (e) HVR-L2 comprising the amino acid sequence of SEQ ID NO:81; and (f) HVR-L3 comprising the amino acid sequence of SEQ ID NO:214; (a) HVR-H1 comprising the amino acid sequence of SEQ ID NO:146; (b) HVR-H2 comprising the amino acid sequence of SEQ ID NO:159; (c) HVR-H3 comprising the amino acid sequence of SEQ ID NO:173; (d) HVR-L1 comprising the amino acid sequence of SEQ ID NO:187; (e) HVR-L2 comprising the amino acid sequence of SEQ ID NO:200; and (f) HVR-L3 comprising the amino acid sequence of SEQ ID NO:215; (a) HVR-H1 comprising the amino acid sequence of SEQ ID NO:147; (b) HVR-H2 comprising the amino acid sequence of SEQ ID NO:160; (c) HVR-H3 comprising the amino acid sequence of SEQ ID NO:174; (d) HVR-L1 comprising the amino acid sequence of SEQ ID NO:188; (e) HVR-L2 comprising the amino acid sequence of SEQ ID NO:201; and (f) HVR-L3 comprising the amino acid sequence of SEQ ID NO:216; (a) HVR-H1 comprising the amino acid sequence of SEQ ID NO:148; (b) HVR-H2 comprising the amino acid sequence of SEQ ID NO:161; (c) HVR-H3 comprising the amino acid sequence of SEQ ID NO:175; (d) HVR-L1 comprising the amino acid sequence of SEQ ID NO:189; (e) HVR-L2 comprising the amino acid sequence of SEQ ID NO:202; and (f) HVR-L3 comprising the amino acid sequence of SEQ ID NO:217; (a) HVR-H1 comprising the amino acid sequence of SEQ ID NO:149; (b) HVR-H2 comprising the amino acid sequence of SEQ ID NO:162; (c) HVR-H3 comprising the amino acid sequence of SEQ ID NO:176; (d) HVR-L1 comprising the amino acid sequence of SEQ ID NO:190; (e) HVR-L2 comprising the amino acid sequence of SEQ ID NO:203; and (f) HVR-L3 comprising the amino acid sequence of SEQ ID NO:218; (a) HVR-H1 comprising the amino acid sequence of SEQ ID NO:150; (b) HVR-H2 comprising the amino acid sequence of SEQ ID NO:163; (c) HVR-H3 comprising the amino acid sequence of SEQ ID NO:177; (d) HVR-L1 comprising the amino acid sequence of SEQ ID NO:191; (e) HVR-L2 comprising the amino acid sequence of SEQ ID NO:204; and (f) HVR-L3 comprising the amino acid sequence of SEQ ID NO:219; (a) HVR-H1 comprising the amino acid sequence of SEQ ID NO:151; (b) HVR-H2 comprising the amino acid sequence of SEQ ID NO:164; (c) HVR-H3 comprising the amino acid sequence of SEQ ID NO:178; (d) HVR-L1 comprising the amino acid sequence of SEQ ID NO:192; (e) HVR-L2 comprising the amino acid sequence of SEQ ID NO:205; and (f) HVR-L3 comprising the amino acid sequence of SEQ ID NO:220; (a)

HVR-H1 comprising the amino acid sequence of SEQ ID NO:147; (b) HVR-H2 comprising the amino acid sequence of SEQ ID NO:160; (c) HVR-H3 comprising the amino acid sequence of SEQ ID NO:179; (d) HVR-L1 comprising the amino acid sequence of SEQ ID NO:193; (e) HVR-L2 comprising the amino acid sequence of SEQ ID NO:206; and (f) HVR-L3 comprising the amino acid sequence of SEQ ID NO:221; (a) HVR-H1 comprising the amino acid sequence of SEQ ID NO:152; (b) HVR-H2 comprising the amino acid sequence of SEQ ID NO:165; (c) HVR-H3 comprising the amino acid sequence of SEQ ID NO:180; (d) HVR-L1 comprising the amino acid sequence of SEQ ID NO:194; (e) HVR-L2 comprising the amino acid sequence of SEQ ID NO:207; and (f) HVR-L3 comprising the amino acid sequence of SEQ ID NO:222; (a) HVR-H1 comprising the amino acid sequence of SEQ ID NO:153; (b) HVR-H2 comprising the amino acid sequence of SEQ ID NO:166; (c) HVR-H3 comprising the amino acid sequence of SEQ ID NO:181; (d) HVR-L1 comprising the amino acid sequence of SEQ ID NO:195; (e) HVR-L2 comprising the amino acid sequence of SEQ ID NO:208; and (f) HVR-L3 comprising the amino acid sequence of SEQ ID NO:223; and (a) HVR-H1 comprising the amino acid sequence of SEQ ID NO:151; (b) HVR-H2 comprising the amino acid sequence of SEQ ID NO:167; (c) HVR-H3 comprising the amino acid sequence of SEQ ID NO:182; (d) HVR-L1 comprising the amino acid sequence of SEQ ID NO:196; (e) HVR-L2 comprising the amino acid sequence of SEQ ID NO:209; and (f) HVR-L3 comprising the amino acid sequence of SEQ ID NO:224.

In some embodiments, an anti-MS4A4A antibody of the present disclosure comprises an HVR-H1 comprising the amino acid sequence of SEQ ID NO:143, an HVR-H2 comprising the amino acid sequence of SEQ ID NO:155, an HVR-H3 comprising the amino acid sequence of SEQ ID NO:169, an HVR-L1 comprising the amino acid sequence of SEQ ID NO:184, an HVR-L2 comprising the amino acid sequence of SEQ ID NO:198, and an HVR-L3 comprising the amino acid sequence of SEQ ID NO:211.

In some embodiments, provided herein are anti-MS4A4A antibodies comprising at least one, at least two, or all three $V_H$ HVR sequences selected from (a) HVR-H1 comprising an amino acid sequence selected from the group consisting of SEQ ID NOs: 142, 143, 144, 145, 146, 147, 148, 149, 150, 151, 152, and 153, or an amino acid sequence with at least about 95% homology to an amino acid sequence selected from the group consisting of 142, 143, 144, 145, 146, 147, 148, 149, 150, 151, 152, and 153; (b) HVR-H2 comprising an amino acid sequence selected from the group consisting of SEQ ID NOs: 154, 155, 156, 157, 158, 159, 160, 161, 162, 163, 164, 165, 166, and 167, or an amino acid sequence with at least about 95% homology to an amino acid sequence selected from the group consisting of SEQ ID NOs: 154, 155, 156, 157, 158, 159, 160, 161, 162, 163, 164, 165, 166, and 167; and (c) HVR-H3 comprising an amino acid sequence selected from the group consisting of SEQ ID NOs: 168, 169, 170, 171, 172, 173, 174, 175, 176, 177, 178, 179, 180, 181, and 182, or an amino acid sequence with at least about 95% homology to an amino acid sequence selected from the group consisting of SEQ ID NOs: 168, 169, 170, 171, 172, 173, 174, 175, 176, 177, 178, 179, 180, 181, and 182.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs: 183, 184, 185, 186, 187, 188, 189, 190, 191, 192, 193, 194, 195, and 196, or an amino acid sequence with at least about 95% homology to an amino acid sequence selected from the group consisting of SEQ ID NOs: 183, 184, 185, 186, 187, 188, 189, 190, 191, 192, 193, 194, 195, and 196; (e) HVR-L2 comprising an amino acid sequence selected from the group consisting of SEQ ID NOs: 81, 197, 198, 199, 200, 201, 202, 203, 204, 205, 206, 207, 208, and 209, or an amino acid sequence with at least about 95% homology to an amino acid sequence selected from the group consisting of SEQ ID NOs: 81, 197, 198, 199, 200, 201, 202, 203, 204, 205, 206, 207, 208, and 209; and (f) HVR-L3 comprising an amino acid sequence selected from the group consisting of SEQ ID NOs: 210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs: 210, 211, 212, 213, 214, 215, 216, 217, 218, 219, 220, 221, 222, 223, and 224.

In some embodiments, provided herein are anti-MS4A4A antibodies comprising (a) a $V_H$ domain comprising at least one, at least two, or all three $V_H$ HVR sequences selected from (i) HVR-H1 comprising an amino acid sequence selected from the group consisting of SEQ ID NO: 142, 143, 144, 145, 146, 147, 148, 149, 150, 151, 152, and 153, or an amino acid sequence with at least about 95% homology to an amino acid sequence selected from the group consisting of SEQ ID NO: 142, 143, 144, 145, 146, 147, 148, 149, 150, 151, 152, and 153, (ii) HVR-H2 comprising an amino acid sequence selected from the group consisting of SEQ ID NO: 154, 155, 156, 157, 158, 159, 160, 161, 162, 163, 164, 165, 166, and 167, or an amino acid sequence with at least about 95% homology to an amino acid sequence selected from the group consisting of SEQ ID NO: 154, 155, 156, 157, 158, 159, 160, 161, 162, 163, 164, 165, 166, and 167, and (iii) HVR-H3 comprising an amino acid sequence selected from the group consisting of SEQ ID NO: 168, 169, 170, 171, 172, 173, 174, 175, 176, 177, 178, 179, 180, 181, and 182, or an amino acid sequence with at least about 95% homology to an amino acid sequence selected from the group consisting of SEQ ID NO: 168, 169, 170, 171, 172, 173, 174, 175, 176, 177, 178, 179, 180, 181, and 182, and (b) a $V_L$ domain comprising at least one, at least two, or all three $V_L$ HVR sequences selected from (i) HVR-L1 comprising an amino acid sequence selected from the group consisting of SEQ ID NO: 183, 184, 185, 186, 187, 188, 189, 190, 191, 192, 193, 194, 195, and 196, or an amino acid sequence with at least about 95% homology to an amino acid sequence selected from the group consisting of SEQ ID NO: 183, 184, 185, 186, 187, 188, 189, 190, 191, 192, 193, 194, 195, and 196, (ii) HVR-L2 comprising an amino acid sequence selected from the group consisting of SEQ ID NO: 81, 197, 198, 199, 200, 201, 202, 203, 204, 205, 206, 207, 208, and 209, or an amino acid sequence with at least about 95% homology to an amino acid sequence selected from the group consisting of SEQ ID NO: 81, 197, 198, 199, 200, 201, 202, 203, 204, 205, 206, 207, 208, and 209, and (iii) HVR-L3 comprising an amino acid sequence selected from the group consisting of SEQ ID NO: 210, 211, 212, 213, 214, 215, 216, 217, 218, 219, 220, 221, 222, 223, and 224, or an amino acid sequence with at least about 95% homology to an amino acid sequence selected from the group consisting of SEQ ID NO: 210, 211, 212, 213, 214, 215, 216, 217, 218, 219, 220, 221, 222, 223, and 224.

In some embodiments, provided herein are anti-MS4A4A antibodies comprising (a) a $V_H$ domain comprising (i) HVR-H1 comprising an amino acid sequence selected from the group consisting of SEQ ID NO: 142, 143, 144, 145, 146, 147, 148, 149, 150, 151, 152, and 153, or an amino acid sequence with at least about 95% homology to an amino acid sequence selected from the group consisting of SEQ ID NO: 142, 143, 144, 145, 146, 147, 148, 149, 150, 151, 152, and 153, (ii) HVR-H2 comprising an amino acid sequence selected from the group consisting of SEQ ID NO: 154, 155, 156, 157, 158, 159, 160, 161, 162, 163, 164, 165, 166, and 167, or an amino acid sequence with at least about 95% homology to an amino acid sequence selected from the group consisting of SEQ ID NO: 154, 155, 156, 157, 158, 159, 160, 161, 162, 163, 164, 165, 166, and 167, and (iii) HVR-H3 comprising an amino acid sequence selected from the group consisting of SEQ ID NO: 168, 169, 170, 171, 172, 173, 174, 175, 176, 177, 178, 179, 180, 181, and 182, or an amino acid sequence with at least about 95% homology to an amino acid sequence selected from the group consisting of SEQ ID NO: 168, 169, 170, 171, 172, 173, 174, 175, 176, 177, 178, 179, 180, 181, and 182, and (b) a $V_L$ domain comprising (i) HVR-L1 comprising an amino acid sequence selected from the group consisting of SEQ ID NO: 183, 184, 185, 186, 187, 188, 189, 190, 191, 192, 193, 194, 195, and 196, or an amino acid sequence with at least about 95% homology to an amino acid sequence selected from the group consisting of SEQ ID NO: 183, 184, 185, 186, 187, 188, 189, 190, 191, 192, 193, 194, 195, and 196, (ii) HVR-L2 comprising an amino acid sequence selected from the group consisting of SEQ ID NO: 81, 197, 198, 199, 200, 201, 202, 203, 204, 205, 206, 207, 208, and 209, or an amino acid sequence with at least about 95% homology to an amino acid sequence selected from the group consisting of SEQ ID NO: 81, 197, 198, 199, 200, 201, 202, 203, 204, 205, 206, 207, 208, and 209, and (iii) HVR-L3 comprising an amino acid sequence selected from the group consisting of SEQ ID NO: 210, 211, 212, 213, 214, 215, 216, 217, 218, 219, 220, 221, 222, 223, and 224, or an amino acid sequence with at least about 95% homology to an amino acid sequence selected from the group consisting of SEQ ID NO: 210, 211, 212, 213, 214, 215, 216, 217, 218, 219, 220, 221, 222, 223, and 224.

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs:142, 143, 144, 145, 146, 147, 148, 149, 150, 151, 152, and 153, or an amino acid sequence with at least about 95% homology to an amino acid sequence selected from the group consisting of SEQ ID NOs:142, 143, 144, 145, 146, 147, 148, 149, 150, 151, 152, and 153; (b) HVR-H2 comprising an amino acid sequence selected from the group consisting of SEQ ID NOs:154, 155, 156, 157, 158, 159, 160, 161, 162, 163, 164, 165, 166, and 167, or an amino acid sequence with at least about 95% homology to an amino acid sequence selected from the group consisting of SEQ ID NOs:154, 155, 156, 157, 158, 159, 160, 161, 162, 163, 164, 165, 166, and 167; (c) HVR-H3 comprising an amino acid sequence selected from the group consisting of SEQ ID NOs:168, 169, 170, 171, 172, 173, 174, 175, 176, 177, 178, 179, 180, 181, and 182, or an amino acid sequence with at least about 95% homology to an amino acid sequence selected from the group consisting of SEQ ID NOs:168, 169, 170, 171, 172, 173, 174, 175, 176, 177, 178, 179, 180, 181, and 182; (d) HVR-L1 comprising an amino acid sequence selected from the group consisting of SEQ ID NOs:183, 184, 185, 186, 187, 188, 189, 190, 191, 192, 193, 194, 195, and 196, or an amino acid sequence with at least about 95% homology to an amino acid sequence selected from the group consisting of SEQ ID NOs:183, 184, 185, 186, 187, 188, 189, 190, 191, 192, 193, 194, 195, and 196; (e) HVR-L2 comprising an amino acid sequence selected from the group consisting of SEQ ID NOs:81, 197, 198, 199, 200, 201, 202, 203, 204, 205, 206, 207, 208, and 209, or an amino acid sequence with at least about 95% homology to an amino acid sequence selected from the group consisting of SEQ ID NOs:81, 197, 198, 199, 200, 201, 202, 203, 204, 205, 206, 207, 208, and 209; and (f) HVR-L3 comprising an amino acid sequence selected from the group consisting of SEQ ID NOs:210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs:210, 211, 212, 213, 214, 215, 216, 217, 218, 219, 220, 221, 222, 223, and 224.

In some embodiments, provided herein are anti-MS4A4A antibodies comprising at least one, two, three, four, five, or six HVRs selected from: (a) HVR-H1 comprising the amino acid sequence of SEQ ID NO:304; (b) HVR-H2 comprising the amino acid sequence of SEQ ID NO:310; (c) HVR-H3 comprising the amino acid sequence of SEQ ID NO:316; (d) HVR-L1 comprising the amino acid sequence of SEQ ID NO:322; (e) HVR-L2 comprising the amino acid sequence of SEQ ID NO:328; and (f) HVR-L3 comprising the amino acid sequence of SEQ ID NO:334; (a) HVR-H1 comprising the amino acid sequence of SEQ ID NO:305; (b) HVR-H2 comprising the amino acid sequence of SEQ ID NO:311; (c) HVR-H3 comprising the amino acid sequence of SEQ ID NO:317; (d) HVR-L1 comprising the amino acid sequence of SEQ ID NO:323; (e) HVR-L2 comprising the amino acid sequence of SEQ ID NO:329; and (f) HVR-L3 comprising the amino acid sequence of SEQ ID NO:335; (a) HVR-H1 comprising the amino acid sequence of SEQ ID NO:306; (b) HVR-H2 comprising the amino acid sequence of SEQ ID NO:312; (c) HVR-H3 comprising the amino acid sequence of SEQ ID NO:318; (d) HVR-L1 comprising the amino acid sequence of SEQ ID NO:324; (e) HVR-L2 comprising the amino acid sequence of SEQ ID NO:330; and (f) HVR-L3 comprising the amino acid sequence of SEQ ID NO:336; (a) HVR-H1 comprising the amino acid sequence of SEQ ID NO:307; (b) HVR-H2 comprising the amino acid sequence of SEQ ID NO:313; (c) HVR-H3 comprising the amino acid sequence of SEQ ID NO:319; (d) HVR-L1 comprising the amino acid sequence of SEQ ID NO:325; (e) HVR-L2 comprising the amino acid sequence of SEQ ID NO:331; and (f) HVR-L3 comprising the amino acid sequence of SEQ ID NO:337; (a) HVR-H1 comprising the amino acid sequence of SEQ ID NO:308; (b) HVR-H2 comprising the amino acid sequence of SEQ ID NO:314; (c) HVR-H3 comprising the amino acid sequence of SEQ ID NO:320; (d) HVR-L1 comprising the amino acid sequence of SEQ ID NO:326; (e) HVR-L2 comprising the amino acid sequence of SEQ ID NO:332; and (f) HVR-L3 comprising the amino acid sequence of SEQ ID NO:338; (a) HVR-H1 comprising the amino acid sequence of SEQ ID NO:309; (b) HVR-H2 comprising the amino acid sequence of SEQ ID NO:315; (c) HVR-H3 comprising the amino acid sequence of SEQ ID NO:321; (d) HVR-L1 comprising the amino acid sequence of SEQ ID NO:327; (e) HVR-L2 comprising the amino acid sequence of SEQ ID NO:333; and (f) HVR-L3 comprising the amino acid sequence of SEQ ID NO:339

In some embodiments, provided herein are anti-MS4A4A antibodies comprising at least one, at least two, or all three $V_H$ HVR sequences selected from (a) HVR-H1 comprising an amino acid sequence selected from the group consisting of SEQ ID NOs: 304, 305, 306, 307, 308, and 309, or an amino acid sequence with at least about 95% homology to an amino acid sequence selected from the group consisting of 304, 305, 306, 307, 308, and 309; (b) HVR-H2 comprising an amino acid sequence selected from the group consisting of SEQ ID NOs: 310, 311, 312, 313, 314, and 315; or an amino acid sequence with at least about 95% homology to an amino acid sequence selected from the group consisting of SEQ ID NOs: 310, 311, 312, 313, 314, and 315; and (c) HVR-H3 comprising an amino acid sequence selected from the group consisting of SEQ ID NOs: 316, 317, 318, 319, 320, and 321, or an amino acid sequence with at least about 95% homology to an amino acid sequence selected from the group consisting of SEQ ID NOs: 316, 317, 318, 319, 320, and 321.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs: 322, 323, 324, 325, 326, and 327, or an amino acid sequence with at least about 95% homology to an amino acid sequence selected from the group consisting of SEQ ID NOs: 322, 323, 324, 325, 326, and 327; (e) HVR-L2 comprising an amino acid sequence selected from the group consisting of SEQ ID NOs: 328, 329, 330, 331, 332, and 333, or an amino acid sequence with at least about 95% homology to an amino acid sequence selected from the group consisting of SEQ ID NOs: 328, 329, 330, 331, 332, and 333; and (f) HVR-L3 comprising an amino acid sequence selected from the group consisting of SEQ ID NOs: 334, 335, 336, 337, 338, and 339, or an amino acid sequence with at least about 95% homology to an amino acid sequence selected from the group consisting of SEQ ID NOs: 334, 335, 336, 337, 338, and 339.

In some embodiments, provided herein are anti-MS4A4A antibodies comprising (a) a $V_H$ domain comprising at least one, at least two, or all three $V_H$ HVR sequences selected from (i) HVR-H1 comprising an amino acid sequence selected from the group consisting of SEQ ID NO: 304, 305, 306, 307, 308, and 309, or an amino acid sequence with at least about 95% homology to an amino acid sequence selected from the group consisting of SEQ ID NO: 304, 305, 306, 307, 308, and 309, (ii) HVR-H2 comprising an amino acid sequence selected from the group consisting of SEQ ID NO: 310, 311, 312, 313, 314, and 315, or an amino acid sequence with at least about 95% homology to an amino acid sequence selected from the group consisting of SEQ ID NO: 310, 311, 312, 313, 314, and 315, and (iii) HVR-H3 comprising an amino acid sequence selected from the group consisting of SEQ ID NO: 316, 317, 318, 319, 320, and 321, or an amino acid sequence with at least about 95% homology to an amino acid sequence selected from the group consisting of SEQ ID NO: 316, 317, 318, 319, 320, and 321, and (b) a $V_L$ domain comprising at least one, at least two, or all three $V_L$ HVR sequences selected from (i) HVR-L1 comprising an amino acid sequence selected from the group consisting of SEQ ID NO: 322, 323, 324, 325, 326, and 327, or an amino acid sequence with at least about 95% homology to an amino acid sequence selected from the group consisting of SEQ ID NO: 322, 323, 324, 325, 326, and 327, (ii) HVR-L2 comprising an amino acid sequence selected from the group consisting of SEQ ID NO: 328, 329, 330, 331, 332, and 333, or an amino acid sequence with at least about 95% homology to an amino acid sequence selected from the group consisting of SEQ ID NO: 328, 329, 330, 331, 332, and 333, and (iii) HVR-L3 comprising an amino acid sequence selected from the group consisting of SEQ ID NO: 334, 335, 336, 337, 338, and 339, or an amino acid sequence with at least about 95% homology to an amino acid sequence selected from the group consisting of SEQ ID NO: 334, 335, 336, 337, 338, and 339.

In some embodiments, provided herein are anti-MS4A4A antibodies comprising (a) a $V_H$ domain comprising (i) HVR-H1 comprising an amino acid sequence selected from the group consisting of SEQ ID NO: 304, 305, 306, 307, 308, and 309, or an amino acid sequence with at least about 95% homology to an amino acid sequence selected from the group consisting of SEQ ID NO: 304, 305, 306, 307, 308, and 309, (ii) HVR-H2 comprising an amino acid sequence selected from the group consisting of SEQ ID NO: 310, 311, 312, 313, 314, and 315, or an amino acid sequence with at least about 95% homology to an amino acid sequence selected from the group consisting of SEQ ID NO: 310, 311, 312, 313, 314, and 315, and (iii) HVR-H3 comprising an amino acid sequence selected from the group consisting of SEQ ID NO: 316, 317, 318, 319, 320, and 321, or an amino acid sequence with at least about 95% homology to an amino acid sequence selected from the group consisting of SEQ ID NO: 316, 317, 318, 319, 320, and 321, and (b) a $V_L$ domain comprising (i) HVR-L1 comprising an amino acid sequence selected from the group consisting of SEQ ID NO: 322, 323, 324, 325, 326, and 327, or an amino acid sequence with at least about 95% homology to an amino acid sequence selected from the group consisting of SEQ ID NO: 322, 323, 324, 325, 326, and 327, (ii) HVR-L2 comprising an amino acid sequence selected from the group consisting of SEQ ID NO: 328, 329, 330, 331, 332, and 333, or an amino acid sequence with at least about 95% homology to an amino acid sequence selected from the group consisting of SEQ ID NO: 328, 329, 330, 331, 332, and 333, and (iii) HVR-L3 comprising an amino acid sequence selected from the group consisting of SEQ ID NO: 334, 335, 336, 337, 338, and 339, or an amino acid sequence with at least about 95% homology to an amino acid sequence selected from the group consisting of SEQ ID NO: 334, 335, 336, 337, 338, and 339.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:101, 102, 103, 104, 105, 106, 107, 108, 109, 110, 111, 112, 113, 114, 115, 116, 117, 118, 119, and 120. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 101, 102, 103, 104, 105, 106, 107, 108, 109, 110, 111, 112, 113, 114, 115, 116, 117, 118, 119, and 120 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 101, 102, 103, 104, 105, 106, 107, 108, 109, 110, 111, 112, 113, 114, 115, 116, 117, 118, 119, or 120. In certain embodiments, a total of 1 to 5 amino acids have been substituted, inserted and/or deleted in SEQ ID NO: 101, 102, 103, 104, 105, 106, 107, 108, 109, 110, 111, 112, 113, 114, 115, 116, 117, 118, 119, or 120. In certain embodiments, substitutions, insertions, or deletions occur in regions outside the HVRs (i.e., in the FRs). Optionally, the anti-MS4A4A antibody comprises the $V_H$ sequence of SEQ ID NO: 101, 102, 103, 104, 105, 106, 107, 108, 109, 110, 111, 112, 113, 114, 115, 116, 117, 118, 119, or 120, including post-translational modifications of that sequence. In a particular embodiment, the $V_H$ comprises one, two or three HVRs selected from: (a) HVR-H1 comprising an amino acid sequence selected from the group consisting of SEQ ID NOs:4, 5, 6, 7, 8, 9, 10, 11, 12, 13, 14, 15, 16, 17, 18, and 19, (b) HVR-H2 comprising an amino acid sequence selected from the group consisting of SEQ ID NOs: 20, 21, 22, 23, 24, 25, 26, 27, 28, 29, 30, 31, 32, 33, 34, 35, 36, and 37, and (c) HVR-H3 comprising an amino acid sequence selected from the group consisting of SEQ ID NOs: 38, 39, 40, 41, 42, 43, 44, 45, 46, 47, 48, 49, 50, 51, 52, 53, 54, and 55.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:121, 122, 123, 124, 125, 126, 127, 128, 129, 130, 131, 132, 133, 134, 135, 136, 137, 138, and 139. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 121, 122, 123, 124, 125, 126, 127, 128, 129, 130, 131, 132, 133, 134, 135, 136, 137, 138, and 139, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 121, 122, 123, 124, 125, 126, 127, 128, 129, 130, 131, 132, 133, 134, 135, 136, 137, 138, or 139. In certain embodiments, a total of 1 to 5 amino acids have been substituted, inserted and/or deleted in SEQ ID NO: 121, 122, 123, 124, 125, 126, 127, 128, 129, 130, 131, 132, 133, 134, 135, 136, 137, 138, or 139. In certain embodiments, the substitutions, insertions, or deletions occur in regions outside the HVRs (i.e., in the FRs). Optionally, the anti-MS4A4A antibody comprises the $V_L$ sequence of SEQ ID NO: 121, 122, 123, 124, 125, 126, 127, 128, 129, 130, 131, 132, 133, 134, 135, 136, 137, 138, or 139, including post-translational modifications of that sequence. In a particular embodiment, the $V_L$ comprises one, two or three HVRs selected from (a) HVR-L1 comprising an amino acid sequence selected from the group consisting of SEQ ID NOs: 56, 57, 58, 59, 60, 61, 62, 63, 64, 65, 66, 67, 68, 69, 70, 71, 72, 73, and 74, (b) HVR-L2 comprising an amino acid sequence selected from the group consisting of SEQ ID NOs: 75, 76, 77, 78, 79, 80, 81, 82, 83, 84, and 85, and (c) HVR-L3 comprising an amino acid sequence selected from the group consisting of SEQ ID NOs: 86, 87, 88, 89, 90, 91, 92, 93, 94, 95, 96, 97, 98, 99, and 100.

In some embodiments, an anti-MS4A4A antibody is provided, wherein the antibody comprises a $V_H$ as in any of the embodiments provided above, and a $V_L$ as in any of the embodiments provided above. In some embodiments, provided herein are anti-MS4A4A antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:101-120 and SEQ ID NOs:121-139, respectively, including post-translational modifications of those sequences.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:101 and $V_L$ comprising the amino acid sequence of SEQ ID NO:121; $V_H$ comprising the amino acid sequence of SEQ ID NO:102 and $V_L$ comprising the amino acid sequence of SEQ ID NO:122; $V_H$ comprising the amino acid sequence of SEQ ID NO:103 and $V_L$ comprising the amino acid sequence of SEQ ID NO:123; $V_H$ comprising the amino acid sequence of SEQ ID NO:104 and $V_L$ comprising the amino acid sequence of SEQ ID NO:124; $V_H$ comprising the amino acid sequence of SEQ ID NO:105 and $V_L$ comprising the amino acid sequence of SEQ ID NO:125; $V_H$ comprising the amino acid sequence of SEQ ID NO:106 and $V_L$ comprising the amino acid sequence of SEQ ID NO:126; $V_H$ comprising the amino acid sequence of SEQ ID NO:107 and $V_L$ comprising the amino acid sequence of SEQ ID NO:127; $V_H$ comprising the amino acid sequence of SEQ ID NO:108 and $V_L$ comprising the amino acid sequence of SEQ ID NO:128; $V_H$ comprising the amino acid sequence of SEQ ID NO:109 and $V_L$ comprising the amino acid sequence of SEQ ID NO:129; $V_H$ comprising the amino acid sequence of SEQ ID NO:110 and $V_L$ comprising the amino acid sequence of SEQ ID NO:130; $V_H$ comprising the amino acid sequence of SEQ ID NO:111 and $V_L$ comprising the amino acid sequence of SEQ ID NO:131; $V_H$ comprising the amino acid sequence of SEQ ID NO:112 and $V_L$ comprising the amino acid sequence of SEQ ID NO:132; $V_H$ comprising the amino acid sequence of SEQ ID NO:113 and $V_L$ comprising the amino acid sequence of SEQ ID NO:128; $V_H$ comprising the amino acid sequence of SEQ ID NO:114 and $V_L$ comprising the amino acid sequence of SEQ ID NO:133; $V_H$ comprising the amino acid sequence of SEQ ID NO:115 and $V_L$ comprising the amino acid sequence of SEQ ID NO:134; $V_H$ comprising the amino acid sequence of SEQ ID NO:116 and $V_L$ comprising the amino acid sequence of SEQ ID NO:135; $V_H$ comprising the amino acid sequence of SEQ ID NO:117 and $V_L$ comprising the amino acid sequence of SEQ ID NO:136; $V_H$ comprising the amino acid sequence of SEQ ID NO:118 and $V_L$ comprising the amino acid sequence of SEQ ID NO:137; $V_H$ comprising the amino acid sequence of SEQ ID NO:119 and $V_L$ comprising the amino acid sequence of SEQ ID NO:138; and $V_H$ comprising the amino acid sequence of SEQ ID NO:120 and $V_L$ comprising the amino acid sequence of SEQ ID NO:139.

In some embodiments, the present disclosure provides an anti-MS4A4A antibody, wherein the antibody comprises a heavy chain variable domain and a light chain variable domain, wherein the heavy chain variable domain comprises the amino acid sequence of SEQ ID NO:115 and the light chain variable domain comprises the amino acid sequence of SEQ ID NO:134.

In some embodiments, the present disclosure provides an anti-MS4A4A antibody, wherein the antibody comprises a heavy chain variable domain and a light chain variable domain, wherein the heavy chain variable domain comprises the amino acid sequence of SEQ ID NO:118 and the light chain variable domain comprises the amino acid sequence of SEQ ID NO:137.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 225, 226, 227, 228, 229, 230, 231, 232, 233, 234, 235, 236, 237, 238, and 239. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 225, 226, 227, 228, 229, 230, 231, 232, 233, 234, 235, 236, 237, 238, and 239 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 225, 226, 227, 228, 229, 230, 231, 232, 233, 234, 235, 236, 237, 238, or 239. In certain embodiments, a total of 1 to 5 amino acids have been substituted, inserted and/or deleted in SEQ ID NO: 225, 226, 227, 228, 229, 230, 231, 232, 233, 234, 235, 236, 237, 238, or 239. In certain embodiments, substitutions, insertions, or deletions occur in regions outside the HVRs (i.e., in the FRs). Optionally, the anti-MS4A4A antibody comprises the $V_H$ sequence of SEQ ID NO: 225, 226, 227, 228, 229, 230, 231, 232, 233, 234, 235, 236, 237, 238, or 239, including post-translational modifications of that sequence. In a particular embodiment, the $V_H$ comprises one, two or three HVRs selected from: (a) HVR-H1 comprising an amino acid sequence selected from the group consisting of SEQ ID NOs: 142, 143, 144, 145, 146, 147, 148, 149, 150, 151, 152, and 153, (b) HVR-H2 comprising an amino acid sequence selected from the group consisting of SEQ ID NOs: 154, 155, 156, 157, 158, 159, 160, 161, 162, 163, 164, 165, 166, and 167, and (c) HVR-H3 comprising an amino acid sequence selected from the group consisting of SEQ ID NOs: 168, 169, 170, 171, 172, 173, 174, 175, 176, 177, 178, 179, 180, 181, and 182.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 240, 241, 242, 243, 244, 245, 246, 247, 248, 249, 250, 251, 252, 253, and 254. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 240, 241, 242, 243, 244, 245, 246, 247, 248, 249, 250, 251, 252, 253, and 254, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 240, 241, 242, 243, 244, 245, 246, 247, 248, 249, 250, 251, 252, 253, or 254. In certain embodiments, a total of 1 to 5 amino acids have been substituted, inserted and/or deleted in SEQ ID NO: 240, 241, 242, 243, 244, 245, 246, 247, 248, 249, 250, 251, 252, 253, or 254. In certain embodiments, the substitutions, insertions, or deletions occur in regions outside the HVRs (i.e., in the FRs). Optionally, the anti-MS4A4A antibody comprises the $V_L$ sequence of SEQ ID NO: 240, 241, 242, 243, 244, 245, 246, 247, 248, 249, 250, 251, 252, 253, or 254, including post-translational modifications of that sequence. In a particular embodiment, the $V_L$ comprises one, two or three HVRs selected from (a) HVR-L1 comprising an amino acid sequence selected from the group consisting of SEQ ID NOs: 183, 184, 185, 186, 187, 188, 189, 190, 191, 192, 193, 194, 195, and 196, (b) HVR-L2 comprising an amino acid sequence selected from the group consisting of SEQ ID NOs: 81, 197, 198, 199, 200, 201, 202, 203, 204, 205, 206, 207, 208, and 209, and (c) HVR-L3 comprising an amino acid sequence selected from the group consisting of SEQ ID NOs: 210, 211, 212, 213, 214, 215, 216, 217, 218, 219, 220, 221, 222, 223, and 224.

In some embodiments, an anti-MS4A4A antibody is provided, wherein the antibody comprises a $V_H$ as in any of the embodiments provided above, and a $V_L$ as in any of the embodiments provided above. In some embodiments, provided herein are anti-MS4A4A antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:225-239 and SEQ ID NOs:240-254, respectively, including post-translational modifications of those sequences.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:225 and $V_L$ comprising the amino acid sequence of SEQ ID NO:240; $V_H$ comprising the amino acid sequence of SEQ ID NO:226 and $V_L$ comprising the amino acid sequence of SEQ ID NO:241; $V_H$ comprising the amino acid sequence of SEQ ID NO:227 and $V_L$ comprising the amino acid sequence of SEQ ID NO:242; $V_H$ comprising the amino acid sequence of SEQ ID NO:228 and $V_L$ comprising the amino acid sequence of SEQ ID NO:243; $V_H$ comprising the amino acid sequence of SEQ ID NO:229 and $V_L$ comprising the amino acid sequence of SEQ ID NO:244; $V_H$ comprising the amino acid sequence of SEQ ID NO:230 and $V_L$ comprising the amino acid sequence of SEQ ID NO:245; $V_H$ comprising the amino acid sequence of SEQ ID NO:231 and $V_L$ comprising the amino acid sequence of SEQ ID NO:246; $V_H$ comprising the amino acid sequence of SEQ ID NO:232 and $V_L$ comprising the amino acid sequence of SEQ ID NO:247; $V_H$ comprising the amino acid sequence of SEQ ID NO:233 and $V_L$ comprising the amino acid sequence of SEQ ID NO:248; $V_H$ comprising the amino acid sequence of SEQ ID NO:234 and $V_L$ comprising the amino acid sequence of SEQ ID NO:249; $V_H$ comprising the amino acid sequence of SEQ ID NO:235 and $V_L$ comprising the amino acid sequence of SEQ ID NO:250; $V_H$ comprising the amino acid sequence of SEQ ID NO:236 and $V_L$ comprising the amino acid sequence of SEQ ID NO:251; $V_H$ comprising the amino acid sequence of SEQ ID NO:237 and $V_L$ comprising the amino acid sequence of SEQ ID NO:252; $V_H$ comprising the amino acid sequence of SEQ ID NO:238 and $V_L$ comprising the amino acid sequence of SEQ ID NO:253; and $V_H$ comprising the amino acid sequence of SEQ ID NO:239 and $V_L$ comprising the amino acid sequence of SEQ ID NO:254.

In some embodiments, the present disclosure provides an anti-MS4A4A antibody, wherein the antibody comprises a heavy chain variable domain and a light chain variable domain, wherein the heavy chain variable domain comprises the amino acid sequence of SEQ ID NO:226 and the light chain variable domain comprises the amino acid sequence of SEQ ID NO:241.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 340, 341, 342, 343, 344, and 345. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 340, 341, 342, 343, 344, and 345 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 340, 341, 342, 343, 344, and 345. In certain embodiments, a total of 1 to 5 amino acids have been substituted, inserted and/or deleted in SEQ ID NO: 340, 341, 342, 343, 344, and 345. In certain embodiments, substitutions, insertions, or deletions occur in regions outside the HVRs (i.e., in the FRs). Optionally, the anti-MS4A4A antibody comprises the $V_H$ sequence of SEQ ID NO: 340, 341, 342, 343, 344, and 345, including post-translational modifications of that sequence. In a particular embodiment, the $V_H$ comprises one, two or three HVRs selected from: (a) HVR-H1 comprising an amino acid sequence selected from the group consisting of SEQ ID NOs: 304, 305, 306, 307, 308, and 309, (b) HVR-H2 comprising an amino acid sequence selected from the group consisting of SEQ ID NOs: 310, 311, 312, 313, 314, and 315, and (c) HVR-H3 comprising an amino acid sequence selected from the group consisting of SEQ ID NOs: 316, 317, 318, 319, 320, and 321.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 346, 347, 348, 349, 350, and 351. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 346, 347, 348, 349, 350, and 351, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 346, 347, 348, 349, 350, or 351. In certain embodiments, a total of 1 to 5 amino acids have been substituted, inserted and/or deleted in SEQ ID NO: 346, 347, 348, 349, 350, or 351. In certain embodiments, the substitutions, insertions, or deletions occur in regions outside the HVRs (i.e., in the FRs). Optionally, the anti-MS4A4A antibody comprises the $V_L$ sequence of SEQ ID NO: 346, 347, 348, 349, 350, or 351, including post-translational modifications of that sequence. In a particular embodiment, the $V_L$ comprises one, two or three HVRs selected from (a) HVR-L1 comprising an amino acid sequence selected from the group consisting of SEQ ID NOs: 322, 323, 324, 325, 326, and 327, (b) HVR-L2 comprising an amino acid sequence selected from the group consisting of SEQ ID NOs: 334, 335, 336, 337, 338, and 339, and (c) HVR-L3 comprising an amino acid sequence selected from the group consisting of SEQ ID NOs: 334, 335, 336, 337, 338, and 339.

In some embodiments, an anti-MS4A4A antibody is provided, wherein the antibody comprises a $V_H$ as in any of the embodiments provided above, and a $V_L$ as in any of the embodiments provided above. In some embodiments, provided herein are anti-MS4A4A antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:340-345 and SEQ ID NOs:346-351, respectively, including post-translational modifications of those sequences.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:340 and $V_L$ comprising the amino acid sequence of SEQ ID NO:346; $V_H$ comprising the amino acid sequence of SEQ ID NO:341 and $V_L$ comprising the amino acid sequence of SEQ ID NO:347; $V_H$ comprising the amino acid sequence of SEQ ID NO:342 and $V_L$ comprising the amino acid sequence of SEQ ID NO:348; $V_H$ comprising the amino acid sequence of SEQ ID NO:343 and $V_L$ comprising the amino acid sequence of SEQ ID NO:349; $V_H$ comprising the amino acid sequence of SEQ ID NO:344 and $V_L$ comprising the amino acid sequence of SEQ ID NO:350; and $V_H$ comprising the amino acid sequence of SEQ ID NO:345 and $V_L$ comprising the amino acid sequence of SEQ ID NO:351.

In some embodiments, an anti-MS4A4A antibody of the present disclosure competitively inhibits binding of at least one reference antibody selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

In some embodiments, an anti-MS4A4A antibody of the present disclosure competes with one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, 4A-220, and any combination thereof, for binding to MS4A4A when the anti-MS4A4A antibody reduces the binding of one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof to MS4A4A by an amount the ranges from about 50% to 100%, as compared to binding to MS4A4A in the absence of the anti-MS4A4A antibody.

In some embodiments, an anti-MS4A4A antibody of the present disclosure competes with one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof for binding to MS4A4A when the anti-MS4A4A antibody reduces the binding of one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof to MS4A4A by at least 50%, at least 55%, by at least 60%, at least 65%, at least 70%, at least 75%, at least 80%, at least 85%, at least 90%, at least 95%, or 100%, as compared to binding to MS4A4A in the absence of the anti-MS4A4A antibody. In some embodiments, an anti-MS4A4A antibody of the present disclosure that reduces the binding of one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof to MS4A4A by 100% indicates that the anti-MS4A4A antibody essentially completely blocks the binding of one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof to MS4A4A. In some embodiments, the anti-MS4A4A antibody and the one or more antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-MS4A4A antibody to one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof. In some embodiments, the anti-MS4A4A antibody is present in excess by an amount that ranges from about 1.5-fold to 100-fold, or greater than 100-fold compared to the amount of the one or more antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof. In some embodiments, the anti-MS4A4A antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof.

In some embodiments, an anti-MS4A4A antibody of the present disclosure binds to an epitope of human MS4A4A that is the same as or overlaps with the MS4A4A epitope bound by at least one reference antibody selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220.

In some embodiments, an anti-MS4A4A antibody of the present disclosure binds essentially the same MS4A4A epitope bound by at least one reference antibody selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220. Detailed exemplary methods for mapping an epitope to which an antibody binds are provided in Morris (1996) "Epitope Mapping Protocols," in Methods in Molecular Biology vol. 66 (Humana Press, Totowa, N.J.).

In some embodiments, an anti-MS4A4A antibody of the present disclosure competes with one or more reference antibodies selected from 4A-1, 4A-2, 4A-3, 4A-4, 4A-6, 4A-7, 4A-8, 4A-9, 4A-10, 4A-11, 4A-14, 4A-15, 4A-16, 4A-19, 4A-20, 4A-21, and 4A-23, and any combination thereof, for binding to MS4A4A. In some embodiments, an anti-MS4A4A antibody of the present disclosure competes with one or more reference antibodies selected from 4A-5, 4A-12, 4A-13, 4A-17, 4A-18, 4A-22, and 4A-24, and any combination thereof for binding to MS4A4A.

In some embodiments, an anti-MS4A4A antibody of the present disclosure competitively inhibits binding of at least one reference antibody selected from 4A-1, 4A-2, 4A-3, 4A-4, 4A-6, 4A-7, 4A-8, 4A-9, 4A-10, 4A-11, 4A-14, 4A-15, 4A-16, 4A-19, 4A-20, 4A-21, and 4A-23, and any combination thereof, for binding to MS4A4A. In some embodiments, an anti-MS4A4A antibody of the present disclosure competitively inhibits binding of at least one reference antibody selected from 4A-5, 4A-12, 4A-13, 4A-17, 4A-18, 4A-22, and 4A-24, and any combination thereof, for binding to MS4A4A.

In some embodiments, an anti-MS4A4A antibody of the present disclosure has the same or overlapping epitope on MS4A4A as at least one reference antibody selected from 4A-1, 4A-2, 4A-3, 4A-4, 4A-6, 4A-7, 4A-8, 4A-9, 4A-10, 4A-11, 4A-14, 4A-15, 4A-16, 4A-19, 4A-20, 4A-21, and 4A-23, and any combination thereof, for binding to MS4A4A. In some embodiments, an anti-MS4A4A antibody of the present disclosure has the same or overlapping epitope on MS4A4A as at least one reference antibody selected from 4A-5, 4A-12, 4A-13, 4A-17, 4A-18, 4A-22, and 4A-24, and any combination thereof, for binding to MS4A4A.

In some embodiments, an anti-MS4A4A antibody of the present disclosure binds to one or more amino acids within amino acid residues 1-64 of human MS4A4A (SEQ ID NO:1). In some embodiments, an anti-MS4A4A antibody of the present disclosure binds to one or more amino acids within amino acid residues 65-85 of human MS4A4A (SEQ ID NO:1). In some embodiments, an anti-MS4A4A antibody of the present disclosure bind to one or more amino acids within amino acid residues 86-98 of human MS4A4A (SEQ ID NO:1). In some embodiments, an anti-MS4A4A antibody of the present disclosure binds to one or more amino acids within amino acid residues 99-119 of human MS4A4A. In some embodiments, an anti-MS4A4A of the present disclosure binds to one or more amino acids within amino acid residues 120-137 of human MS4A4A. In some embodiments, an anti-MS4A4A of the present disclosure binds to one or more amino acids within amino acid residues 138-158 of human MS4A4A. In some embodiments, an anti- MS4A4A of the present disclosure binds to one or more amino acids within amino acid residues 159-179 of human MS4A4A. In some embodiments, an anti-MS4A4A of the present disclosure binds to one or more amino acids within amino acid residues 180-200 of human MS4A4A. In some embodiments, an anti-MS4A4A of the present disclosure binds to one or more amino acids within amino acid residues 201-239 of human MS4A4A. In some embodiments, an anti-MS4A4A antibody of the present disclosure binds to extracellular domain 1 (ECL1) of MS4A4A. In some embodiments, an anti-MS4A4A antibody of the present disclosure binds to one or more amino acids within the amino acid sequence CMASNTYGSNPIS (SEQ ID NO:289) of SEQ ID NO:1. In some embodiments, an anti-MS4A4A antibody of the present disclosure binds to extracellular domain 2 (ECL2) of MS4A4A. In some embodiments, an anti-MS4A4A antibody of the present disclosure binds to one or more amino acids within the amino acid sequence SFHHPYCNYYGNSNNCHGTMS (SEQ ID NO:290) of SEQ ID NO:1

In some embodiments, an anti-MS4A4A antibody of the present disclosure binds to a region or epitope in human MS4A4A comprising amino acid residues 155-177 of human MS4A4A of SEQ ID NO:1. In some embodiments, an anti-MS4A4A antibody of the present disclosure binds to one or more amino acids within amino acid residues 155-177 of human MS4A4A of SEQ ID NO:1. In some embodiments, an anti-MS4A4A antibody of the present disclosure binds to a region or epitope in human MS4A4A comprising the amino acid sequence LAFYSFHHPYCNYYG (SEQ ID NO:296). In some embodiments, an anti-MS4A4A antibody of the present disclosure binds to one or more amino acid residues within the amino acid sequence LAFYSFHHPYCNYYG (SEQ ID NO:296). In some embodiments, an anti-MS4A4A antibody of the present disclosure binds to a region or epitope in human MS4A4A comprising the amino acid sequence FYSFHHPYCNYYGNS (SEQ ID NO:297). In some embodiments, an anti-MS4A4A antibody of the present disclosure binds to one or more amino acid residues within the amino acid sequence FYSFHHPYCNYYGNS (SEQ ID NO:297). In some embodiments, an anti-MS4A4A antibody of the present disclosure binds to a region or epitope in human MS4A4A comprising the amino acid sequence SFHHPYCNYYGNSNN (SEQ ID NO:298). In some embodiments, an anti-MS4A4A antibody of the present disclosure binds to one or more amino acid residues within the amino acid sequence SFHHPYCNYYGNSNN (SEQ ID NO:298). In some embodiments, an anti-MS4A4A antibody of the present disclosure binds to a region or epitope in human MS4A4A comprising the amino acid sequence HHPYCNYYGNSNNCH (SEQ ID NO:299). In some embodiments, an anti-MS4A4A antibody of the present disclosure binds to one or more amino acid residues within the amino acids sequence HHPYCNYYGNSNNCH (SEQ ID NO:299). In some embodiments, an anti-MS4A4A antibody of the present disclosure binds to a region or epitope in human MS4A4A comprising the amino acid sequence PYCNYYGNSNNCHGT (SEQ ID NO:300). In some embodiments, an anti-MS4A4A antibody of the present disclosure binds to one or more amino acid residues within the amino acid sequence PYCNYYGNSNNCHGT (SEQ ID NO:300).

Any suitable competition assay or MS4A4A binding assay known in the art, such as BIAcore analysis, ELISA assays, or flow cytometry, may be utilized to determine whether an anti-MS4A4A antibody competes with (or competitively inhibits the binding of) one or more reference antibodies selected from 4A-2, 4A-3, 4A-4, 4A-5, 4A-6, 4A-7, 4A-8, 4A-9, 4A-10, 4A-11, 4A-12, 4A-13, 4A-14, 4A-15, 4A-16, 4A-17, 4A-18, 4A-19, 4A-20, 4A-21, 4A-23, 4A-24, 4A-201, 4A-202, 4A-203, 4A-204, 4A-205, 4A-206, 4A-207, 4A-208, 4A-209, 4A-210, 4A-213, 4A-214, 4A-216, 4A-217, 4A-219, 4A-25, 4A-26, 4A-239, 4A-225, and 4A-220, and any combination thereof for binding to MS4A4A. In an exemplary competition assay, immobilized MS4A4A or cells expressing MS4A4A on the cell surface are incubated in a solution comprising a first labeled antibody that binds to MS4A4A (e.g., human or non-human primate) and a second unlabeled antibody that is being tested for its ability to compete with the first antibody for binding to MS4A4A. The second antibody may be present in a hybridoma supernatant. As a control, immobilized MS4A4A or cells expressing MS4A4A is incubated in a solution comprising the first labeled antibody but not the second unlabeled antibody. After incubation under conditions permissive for binding of the first antibody to MS4A4A, excess unbound antibody is removed, and the amount of label associated with immobilized MS4A4A or cells expressing MS4A4A is measured. If the amount of label associated with immobilized MS4A4A or cells expressing MS4A4A is substantially reduced in the test sample relative to the control sample, then that indicates that the second antibody is competing with the first antibody for binding to MS4A4A. See, Harlow and Lane (1988) *Antibodies: A Laboratory Manual* ch. 14 (Cold Spring Harbor Laboratory, Cold Spring Harbor, N.Y.).

Further provided herein are anti-MS4A4A antibodies which competitively inhibit binding of and/or compete for binding with an anti-MS4A4A antibody comprising (a) a $V_H$ domain comprising (i) HVR-H1 comprising an amino acid sequence selected from the group consisting of SEQ ID NO:4, 5, 6, 7, 8, 9, 10, 11, 12, 13, 14, 15, 16, 17, 18, and 19, (ii) HVR-H2 comprising an amino acid sequence selected from the group consisting of SEQ ID NO: 20, 21, 22, 23, 24, 25, 26, 27, 28, 29, 30, 31, 32, 33, 34, 35, 36, and 37, and (iii) HVR-H3 comprising an amino acid sequence selected from the group consisting of SEQ ID NO: 38, 39, 40, 41, 42, 43, 44, 45, 46, 47, 48, 49, 50, 51, 52, 53, 54, and 55, and (b) a $V_L$ domain comprising (i) HVR-L1 comprising an amino acid sequence selected from the group consisting of SEQ ID NO: 56, 57, 58, 59, 60, 61, 62, 63, 64, 65, 66, 67, 68, 69, 70, 71, 72, 73, and 74, (ii) HVR-L2 comprising an amino acid sequence selected from the group consisting of SEQ ID NO: 75, 76, 77, 78, 79, 80, 81, 82, 83, 84, and 85, and (iii) HVR-L3 comprising an amino acid sequence selected from the group consisting of SEQ ID NO: 86, 87, 88, 89, 90, 91, 92, 93, 94, 95, 96, 97, 98, 99, and 100. In some embodiments, the antibody comprises the $V_H$ and $V_L$ sequences in SEQ ID NOs:101-120 and SEQ ID NOs:121-139, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising an amino acid sequence selected from the group consisting of SEQ ID NO:4, 5, 6, 7, 8, 9, 10, 11, 12, 13, 14, 15, 16, 17, 18, and 19, (ii) HVR-H2 comprising an amino acid sequence selected from the group consisting of SEQ ID NO: 20, 21, 22, 23, 24, 25, 26, 27, 28, 29, 30, 31, 32, 33, 34, 35, 36, and 37, and (iii) HVR-H3 comprising an amino acid sequence selected from the group consisting of SEQ ID NO: 38, 39, 40, 41, 42, 43, 44, 45, 46, 47, 48, 49, 50, 51, 52, 53, 54, and 55, and (b) a $V_L$ domain comprising (i) HVR-L1 comprising an amino acid sequence selected from the group consisting of SEQ ID NO: 56, 57, 58, 59, 60, 61, 62, 63, 64, 65, 66, 67, 68, 69, 70, 71, 72, 73, and 74, (ii) HVR-L2 comprising an amino acid sequence selected from the group consisting of SEQ ID NO: 75, 76, 77, 78, 79, 80, 81, 82, 83, 84, and 85, and (iii) HVR-L3 comprising an amino acid sequence selected from the group consisting of SEQ ID NO: 86, 87, 88, 89, 90, 91, 92, 93, 94, 95, 96, 97, 98, 99, and 100. In some embodiments, the antibody comprises the $V_H$ and $V_L$ sequences in SEQ ID NOs:101-120 and SEQ ID NOs: 121-139, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising an amino acid sequence selected from the group consisting of SEQ ID NO: 142, 143, 144, 145, 146, 147, 148, 149, 150, 151, 152, and 153, (ii) HVR-H2 comprising an amino acid sequence selected from the group consisting of SEQ ID NO: 154, 155, 156, 157, 158, 159, 160, 161, 162, 163, 164, 165, 166, and 167, and (iii) HVR-H3 comprising an amino acid sequence selected from the group consisting of SEQ ID NO: 168, 169, 170, 171, 172, 173, 174, 175, 176, 177, 178, 179, 180, 181, and 182, and (b) a $V_L$ domain comprising (i) HVR-L1 comprising an amino acid sequence selected from the group consisting of SEQ ID NO: 183, 184, 185, 186, 187, 188, 189, 190, 191, 192, 193, 194, 195, and 196, (ii) HVR-L2 comprising an amino acid sequence selected from the group consisting of SEQ ID NO: 81, 197, 198, 199, 200, 201, 202, 203, 204, 205, 206, 207, 208, and 209, and (iii) HVR-L3 comprising an amino acid sequence selected from the group consisting of SEQ ID NO: 210, 211, 212, 213, 214, 215, 216, 217, 218, 219, 220, 221, 222, 223, and 224. In some embodiments, the antibody comprises the $V_H$ and $V_L$ sequences in SEQ ID NOs:225-239 and SEQ ID NOs:240-254, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising an amino acid sequence selected from the group consisting of SEQ ID NO: 142, 143, 144, 145, 146, 147, 148, 149, 150, 151, 152, and 153, (ii) HVR-H2 comprising an amino acid sequence selected from the group consisting of SEQ ID NO: 154, 155, 156, 157, 158, 159, 160, 161, 162, 163, 164, 165, 166, and 167, and (iii) HVR-H3 comprising an amino acid sequence selected from the group consisting of SEQ ID NO: 168, 169, 170, 171, 172, 173, 174, 175, 176, 177, 178, 179, 180, 181, and 182, and (b) a $V_L$ domain comprising (i) HVR-L1 comprising an amino acid sequence selected from the group consisting of SEQ ID NO: 183, 184, 185, 186, 187, 188, 189, 190, 191, 192, 193, 194, 195, and 196, (ii) HVR-L2 comprising an amino acid sequence selected from the group consisting of SEQ ID NO: 81, 197, 198, 199, 200, 201, 202, 203, 204, 205, 206, 207, 208, and 209, and (iii) HVR-L3 comprising an amino acid sequence selected from the group consisting of SEQ ID NO: 210, 211, 212, 213, 214, 215, 216, 217, 218, 219, 220, 221, 222, 223, and 224. In some embodiments, the antibody comprises the $V_H$ and $V_L$ sequences in SEQ ID NOs:225-239 and SEQ ID NOs:240-254, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising an amino acid sequence selected from the group consisting of SEQ ID NO: 304, 305, 306, 307, 308, and 309, (ii) HVR-H2 comprising an amino acid sequence selected from the group consisting of SEQ ID NO: 310, 311, 312, 313, 314, and 315, and (iii) HVR-H3 comprising an amino acid sequence selected from the group consisting of SEQ ID NO: 316, 317, 318, 319, 320, and 321, and (b) a $V_L$ domain comprising (i) HVR-L1 comprising an amino acid sequence selected from the group consisting of SEQ ID NO: 322, 323, 324, 325, 326, and 327, (ii) HVR-L2 comprising an amino acid sequence selected from the group consisting of SEQ ID NO: 328, 329, 330, 331, 332, and 333, and (iii) HVR-L3 comprising an amino acid sequence selected from the group consisting of SEQ ID NO: 334, 335, 336, 337, 338, and 339. In some embodiments, the antibody comprises the $V_H$ and $V_L$ sequences in SEQ ID NOs:340-345 and SEQ ID NOs:346-351, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising an amino acid sequence selected from the group consisting of SEQ ID NO: 304, 305, 306, 307, 308, and 309, (ii) HVR-H2 comprising an amino acid sequence selected from the group consisting of SEQ ID NO: 310, 311, 312, 313, 314, and 315, and (iii) HVR-H3 comprising an amino acid sequence selected from the group consisting of SEQ ID NO: 316, 317, 318, 319, 320, and 321, and (b) a $V_L$ domain comprising (i) HVR-L1 comprising an amino acid sequence selected from the group consisting of SEQ ID NO: 322, 323, 324, 325, 326, and 327, (ii) HVR-L2 comprising an amino acid sequence selected from the group consisting of SEQ ID NO: 328, 329, 330, 331, 332, and 333, and (iii) HVR-L3 comprising an amino acid sequence selected from the group consisting of SEQ ID NO: 334, 335, 336, 337, 338, and 339. In some embodiments, the antibody comprises the $V_H$ and $V_L$ sequences in SEQ ID NOs:340-345 and SEQ ID NOs: 346-351, respectively. In some embodiments, the epitope of human MS4A4A is the same epitope as bound by an anti-MS4A4A antibody.

In some embodiments, the anti-MS4A4A antibody according to any of the above embodiments is a monoclonal antibody, including a humanized and/or human antibody. In some embodiments, the anti-MS4A4A antibody is an antibody fragment, e.g., a Fv, Fab, Fab', scFv, diabody, or F(ab')2 fragment. In some embodiments, the anti-MS4A4A antibody is a substantially full-length antibody, e.g., an IgG1 antibody, IgG2a antibody or other antibody class or isotype as defined herein.

In some embodiments, an anti-MS4A4A antibody according to any of the above embodiments may incorporate any of the features, singly or in combination, as described in Sections 1-7 below:

(1) Anti-MS4A4A Antibody Binding Affinity

In some embodiments of any of the antibodies provided herein, the antibody has a dissociation constant (Kd) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881(1999)). In some embodiments, Kd is measured using a BIACORE surface plasmon resonance assay, for example, an assay using a BIACORE-2000 or a BIACORE-3000 (BIAcore, Inc., Piscataway, N.J.) is performed at 25° C. with immobilized antigen CM5 chips at ~10 response units (RU). In some embodiments, the $K_D$ is determined using a monovalent antibody (e.g., a Fab) or a full-length antibody. In some embodiments, the $K_D$ is determined using a full-length antibody in a monovalent form.

(2) Antibody Fragments

In some embodiments of any of the antibodies provided herein, the antibody antibodies is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087,409 Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology Human variable regions from intact antibodies generated by such animals may be further modified, e.g., by combining with a different human constant region.

Human antibodies can also be made by hybridoma-based methods Human myeloma and mouse-human heteromyeloma cell lines for the production of human monoclonal antibodies have been described. (See, e.g., Kozbor J. Immunol. 133:3001 (1984) and Boerner et al. J. Immunol. 147:86 (1991)) Human antibodies generated via human B-cell hybridoma technology are also described in Li et al. Proc. Natl. Acad. Sci. USA, 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. Histology and Histopathology 20(3):927-937 (2005) and Vollmers et al. Methods and Findings in Experimental and Clinical Pharmacology 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(−2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more MS4A4A activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to MS4A4A.

It may also be desirable to modify an anti-MS4A4A antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-MS4A4A antibody of the present disclosure to modify effector function to increase finding selectivity toward the ITIM-containing FcgRIIb (CD32b) to increase clustering of MS4A4A antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or IgG$_4$) that is responsible for increasing the in vivo serum half-life of the IgG molecule. Other amino acid sequence modifications.

(6) Multispecific Antibodies

Multispecific are antibodies that have binding specificities for at least two different epitopes, including those on the same or another polypeptide (e.g., one or more MS4A4A polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab')$_2$ bispecific antibodies). In some embodiments, the multispecific antibody comprises a first antigen binding region which binds to first site on MS4A4A and comprises a second antigen binding region which binds to a second site on MS4A4A. In some embodiment, the multispecific antibodies comprises a first antigen binding region which binds to MS4A4A and a second antigen binding region that binds to a second polypeptide.

Provided herein are multispecific antibodies comprises a first antigen binding region, wherein the first antigen binding region comprises the six HVRs of an antibody described herein, which binds to MS4A4A and a second antigen binding region that binds to a second polypeptide. In some embodiments, the first antigen binding region comprises the $V_H$ or $V_L$ of an antibody described herein.

In some embodiments of any of the multispecific antibodies, the second polypeptide is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and/or (e) a protein, lipid, polysaccharide, or glycolipid expressed on one or more tumor cells and any combination thereof.

Numerous antigens are known in the art that facilitate transport across the blood-brain barrier (see, e.g., Gabathuler R. *Neurobiol. Dis.* 37:48-57 (2010)). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10):e13741 (2010)).

The multivalent antibodies may recognize the MS4A4A antigen as well as without limitation additional antigens Aβ peptide, antigen or an α-synuclein protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier. In some embodiments, the second polypeptide is transferrin. In some embodiments, the second polypeptide is Tau. In some embodiments, the second polypeptide is Aβ. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1 Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple MS4A4A (see, US 2008/0069820, for example).

(7) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE A

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.*, 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fc is an antibody Fc isotypes and/or modification. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci* USA, 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA*, 103:4005-4010 (2006)), or one or more of L234F, L235E, and/or P331S mutations (Sazinsky et al. *Proc Natl Acad Sci USA*, 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-MS4A4A antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol,* 200:16-26 (2000)); G237A (Cole et al. *Transplantation,* 68:563-571 (1999)); H268Q, V309L, A330S, P331S (US 2007/0148167; Armour et al. *Eur J Immunol* 29: 2613-2624 (1999); Armour et al. *The Haematology Journal* 1(Suppl.1):27 (2000); Armour et al. *The Haematology Journal* 1(Suppl.1):27 (2000)), C219S, and/or C220S (White et al. *Cancer Cell* 27, 138-148 (2015)); S267E, L328F (Chu et al. *Mol Immunol,* 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1(CH1) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(8) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxypolyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. *J. Med. Chem.*, 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH- (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates, and Ducry et al. *Bioconjugate Chemistry* 21 (1):5-13 (2010).

II. Nucleic Acids, Vectors, and Host Cells

Anti-MS4A4A antibodies of the present disclosure may be produced using recombinant methods and compositions, e.g., as described in U.S. Pat. No. 4,816,567. In some embodiments, isolated nucleic acids having a nucleotide sequence encoding any of the anti-MS4A4A antibodies of the present disclosure are provided. Such nucleic acids may encode an amino acid sequence comprising the V$_L$ and/or an amino acid sequence comprising the V$_H$ of the anti-MS4A4A antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the V$_L$ of the antibody and an amino acid sequence comprising the V$_H$ of the antibody, or (2) a first vector comprising a nucleic acid that encodes an amino acid sequence comprising the V$_L$ of the antibody and a second vector comprising a nucleic acid that encodes an amino acid sequence comprising the V$_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-MS4A4A antibody of the present disclosure are provided. In some embodiments, the method includes culturing a host cell of the present disclosure comprising a nucleic acid encoding the anti-MS4A4A antibody, under conditions suitable for expression of the antibody. In some embodiments, the antibody is subsequently recovered from the host cell (or host cell culture medium).

For recombinant production of an anti-MS4A4A antibody of the present disclosure, a nucleic acid encoding the anti-MS4A4A antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-MS4A4A antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-MS4A4A antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

III. Pharmaceutical Compositions/Formulations

Provided herein are pharmaceutical compositions and/or pharmaceutical formulations comprising the anti-MS4A4A antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy*, Pharmaceutical Press 22nd ed. (2013). For a brief review of methods for drug delivery, see, Langer, *Science* 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-MS4A4A antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid.

IV. Therapeutic Uses

As disclosed herein, anti-MS4A4A antibodies of the present disclosure may be used for preventing, reducing risk, or treating diseases and disorders. In some embodiments, an anti-MS4A4A antibody of the present disclosure is effective at preventing, reducing risk, or treating Alzheimer's disease, late onset Alzheimer's disease, and cognitive impairment.

MS4A4A as a Disease Target

Genome wide association studies have identified various members of the MS4A family are associated with Alzheimer's disease. These are MS4A2, MS4A3, MS4A4A, MS4A4E, MS4A6A, and MS4A6E. The associated SNPs are found in the 3' UTR of MS4A6A (r5610932) and the intergenic region between MS4A4E and MS4A6A (r5670139). There are three SNPs in the MS4A gene cluster that have been associated with an increased risk of late-onset Alzheimer's disease. These include rs4938933 in MS4A4A, rs670139 in MS4A4E, and rs610932 in MS4A6A (Hollingworth et al, 2011, Nat Genetics, 43:429-435; Naj et al, 2011, Nature Genetics, 43:436-441; Antunez et al, 2011, Genome Medicine, 3, article 33). Additionally, MS4A4A locus SNPs (r52304933 and r52304935) associated with higher levels of MS4A4A and increased Alzheimer's disease risk, including late-onset Alzheimer's disease (LOAD) (Allen et al, 2012, Neurology, 79:221-228).

The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disorder, the method comprising administering to the individual in need thereof a therapeutically effective amount of an anti-MS4A4A antibody.

In some embodiments, the present disclosure provides a method for preventing, reducing the risk, or treating an individual having Alzheimer's disease, the method comprising administering to the individual in need thereof a therapeutically effective amount of an anti-MS4A4A antibody.

In some embodiments, the present disclosure provides a method for preventing, reducing the risk, or treating an individual having late onset Alzheimer's disease, the method comprising administering to the individual in need thereof a therapeutically effective amount of an anti-MS4A4A antibody.

In some embodiments, the present disclosure provides a method for preventing, reducing the risk, or treating an individual having mild cognitive impairment, the method comprising administering to the individual in need thereof a therapeutically effective amount of an anti-MS4A4A antibody.

In some embodiments, the present disclosure provides a method for preventing, reducing risk, or treating an individual having a disease, disorder, or condition associated with over expression or increased activity of MS4A4A, the method comprising administering to an individual in need thereof a therapeutically effective amount of an anti-MS4A4A antibody.

In some embodiments, the present disclosure provides a method for preventing, reducing risk, or treating an individual having a disease, disorder, or condition associated with decreased expression or activity of MS4A4A, the method comprising administering to an individual in need thereof a therapeutically effective amount of an anti-MS4A4A antibody.

Other aspects of the present disclosure relate to a method of preventing, reducing risk, or treating an individual having a disease, disorder, or injury selected from the group consisting of frontotemporal dementia, Alzheimer's disease, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A4A antibody of any of the preceding embodiments. Other aspects of the present disclosure relate to an anti-MS4A4A antibody of any of the preceding embodiments for use in preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of older individual, and one or more undesirable symptoms of normal aging. Other aspects of the present disclosure relate to an anti-MS4A4A antibody of any of the preceding embodiments for use in preventing or reducing metastasis. Other aspects of the present disclosure relate to an anti-MS4A4A antibody of any of the preceding embodiments for use in preventing, reducing risk, or treating an individual having cancer.

Other aspects of the present disclosure relate to use of an anti-MS4A4A antibody of any of the preceding embodiments in the manufacture of a medicament for preventing, reducing risk, or treating an individual having a disease, disorder, or injury selected from the group consisting of frontotemporal dementia, Alzheimer's disease, late-onset Alzheimer's disease, mild cognitive impairment, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitations inflammation, neuronal loss, and cognitive deficits, such as cognitive deficits in the absence of known brain disease, including cognitive deficits of the frontal cerebral cortex of older individual and one or more undesirable symptoms of normal aging. Other aspects of the present disclosure relate to a method of preventing, reducing risk, or treating an individual having a disease, disorder, or injury selected from the group consisting of frontotemporal dementia, progressive supranuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis, comprising administering to the individual a therapeutically effective amount of the anti-MS4A4A antibody of any of the preceding embodiments. Other aspects of the present disclosure relate to an anti-MS4A4A antibody of any of the preceding embodiments for use in preventing, reducing risk, or treating an individual having a disease, disorder, or injury selected from the group consisting of frontotemporal dementia, progressive supranuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis. Other aspects of the present disclosure relate to use of an anti-MS4A4A antibody of any of the preceding embodiments in the manufacture of a medicament for preventing, reducing risk, or treating an individual having a disease, disorder, or injury selected from the group consisting of frontotemporal dementia, progressive supranuclear palsy. Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis.

Several genes in the MS4A locus have been associated with the inflammatory response, including MS4A4A. (Karch and Goate, 2015, Biol Psychiatry, 77:43-51). Additionally, overexpression of MS4A family genes increased activation of T cells and promoted trafficking of T cells across the blood brain barrier. Activated T cells interact with microglia, causing microglia to activate, resulting in the release of pro-inflammatory cytokines, leading to damage of neurons. Overexpression of MS4A4B reduced T cell apoptosis, whereas knockdown of MS4A4B promoted T cells to undergo apoptosis. (Ma et al, 2015, Mol Neurobiol, 51:1240-1248.)

Autoinflammatory diseases are a group of clinical conditions, different from autoimmune syndromes. Autoinflammatory diseases are characterized by episodes of unprovoked inflammation, due to dysregulation of the innate immune system, without autoreactive T lymphocytes and autoantibodies and are therefore different from classical autoimmune diseases. Two groups of autoinflammatory diseases have been classified: monogenic autoinflammatory diseases and multifactorial autoinflammatory diseases. In some embodiments, an autoinflammatory disorder to be prevented or treated by the methods of the present disclosure includes, but is not limited to, monogenic autoinflammatory diseases such as familial Mediterranean fever (FMF), periodic fever associated with mevalonate kinase deficiency (hyperimmunoglobulin D syndrome), TNF receptor-associated periodic syndrome (TRAPS), cryopyrin-associated periodic syndrome (CAPS), NLRP12-associated autoinflammatory disorders (e.g., NALP12-associated periodic fever), deficiency of interleukin-1 receptor antagonist (DIRA), pyogenic arthritis-pyoderma gangrenosum and acne (PAPA) syndrome, Majeed syndrome, Blau's syndrome, hyperimmuno globulinemia W with periodic fever syndrome (HIDS), familial cold autoinflammatory syndrome (FCAS), Muckle-Wells syndrome (MWS), and neonatal onset of multisystemic inflammatory disorder (NOMID). In some embodiments, an autoinflammatory disorder to be prevented or treated by the methods of the present disclosure includes, but is not limited to, multifactorial autoinflammatory diseases such as include periodic fever, aphthous stomatitis, pharyngitis, and adenopathy syndrome (PFAPA), Behcet's disease, systemic juvenile idiopathic arthritis (sJIA), Still's disease, adult-onset Still's disease (AOSD), Crohn's disease, Schnitzler's syndrome, Sweet's syndrome, Chronic recurrent multifocal osteomyelitis (CRMO), synovitis acne pustulosis hyperostosis osteitis syndrome (SAPHO), and adult-onset Still disease. (See Ciccarelli et al, 2013, Curr Med Chem, 21:261-269.)

Although MS4A genes are poorly characterized, an important role in immunity has been shown for several members of this cluster, including MS4A1, MS4A2, and MS4A4B (Zuccolo et al, 2010, PLoS One; Zuccolo et al, 2013, Front Immmunol, 4:195).

Autoimmune diseases arise from an abnormal immune response to normal body tissue. In some embodiments, an autoimmune disease or disorder to be prevented or treated by the method of the present disclosure includes, but is not limited to, Addison's disease, agammaglobulinemia, alopecia areata, amyloidosis, ankylosing spondylitis, Anti-GBM/Anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune pancreatitis, autoimmune retinopathy, autoimmune urticaria, axonal & neuronal neuropathy (AMAN), Baló disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Churg-Strauss, cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with Polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hypogammalglobulinemia, IgA Nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosis, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, multiple sclerosis, myasthenia gravis, myositis, narcolepsy, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, and III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome (SPS), subacute bacterial endocarditis (SBE), Susac's syndrome, sympathetic ophthalmia (SO), Takayasu's arteritis, temporal arteritis/giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, and Wegener's granulomatosis (or Granulomatosis with Polyangiitis (GPA)).

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

V. Diagnostic Uses

In some embodiments of any of the antibodies, any of the anti-MS4A4A antibodies provided herein is useful for detecting the presence of MS4A4A in a sample or an individual. The term "detecting" as used herein encompasses quantitative or qualitative detection. Provided herein are methods of using the antibodies of this disclosure for diagnostic purposes, such as the detection of MS4A4A in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VI. Articles of Manufacture

Provided herein are articles of manufacture (e.g., kit) comprising an anti-MS4A4A antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-MS4A4A antibody described herein) to prevent, reduce risk, or treat an individual having a disease, disorder, or injury selected from of frontotemporal dementia, Alzheimer's disease, late onset Alzheimer's disease, cognitive decline or impairment, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A4A antibody of any of the preceding embodiments.

In some embodiments, the instructions include instructions for use of the anti-MS4A4A antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1: Construction of MS4A4A Expression Plasmids for DNA Immunization

A DNA immunization approach was used for developing antibodies directed against MS4A4A. cDNA sequences encoding human MS4A4A (SEQ ID NO:1) and cynomolgus (cyno) MS4A4A (SEQ ID NO:3) were cloned into the pCAGGS expression vector (KeraFAST EH1017) for DNA immunization. Expression of each MS4A4A polypeptide was confirmed by transient transfection of the expression constructs into HEK293T cells, followed by extracellular flow cytometry using commercially-available anti-MS4A4A antibodies (clone 5C12, BioLegend Cat #372502; clone 3F2, Millipore Cat #MABC1174; clone 4H2, Kerafast Cat #EUC003). The expression constructs were then used for DNA immunization in mice as described below.

Example 2: Generation of Anti-MS4A4A Hybridoma Antibodies

In order to obtain antibodies against MS4A4A, the following procedures were used to generate hybridomas. Balb/c or SJL mice (Jackson Laboratory, Bar Harbor, Me.) were co-immunized weekly with 50 µg each of plasmid DNA expression construct encoding full-length human or cyno MS4A4A with or without mFlt3 ligand (DNA) and mGM-CSF (DNA) (Invitrogen, San Diego, Calif.) diluted in lactated Ringer's solution. A total of 8 injections of the MS4A4A expression plasmids for DNA immunization were performed per mouse. Spleens were harvested from the mice three days following the final DNA immunization. Sera from the mice were analyzed for reactivity to MS4A4A by FACS analyses using HEK293 cells overexpressing human and/or cyno MS4A4A. Splenocytes from mice whose sera demonstrated strong binding to HEK293 cells overexpressing human and/or cyno MS4A4A by FACS were fused with P3X63Ag8.653 mouse myeloma cells (CRL-1580, American Type Culture Collection, Rockville, Md.) via electrofusion (ECM 2001, BTX, Holliston, Mass.) and incubated at 37° C., 5% $CO_2$, overnight in Clonacell-HY Medium C (StemCell Technologies, Vancouver, BC, Canada).

The following day, the fused cells were centrifuged and resuspended in 10 mls of ClonaCell-HY Medium C with anti-mouse IgG Fc-FITC (Jackson Immunoresearch, West Grove, Pa.) and then gently mixed with 90 mls of methylcellulose-based ClonaCell-HY Medium D (Stemcell Technologies) containing HAT components. The cells were plated into Nunc OmniTrays (Thermo Fisher Scientific, Rochester, N.Y.) and allowed to grow at 37° C., 5% $CO_2$ for eight days. Fluorescent colonies were selected and transferred into 96-well plates containing Clonacell-HY Medium E (StemCell Technologies) using a Clonepix 2 (Molecular Devices, Sunnyvale, Calif.). After five days, tissue culture supernatants from the hybridomas were screened by FACS against HEK293 cells overexpressing full length human MS4A4A, as described below. In total 706 hybridoma clones were generated from four independent rounds of fusion.

Example 3: Transfection of HEK293 Cells with MS4A4A cDNA

HEK293 cells were transfected with an expression plasmid encoding human MS4A4A as follows. HEK293 (ATCC CRL-1573) cells were cultured in Dulbecco's Modified Eagle's Medium ((DMEM), Sigma)+10% FBS (Gibco) until >80% confluent. The cells were then dissociated with a non-enzymatic cell dissociation buffer (CellStripper, Corning) and plated at 40-50% confluency in T150 flasks (ThermoFischerScientific Cat #08-772-48) 24 hours prior to transfection. Transfection was carried out using Lipofectamine 3000 (ThermoFischerScientific), according to the manufacturer's protocol. Cells were harvested 24 hours after transfection in order to precede any toxic effects of MS4A4A over-expression in HEK293 cells. Harvested cells were either immediately used for FACS analyses to confirm cell surface expression of MS4A4A, or frozen in 10% DMSO for subsequent use.

Flow cytometry was performed as follows. Briefly, transiently transfected cells were labeled with LIVE/DEAD Fixable Aqua Dead Cell Stain Kit (ThermoFisher Scientific, Cat #L34957) on ice for 30 minutes. After a wash with PBS, $2 \times 10^5$ cells were aliquoted per well in 96-well U-bottom plates and incubated with 500 of culture supernatant on ice for 30 minutes. After primary incubation, the supernatant was removed via centrifugation, the cells were washed twice with 175 µl of ice-cold FACS buffer (PBS+1% FBS+2 mM EDTA), and then incubated on ice for 20 minutes with anti-mouse IgG Fc-APC (Jackson ImmunoResearch Labs, West Grove, Pa., Cat #115-136-071) diluted 1:200. Following this secondary incubation, the cells were again washed twice with ice-cold FACS buffer and resuspended in a final volume of 200 µl of FACS buffer. Analysis was performed on a FACS Canto system (BD Biosciences), with gates drawn to exclude dead (Aqua-positive) cells.

Figure 1B:
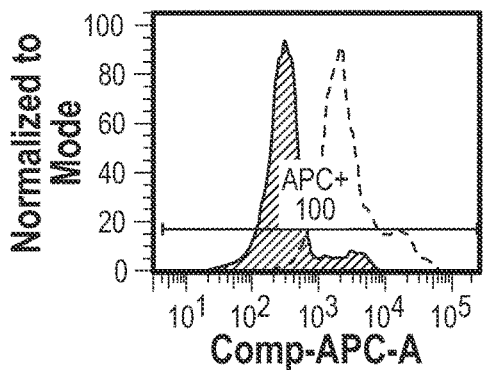
FIG. 1B shows representative FACS plots of HEK293 cells transiently transfected with cyno MS4A4A (clear trace) and non-transfected cells (shaded trace) stained with hybridoma supernatant containing anti-MS4A4A antibody of the present disclosure.
Figure 1C:
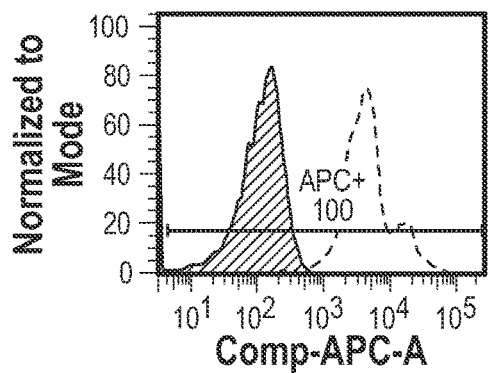
FIG. 1C shows representative FACS plots of HEK293 cells transiently transfected with human MS4A4A (clear trace) and non-transfected cells (shaded trace) stained with anti-MS4A4A antibody 5C12 (BioLegend).
Figure 1D:
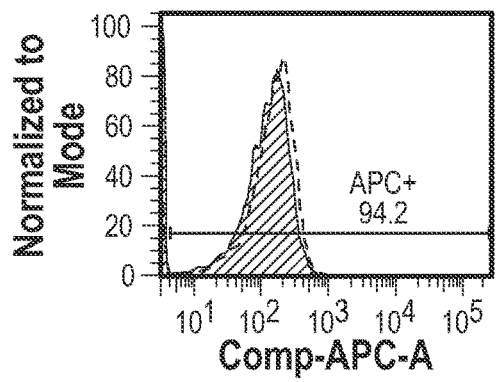
FIG. 1D shows representative FACS plots of HEK293 cells transiently transfected with cyno MS4A4A (clear trace) and non-transfected cells (shaded trace) stained with anti-MS4A4A antibody 5C12.

Representative FACS plots are shown in FIG. 1. In FIG. 1A, HEK293 cells transiently transfected with human MS4A4A (clear trace) and parental (non-transfected) HEK293 cells (shaded trace) were stained with hybridoma supernatant from one of the clones generated above. There was a 46-fold increase in mean fluorescence intensity (MFI) in this particular flow cytometry experiment. In FIG. 1B, HEK293 cells transfected with cyno MS4A4A (clear trace) or control cells (shaded trace) were labeled with the same supernatant, and a 8.5-fold increase in MFI is observed. In FIG. 1C, HEK293 cells transiently transfected with human MS4A4A (clear trace) and parental (non-transfected) HEK293 cells (shaded trace) were stained with antibody 5C12, a commercially available anti-MS4A4A antibody, with a 54-fold increase in MFI. In FIG. 1D, HEK293 cells transfected with cyno MS4A4A (clear trace) and parental (non-transfected) HEK cells (shaded trace) were stained with antibody 5C12. No cross-reactivity of 5C12 to cyno MS4A4A was observed.

Example 4: Transfection of Other Cell Lines with MS4A4A Expression Plasmids, and Generation of MS4A4A Knockout Cell Lines Given the difficulty for generating stably-transfected HEK293 cell lines expressing recombinant human MS4A4A, other DNA vectors and cell lines were tested to determine if they would be more compatible for MS4A4A expression. For stable transfection, MS4A4A coding sequence was introduced into expression vectors pD2533-G418 or pD3539-puro (Atum, Newark, Calif., USA).

MS4A4A is expressed natively in myeloid cells in vivo. Therefore, to overcome the observed toxicity issues using cells described above, several myeloid-derived cell lines were used for transient expression of recombinant MS4A4A. The panel of myeloid-derived cell lines included THP-1 cells (ATCC TIB202), U937 cells (ATCC CRL-1593.2), K562 cells (ATCC CCL243), HL60 cells (ATCC CCL240), and Kasumi-1 cells (ATCC CRL-2724). 300.19 cells (Tufts University T000710), a mouse pre-B cell line, was also tested as it is commonly used for recombinant protein expression purposes. Each of these cell lines were screened for antibiotic susceptibility in order to determine a suitable dose of G418 or puromycin for selection and transfection efficiency. Transfectants from U937 cells, K562 cells, and 300.19 cells were found to be viable after MS4A4A expression plasmid transfection and antibiotic selection. After cloning by limiting-dilution, individual clones were generated and screened for human MS4A4A protein cell surface expression using flow cytometry using methodology described above.

Figure 2A:
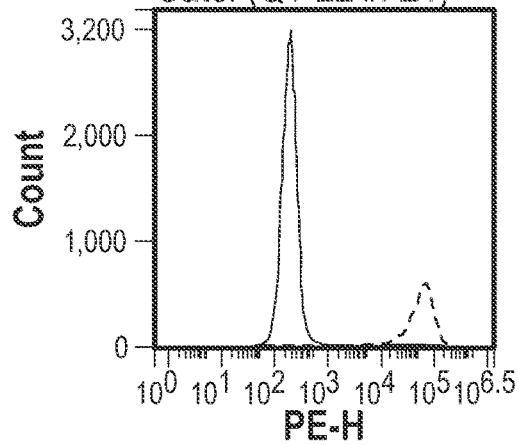
FIG. 2 shows FACS analysis of 300.19 cells (FIG. 2A), K562 cells (FIG. 2B) and U937 cells (FIG. 2C) transfected with human MS4A4A and stained with anti-MS4A4A antibody 5C12 (Biolegend); FACS analysis of 300.19 cells (FIG. 2D), K562 cells (FIG. 2E) and U937 cells (FIG. 2F) transfected with cyno MS4A4A, and stained with a hybridoma supernatant containing anti-MS4A4A of the present disclosure. In each panel of FIG. 2, solid traces on the left side correspond to untransfected cells and dashed traces on the right side correspond to transfected cells.
Figure 2B:
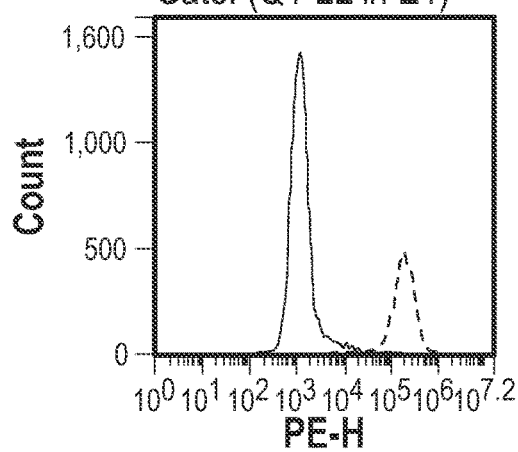
Figure 2C:
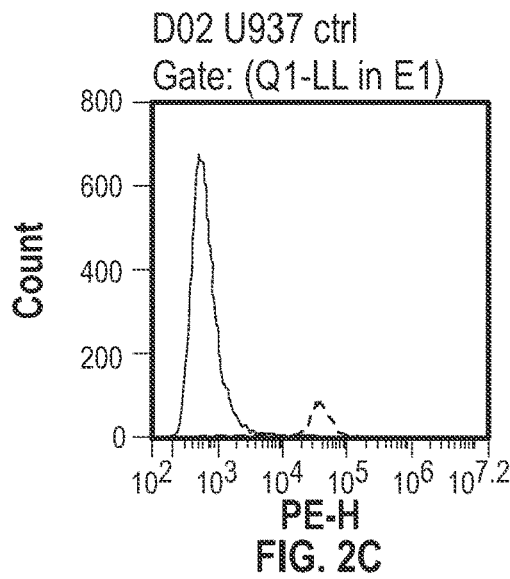
Figure 2D:
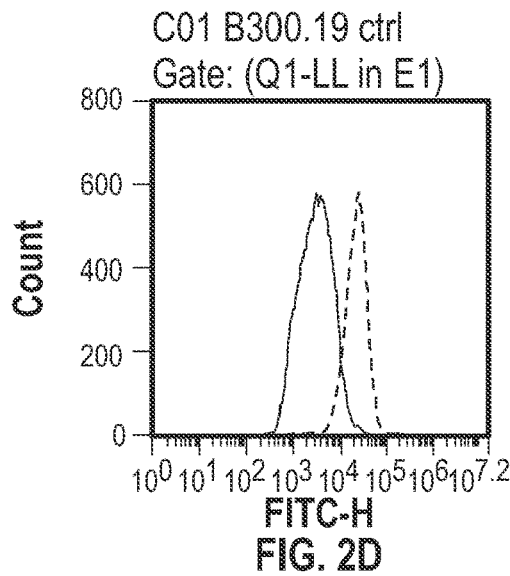
Figure 2E:
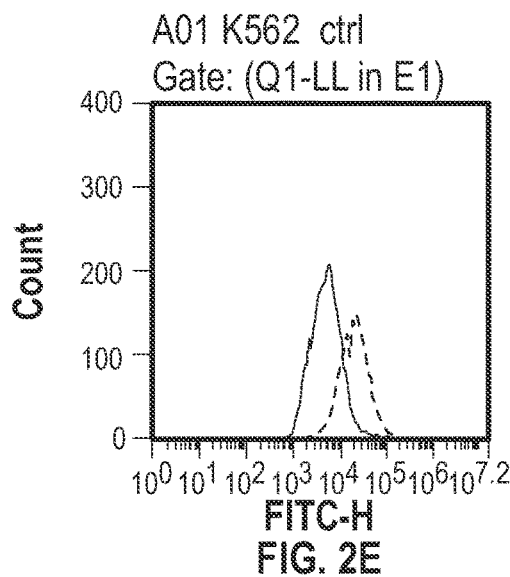
Figures 2F, 3A:
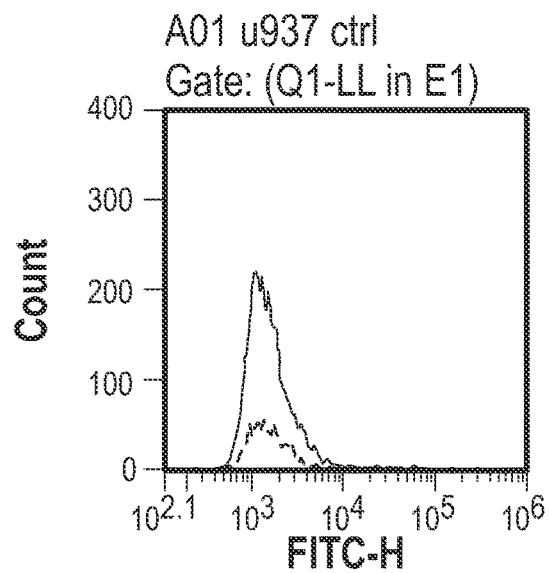
FIGS. 3A-3K show FACS analyses of anti-MS4A4A antibodies of the present disclosure binding to untransfected 300.19 cells (shading), 300.19 cells transfected with human MS4A4A (trace with dashed lines and dots), and 300.19 cells transfected with cyno MS4A4A (trace with dashed lines).

These results of these experiments are shown in FIG. 2. 300.19 cells (FIG. 2A), K562 (FIG. 2B), and U937 (FIG. 2C) were transfected with human MS4A4A and stained with antibody 5C12 (Biolegend). 300.19 cells (FIG. 2D), K562 (FIG. 2E), and U937 (FIG. 2F) were transfected with cyno MS4A4A, and stained with a hybridoma supernatant generated from Example 2 for flow cytometry. This was used as none of the prior art commercially available reagents (5C12, 4H2, 3F2) bind to cynomolgous MS4A4A. In each panel of FIG. 2, traces on the left side correspond to non-transfected cells; traces on the right side correspond to transfected cells. All clones were positive for anti-MS4A4A reactivity except for U937 cells transfected with cyno MS4A4A, despite the clone being subjected to antibiotic selection. These results indicate that anti-MS4A4A hybridoma supernatant of the present disclosure are capable of binding MS4A4A expressed on the surface of cells. The above-generated stable cell lines were then used for cell-based immunizations in mice and in subsequent screening methods as described below.

MS4A4A knockout cell lines were also produced to serve as negative control in binding and functional studies. U937 cell lines in which the MS4A4A gene was knocked-out were generated by CRISPR/Cas9 technology, using established methods in the art by Applied StemCell (Milpitas, Calif., USA). Two independent U937 cells lines with MS4A4A gene knockout were selected for subsequent studies. The absence of MS4A4A protein expression in these knockout cell lines was confirmed by flow cytometry after the cells were differentiated with 40 ng/ml PMA for two days, which induces MS4A4A expression on the surface of wildtype cells (data not shown).

Example 5: Primary Screening of Anti-MS4A4A Hybridomas

Initial screening of the anti-MS4A4A hybridomas was performed as follows. Tissue culture supernatants from 706 hybridomas obtained were initially screened for their ability to differentially bind human MS4A4A-transfected HEK293 cells by comparing the extent of binding to parental (non-transfected) HEK293 cells compared to transfected cells. MS4A4A-expressing cells were produced via transient transfection of HEK293 cells using the lipofectamine system, according to the manufacturer's protocol with modifications as described above in Example 3. To ensure reproducibility across screening experiments, a large bank of transfected cells ($\sim 1 \times 10^9$) was prepared in a single round of transient transfection, and aliquoted and frozen for all further screening experiments.

For screening of the hybridoma cell culture supernatants, human MS4A4A-transfected HEK293 cells were aliquoted in 96-well U-bottom plates ($2 \times 10^5$ cells per well) and incubated with 50 µL of hybridoma cell culture supernatant on ice for 30 minutes. After this primary incubation, the supernatant was removed via centrifugation, the cells were washed twice with 175 µL of ice-cold FACS buffer (PBS+1% FBS+2 mM EDTA), and then further incubated on ice for 20 minutes with anti-mouse IgG Fc-allophycocyanin (APC) (Jackson Labs, Cat #115-136-071) (diluted 1:200). Following this secondary incubation, the cells were again washed twice with ice-cold FACS buffer and resuspended in a final volume of 30 µL of FACS buffer+0.25 µl/well propidium iodide (BD Biosciences Cat #556463). Binding intensity on cells were analyzed by the FACS Canto system (BD Biosciences), with sort gates drawn to exclude propidium iodide-positive dead cells. Ratio of APC mean fluorescence intensity (MFI) on MS4A4A-transfectants vs. HEK293 parental cells was calculated for each hybridoma supernatant. A total of 47 clones were identified that displayed greater than 1.5-fold difference in binding to MS4A4A-transiently transfected HEK293 cells compared to binding to parental (non-transfected) HEK293 cells.

Positive clones identified above were expanded and then rescreened for specificity against HEK293 cells overexpressing human MS4A4A or cyno MS4A4A and parental HEK293 cells. These experiments were performed using supernatants from hybridoma clones which had undergone further expansion after initial selection. Briefly, previously prepared, cryopreserved transiently-transfected cells were labeled with LIVE/DEAD Fixable Aqua Dead Cell Stain Kit (ThermoFisher Scientific L34957) on ice for 30 minutes. After a wash with PBS, $2 \times 10^5$ cells were aliquoted per well in 96-well U-bottom plates and incubated with 50 µl of culture supernatant on ice for 30 minutes. After primary incubation, the supernatant was removed via centrifugation, the cells were washed twice with 175 µl of ice-cold FACS buffer (PBS+1% FBS+2 mM EDTA) and then incubated on ice for 20 minutes with anti-mouse IgG Fc-APC (Jackson ImmunoResearch Labs, West Grove, Pa., Cat #115-136-071) diluted 1:200. Following this secondary incubation, the cells were again washed twice with ice-cold FACS buffer and resuspended in a final volume of 200 µl of FACS buffer. Analysis was performed on a FACS Canto system (BD Biosciences), with sort gates drawn to exclude dead (Aqua-positive) cells. Ratio of APC MFI on MS4A4A+/HEK293 parental cells was calculated for each hybridoma; the results are shown in Table 1. Positive clones (fold change of 1.8 or greater) were carried forward for further testing. These clones were named as anti-MS4A4A antibodies 4A-1 to 4A-24 and further characterized as described below.

TABLE 1

| Ab ID | Human 4A:parental cell ratio | Cyno 4A:parental cell ratio |
|---|---|---|
| 4A-1 | 15.726 | 4.541 |
| 4A-2 | 20.151 | 9.626 |
| 4A-3 | 7.314 | 2.580 |
| 4A-4 | 4.779 | 2.001 |
| 4A-5 | 27.276 | 8.489 |
| 4A-6 | 33.148 | 7.630 |
| 4A-7 | 7.966 | 3.976 |
| 4A-8 | 5.698 | 3.302 |
| 4A-9 | 8.197 | 3.463 |
| 4A-10 | 6.547 | 2.326 |
| 4A-11 | 9.122 | 2.112 |
| 4A-12 | 9.583 | 3.965 |
| 4A-13 | 43.840 | 9.944 |
| 4A-14 | 4.204 | 0.647 |
| 4A-15 | 8.127 | 4.665 |
| 4A-16 | 5.927 | 2.654 |
| 4A-17 | 4.828 | 1.674 |
| 4A-18 | 46.273 | 8.387 |
| 4A-19 | 1.859 | 1.510 |
| 4A-20 | 1.918 | 0.951 |
| 4A-21 | 4.297 | 1.312 |
| 4A-22 | 2.654 | 1.477 |

TABLE 1-continued

| Ab ID | Human 4A:parental cell ratio | Cyno 4A:parental cell ratio |
|---|---|---|
| 4A-23 | 1.964 | 1.219 |
| 4A-24 | 7.518 | 0.771 |

Example 6: Anti-MS4A4A Antibody Binding to Peptides Corresponding to MS4A4A Extracellular Domains Anti-MS4A4A hybridoma supernatants were tested for binding to MS4A4A peptides corresponding to ECL1 (amino acid residues 86-98 of human MS4A4A of SEQ ID NO:1) and ECL2 (amino acid residues 159-179 of human MS4A4A of SEQ ID NO:1), using an enzyme-linked immunosorbent assay (ELISA). Briefly, 96-well polystyrene plates were coated with 1-10m/ml of synthetic free or BSA-conjugated peptides in coating buffer (0.05M carbonate buffer, pH9.6, Millipore Sigma C3041) overnight at 4° C. Coated plates were then blocked with ELISA diluent (PBS+0.5% BSA+0.05% Tween20) for 1-hour, washed 3×300 μL in PBST (PBS+0.05% Tween20, Thermo Cat #28352), and then the antibodies were added to the plate (50 μl/ml). After 30 mins incubation (room temperature, with shaking), the plates were washed 3×300 μL in PBST. A secondary anti-mouse HRP antibody (Jackson Immunoresearch Cat #115-035-003) was added at a 1:1000 dilution in ELISA diluent (50 μl/well) and incubated for 30 minutes at room temperature with shaking. After a final set of washes (3×300 μL in PBST), 504, of TMB substrate (BioFx TMBW-1000-01) was added and the reaction was then quenched after 5-10 mins with 504, of stop solution (BioFx BSTP-1000-01). The quenched reaction wells were detected for absorbance at 650 nm with a BioTek Synergy Microplate Reader using GEN5 2.04 software.

Of the 24 anti-MS4A4A positive hybridoma clones identified above, supernatants from 17 hybridoma clones displayed strong binding to the BSA-MS4A4A-ELC2 peptide compared to BSA-mouse DAP12, an irrelevant negative control peptide. The hybridoma clones displaying no binding may be accounted for by several factors, e.g., these anti-MS4A4A antibodies may bind to conformational epitopes that were not modeled by this methodology, or these antibodies may recognize epitopes that are made up of both ECL1 and ECL2.

Binding to ECL1, on the other hand, was not detected for any of the hybridoma clones screened using this method. This may be due to the smaller size of ECL1, which is 13 amino acid residues in length compared that of ECL2, which is 21 amino acid residues in length. If MS4A4A forms a four-helix bundle, then the larger ECL2 domain may dominate the exposed surface available for antibody binding. It is possible that certain antibodies identified herein recognize epitopes formed by a combination of amino acid residues located in ECL1 and ECL2, and thus would not be detected by this methodology.

The results of the ELISA binding experiments are shown below in Table 2.

TABLE 2

| Strong binding to MS4A4A-ECL2 BSA conjugated peptide | No binding detected |
|---|---|
| 4A-1, 4A-2, 4A-3, 4A-4, 4A-6, 4A-7, 4A-8, 4A-9, 4A-10, 4A-11, 4A-14, 4A-15, 4A-16, 4A-19, 4A-20, 4A-21, 4A-23 | 4A-5, 4A-12, 4A-13, 4A-17, 4A-18, 4A-22, 4A-24 |

Example 7: Anti-MS4A4A Screen on Stable Transfected Cell Lines

Anti-human MS4A4A antibody hybridoma clones identified from the initial rounds of selection were also screened for their ability to bind MS4A4A expressed on human myeloid cell lines K562 and U937, as well as murine myeloma cell line 300.19.

Flow cytometry was performed as follows. Briefly, transiently-transfected cells were labeled with LIVE/DEAD Fixable Aqua Dead Cell Stain Kit (ThermoFisher Scientific Cat #L34957) on ice for 30 minutes. After a wash with PBS, non-specific binding through Fc receptors, which are abundantly expressed on these cells, was blocked by incubating the cells with 1% BSA, 33% human serum (Sigma H4522) and 33% Human Fc block (Invitrogen 14-9161-73). $2 \times 10^5$ cells were aliquoted per well in 96-well U-bottom plates and incubated with 500 of culture supernatant on ice for 30 minutes. After this primary incubation, the supernatant was removed via centrifugation, the cells were washed twice with 175 μl of ice-cold FACS buffer (PBS+1% FBS+2 mM EDTA), and then incubated on ice for 20 minutes with anti-mouse IgG Fc-APC (Jackson ImmunoResearch Labs, West Grove, Pa., Cat #115-136-071) diluted 1:200. Following this secondary incubation, the cells were again washed twice with ice-cold FACS buffer and resuspended in a final volume of 200 μl of FACS buffer. Analysis was performed on a FACS Canto system (BD Biosciences), with gates drawn to exclude dead (Aqua-positive) cells.

Figure 3B:
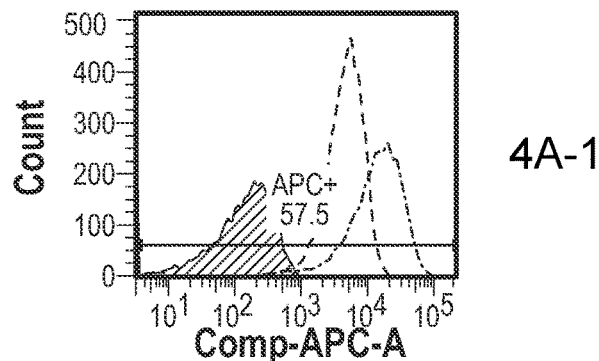
Figure 3B:
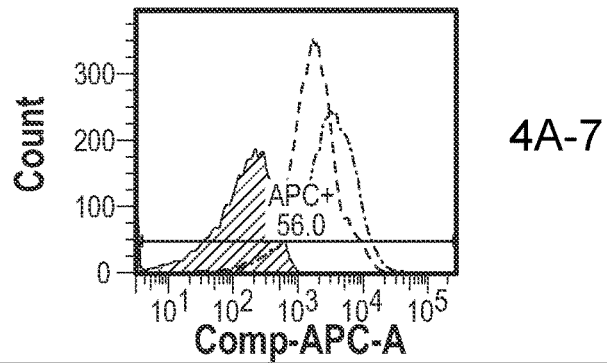
Figure 3B:
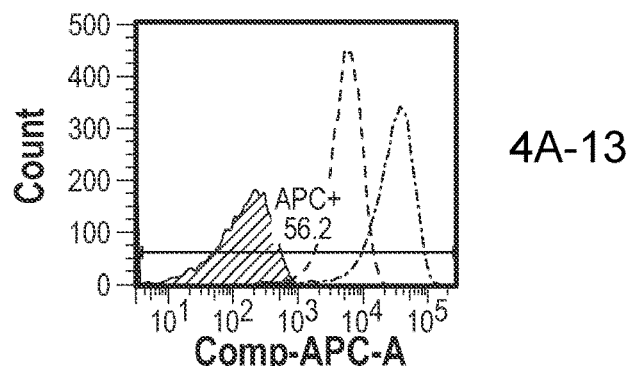
Figure 3C:
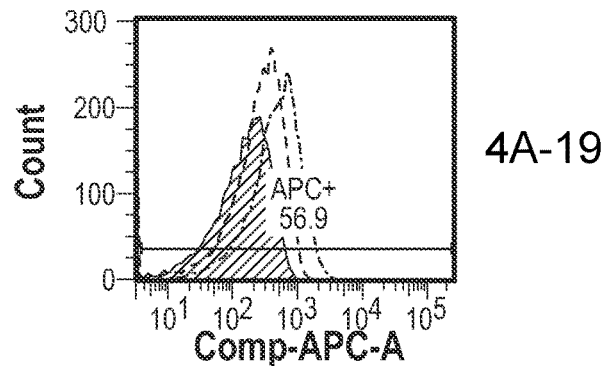
Figure 3C:
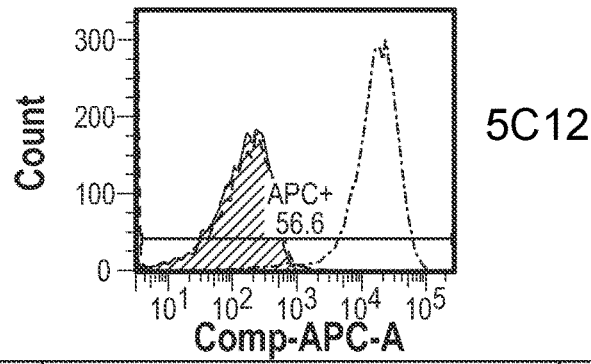
Figure 3C:
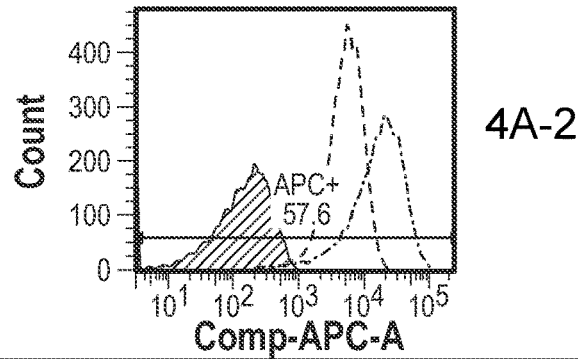
Figure 3D:
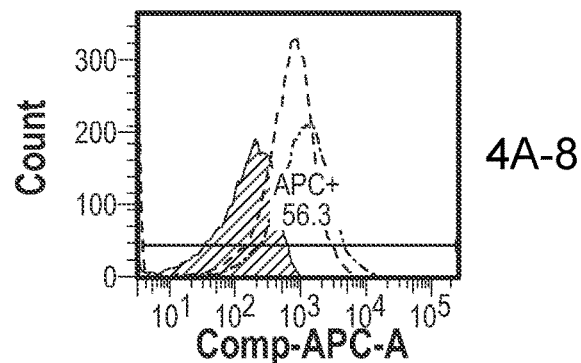
Figure 3D:
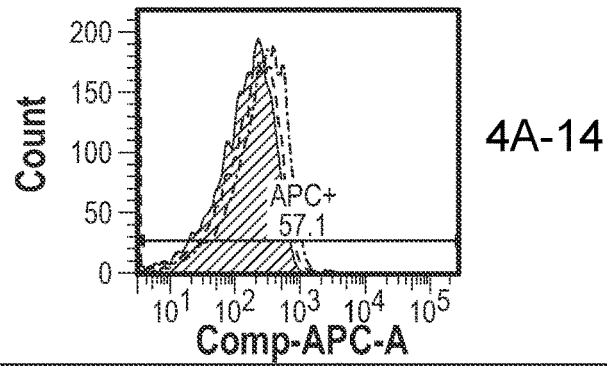
Figure 3D:
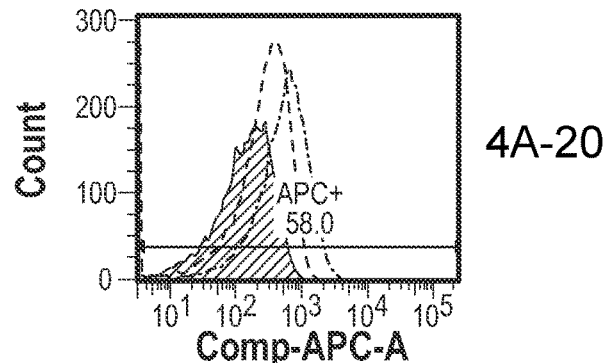
Figure 3E:
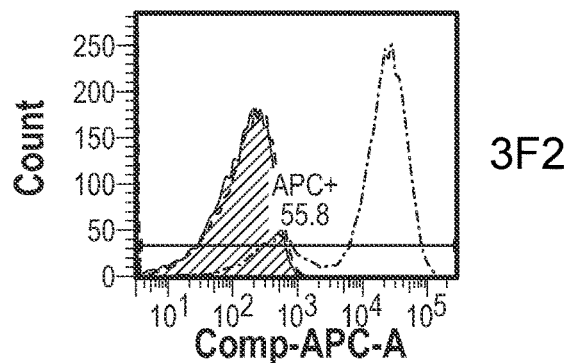
Figure 3E:
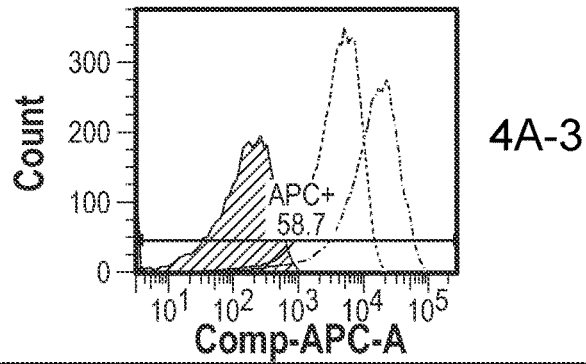
Figure 3E:
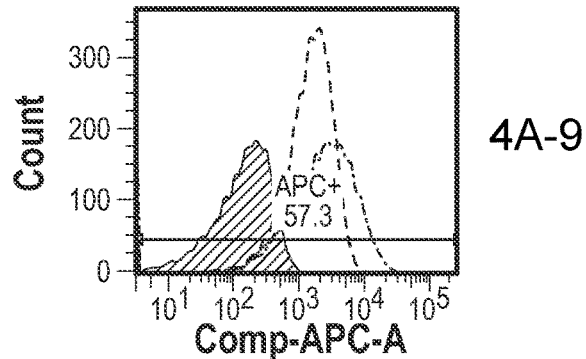
Figure 3F:
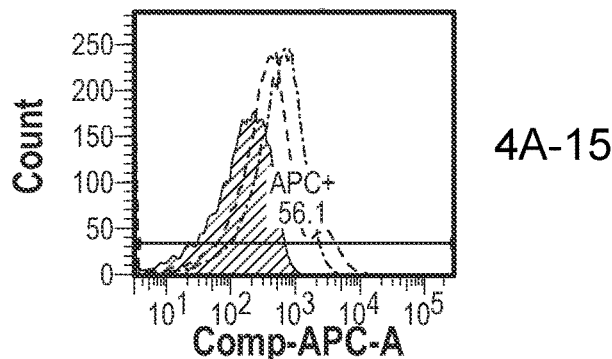
Figure 3F:
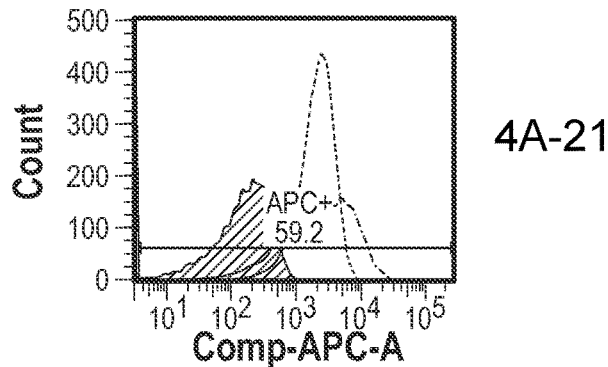
Figure 3F:
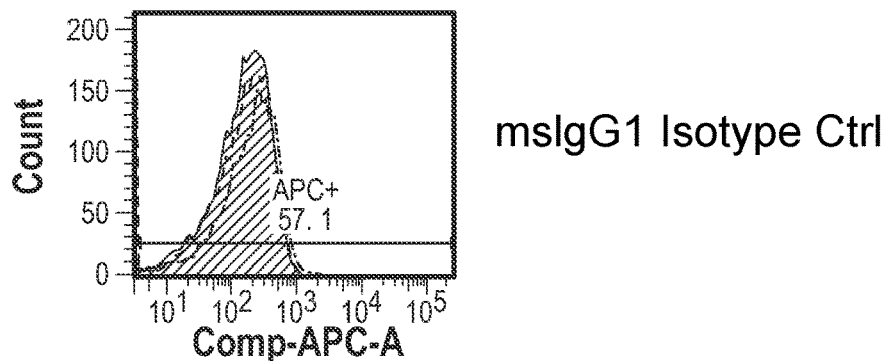
Figure 3G:
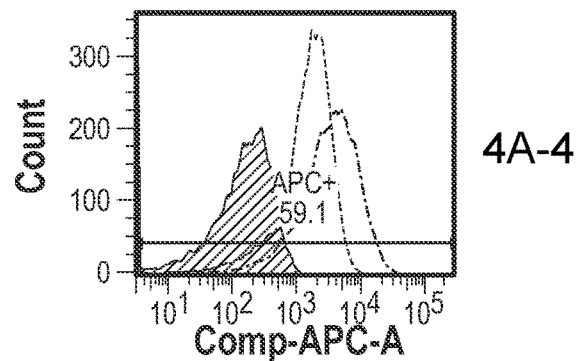
Figure 3G:
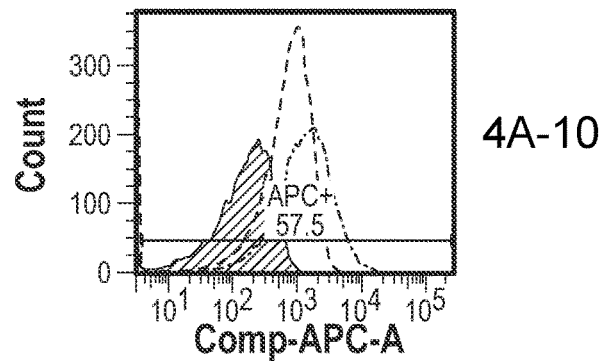
Figure 3G:
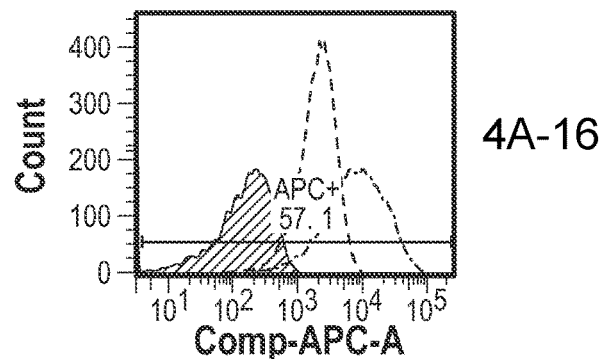
Figure 3H:
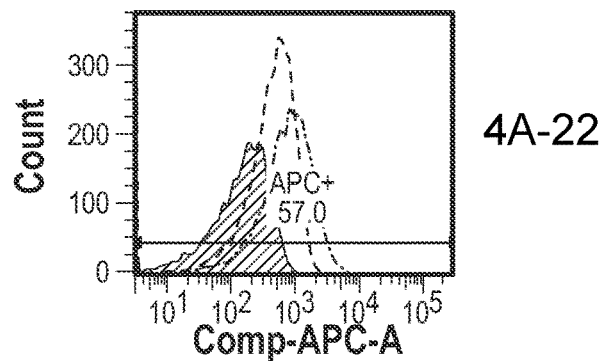
Figure 3H:
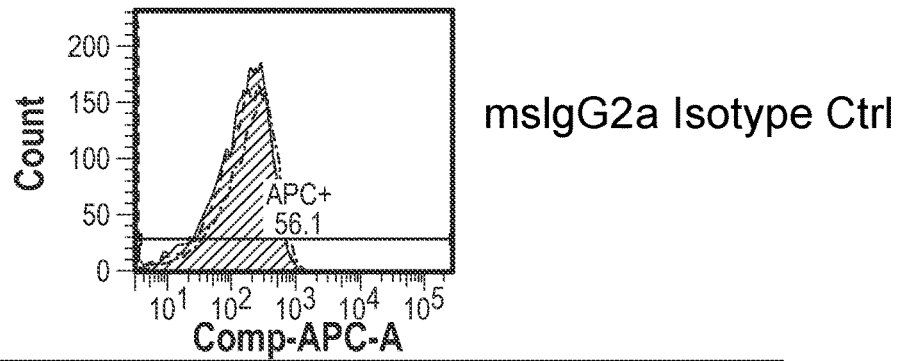
Figure 3H:
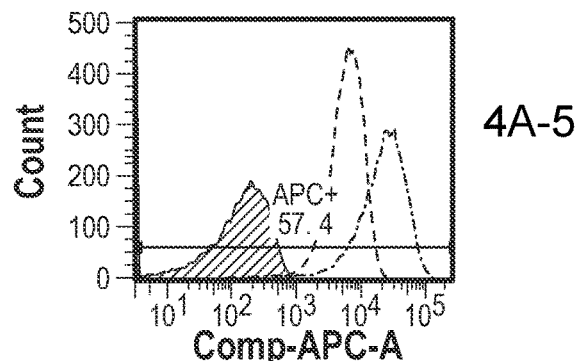
Figure 3I:
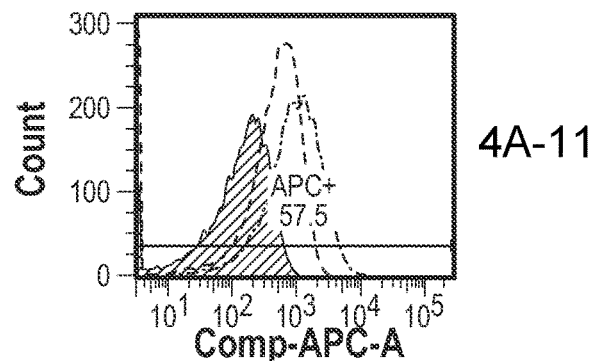
Figure 3I:
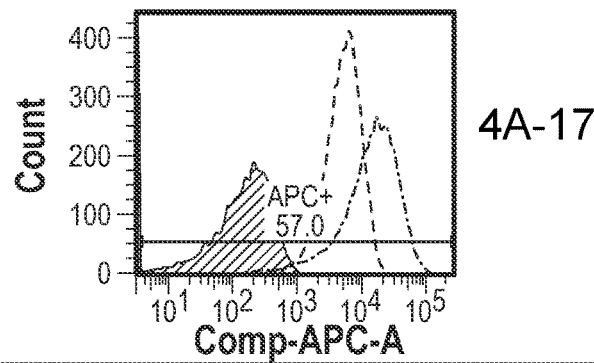
Figure 3I:
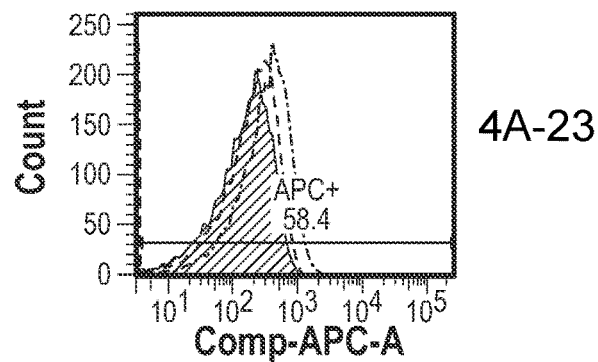
Figure 3J:
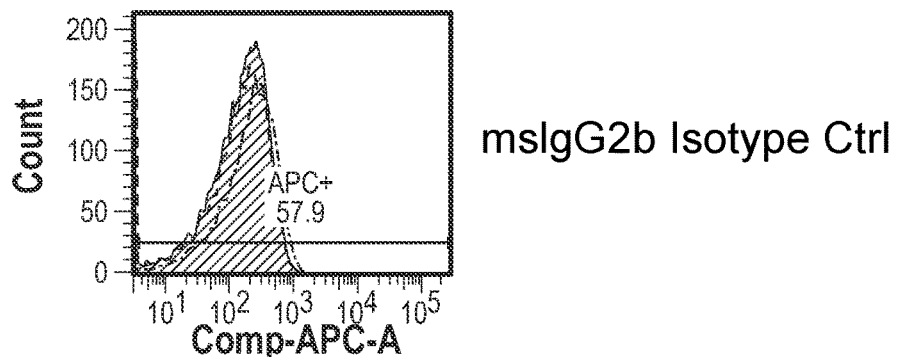
Figure 3J:
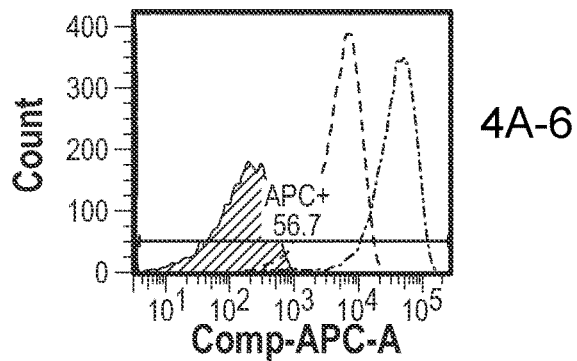
Figure 3J:
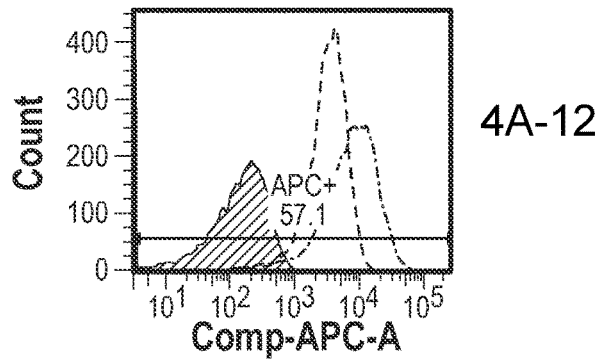
Figure 3K:
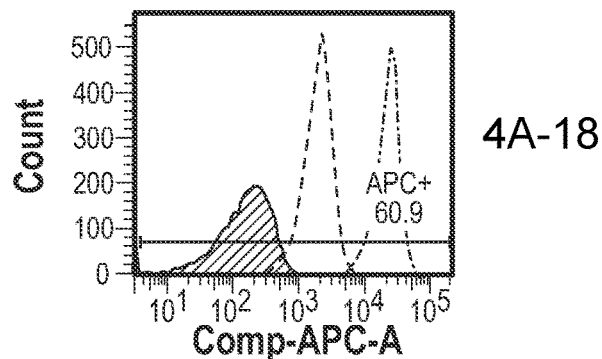
Figure 3K:
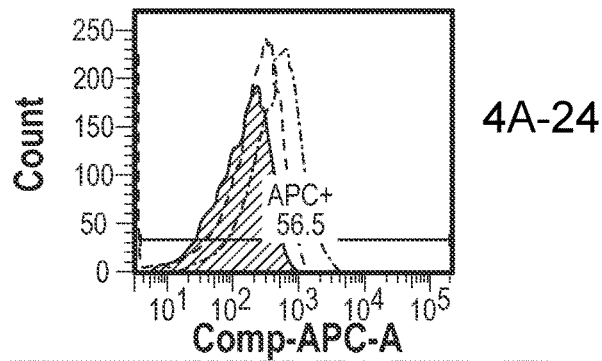
Figure 3K:
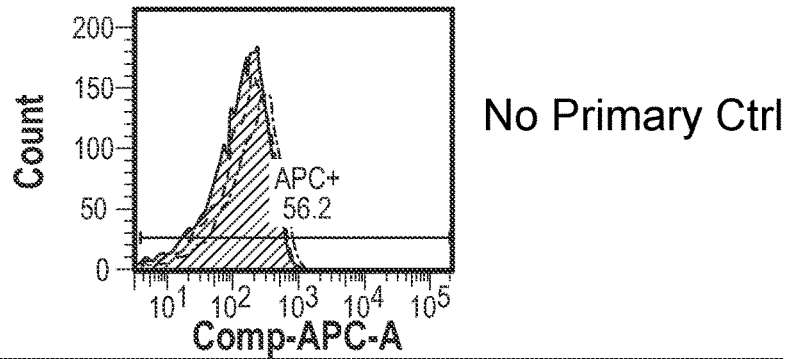
Figure 4B:
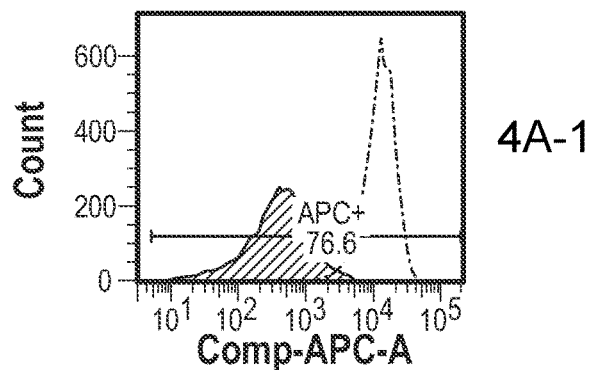
Figure 4B:
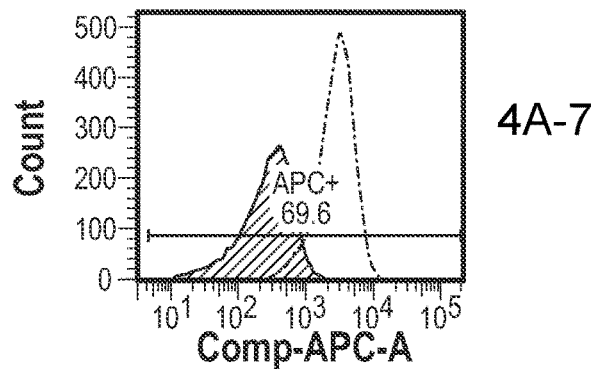
Figure 4B:
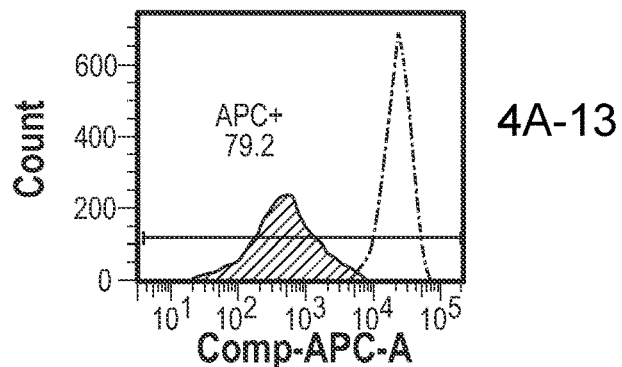
Figure 4C:
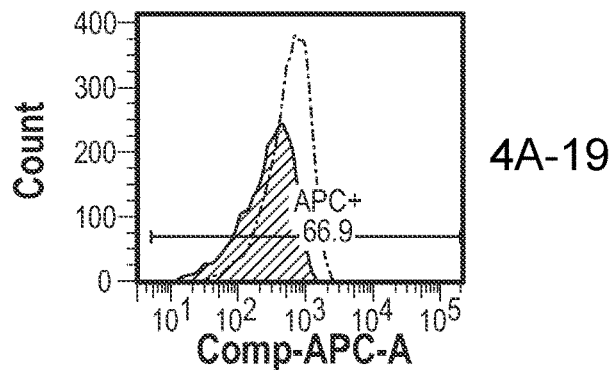
Figure 4C:
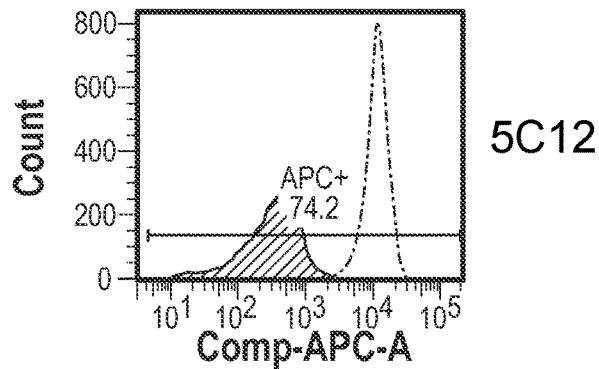
Figure 4C:
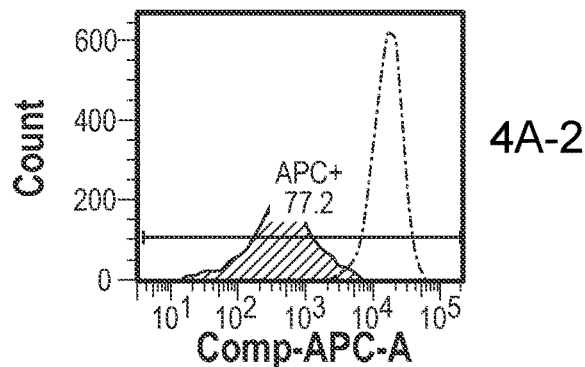
Figure 4D:
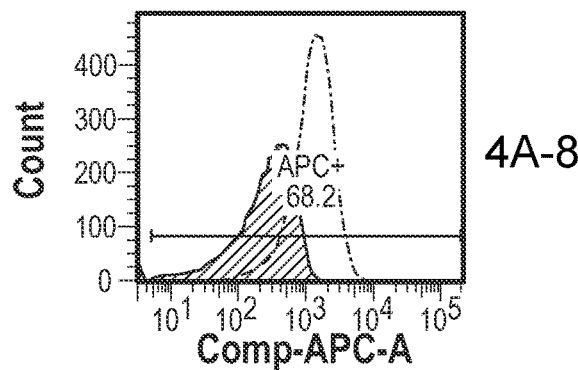
Figure 4D:
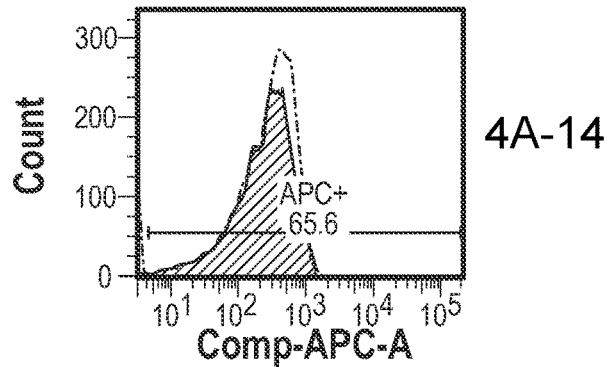
Figure 4D:
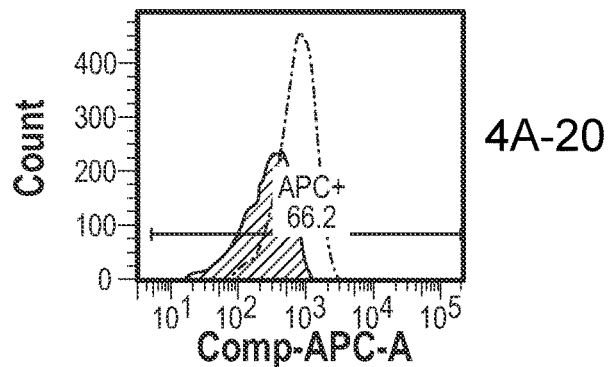
Figure 4E:
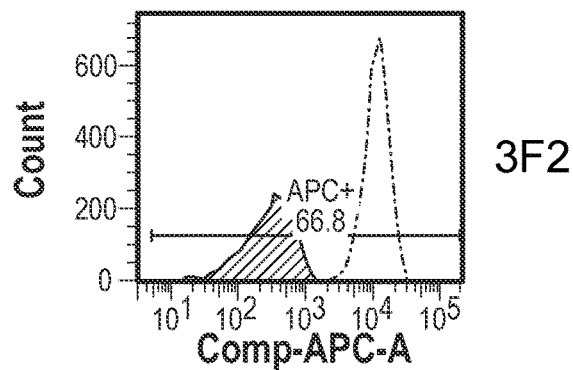
Figure 4E:
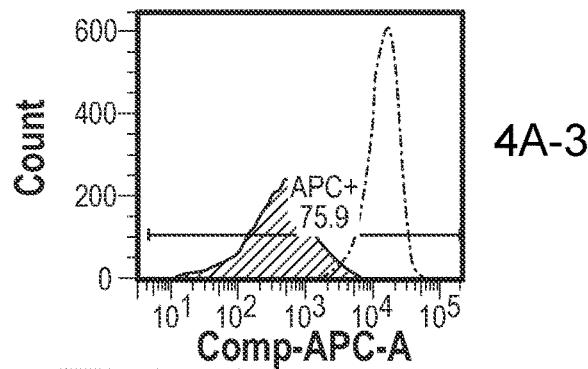
Figure 4E:
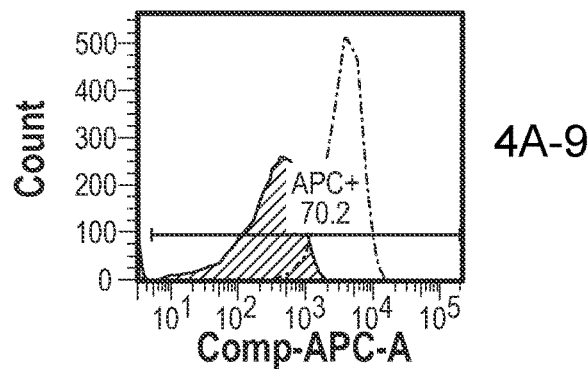
Figure 4F:
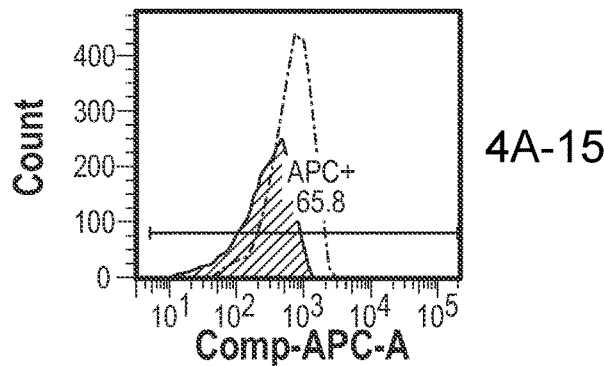
Figure 4F:
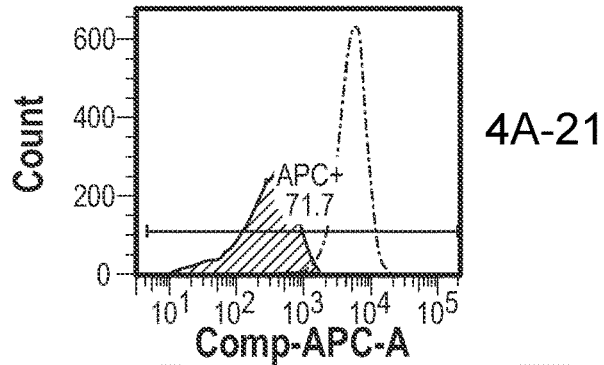
Figure 4F:
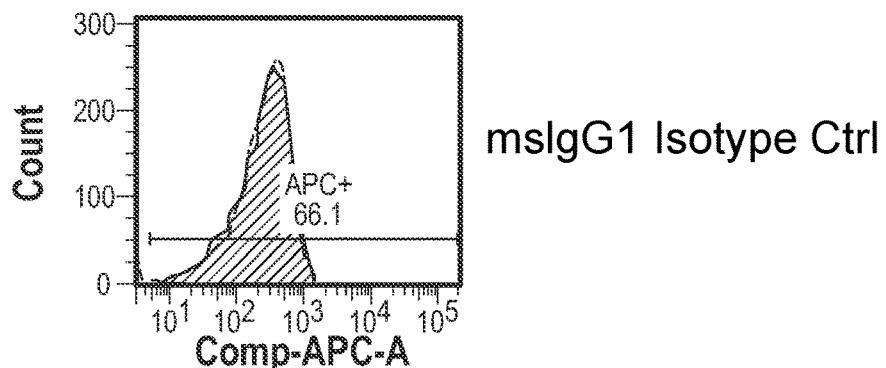
Figure 4G:
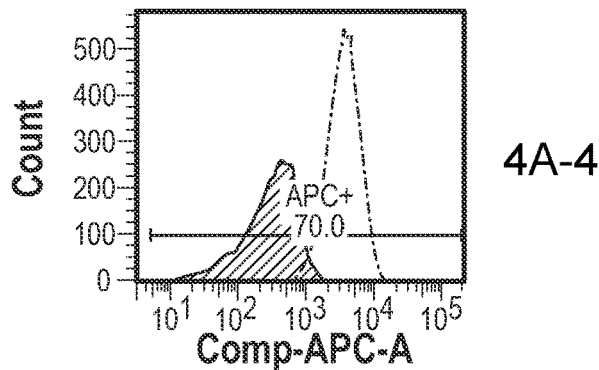
Figure 4G:
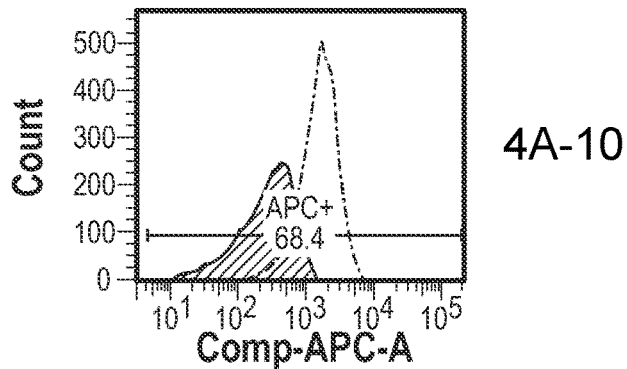
Figure 4G:
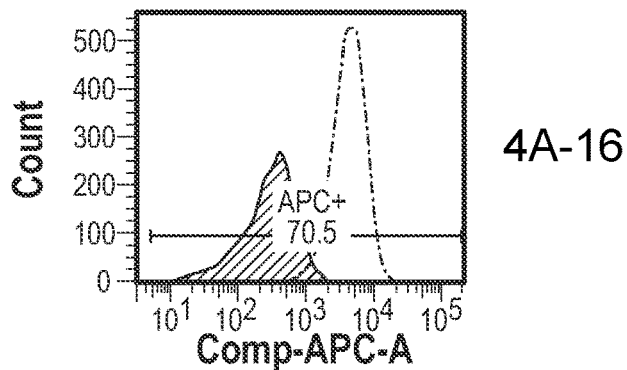
Figure 4H:
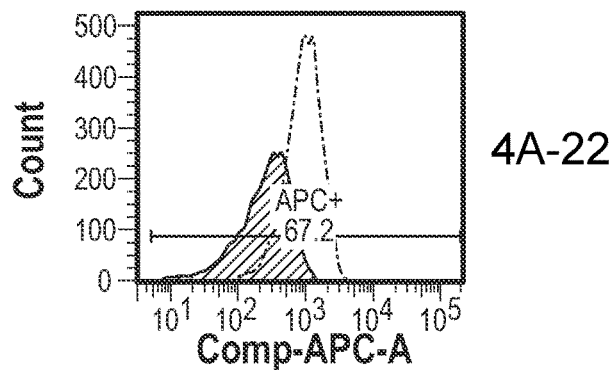
Figure 4H:
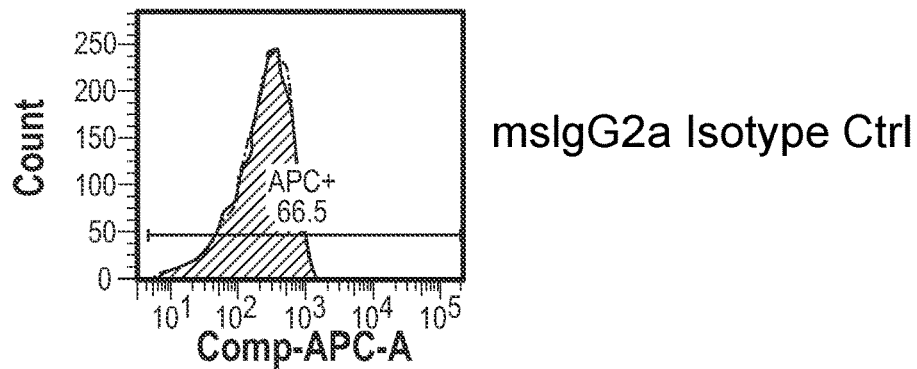
Figure 4H:
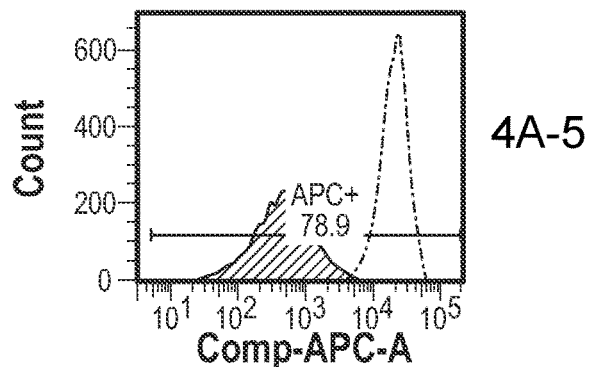
Figure 4I:
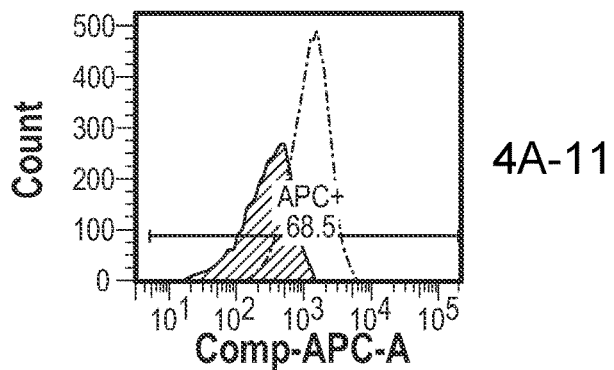
Figure 4I:
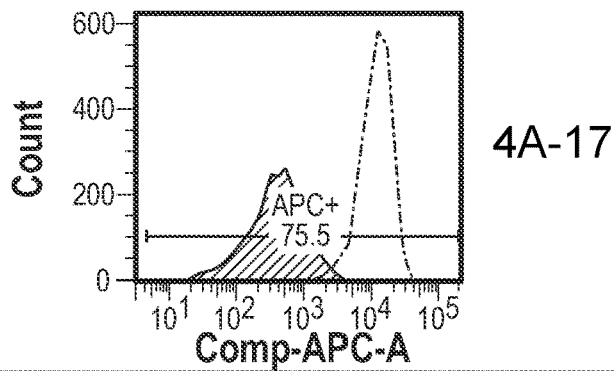
Figure 4I:
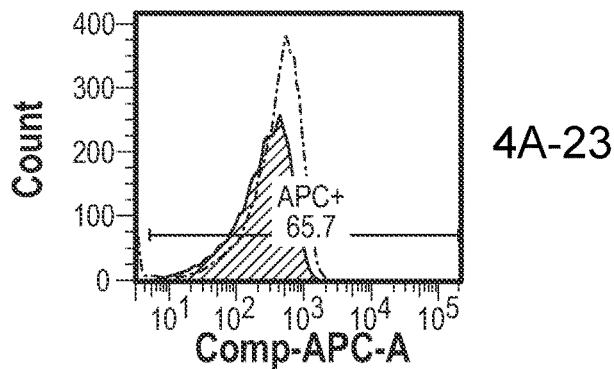
Figure 4J:
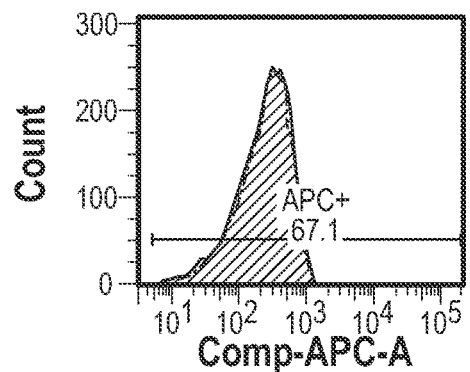
Figure 4J:
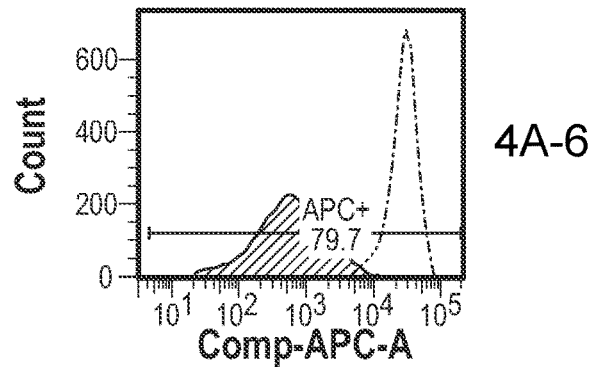
Figure 4J:
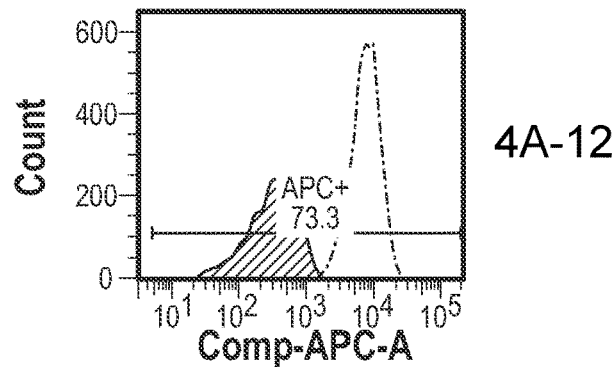
Figure 4K:
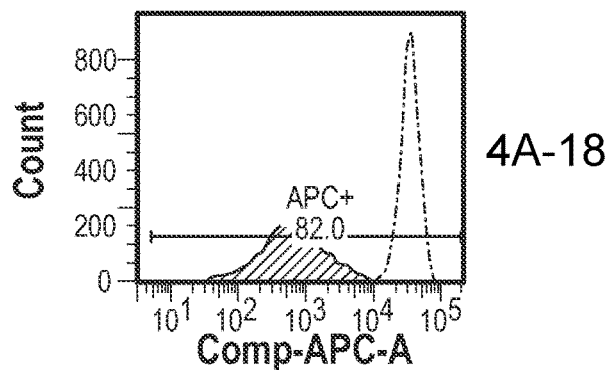
Figure 4K:
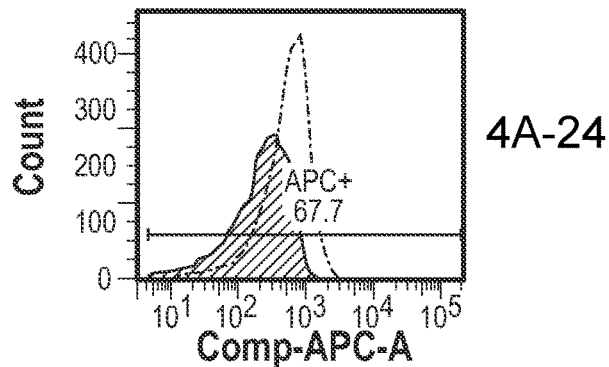
Figure 4K:
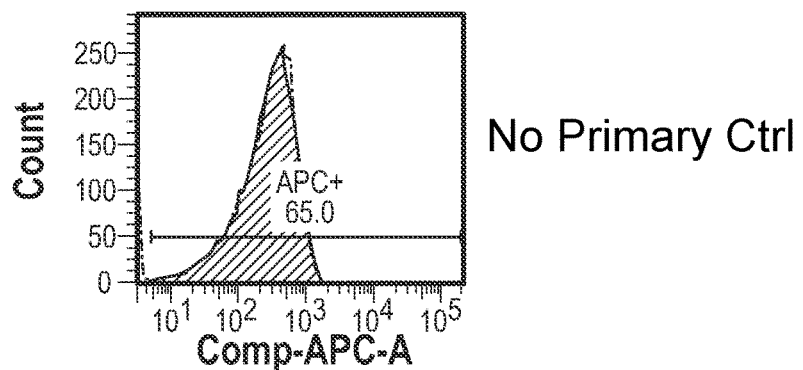

The results of this FACS analysis of anti-MS4A4A antibodies binding to 300.19 cells transiently-transfected with human MS4A4A and to 300.19 cells transiently-transfected with cyno MS4A4A are shown in FIG. 3. The results of anti-MS4A4A antibodies antibody binding to U937 cells transiently-transfected with human MS4A4A are shown in FIG. 4. Among the antibodies tested, all 24 anti-MS4A4A antibodies bound to human MS4A4A presented on these transiently-transfected cell lines. Furthermore, it was noted that 19 of the 24 anti-MS4A4A antibodies were cross-reactive to both human MS4A4A and cyno MS4A4A, with an additional three anti-MS4A4A antibodies showing some binding reactivity. Commercially available anti-MS4A4A antibodies 5C12, 3F2, and 4H2 did not exhibit cyno MS4A4A cross-reactivity. The list of antibodies that displayed cross-reactivity of binding to cells transfected with human MS4A4A or with cyno MS4A4A are shown below in Table 3.

TABLE 3

| Antibodies that fully cross-react to cyno MS4A4A | Antibodies that partially cross-react to cyno MS4A4A | Antibodies that do not cross-react to cyno MS4A4A |
|---|---|---|
| 4A-1, 4A-2, 4A-3, 4A-4, 4A-5, 4A-6, 4A-7, 4A-8, 4A-9, 4A-10, 4A-11, 4A-12, 4A-13, 4A-15, 4A-16, 4A-17, 4A-18, 4A-19, 4A-22 | 4A-20, 4A-21, 4A-24 | 4A-14, 4A-23 |

Example 8: Molecular Cloning of Anti-MS4A4A Hybridoma Antibodies

Anti-MS4A4A antibodies obtained from the hybridomas described above were cloned as follows. 5×10$^5$ hybridoma cells were resuspended in 0.5 ml Trizol solution (Thermo Fisher Scientific, cat #15596026). Total RNA was extracted from the cells by chloroform extraction and ethanol precipitation. cDNA was generated by using Clontech's SMARTer® RACE 5'/3' Kit (Takara Bio USA Inc, Cat. No. 634859) following the manufacturer's protocol.

Variable heavy and light immunoglobulin regions were cloned separately by touchdown PCR using the 5' UPM primer provided in the RACE kit and heavy chain constant region primer (5'-AGCTGGGAAGGTGTGCACA-3') [SEQ ID NO:140] and light constant region primer (5'-CCAT-TTTGTCGTTCACTGCCA-3') [SEQ ID NO:141].

PCR products were purified by QIAquick PCR Purification Kit (QIAGEN, Cat No. 28106) and ligated into a pCR2.1®-TOPO® cloning vector (TOPO® TA cloning Kit, Invitrogen) and transformed into ONESHOT® TOP10 Competent cells.

Transformed *Escherichia coli* (*E. coli*) colonies were isolated and the variable heavy chain (VH) and variable light chain (VL) nucleic acids were sequenced for each corresponding hybridoma cell line. Following the sequence determination, variable heavy chain regions and variable light chain regions were amplified by PCR using primers containing endonuclease restriction sites (BsrGI and BstEII for HV and BssHII and BsiWI for LV) and subcloned into pJG mammalian expression vector (Alector Inc.) encoding human IgG1 and IgGK, respectively.

Example 9: Antibody Heavy Chain and Light Chain Variable Domain Sequences

Using standard techniques, the amino acid sequences encoding the light chain variable regions and the heavy chain variable regions for 21 of the 24 generated antibodies were determined. The Kabat light chain CDR sequences and heavy chain CDR sequences of the antibodies are set forth in Table 4A below. The light chain variable region and heavy chain variable region sequences of the antibodies are set forth in Table 4B below.

TABLE 4A

Antibody CDR sequences

| Ab ID | CDR-H1 | CDR-H2 | CDR-H3 | CDR-L1 | CDR-L2 | CDR-L3 |
|---|---|---|---|---|---|---|
| 4A-2 | DYEMN (SEQ ID NO: 4) | WINTYTGEPT YADDFQG (SEQ ID NO: 20) | NYYYGNGDVM DY (SEQ ID NO: 38) | SASSSVSYIH (SEQ ID NO: 56) | STSNLAS (SEQ ID NO: 75) | QQRTGFPL T (SEQ ID NO: 86) |
| 4A-3 | KYGMN (SEQ ID NO: 5) | WINTYTAEPT YGDDFKG (SEQ ID NO: 21) | SAELVRHYYAL DY (SEQ ID NO: 39) | RSSQSLVHS NGNIYLE (SEQ ID NO: 57) | KVSNRFS (SEQ ID NO: 76) | SQGSHVPP T (SEQ ID NO: 87) |
| 4A-4 | DYVLV (SEQ ID NO: 6) | NINPYYGNSD YNLKFEG (SEQ ID NO: 22) | YGLYAMDF (SEQ ID NO: 40) | RSSQTIVHS NGNSYLE (SEQ ID NO: 58) | KVSNRFS (SEQ ID NO: 76) | FQSSHVPLT (SEQ ID NO: 88) |
| 4A-5 | DAWMD (SEQ ID NO: 7) | EIRSKTNSHA TYYAESVKG (SEQ ID NO: 23) | DYYGIF (SEQ ID NO: 41) | KSTQSLLDS DGKTFLN (SEQ ID NO: 59) | LVSKLDS (SEQ ID NO: 77) | WQGTHFPQ T (SEQ ID NO: 89) |
| 4A-7 | DYVMI (SEQ ID NO: 8) | NINPYYGSTS YNLKFKG (SEQ ID NO: 24) | YGYDALDN (SEQ ID NO: 42) | RSSQSIVHSN GNTYLD (SEQ ID NO: 60) | RVSNRFS (SEQ ID NO: 78) | FQGSHVPL T (SEQ ID NO: 90) |
| 4A-8 | DYYMY (SEQ ID NO: 9) | YINNGGGSTY YPDTVKG (SEQ ID NO: 25) | QGNLIYYSGSS LFAY (SEQ ID NO: 43) | RSSQSIVHSN RNTYLE (SEQ ID NO: 61) | KVSNRFS (SEQ ID NO: 76) | FQGSHVPW T (SEQ ID NO: 91) |
| 4A-9 | SGYYWN (SEQ ID NO: 10) | YISYDGNNK YNPSLKN (SEQ ID NO: 26) | RDY (SEQ ID NO: 44) | RSSQNIVHS NGITYLE (SEQ ID NO: 62) | KISNRFS (SEQ ID NO: 79) | FQGSHVPY T (SEQ ID NO: 92) |
| 4A-10 | DAWMD (SEQ ID NO: 7) | EIRSKANDHA TYYAESVKG (SEQ ID NO: 27) | DYYGFF (SEQ ID NO: 45) | KSSQSLLDR DGKTFLN (SEQ ID NO: 63) | LVSKLDS (SEQ ID NO: 77) | WQGTHFPQ T (SEQ ID NO: 89) |
| 4A-11 | DAWMD (SEQ ID NO: 7) | EIRSKTDNHA TYFAESVKG (SEQ ID NO: 28) | STFAS (SEQ ID NO: 46) | KSSQSLLDS DGKTYLN (SEQ ID NO: 64) | LVSKLDS (SEQ ID NO: 77) | WQGTHFPQ T (SEQ ID NO: 89) |
| 4A-12 | SYWMY (SEQ ID NO: 11) | YINPGTGYTE YNQKFKD (SEQ ID NO: 29) | FYYGSPYYYA MDY (SEQ ID NO: 47) | KASQSVDTD VA (SEQ ID NO: 65) | SASNRYT (SEQ ID NO: 80) | HQYNSYPL T (SEQ ID NO: 93) |

TABLE 4A-continued

Antibody CDR sequences

| Ab ID | CDR-H1 | CDR-H2 | CDR-H3 | CDR-L1 | CDR-L2 | CDR-L3 |
|---|---|---|---|---|---|---|
| 4A-13 | DAWMD (SEQ ID NO: 7) | EIRSKANDHA TYYAESVKG (SEQ ID NO: 27) | DYYGFF ID NO: 45) | KSSQSLLDR DGKTFLN (SEQ ID NO: 63) | LVSKLDS (SEQ ID NO: 77) | WQGTHFPQ T (SEQ ID NO: 89) |
| 4A-14 | DAWLD (SEQ ID NO: 12) | EIRSKANDHA TYYAESVKG (SEQ ID NO: 27) | DYYGFF (SEQ ID NO: 45) | KSSQSLLDR DGKTYLN (SEQ ID NO: 66) | LVSKLDS (SEQ ID NO: 77) | WQGTHFPQ T (SEQ ID NO: 89) |
| 4A-15 | DYVIL (SEQ ID NO: 13) | HINPYYANSD YNVNFRG (SEQ ID NO: 30) | YGSGMDY (SEQ ID NO: 48) | RSSQSIVHSD GNTYLE (SEQ ID NO: 67) | KVSNRFS (SEQ ID NO: 76) | FQGSHFPLT SEQ ID NO: 94) |
| 4A-16 | DAWMD (SEQ ID NO: 7) | EIRSKANDHA TYYAESVKG (SEQ ID NO: 27) | DYYGFF (SEQ ID NO: 45) | KSSQSLLDR DGKTFLN (SEQ ID NO: 63) | LVSKLDS (SEQ ID NO: 77) | WQGTHFPQ T (SEQ ID NO: 89) |
| 4A-17 | GYWIE (SEQ ID NO: 14) | EILPGIGNTK YSEKFKG (SEQ ID NO: 31) | SLLRAMDY (SEQ ID NO: 49) | SAISSISYMH (SEQ ID NO: 68) | DTSKLAS (SEQ ID NO: 81) | HQRSSYPY (SEQ ID NO: 95) |
| 4A-18 | SYWIH (SEQ ID NO: 15) | NINPTNGGTN YNERFKS (SEQ ID NO: 32) | AYYYGSSLFAY (SEQ ID NO: 50) | KASQNVGT AVA (SEQ ID NO: 69) | SASYRHT (SEQ ID NO: 82) | QQYSTYPW T (SEQ ID NO: 96) |
| 4A-19 | DYGIS (SEQ ID NO: 16) | EIYPRSGNTY YNEKFKG (SEQ ID NO: 33) | KGLLRDFDY (SEQ ID NO: 51) | KSSQSLLES DGKTYLN (SEQ ID NO: 70) | LVSKLDS (SEQ ID NO: 77) | WQGTHFPH T (SEQ ID NO: 97) |
| 4A-20 | DYNMD (SEQ ID NO: 17) | DINPNNGYTI YNQKFKG (SEQ ID NO: 34) | STGPYFDY (SEQ ID NO: 52) | RASENIYSY LA (SEQ ID NO: 71) | NGKTLAE (SEQ ID NO: 83) | QHHYGIPR T (SEQ ID NO: 98) |
| 4A-21 | SYGLS (SEQ ID NO: 18) | WINTYSGVPT YANDFKG (SEQ ID NO: 35) | SLVDY (SEQ ID NO: 53) | KSSQSLLYS DGKTYLS (SEQ ID NO: 72) | LVSKLDS (SEQ ID NO: 77) | WQGIDFHQ T (SEQ ID NO: 99) |
| 4A-23 | DYNIH (SEQ ID NO: 19) | YINPNNDDTT FNQKFKG (SEQ ID NO: 36) | SPYCYFDV (SEQ ID NO: 54) | KASQDINKY IV (SEQ ID NO: 73) | YTSTLQP (SEQ ID NO: 84) | LQYDNLWT (SEQ ID NO: 100) |
| 4A-24 | DAWMD (SEQ ID NO: 7) | EIRDNADNHP TYYAESVKG (SEQ ID NO: 37) | DYYGSH (SEQ ID NO: 55) | KASQSLLDS DGKTYLN (SEQ ID NO: 74) | LVSKMDS (SEQ ID NO: 85) | WQGTHFPQ T (SEQ ID NO: 89) |

TABLE 4B

V_H and V_L sequences

| Ab ID | V_H: | V_L: |
|---|---|---|
| 4A-2 | QIQLVQSGPELKKPGETVKISCKASGYTFVDYE MNWVKQAPGKGLEWLGWINTYTGEPTYADD FQGRFAFSLVTSVSTAYLQINNLKHEDMATYL CTRNYYYGNGDVMDYWGQGTSVTVSS (SEQ ID NO: 101) | QIVLTQSPAIMSASPGEKVTITCSASSSV SYIHWFQQKPGTSPKLWIYSTSNLASGV PARFSGSGSGTSYSLTISRMEAEDAATY YCQQRTGFPLTFGGGTQLEIK (SEQ ID NO: 121) |
| 4A-3 | QIQLVQSGPELKTPGETVKISCKSSGYTFTKYG MNWVKQAPGKGLKWMAWINTYTAEPTYGDD FKGRFAFSLETSANTAYLQINNLKNEDTATYFC ARSAELVRHYYALDYWGQGTSVTVSS (SEQ ID NO: 102) | DVLMTQTPLSLPVSLGDQASISCRSSQS LVHSNGNIYLEWFLQKPGQSLKILIYKV SNRFSGVPDRFSGSGSGTDFTLKISRVE ADDLGVYYCSQGSHVPPTFGAGTKLEL R (SEQ ID NO: 122) |

TABLE 4B-continued

V_H and V_L sequences

| Ab ID | V_H: | V_L: |
|---|---|---|
| 4A-4 | EIQLQQTGPDLVKPGTSVKISCKASGYSFTDYV LVWVKQSHGKSLEWIGNINPYYGNSDYNLKFE GKARLTVDRSSSTAYMQLNSLTSEDSAVYYCA RYGLYAMDFWGQGTSVTVSS (SEQ ID NO: 103) | DVLMTQTPLSLPVSLGDQASISCRSSQTI VHSNGNSYLEWYLQKPGQSPKLLIYKV SNRFSGVPDRFSGSGSGTVFTLKISRVE AEDLGVYFCFQSSHVPLTFGVGTKLEL K (SEQ ID NO: 123) |
| 4A-5 | EVKVEESGGGLVQPGGSMKLSCAASGFTFSDA WMDWVRQSPEKGLEWVAEIRSKTNSHATYYA ESVKGRFTISRDDSKSSVYLQMNSLRAEDTGIY YCTVDYYGIFWGQGTLVTVSS (SEQ ID NO: 104) | DVVMTQTPLTLSVTIGQPASISCKSTQSL LDSDGKTFLNWLLQRPGQSPKRLIYLVS KLDSGVPDRFTGSGSGTDFTLKISRVEA EDLGVYFCWQGTHFPQTFGGGTKLEIK (SEQ ID NO: 124) |
| 4A-7 | EIQLQQTGPELVKPGASVKISCKASGYSFTDYV MIWVKQSHGKSLEWIGNINPYYGSTSYNLKFK GKATLTVDKSSSTAYMQLKSLTSEDSAVYYCA RYGYDALDNWGQGTSVTVSS (SEQ ID NO: 105) | DVLLTQTPLSLPVSLGDQASISCRSSQSI VHSNGNTYLDWSLQKPGQSPKLLIYRV SNRFSGVPDRFSGSGSGTDFTLKISRVE AEDLGVYYCFQGSHVPLTFGAGTKLEL K (SEQ ID NO: 125) |
| 4A-8 | EVKLVESGGGLVQPGGSLKLSCATSGFTFSDY YMYWVRQTPEKRLEWVAYINNGGSTYYPDT VKGRFTISRDNAKNTLYLQMSRLKSEDTAMY YCARQGNLIYYSGSSLFAYWGQGTMVTVSS (SEQ ID NO: 106) | DVLMTQTPLSLPVSLGDQASISCRSSQSI VHSNRNTYLEWYVQKPGQSPKLLIYKV SNRFSGVPDRFSGSGSGTDFTLKISRVE AEDLGVYYCFQGSHVPWTFGGGTKLEI K (SEQ ID NO: 126) |
| 4A-9 | DVQLQESGPGLVKPSQSLSLTCSVTGYSITSGY YWNWIRQFPGNKLEWMGYISYDGNNKYNPSL KNRISITRDTSKNQFFLKLNSVTTEDTATYYCA NRDYWGQGTTLTVSS (SEQ ID NO: 107) | DVLMTQTPLSLPVSLGDQASISCRSSQNI VHSNGITYLEWFLQKPGQSPTLLIYKISN RFSGVPDRFSGSGSGTDFTLKISRVEAE DLGVYYCFQGSHVPYTFGGGTKLDIK (SEQ ID NO: 127) |
| 4A-10 | EVKLEESGGGLVQPGGSMKLSCAASGFTFSDA WMDWVRQSPEKGLEWVAEIRSKANDHATYY AESVKGRFTISRDDSKSSVYLQMNSLRAEDTGI YYCSVDYYGFFWGQGTLVTVSA (SEQ ID NO: 108) | DVVMTQTPLTLSVTIGQTASISCKSSQSL LDRDGKTFLNWLLQRPGQSPKRLIYLV SKLDSGVPDRFTGSGSGTDFTLKISRVE AEDLGVYYCWQGTHFPQTFGGGTKLEI K (SEQ ID NO: 128) |
| 4A-11 | EVKLEESGGGLVQPGGSMKLSCAASGFTFSDA WMDWVRQSPEKGLEWVAEIRSKTDNHATYFA ESVKGRFTISRDDSKSSVYLQMNSLRAGDTGIY YCYGSTFASWGQGTLVTVSS (SEQ ID NO: 109) | DVVMTQTPLTLSVTLGQPASISCKSSQS LLLDSDGKTYLNWLFQRPGQSPKRLIYL VSKLDSGVPDRFTGSGSGTDFTLKISRV EAEDLGVYYCWQGTHFPQTFGGGTNL EIK (SEQ ID NO: 129) |
| 4A-12 | QVQLQQSGAELAQPGASVKMSCKASGYTFSS YWMYWVKQGPGQGLEWIGYINPGTGYTEYN QKFKDKATLTADKSSSTAYMQLSSLTSEDSAV YYCARFYYGSPYYYAMDYWGQGTSVTVSS (SEQ ID NO: 110) | DIVMTQSQKFMSTSVGDRVTFTCKASQ SVDTDVAWYQQKPGQSPKLLIYSASNR YTGVPDRFTGSGSGTDFTLTISNVQSED LADYFCHQYNSYPLTFGAGTKLELK (SEQ ID NO: 130) |
| 4A-13 | EVKLEESGGGLVQPGGSMKLSCAASGFTFSDA WMDWVRQSPEKGLEWVAEIRSKANDHATYY AESVKGRFTISRDDSKSSVYLQMNSLRAEDTGI YYCSVDYYGFFWGQGTLVTVSA (SEQ ID NO: 108) | DVVMTQTPLTLSVTIGQTASISCKSSQSL LDRDGKTFLNWLLQRPGQSPKRLIYLV SKLDSGVPDRFTGSGSGTDFTLKISRVE AEDLGVYYCWQGTHFPQTFGGGTKLEI K (SEQ ID NO: 128) |
| 4A-14 | EVKLEESGGGLVQPGGSMKLSCAASGFTFSDA WLDWVRQSPEKGLEWVAEIRSKANDHATYYA ESVKGRFTISRDDSKSRFYLQMNSLRAEDTGIY YCSVDYYGFFWGQGTLVTVSA (SEQ ID NO: 111) | AVVMTQTPLTLSVTIGQPASISCKSSQSL LDRDGKTYLNWLLQRPGQSPKRLIYLV SKIDSGVPDRFTGSGSGTDFTLKISRVE AEDLGVYYCWQGTHFPQTFGGGTKLEI K (SEQ ID NO: 131) |
| 4A-15 | EIQLQQTGPDLVKPGASVKISCKASGYSFTDYV ILWVKQSHGKTLEWIGHINPYYANSDYNVNFR GKATLTVDKSSSTAHMQLNSLTSEDSAVYYCV RYGSGMDYWGQGTSVTVSS (SEQ ID NO: 112) | DVLMTQTPLSLPVSLGDQASISCRSSQSI VHSDGNTYLEWYLQKPGQSPKLLIYKV SNRFSGVPDRFSGSGSGTDFTLKISRVE AEDLGVYYCFQGSHFPLTFGAGTKLEL K (SEQ ID NO: 132) |
| 4A-16 | EVKLEESGGGLVQPGGSMKLSCAASGFTFSDA WMDWVRQSPEKGLEWVAEIRSKANDHATYY AESVKGRFTISRDDSKSSVYLQMNSLRAEDTGI YYCSVDYYGFFWGQGTMVTVSA (SEQ ID NO: 113) | DVVMTQTPFTLSVTIGQSASISCKSSQSL LDRDGKTFLNWLLQRPGQSPKRLIYLV SKLDSGVPDRFTGSGSGTDFTLKISRVE AEDLGVYYCWQGTHFPQTFGGGTKLEI K (SEQ ID NO: 128) |

TABLE 4B-continued

V_H and V_L sequences

| Ab ID | V_H: | V_L: |
|---|---|---|
| 4A-17 | QVQLQQSAAELMKPGASVKLSCKATGYTFTG YWIEWLKQRPGHGLEWIGEILPGIGNTKYSEKF KGKATFTADTSSNTAYMQLSSLTTEDSAIYYC ARSLLRAMDYWGQGTSVTVSS (SEQ ID NO: 114) | QIVLTQSPAIMSASPGEKVTMTCSAISSI SYMHWYQLKPGTSPKRWIYDTSKLASG VPARFSGSGSGTSYSLTISSMEAEDAAT YYCHQRSSYPYTFGGGTKLEIK (SEQ ID NO: 133) |
| 4A-18 | QVQLQQPGTELVKPGASVKLSCKASGYTFTSY WIHWVKQRPGQGLEWIGNINPTNGGTNYNER FKSKATLTVDKSSSTAYMQLSSLTSEDSAVYY CARAYYYGSSLFAYWGQGTLVTVSA (SEQ ID NO: 115) | DIVMTQSQKFMSTTVGDRVSITCKASQ NVGTAVAWSQQKPGQSPKLLIYSASYR HTGVPDRFTGSGSGTDFTLTITNMQSED LADYFCQQYSTYPWTFGGGTKLEIK (SEQ ID NO: 134) |
| 4A-19 | QVQLQQSGAELARPGASVKLSCKASGYSFIDY GISWVKQRTGQGLEWIGEIYPRSGNTYYNEKF KGKATLTADKSSSTAYMELRSLTSEDSAVYFC ARKGLLRDFDYWGQGTTLTVSS (SEQ ID NO: 116) | DIQMTQTPLTLSVTIGQPASISCKSSQSL LESDGKTYLNWLLQRPGQSPKRLIYLVS KLDSGVPDRFTGSGSGTDFTLKISRVEA EDLGVYYCWQGTHFPHTFGGGTKLEIK (SEQ ID NO: 135) |
| 4A-20 | EVQLQQSGPELVKPGASVKIPCKASGYTFTDY NMDWVKQSHGKSLDWIGDINPNNGYTIYNQK FKGKATLTVDKSSSTAYMELRRLTSEDTAVYY CARSTGPYFDYWGQGTTLTVSS (SEQ ID NO: 117) | DIQMTQSPASLSASVGETVTITCRASENI YSYLAWYQQKQGKSPQFLVYNGKTLA EGVPSRFSGCGSGTQFSLKINSLQPEDFG SYYCQHHYGIPRTFGGGTKLEIK (SEQ ID NO: 136) |
| 4A-21 | QIQLVQSGPELKKPGETVKISCKASGYIFTSYGL SWVKQTPGKGLKWMGWINTYSGVPTYANDF KGRFAFSLETSASTTYLRINNLKNDDTATYFCA RSLVDYWGQGTPLTVSS (SEQ ID NO: 118) | DVVMTQTPFTLSVTIGQSASISCKSSQSL LYSDGKTYLSWLLQRPGQSPKRLIYLVS KLDSGVPDRFTGSGSGTDFTLKISRVEA EDLGVYYCWQGIDFHQTFGGGTKLEIK (SEQ ID NO: 137) |
| 4A-23 | EVQLQQSGPELVKPGASVKMSCQASGYTFTDY NIHWVKQSHGKSLKWIGYINPNNDDTTFNQKF KGKATLTVNKSSSTAYMELRSLTSEDSAVYYC ARSPYCYFDVWGTGTTVTVSS (SEQ ID NO: 119) | DIQMTQSPSSLSASLGGKVTITCKASQDI NKYIVWYQHKPGKGPRLLINYTSTLQP GIPSRFSGGGSGGDYSFSISNLEPEDIAT YYCLQYDNLWTFGGGTKLEIK (SEQ ID NO: 138) |
| 4A-24 | EVKLEESGGGLVQPGGSMKLSCAASGFTFSDA WMDWVRQSPEKGLEWVAEIRDNADNHPTYY AESVKGRFTISRDDSKSSVYLQMNSLRAEDTGI YYCTSDYYGSHWGQGTTLTVSS (SEQ ID NO: 120) | DVVMTQTPFTLSVTIGQPASISCKASQS LLDSDGKTYLNWLLQRPGQSPKRLIYL VSKMDSGVPDRFTGSGSGTDFTLKISRV EAEDLGVYYCWQGTHFPQTFGGGTKL EIK (SEQ ID NO: 139) |

Example 10: Production of Recombinant Anti-MS4A4A Antibodies

Purified hybridoma-derived anti-MS4A4A antibodies are purified using Protein A from hybridoma supernatants after culturing the hybridomas in low-IgG or chemically defined media. Some of the anti-MS4A4A antibodies are also produced via direct cloning of the variable gene regions obtained from the hybridomas into a recombinant expression plasmid for production of chimeric antibodies containing a human Fc domain (human IgG1). The expression plasmids are transiently transfected into Expi293 cells and the resulting anti-MS4A4A antibodies purified via Protein A.

Recombinant production of anti-MS4A4A antibodies is performed as follows. Transfection of expression plasmids containing nucleic acid encoding the anti-MS4A4A antibody VH and VL chains is carried out using the Expifectamine-293 system (ThermoFischerScientific Cat #A14524) according to the manufacturer's protocol. Briefly, for each anti-MS4A4A antibody, 12 μg of light chain plasmid DNA and 18 μg of heavy chain plasmid DNA is diluted into 1.5 mL OptiMEM (ThermoFischerScientific Cat #31985070), to which 80὿, of Expifectamine reagent is added. The resulting solution is mixed and incubated at room temperature for 30 minutes prior to addition to 30 mL of Expi293 cells (ThemoFischerScientific A14527) in Expi293 expression media (ThermoFischerScientific Cat #A1435101) in 125 mL flasks (Fischer Scientific FIS #PBV12-5). Transfected cells are cultured to approximately $3\times10^{-6}$ cells/ml prior to transfection. Culture conditions for Expi293 cells are 37° C./8% CO2 with orbital shaking at 125 rpm. 16-24 hours after transfection, 150 μL of ExpiFectamine™ 293 Transfection Enhancer 1 and 1.5 mL of ExpiFectamine™ 293 Transfection Enhancer 2 are added to each flask to enhance recombinant antibody yield. Culture supernatants are harvested 5-7 days after transfection, filtered (0.2 micron), and purified via Protein A chromatography.

Example 11: Kinetic Characterization of Anti-MS4A4A Antibodies

Binding kinetic characterization of the anti-MS4A4A antibodies to MS4A4A ECL1 and ECL2 and to MS4A6A ECL1 and ECL2 peptides was performed by Carterra (South San Francisco, Calif.) using a proprietary array Surface Plasmon Resonance (SPR) instrument (MX-96) as follows. Antibodies were captured onto a CMD500D chip (Xantec #SPMX CMD500D) using the Continous Flow Microspotter (CFM). First, the chip was activated with 100 mM MES pH 5.5, 100 μL EDC (133 mM final), 100 μL of S-NHS (33.3 mM final), for 7 minutes. A lawn of anti-mouse IgG-Fc (Jackson ImmunoResearch cat #115-005-071) was injected for 15 minutes to establish a surface density of 10000-12000 RU, after which the chip surface was deactivated with 1M ethanolamine at pH 8.5 for 10 minutes. Anti-MS4A4A hydridoma supernatant or purified anti-MS4A4A antibodies were diluted in HBS-EP+ buffer (Teknova Cat #H8022) and then printed as duplicates with a 20 minute and a 5-minute print from the same sample solution.

To perform kinetic analysis, human MS4A4A peptides corresponding to ECL1 (amino acid residues 86-98 of human MS4A4A of SEQ ID NO:1) and ECL2 (amino acid residues 159-179 of human MS4A4A of SEQ ID NO:1), or human MS4A6A peptides corresponding to ECL1 (amino acid residues 68-85 of human MS4A6A of SEQ ID NO:291) and ECL2 (amino acid residues 138-185 of human MS4A6A of SEQ ID NO:291) were prepared in HBS-EP+ buffer with 1 mg/ml BSA at final assay concentrations of 2000 nM, 400 nM, 80 nM, 16 nm, and 3.2 nM. These were then injected on the chip for five minutes, followed by a seven-minute dissociation period at 8 uL per second in a non-regenerative kinetic series. Duplicate measurements for each anti-MS4A4A antibody were taken to ensure reproducibility. Association rates (Kon) and dissociation rates (Koff) were calculated using a single one-to-one Langmuir binding model. The equilibrium dissociation constant (KD) was calculated as the ration of Koff/Kon.

Of the 24 hybridoma supernatants from the present disclosure and the three commercially-available murine anti-MS4A4A antibodies (5C12, 4H2 and 3F2) tested, anti-MS4A4A antibody 4A-21 showed binding to the human MS4A4A ECL2 peptide using the methods described above. The kinetic constants determined for anti-MS4A4A antibody 4A-21 from these experiments were: Kon ((M−1 s−1), 2.5E+05; Koff (s−1), 7.8E-03; and KD of 31 nM. Using the methodology described above, no other anti-MS4A4A antibodies tested bound MS4A4A ECL1, MS4A6A ECL1, or MS4A6A ECL2 peptides.

Example 12: Affinity Measurement of MS4A4A Antibodies to Transiently and Natively-Expressing Cell Lines Purified anti-MS4A4A antibodies are evaluated for their binding affinity to various MS4A4A-expressing cell lines. These include transfected cells as described above in Example 8, as well as myeloid cell lines and primary cells that endogenously express MS4A4A. Anti-MS4A4A antibodies tested are either mouse IgGs purified from hybridoma supernatant or human IgG1 Fc chimeras produced recombinantly in Expi293 cells. Affinity binding to cells is determined as follows. Briefly, cells are harvested, washed and labeled with Aqua Live/Dead for viability discrimination. After a wash with PBS, 2×10^5 cells are aliquoted per well in 96-well U-bottom plates and incubated with 504, of purified anti-MS4A4A antibody at various concentrations (3× dilutions starting at 10 μg/ml) in FACS buffer (PBS+2% FBS+1 mM EDTA). After primary incubation, the supernatant was removed via centrifugation, washed 2× with 150 μL of ice-cold FACS buffer and incubated with the appropriate secondary antibody on ice for 30 minutes. Following the secondary incubation, the cells are again washed 2× with ice-cold FACS buffer and resuspended in a final volume of 200 μL of FACS buffer. Flow cytometry analysis is performed on a FACS Canto system (BD Biosciences). Binding data was analyzed using Median fluorescent intensity and curves were fit in Prism (nonlinear regression: log inhibitor vs. dose response with four parameters) to determine EC50 values.

Example 13: Epitope Determination of Anti-MS4A4A Antibodies by Peptide Binding Epitope binding characteristics of anti-MS4A4A antibodies are determined by two complementary approaches. First, a panel of overlapping peptides derived from the extracellular loops (ECLs) of human MS4A4A (SEQ ID NO:1) and human MS4A6A (SEQ ID NO: 291) were synthesized by JPT peptides (Berlin, Germany). These peptides were 15 amino acids in length, each offset by 2 amino acids. The peptides were biotinylated on the N-terminus. Peptides 4A.1 through 4A.4 were derived from human MS4A4A ECL1 and surrounding regions. Peptides 4A.5 through 4A.12 were derived from human MS4A4A ECL2 and surrounding regions. Anti-MS4A4A antibodies of the present disclosure and commercially-available anti-MS4A4A antibodies were tested for binding to the various linear peptides by Carterra (South San Francisco, Calif., USA) using a proprietary array SPR instrument (MX-96).

The peptide library was printed onto a streptavidin-coated chip (Xantec SAD50M, Dusseldorf, Germany) using the Continuous Flow Microspotter (CFM). First, the chip was activated with 100 mM MES, pH 5.5, 100 μL EDC (133 mM final), 100 μL of S-NHS (33.3 mM final). The peptide library was immobilized onto the chip at 250 nM per peptide diluted into HBS-EP+ buffer (Teknova Cat #H8022) with 1 mg/ml BSA and 1 μg/ml mouse IgG-Biotin. Following immobilization, the chip surface was deactivated with 1M ethanolamine at pH 8.5 for 10 minutes. Hybridoma supernatants and purified anti-MS4A4A antibodies were diluted in HBS-EP+ buffer with 1 mg/ml BSA and injected onto the chip. Duplicate measurements for each anti-MS4A4A antibody were taken to ensure reproducibility. Binding characteristics were determined for each peptide-antibody combination, allowing the mapping of the linear peptide region each antibody interacts with.

Anti-MS4A4A antibody 4A-21 and commercially available anti-MS4A4A antibody 5C12 displayed robust binding to peptides corresponding to regions in human MS4A4A ECL2, as indicated in bold in Table 5 below. Anti-MS4A4A antibody 4A-21 binds peptides 4A.5 through 4A.9, spanning amino acid residues 155 to 177 of human MS4A4A. Anti-MS4A4A antibody 5C12 binds peptides 4A.6 through 4A.9, spanning amino acid residues 157 to 177 of human MS4A4A. The binding regions of these two antibodies are overlapping but not identical, indicating that they interact with different residues within ECL2 of human MS4A4A. Neither of these two antibodies showed binding to human MS4A4A ECL1 using the methodology described above.

TABLE 5

| Peptide | Sequence | 4A-21 | 5C12 |
|---|---|---|---|
| 4A.1 | ITMMCMASNTYGSNP (SEQ ID NO: 292) | −11.16 | −1.49 |
| 4A.2 | MMCMASNTYGSNPIS (SEQ ID NO: 293) | −11.53 | −0.19 |
| 4A.3 | CMASNTYGSNPISVY (SEQ ID NO: 294) | −10.55 | −1.54 |

TABLE 5-continued

| Peptide | Sequence | 4A-21 | 5C12 |
|---|---|---|---|
| 4A.4 | ASNTYGSNPISVYIG (SEQ ID NO: 295) | -7.90 | -0.46 |
| 4A.5 | LAFYSFHHPYCNYYG (SEQ ID NO: 296) | 382.80 | 1.60 |
| 4A.6 | FYSFHHPYCNYYGNS (SEQ ID NO: 297) | 485.67 | 44.38 |
| 4A.7 | SFHHPYCNYYGNSNN (SEQ ID NO: 298) | 446.10 | 17.75 |
| 4A.8 | HHPYCNYYGNSNNCH (SEQ ID NO: 299) | 308.63 | 22.30 |
| 4A.9 | PYCNYYGNSNNCHGT (SEQ ID NO: 300) | 225.21 | 30.86 |
| 4A.10 | CNYYGNSNNCHGTMS (SEQ ID NO: 301) | -4.50 | 1.13 |
| 4A.11 | YYGNSNNCHGTMSIL (SEQ ID NO: 302) | -6.50 | -2.73 |
| 4A.12 | GNSNNCHGTMSILMG (SEQ ID NO: 303) | -5.20 | -4.08 |

Some MS4A4A antibodies bind to discontinuous epitopes. Pepscan (Lelstad, The Netherlands) has developed a technology, known as CLIPS, designed to address such epitopes. In this technology, a library of tertiary-structure mimics is designed and synthesized onto a solid support. These mimics can model secondary structural elements in proteins, such as loops, alpha-helices and beta-strands. The binding of the antibody to each peptide construct is determined and quantified. The extent of binding to the library indicates the region to which a given antibody interacts with, thus its epitope.

Example 14: Epitope Binning of Anti-MS4A4A Antibodies by Cell Binding

As MS4A4A is a multi-pass transmembrane protein, recombinantly produced soluble proteins are not appropriate reagents for investigating antibody:protein interactions. Anti-MS4A4A antibodies are binned using a modified classical sandwich method. For example, to determine whether antibodies A and B are in the same bin, cells expressing MS4A4A are first incubated with saturating levels of anti-MSSASA antibody A. After washes with FACS buffer, anti-MS4A4A antibody B, labeled with fluorophore allophycocyanin (APC), is added to the cells for incubation on ice for 15 minutes. The cells are analyzed by FACS Canto system (BD Biosciences), with gates drawn to exclude dead cells. The level of anti-MS4A4A antibody B binding in the presence or absence of anti-MS4A4A antibody A are compared. Reduction or extinction of binding in the presence of anti-MS4A4A antibody A indicates competition between these two antibodies. This procedure is repeated against other anti-MS4A4A antibodies so the entire anti-MS4A4A antibody panel is binned.

Example 15: Downregulation of MS4A4A Protein by Anti-MS4A4A Antibodies

The ability of anti-MS4A4A antibodies to reduce cell surface and total cellular protein levels of MS4A4A in various cell lines and primary cells is evaluated. Reduction in MS4A4A protein in either compartment indicates a reduction in MS4A4A activity in the cells.

Cells are incubated with anti-MS4A4A antibodies of the present disclosure for various time periods and then the levels of MS4A4A protein remaining associated with the cells is assayed by either FACS (cell surface) or western blot (total cell protein level). For FACS assays, detection of the remaining MS4A4A is carried out with direct-allophycocyanin (APC) conjugated, non-competing antibodies. For Western blot detection, cells are lysed by the addition of 50 μL lysis buffer (RIPA lysis buffer (ThermoFischerScientific Cat #89900)+1:100 HALT protease inhibitor cocktail (ThermoFischerScientific Cat #87786), and cleared for insoluble debris by centrifugation at 14,000×g for 15 minutes. Soluble fraction is assayed with bicinchoninic acid (BCA) reagent for protein quantification. Equal amounts of proteins from each sample are loaded on a 4-12% Bis-Tris Plus polyacrylamide gel (ThermoFisher Scientific NW04120) and subjected to electrophoresis separation, after which proteins in the gel are transferred onto a polyvinylidene difluoride (PVDF) membrane using iBlot2 (ThermoFisher Scientific IM21001) and Transfer Stacks (ThermoFisher Scientific IB24002). The membrane is blocked with either 1% bovine serum albumin or 5% non-fat milk to prevent non-specific binding. It is then incubated with in-house or commercial detection antibodies, washed, and incubated with HRP-conjugated secondary antibody (rabbit, Abcam #205718; mouse, Abcam #205719). Binding is visualized by developing with SuperSignal West Pico Plus chemiluminescent substrate (ThermoFisher Scientific #34577), and recorded digitally with iBright FL1000 (ThermoFisher Scientific A32752) or other compatible systems.

Example 16: Intracellular Signal Transduction Triggered by Anti-MS4A4A Antibodies As a cell surface molecule, it is likely that MS4A4A is involved directly or indirectly in the cells' interaction with extracellular signals. Other molecules in the MS4A family are components of surface receptor complexes and modulate signal transduction.

The topology of MS4A4A suggests that it has the capacity to act as an ion-channel, by forming a bundled barrel across the plasma membrane. Calcium is a common second messenger for such ion channels. The potential for anti-MS4A4A antibodies to trigger calcium flux in cell lines and primary cells is investigated as follows. Cells expressing MS4A4A are loaded with a calcium-sensitive dye (e.g., Fura-2, Indo-1 or Fluo-4 (ThermoFisher Scientific)). Cells are then incubated with anti-MS4A4A antibodies for up to thirty minutes and the level of fluorescence monitored by a flow cytometer, a fluorescent microscope, or a fluorospectrometer.

MS4A4A may also modulate other cell signaling events directly or indirectly. Protein phosphorylation/dephosphorylation is a mechanism associated with intracellular signal transduction. While MS4A4A contains no known protein kinase motifs, and is therefore unlikely to be a kinase or a phosphatase itself, MS4A4A may modulate downstream phosphorylation or dephosphorylation events through its interaction with other signaling molecules. To examine this, MS4A4A-expressing cell lines and primary cells are incubated with anti-MS4A4A antibodies. At various treatment time points, cells are harvested and analyzed for their intracellular protein serine/threonine phosphorylation or tyrosine phosphorylation by Western Blotting. For Western blot detection, cells are lysed by the addition of 50 μL lysis buffer (RIPA lysis buffer (ThermoFischerScientific Cat #89900)+1:100 HALT protease inhibitor cocktail (ThermoFischerScientific Cat #87786), and cleared for insoluble debris by centrifugation at 14,000×g for 15 minutes. Soluble fraction is assayed with bicinchoninic acid (BCA) reagent for protein quantification. Equal amounts of proteins from each sample are loaded on a 4-12% Bis-Tris Plus polyacrylamide gel (ThermoFisher Scientific NW04120) and subjected to electrophoresis separation, after which proteins in the gel are transferred onto a polyvinylidene difluoride (PVDF) membrane using iBlot2 (ThermoFisher Scientific IM21001) and Transfer Stacks (ThermoFisher Scientific IB24002). The membrane is blocked with either 1% bovine serum albumin or 5% non-fat milk to prevent non-specific binding. It is then incubated with in-house or commercial detection antibodies directed against serine/threonine phosphorylation or tyrosine phosphorylation. The membrane is then washed, and incubated with HRP-conjugated secondary antibody (rabbit, Abcam #205718; mouse, Abcam #205719). Binding is visualized by developing with SuperSignal West Pico Plus chemiluminescent substrate (ThermoFisher Scientific #34577), and recorded digitally with iBright FL1000 (ThermoFisher A32752) or other compatible systems.

It is possible that MS4A4A does not engage extracellular ligands directly, but rather exerts its effects on other cellular receptors in a receptor protein complex on the plasma membrane. For example, MS4A4A may form protein complexes with toll-like receptors (TLRs), cytokine receptors, chemokine receptors, scavenger receptors, Triggering Receptors Expressed on Myeloid cells 1 or 2, inhibitory receptors such as CD33, Siglec family or CD200, Fc receptors, or other cell surface receptors that modulate myeloid cell or microglia cell function. To examine this experimentally, we co-engage MS4A4A-expressing cell lines and primary cells with both the cognate ligands of these receptors and anti-MS4A4A antibodies. Downstream signaling events such as calcium mobilization and protein phosphorylation are examined as described above. In addition, changes in gene expression are analyzed through RT-PCR or global profiling methods such as RNASeq or microarrays.

Example 17: Characterization of Interactions Between MS4A4A and Binding Partners Use of anti-MS4A4A antibodies to block the interaction of MS4A4A with various binding partners may be tested. Little is known about proteins that interact with MS4A4A in vivo. To identify such binding partners, MS4A4A is immunoprecipitated from myeloid cell lines and primary cells using an anti-MS4A4A antibody of the present disclosure. The immunoprecipitated material is subjected to tandem mass spectrometry to identify proteins that have co-precipitated with MS4A4A protein. Once identified, this interaction is confirmed by western blotting or fluorescence resonance energy transfer (FRET) analyses. Alternatively, MS4A4A-expressing cell lines may be administered anti-MS4A4A antibodies and then stained for both MS4A4A and a potential binding partner, with the readout being either co-localization or fluorescence resonance energy transfer (FRET).

Example 18: Characterization of the Effects of Anti-MS4A4A Antibodies on Myeloid Cell Metabolism, Biology, and Function The downstream sequelae of engagement of anti-MS4A4A antibodies to their targets on myeloid cells, including microglia in the CNS, is examined in detailed using cultures of myeloid cell lines and primary cells such as monocyte-derived macrophages and dendritic cells as model systems. These cells are widely used to investigate the biology of myeloid cells as their functions are regularly studied in vitro. These functions include energy metabolism, cytokine production, phagocytosis, cell surface molecule expression, polarization, migration, and antigen presentation.

Briefly, MS4A4A-expressing cells are incubated with anti-MS4A4A antibodies presented in plate-bound, soluble or pre-complexed formats, which mimic the different ways antibodies are presented to their cellular target in vivo. The incubation condition and time line depend on the readout to be analyzed, but in general range from 1 hour to seven days. After incubation, cells can be harvested and lysed for mRNA or protein analyses. They are also subjected to flow cytometry analysis for cell surface molecule expression. For metabolic studies, cells are incubated with CellTiter-Glo (Promega) or other compatible reagents, which measures ATP content within the cells or other parameters for cell viability. Culture supernatants will also be harvested and subjected to ELISA or other similar methods to determine secretion of cytokines, chemokines and other molecules by treated cells. Phagocytosis capacity of treated cells is determined by feeding cells with fluorescently-labelled substrates such as latex beads, bacterial or fungal particles, and aggregate particles of protein such as A-beta, Tau or prion molecules. Cell migration is determined by the macrophage scratch assay (Liang et. al., Nature Protocols 2007; 2(2): 329) or the transwell assay (Corning, Corning, N.Y., USA).

Example 19: Characterization of the Activity of Anti-MS4A4A Antibodies Utilizing Animal Models for Aging, Seizures, Spinal Cord Injury, Retinal Dystrophy, Frontotemporal Dementia, and Alzheimer's Disease The therapeutic utility of anti-MS4A4A antibodies can also be tested in animal models for aging, seizures, spinal cord injury, retinal dystrophy, frontotemporal dementia, and Alzheimer disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 20: Characterization of the Effects of Anti-MS4A4A Antibodies Utilizing Animal Models for Oncology Myeloid cells represent a major component of the immune cells present in most solid tumors. Their role in tumor biology is context-dependent—while such cells have the potential to play a key role in the eradication of tumors, they are most often co-opted by the host tumor to assist in providing a pro-tumor phenotype. This is achieved mostly through the polarization of myeloid cells towards an M2-phenotype, which is typically immunosuppressive and thus blocks the immune system from eradicating the tumor. Anti-MS4A4A antibodies, through repolarization of myeloid cells, can reverse this immunosuppressive phenotype and promote an anti-tumor immune response.

Numerous animal tumor models exist. Examples of relevant animal models include humanized mouse models, where the mouse immune system is genetically deleted, as typified by the NSG mice (Jackson Laboratory, Bar Harbor, Me.). These mice act as receptive hosts for human immune cells, leading to the engraftment of human adaptive and innate immune cells. These animals are then inoculated with tumor cells, usually under the skin on the flanks. Tumor size over time represents the balance between the growth of tumor cells and their eradication by the host immune system. Throughout the time course, the animals are treated with anti-MS4A4A antibodies, which modifies tumor progression when compared to isotype-treated animals. At the end of treatment period tumors are extracted and subjected to various analyses to determine the effect of anti-MS4A4A antibodies on the tumor cells and infiltrating immune cells. Tumors can be sectioned, mounted onto slides and analyzed under the microscope for histological changes. mRNA can be analyzed by RT-PCR, RNASeq or microarray to determine changes in gene expression. Single cell suspensions of tumor and infiltrating immune cells can be prepared, stained with antibodies against various cell surface markers and analyzed by flow cytometry, to delineate changes in cell surface phenotype, especially in immune cells such as macrophages and T cells. Changes observed as a result of anti-MS4A4A treatment in any of these analyses will indicate an immune-modulatory function for these antibodies.

Example 21: Generation of Additional Anti-MS4A4A Hybridoma Antibodies

Additional anti-MS4A4A antibodies were obtained using a combined cell and DNA immunization approach using methods described above in Examples 1-4 with the following modifications. Balb/c mice (Jackson Laboratory, Bar Harbor, Me.) were immunized intraperitoneally weekly with 15 million cells each of 300.19 mouse pre-B cells stably overexpressing human or cyno MS4A4A diluted in PBS with or without Sigma Adjuvant System (Millipore Sigma-Aldrich, Burlington, Mass.). After four cell injections, the mice were boosted with two weekly injections of 50 µg each of plasmid DNA encoding full-length human or cyno MS4A4A with mGM-CSF DNA diluted in lactated Ringer's solution. The mice were given a final boost with 300.19 cells stably overexpressing human or cyno MS4A4A, and spleens and lymph nodes were harvested from the mice three days later.

Sera from the mice were analyzed for reactivity to MS4A4A by FACS analyses using 300.19 and K562 cells stably overexpressing human or cyno MS4A4A. Splenocytes from mice whose sera demonstrated strong binding to the cells by FACS were fused with P3X63Ag8.653 (CRL-1580, American Type Culture Collection, Rockville, Md.) or SP2/mIL-6 (CRL-2016, American Type Culture Collection, Rockville, Md.) mouse myeloma cells via electrofusion (ECM 2001, BTX, Holliston, Mass.) and incubated at 37° C., 5% $CO_2$, overnight in Clonacell-HY Medium C (StemCell Technologies, Vancouver, BC, Canada).

The following day, the fused cells were centrifuged and resuspended in 10 mls of ClonaCell-HY Medium C with anti-mouse IgG Fc-FITC (Jackson Immunoresearch, West Grove, Pa.) and then gently mixed with 90 mls of methyl-cellulose-based ClonaCell-HY Medium D (Stemcell Technologies) containing HAT components. The cells were plated into Nunc OmniTrays (Thermo Fisher Scientific, Rochester, N.Y.) and allowed to grow at 37° C., 5% $CO_2$ for seven days. Fluorescent colonies were selected and transferred into 96-well plates containing Clonacell-HY Medium E (StemCell Technologies) using a Clonepix 2 (Molecular Devices, Sunnyvale, Calif.). After six days, tissue culture supernatants from the hybridomas were screened by FACS against 300.19, K562, and/or U937 cells overexpressing full length human MS4A4A, as described below. In total, 1387 hybridoma clones were generated from this immunization campaign.

Example 22: Screening of Anti-MS4A4A Hybridomas

Initial screening of the anti-MS4A4A hybridomas obtained as described in Example 21 above was performed as follows. Tissue culture supernatants from 1387 hybridomas clones were initially screened for their ability to differentially bind U937, K562 and/or 300.19 stably expressing human MS4A4A by comparing the extent of binding to parental U937, K562 and/or 300.19 cells compared to transfected cells.

For screening of the hybridoma cell culture supernatants, a multiplexing FACS was employed where each cell line was labeled with dyes to create a unique fluorescent barcode. Briefly, human MS4A4A-expressing and parental U937, K562, and/or 300.19 cells were stained with either 500 nM of CellTrace Violet dye (ThermoFisher, Cat #C34557), 6 nM or 200 nM of CellTrace CFSE dye (ThermoFisher, Cat #C34570), or a combination of the two according to the manufacturer's protocol. After washing the labeled cells to remove free dye, non-specific binding through the Fc receptors, which are abundantly expressed on these cells, was blocked by incubating the cells with 1% BSA, 33% human serum (Sigma Cat #H4522) and 33% Human Fc block (Invitrogen Cat #14-9161-73). Cells were aliquoted in 96-well U-bottom plates ($8 \times 10^4$ cells per cell line, per well) and incubated with 50 µL of hybridoma cell culture supernatant on ice for 30 minutes. After this primary incubation, the supernatant was removed via centrifugation, the cells were washed twice with 175 µL of ice-cold FACS buffer (PBS+1% FBS+2 mM EDTA), and then further incubated on ice for 20 minutes with anti-mouse IgG Fc-allophycocyanin (APC) (Jackson Labs, Cat #115-136-071) (diluted 1:1000). Following this secondary incubation, the cells were again washed twice with ice-cold FACS buffer and resuspended in a final volume of 100 µL of FACS buffer. Binding intensity on cells were analyzed by the FACS Canto system (BD Biosciences), with sort gates drawn to distinguish each cell line by its unique fluorescent barcode. Ratio of APC mean fluorescence intensity (MFI) on MS4A4A-transfectants vs. parental cells was calculated for each hybridoma supernatant. A total of 121 clones were identified that displayed greater than 2.2-fold difference in binding to MS4A4A-stably transfected cells compared to binding to parental (non-transfected) cells.

Example 23: Secondary Screening of Anti-MS4A4A Hybridomas

Positive clones identified in Example 22 above were expanded and then rescreened for specificity against U937, K562, and/or 300.19 cells stably overexpressing human MS4A4A or cyno MS4A4A and parental U937, K562, and/or 300.19 cells. These experiments were performed using supernatants from hybridoma clones which had undergone further expansion after initial selection. Briefly, stably transfected cells were labeled with LIVE/DEAD Fixable Aqua Dead Cell Stain Kit (ThermoFisher Scientific Cat #L34957) on ice for 30 minutes. After a wash with PBS, non-specific binding through Fc receptors, which are abundantly expressed on these cells, was blocked by incubating the cells with 1% BSA, 33% human serum (Sigma Cat #H4522) and 33% Human Fc block (Invitrogen Cat #14-9161-73). $2 \times 10^5$ cells were aliquoted per well in 96-well U-bottom plates and incubated with 500 of culture supernatant on ice for 30 minutes. After this primary incubation, the supernatant was removed via centrifugation, the cells were washed twice with 175 µl of ice-cold FACS buffer (PBS+1% FBS+2 mM EDTA), and then incubated on ice for 20 minutes with anti-mouse IgG Fc-APC (Jackson ImmunoResearch Labs, West Grove, Pa., Cat #115-136-071) diluted 1:1000. Following this secondary incubation, the cells were again washed twice with ice-cold FACS buffer and resuspended in a final volume of 200 µl of FACS buffer. Analysis was performed on a FACS Canto system (BD Biosciences), with gates drawn to exclude dead (Aqua-positive) cells.

The APC ratio was calculated for each antibody as follows. For the parental (Par) cell lines, the anti-MS4A4A antibody binding ratio was calculated by comparing the binding measured to the binding observed using an irrelevant purified mouse IgG antibody. For cell lines overexpressing human MS4A4A (h4A) or cyno MS4A4A (cy4A), the ration was calculated by comparing the binding measured to the binding observed on the corresponding parental cell lines. Table 6 below shows the extent of antibody binding to each cell line: +/− signifies a 1.5-fold increase in MFI; +, ++, and +++ indicate over 2-fold increase in MFI. Clones that displayed binding to any of the MS4A4A-overexpressing cell lines (having a binding ratio greater than 1.5) and binding to parental cells with a ratio of less than 2 were carried forward for further characterization. These clones were named as anti-MS4A4A antibodies 4A-201 to 4A-240.

TABLE 6

| mAb clone | 300.19 | | | K562 | | U937 | |
|---|---|---|---|---|---|---|---|
| | Par | h4A | cy4A | Par | h4A | Par | h4A |
| 4A-201 | − | +/− | + | − | + | − | +/− |
| 4A-202 | − | +++ | ++ | − | ++ | − | +++ |
| 4A-203 | − | − | − | − | +/− | + | +/− |
| 4A-204 | − | − | − | − | + | − | + |
| 4A-205 | − | +/− | + | − | + | − | + |
| 4A-206 | − | − | +/− | − | + | − | + |
| 4A-207 | − | +/− | + | − | + | − | +/− |
| 4A-208 | − | +/− | + | − | + | − | + |
| 4A-209 | − | +/− | + | − | + | − | +/− |
| 4A-210 | − | − | − | − | +/− | − | − |
| 4A-213 | − | − | +/− | − | + | − | +/− |
| 4A-214 | − | ++ | ++ | − | ++ | − | ++ |
| 4A-216 | − | − | − | − | +/− | − | − |
| 4A-217 | − | +/− | + | − | +/− | − | + |
| 4A-219 | − | − | − | − | − | + | + |
| 4A-220 | − | ++ | − | − | ++ | − | ++ |
| 4A-221 | − | − | − | − | +/− | − | +/− |
| 4A-225 | − | +/− | + | − | + | − | +/− |
| 4A-226 | − | − | − | − | +/− | − | +/− |
| 4A-239 | − | − | − | − | − | − | − |
| 4A-240 | − | − | − | − | − | − | − |

Anti-MS4A4A antibodies that were selected for further characterization, based on their binding to huMS4A4A, are listed in Table 7. Their cross-reactivity to cyno MS4A4A is also listed. Commercially available anti-MS4A4A antibodies 5C12, 3F2, and 4H2 did not exhibit cyno MS4A4A cross-reactivity.

TABLE 7

| Anti-MS4A4A antibodies which cross-react to cyno MS4A4A | Anti-MS4A4A antibodies which do not cross-react to cyno MS4A4A |
|---|---|
| 4A-201, 4A-202, 4A-205, 4A-206, 4A-207, 4A-208, 4A-209, 4A-210, 4A-213, 4A-214, 4A-216, 4A-217, 4A-219, 4A-221, 4A-225, 4A-226 | 4A-203, 4A-204, 4A-220 |

Example 24: Anti-MS4A4A Antibody Binding to Peptides Corresponding to Human MS4A4A Extracellular Domains Anti-MS4A4A hybridoma supernatants (neat) or as purified mIgG (5 µg/ml) were tested for binding to human MS4A4A peptides corresponding to ECL1 (amino acid residues 86-98 of human MS4A4A of SEQ ID NO:1) and ECL2 (amino acid residues 159-179 of human MS4A4A of SEQ ID NO:1) using an enzyme-linked immunosorbent assay (ELISA). Briefly, 96-well polystyrene plates were coated with 2 or 10 µg/ml of synthetic free or BSA-conjugated peptides in coating buffer (0.05M carbonate buffer, pH9.6, Millipore Sigma Cat #C3041) overnight at 4° C. Coated plates were then blocked with ELISA diluent (PBS+0.5% BSA+0.05% Tween20) for 1-hour, washed 3×300 µL in PBST (PBS+0.05% Tween20, Thermo Cat #28352), and then the antibodies were added to the plate (50 µl/well). After 30 mins incubation (room temperature, with shaking), the plates were washed 3×300 µL in PBST. A secondary anti-mouse HRP antibody (Jackson Immunoresearch Cat #115-035-003) was added at a 1:1000 dilution in ELISA diluent (50 µl/well) and incubated for 30 minutes at room temperature with shaking. After a final set of washes (3×300 µL in PBST), 504, of TMB substrate (BioFx Cat #TMBW-1000-01) was added and the reaction was then quenched after 5-10 mins with 504, of stop solution (BioFx Cat #BSTP-1000-01). The quenched reaction wells were detected for absorbance at 650 nm with a BioTek Synergy Microplate Reader using GEN5 2.04 software.

Of the 19 anti-MS4A4A positive hybridoma clones identified above in Example 23, supernatants from 18 of these were tested along with 3 purified anti-MS4A4A murine antibodies (4A-18, 4A-21, and 4A-25; see Example 7 above) and 3 commercially-available murine anti-MS4A4A antibodies (5C12, 3F2, and 4H2). Four anti-MS4A4A antibodies (4A-21, 4A-25, 4A-202, and 4A-214) displayed strong binding to the huMS4A4A-ELC2 free-peptide compared to that observed for BSA mouse DAP12, an irrelevant negative peptide control. The three commercially-available anti-MS4A4A antibodies did not display binding to human MS4A4A ECL1 and ECL2 peptides. The hybridoma clones displaying no binding may be accounted for by several factors, e.g., these anti-MS4A4A antibodies may bind to conformational epitopes that were not modeled by this methodology, or these antibodies may recognize epitopes that are made up of both ECL1 and ECL2 of MS4A4A.

Binding to ECL1 of MS4A4A was not detected for any of the hybridoma clones screened using this methodology. This may be due to the smaller size of ECL1, which is 13 amino acid residues in length compared to that of ECL2, which is 21 amino acid residues in length. It is predicted that MS4A4A forms a 4-helix bundle structure. The larger ECL2 domain may mask the smaller ECL1 domain and prevent antibody binding. It is possible that certain antibodies identified herein bind conformational epitopes of MS4A4A that would not be recapitulated by the linear ECL1 peptides used herein, or recognize epitopes formed by a combination of amino acid residues located in ECL1 and ECL2, and thus would not be detected by this methodology.

The results of the ELISA binding experiments are shown below in Table 8.

TABLE 8

| Anti-MS4A4A antibodies which displayed binding to human MS4A4A-ECL2 peptide | Anti-MS4A4A antibodies for which no binding was detected |
|---|---|
| 4A-21, 4A-25, 4A-202, 4A-214 | 4A-201, 4A-203, 4A-204, 4A-205, 4A-206, 4A-207, 4A-208, 4A-209, 4A-210, 4A-213, 4A-217, 4A-219, 4A-220, 4A-225 |

Example 25: Molecular Cloning of Anti-MS4A4A Hybridoma Antibodies and Generation of Chimeric Antibody-Expressing Vectors The additional anti-MS4A4A antibodies obtained from the hybridomas described above in Examples 21-24 were cloned as follows. $5 \times 10^5$ hybridoma cells were resuspended in 0.35 ml RLT buffer, a component of the RNeasy Mini Kit (Qiagen, Cat. No. 74104). Total RNA was extracted using through binding to spin columns according to manufacturer's instructions. cDNA was generated by using Clontech's SMARTer® RACE 5'/3' Kit (Takara Bio USA Inc, Cat. No. 634859) following the manufacturer's protocol.

Variable heavy and light immunoglobulin regions were cloned separately by touchdown PCR using the 5' UPM primer provided in the RACE kit and heavy chain constant region primer (5'-AGCTGGGAAGGTGTGCACA-3') [SEQ ID NO:140] and light constant region primer (5'-CCAT-TTTGTCGTTCACTGCCA-3') [SEQ ID NO:141].

PCR products were purified by QIAquick PCR Purification Kit (QIAGEN, Cat No. 28106) and ligated into a pCR2.1®-TOPO® cloning vector (TOPO® TA cloning Kit, Invitrogen) and transformed into ONESHOT® TOP10 Competent cells.

Transformed *Escherichia coli* (*E. coli*) colonies were isolated and the variable heavy chain (VH) and variable light chain (VL) nucleic acids were sequenced for each corresponding hybridoma cell line. Following the sequence determination, variable heavy chain regions and variable light chain regions were amplified by PCR using primers containing endonuclease restriction sites (BsrGI and BstEII for HV and BssHII and BsiWI for LV) and subcloned into pcDNA mammalian expression vector (Invitrogen) encoding human IgG1 and IgGK, respectively.

Example 26: Antibody Heavy Chain and Light Chain Variable Domain Sequences

Using standard techniques, the amino acid sequences encoding the light chain variable regions and the heavy chain variable regions for the additional anti-MS4A4A antibodies were determined. The Kabat light chain CDR sequences and heavy chain CDR sequences of the antibodies are set forth in Table 9A below. The light chain variable region and heavy chain variable region sequences of the antibodies are set forth in Table 9B below.

TABLE 9A

| Antibody CDR sequences | | | | | | |
|---|---|---|---|---|---|---|
| Ab ID | CDR-H1 | CDR-H2 | CDR-H3 | CDR-L1 | CDR-L2 | CDR-L3 |
| 4A-201 | SFGVT (SEQ ID NO: 142) | IIWGDGSTNY HSALIS (SEQ ID NO: 154) | RDYDGREDVM GY (SEQ ID NO: 168) | KATQNVRT AVA (SEQ ID NO: 183) | LASNRHT (SEQ ID NO: 197) | LQHWSYPL T (SEQ ID NO: 210) |
| 4A-202 | NYWMQ (SEQ ID NO: 143) | ATHPGHGDT RYTQKFKG (SEQ ID NO: 155) | EEVYYGFRSY WYFDV (SEQ ID NO: 169) | RASESVDNY GVSFMN (SEQ ID NO: 184) | GASNQGS (SEQ ID NO: 198) | QQSKEVPP T (SEQ ID NO: 211) |
| 4A-203 | SFYMS (SEQ ID NO: 144) | AINSNGGSTY YPDTVKG (SEQ ID NO: 156) | QNYYGSSSYW YFDV (SEQ ID NO: 170) | SVSSSISSSN LH (SEQ ID NO: 185) | GTSNLAS (SEQ ID NO: 199) | QQWSRYPL T (SEQ ID NO: 212) |
| 4A-204 | SFYMS (SEQ ID NO: 144) | AINSNGGSTY YPDSVKG (SEQ ID NO: 157) | HLYYGLYYAM DY (SEQ ID NO: 171) | SASSSVSFM Y (SEQ ID NO: 186) | DTSKLAS (SEQ ID NO: 81) | FQGSGFPLT (SEQ ID NO: 213) |
| 4A-205 | HYGMS (SEQ ID NO: 145) | TIGRDGIHTD YRDSVKG (SEQ ID NO: 158) | HLYYGLYYSM DY (SEQ ID NO: 172) | SASSSVSFM Y (SEQ ID NO: 186) | DTSKLAS (SEQ ID NO: 81) | FQGSGYPL T (SEQ ID NO: 214) |
| 4A-206 | SYTMS (SEQ ID NO: 146) | SLSSGGSTYY PDSVKG (SEQ ID NO: 159) | DYYVSSYRWY FDV (SEQ ID NO: 173) | RASQDISNY LN (SEQ ID NO: 187) | YTSNLHS (SEQ ID NO: 200) | QQGKSFPW T (SEQ ID NO: 215) |
| 4A-207 | NYWMN (SEQ ID NO: 147) | EIRLKSNNYA THYAESVKG (SEQ ID NO: 160) | DPPMDY (SEQ ID NO: 174) | SASSSVSYM H (SEQ ID NO: 188) | STSNLVS (SEQ ID NO: 201) | HQRTSYPW T (SEQ ID NO: 216) |

TABLE 9A-continued

Antibody CDR sequences

| Ab ID | CDR-H1 | CDR-H2 | CDR-H3 | CDR-L1 | CDR-L2 | CDR-L3 |
|---|---|---|---|---|---|---|
| 4A-208 | DTYIH (SEQ ID NO: 148) | RIDPANDNTK YDPKFQG (SEQ ID NO: 161) | IAYGSWALDY (SEQ ID NO: 175) | KASQNVDT NVA (SEQ ID NO: 189) | SASFRYS (SEQ ID NO: 202) | QQYNSYPW T (SEQ ID NO: 217) |
| 4A-209 | RYWMS (SEQ ID NO: 149) | EIKSDSSTINY TPSLKD (SEQ ID NO: 162) | RGFYDYDAWF AY (SEQ ID NO: 176) | SASSSVTYM Y (SEQ ID NO: 190) | LTSNRAS (SEQ ID NO: 203) | QQWSSNPP T (SEQ ID NO: 218) |
| 4A-210 | TYTMS (SEQ ID NO: 150) | TISSGGSYTF YPDSVKG (SEQ ID NO: 163) | DNTTGDRGWY FDV (SEQ ID NO: 177) | QASESVSFA GKSLMH (SEQ ID NO: 191) | RASNLES (SEQ ID NO: 204) | MQSMEDPR T (SEQ ID NO: 219) |
| 4A-213 | SYGVH (SEQ ID NO: 151) | VIWVGGSTN YNSALMS (SEQ ID NO: 164) | AVYYYGSSYYF DY (SEQ ID NO: 178) | RASQSIGTSI H (SEQ ID NO: 192) | YASESIS (SEQ ID NO: 205) | QQSNSWPT (SEQ ID NO: 220) |
| 4A-214 | NYWMN (SEQ ID NO: 147) | EIRLKSNNYA THYAESVKG (SEQ ID NO: 160) | MIIVDY (SEQ ID NO: 179) | RASQSVSSS TYSYLH (SEQ ID NO: 193) | YASNLES (SEQ ID NO: 206) | QHSWEIPLT (SEQ ID NO: 221) |
| 4A-216 | NYWLG (SEQ ID NO: 152) | DIFPGGNYLK NNEKFKG (SEQ ID NO: 165) | SSANFPFTY (SEQ ID NO: 180) | TASSSLSYM Y (SEQ ID NO: 194) | LTSNLAS (SEQ ID NO: 207) | QQWSSNPL T (SEQ ID NO: 222) |
| 4A-217 | SYGMS (SEQ ID NO: 153) | HISGGGTFTH YPDSVKG (SEQ ID NO: 166) | EGAGTRFAY (SEQ ID NO: 181) | RPSQDISNSL N (SEQ ID NO: 195) | STSKLHS (SEQ ID NO: 208) | QQDYTLPW T (SEQ ID NO: 223) |
| 4A-219 | SYGVH (SEQ ID NO: 151) | VIWSGGSTD YNAAFIS (SEQ ID NO: 167) | LYYGYDGFAY (SEQ ID NO: 182) | KASQDVSTA VA (SEQ ID NO: 196) | SASYRYT (SEQ ID NO: 209) | QQHYSTPL T (SEQ ID NO: 224) |
| 4A-25 | TSDMGV G (SEQ ID NO: 304) | DIWWDDNKY YNPSLKS (SEQ ID NO: 310) | RANYGNLFDY (SEQ ID NO: 316) | KASQNVRSA VA (SEQ ID NO: 322) | WASNRHT (SEQ ID NO: 328) | LQHWNYLT (SEQ ID NO: 334) |
| 4A-26 | TSDMGV G (SEQ ID NO: 305) | DIWWDDNKY YNPSLKS (SEQ ID NO: 311) | RANYGNLFDY (SEQ ID NO: 317) | KASQSVDY DGDSYMN (SEQ ID NO: 323) | AASNLES (SEQ ID NO: 329) | QQSNEDPR T (SEQ ID NO: 335) |
| 4A-239 | HYGMS (SEQ ID NO: 306) | TISSGGSSTY YPDSVKG (SEQ ID NO: 312) | HLYYGLYYAM DY (SEQ ID NO: 318) | SASSSVSFM Y (SEQ ID NO: 324) | DTSKLAS (SEQ ID NO: 330) | FQGSGFPLT (SEQ ID NO: 336) |
| 4A-225 | SFGVN (SEQ ID NO: 307) | IIWGDGSTNF HSALMS (SEQ ID NO: 313) | RDYDGRDDVM GY (SEQ ID NO: 319) | KASQTVRTA VA (SEQ ID NO: 325) | LASNRHT (SEQ ID NO: 331) | LQHWSYPL T (SEQ ID NO: 337) |
| 4A-214 | NYWMN (SEQ ID NO: 308) | EIRLKSNNYA THYAESVKG (SEQ ID NO: 314) | MIIVDY (SEQ ID NO: 320) | RASQSVSSS TYSYLH (SEQ ID NO: 326) | YASNLES (SEQ ID NO: 332) | QHSWEIPLT (SEQ ID NO: 338) |
| 4A-220 | GYFMN (SEQ ID NO: 309) | RINPYNGDTL YNQKFKG (SEQ ID NO: 315) | VKGYDYDGAM DY (SEQ ID NO: 321) | RSSQSLLQS GNQKSSLA (SEQ ID NO: 327) | WARTRQS (SEQ ID NO: 333) | QQYSDTPF T (SEQ ID NO: 339) |

TABLE 9B

| Ab ID | V$_H$: | V$_L$: |
|---|---|---|
| 4A-201 | QVQLRESGPGLVAPSQSLSITCTVSGFSLSSFGV TWVRQPPGKGLEWLGIIWGDGSTNYHSALISR LSISKDNSKSQVFLKLNRLQTDDTATYYCAKR DYDGREDVMGYWGQGTSVTVSS (SEQ ID NO: 225) | DIVMTQSQKFMSTSVGDRVSITCKATQ NVRTAVAWYQQKPGQSPKPLIYLASNR HTGVPDRFTGSGSGTDFTLTITNVQSED LADYFCLQHWSYPLTFGAGTKLEMK (SEQ ID NO: 240) |
| 4A-202 | QVQLQQSGAELARPGASVKLSCKASGYTFTNY WMQWVKQRPGQGLEWIGATHPGHGDTRYTQ KFKGKATLSADKSSSTAYMQLSNLASEDSAVY YCAREEVYYGFRSYWYFDVWGAGTTVTSS (SEQ ID NO: 226) | DIVLTQSPASLAVSLGQRATISCRASESV DNYGVSFMNWFQQKPGQPPKLLIYGAS NQGSGVPARFSGSGSGTDFSLNIHPMEE DDTAMYFCQQSKEVPPTFGGGTKLEIK (SEQ ID NO: 241) |
| 4A-203 | DVKLVESGGGLVKLGGSLKLSCAASGFTFSSF YMSWVRQTPEKRLELVAAINSNGGSTYYPDTV KGRFTISRDNAKNTLYLQMSSLKSEDTALYYC ARQNYYGSSSYWYFDVWGAGTTVTSS (SEQ ID NO: 227) | EIVLTQSPALMAASPGEKVTITCSVSSSI SSSNLHWYRQKSETSPKPWIYGTSNLAS GVPVRFSGSGSGTSYSLTISSMEAEDAA TYYCQQWSRYPLTFGAGTKLELK (SEQ ID NO: 242) |
| 4A-204 | DVKLVESGGGLAKLGGSLKLSCAASGFTFSSF YMSWVRQTPEKRLELVAAINSNGGSTYYPDSV KGRFTISRDNVKNTLYLQMSSLKSEDTAMYYC ARHLYYGLYYAMDYWGQGTSVTVSS (SEQ ID NO: 228) | ENVLTQSPAIMSASPGEKVTMTCSASSS VSFMYWYQEKSSTSPKLWIYDTSKLAS GVPGRFSGSGSGNSYSLTISSMGAEDVA TYYCFQGSGFPLTFGSGTKLEIK (SEQ ID NO: 243) |
| 4A-205 | EVQLVESGGDLVKPGGSLKLSCAASGFTFSHY GMSWVRQTPDKRLDWVATIGRDGIHTDYRDS VKGRFTISRDNAKNTLYLQMGSLKSEDSAIFYC ARHLYYGLYYSMDYWGQGTSVTVSS (SEQ ID NO: 229) | ENVLTQSPAIMSASPGEKVTMTCSASS SVSFMYWYQQKSSTSPKLWIYDTSKL ASGVPGRFSGSGSGNSYSLTISSMEAE DVATYYCFQGSGYPLTFGSGTKLEIK (SEQ ID NO: 244) |
| 4A-206 | EVKLVESGGGLVKPGGSLKLSCAASGFTFSSYT MSWVRQTPEKRLEWVASLSSGGSTYYPDSVK GRFTISRDNARNILYLQMSSLRSEDTAMYYCA KDYYVSSYRWYFDVWGAGTTVTSS (SEQ ID NO: 230) | DIQMTQITSSLSASLGDRVTISCRASQDI SNYLNWYQQKPDGTVKLLIYYTSNLHS GVPSRFSGSGSGTDYSLTISNLEQEDIAT YFCQQGKSFPWTFGGGTKLEIK (SEQ ID NO: 245) |
| 4A-207 | EVNLEESGGGLVQPGGSMKLSCVASGFTFNNY WMNWVRQSPEKGLEWVAEIRLKSNNYATHY AESVKGRFTISRDDSKSSVYLQMNNLRPEDTAI YYCTTDPPMDYSGQGTPVTVSS (SEQ ID NO: 231) | QIVLTQSPAFMSASPGEKVTITCSASSSV SYMHWFQQKPGTSPKLWIYSTSNLVSG VPDRFSGSGSGTSYSLTISRMEAEYAAT YYCHQRTSYPWTFGGGTKLEIK (SEQ ID NO: 246) |
| 4A-208 | EVHLQQSGAEVVKPGASVKLSCTASGFNIKDT YIHWVMQRPEQGLEWIGRIDPANDNTKYDPKF QGKATITSDTSSNTAYLHLSSLTSEDTAVYYCA RIAYGSWALDYWGQGTSVTVSS (SEQ ID NO: 232) | DIVMTQSQKFMSTSVGDRVIVTCKASQ NVDTNVAWYQQKPGQSPKTLIYSASFR YSGVPDRFTGSGSGTDFTLSISNVQSED LAEYFCQQYNSYPWTFGGGTKLEIK (SEQ ID NO: 247) |
| 4A-209 | EVKLLESGGGLVQPGGSLKLSCAASGFDFSRY WMSWVRQAPGKGLEWIGEIKSDSSTINYTPSL KDKFIISRDNAKNTLYLQMSKVRSEDTALYYC ARRGFYDYDAWFAYWGQGTLVTVSS (SEQ ID NO: 233) | QIVLTQSPTLMSASPGEKVTMTCSASSS VTYMYWYQQKPRSSPKPWIYLTSNRAS GVPTRFSGSGSGTSHSLTISYMEAEDAA TYYCQQWSSNPPTFGAGTKLELR (SEQ ID NO: 248) |
| 4A-210 | DVKLVESGGGLVKPGGSLKLSCAASGFTFGTY TMSWVRQTPEKRLEWVATISSGGSYTFYPDSV KGRFTISRDNAKNTLYLQMSSLKSEDTAMYYC TRDNTTGDRGWYFDVWGAGTTVTSS (SEQ ID NO: 234) | DIVLTQSPVSLAVSLGQRATISCQASESV SFAGKSLMHWFQQKPGQPPKLLIYRAS NLESGVPARFSGSGSESDFTLTIDPVEED DATMYYCMQSMEDPRTFGGGTKLEIK (SEQ ID NO: 249) |
| 4A-213 | QVQLKESGPGLVAPSQSLSITCTVSGFSLTSYG VHWVRQPPGKGLEWLGVIWGGSTNYNSAL MSRLSISKDNSKSQVFLKMNSLQTDDTAMYYC ARAVYYYGSSYYFDYWGQGTTVTVSS (SEQ ID NO: 235) | DILLTQSPAILSVSPGERVSFSCRASQSIG TSIHWYQQRTNGSPRLLIKYASESISGIP SRFSGSGSGTDFTLSINSVESEDIADYYC QQSNSWPTTFGGGTKLEIK (SEQ ID NO: 250) |
| 4A-214 | EVKLEESGGGLVQPGRSMKLSCVASGFTFSNY WMNWVRQSPEKGLEWVAEIRLKSNNYATHY AESVKGRFTISRDDSKSSVYLQMNNLRAEDTGI YYCSSMIIVDYWGQGTTVTSS (SEQ ID NO: 236) | DIVLTQSPASLTVSLGQRATISCRASQSV SSSTYSLHWYQQRPGQPPKLLIKYASN LESGVPARFSGSGSGTVFTLNIHPVEEE DTATYYCQHSWEIPLTFGAGTKLEMK (SEQ ID NO: 251) |
| 4A-216 | QVHLQQSGTELVRPGTSVRISCKASGYTFTNY WLGWVKERTGHGLEWIGDIFPGGNYLKNNEK | QIVLTQSPALMSASPGEKVTMTCTASSS LSYMYWYQQRPRSSPKPWIYLTSNLAS |

TABLE 9B-continued

V_H and V_L sequences

| Ab ID | V_H: | V_L: |
|---|---|---|
| | FKGKATLTADTSSSTAYMQLNGLTSEDSAVYF CARSSANFPFTYWGQGTLVTVSS (SEQ ID NO: 237) | GVPTRFSGSGSGTSYSLTISSMEAEDAA TYYCQQWSSNPLTFGAGTKLEMK (SEQ ID NO: 252) |
| 4A-217 | EVKLVESGGGLVKPGGSLKLSCAASGFTFSSY GMSWVRQTPEKRLEWVAHISGGGTFTHYPDS VKGRFTISRDNAKNNLYLQMSSLRSEDTALYY CAREGAGTRFAYWGQGTLVTVSS (SEQ ID NO: 238) | DIQMTQTTSSLSASLGDRVTISCRPSQDI SNSLNWYQQKPDGTVKLLIYSTSKLHS GVPSRFSGSGSGIDYSLTISNLEQEDIAT YFCQQDYTLPWTFGGGTKLDVK (SEQ ID NO: 253) |
| 4A-219 | QVQMKQSGPGLVQPSQSLSITCTVSGFSLTSYG VHWVRQSPGKGLEWLGVIWSGGSTDYNAAFI SRLSISKDNSKSQVFFKMNSLQADDTAIYYCVR LYYGYDGFAYWGQGTLVTVSS (SEQ ID NO: 239) | DIVMTQSHKFMSTSVGDRVSITCKASQ DVSTAVAWYQQKPGQSPKLLIYSASYR YTGVPDRFTGSGSGTDFTFTISSVQAED LAVYYCQQHYSTPLTFGAGTKLELK (SEQ ID NO: 254) |
| 4A-25 | QVTLKESGPGILQPSQTLSLTCSFSGFSLRTSD MGVGWVRQPSGEGLEWLADIWWDDNKYYN PSLKSRLTISKDTSSNQVFLKITSVDTADTATY YCARRANYGNLFDYWGQGTAVTVSS (SEQ ID NO: 340) | DIVMTQSLKFMSTSVGDRVSITCKASQ NVRSAVAWYQQKPGQSPKVLIYWAS NRHTGVPDRFTGSGSGTDFTLTISNVQ SEDLADYFCLQHWNYLTFGSGTKLEIK (SEQ ID NO: 346) |
| 4A-26 | QVTLKESGPGILQPSQTLSLTCSFSGFSLRTSD MGVGWVRQPSGEGLEWLADIWWDDNKYYN PSLKSRLTISKDTSSNQVFLKITSVDTADTATY YCARRANYGNLFDYWGQGTAVTVSS (SEQ ID NO: 341) | DIVMTQSPASLAVSLGQRATISCKASQ SVDYDGDSYMNWYQQKPGQPPKLLIY AASNLESGIPARFSGSGSGTDFTLNIHP VEEEDAATYYCQQSNEDPRTFGGGTK LEIK (SEQ ID NO: 347) |
| 4A-239 | EVQVVESGGDLVKPGGSLKLSCTASGFTFSHY GMSWVRQTPDKRLEWVATISSGGSSTYYPDS VKGRFTISRDNVKNTLYLQMSSLKSEDTAMY YCARHLYYGLYYAMDYWGQGTSVTVSS (SEQ ID NO: 342) | ENVLTQSPAIMSASPGEKVTMTCSASS SVSFMYWYQEKSSTSPKLWIYDTSKL ASGVPGRFSGSGSGNSYSLTISSMGAE DVATYYCFQGSGFPLTFGSGTKLEIK (SEQ ID NO: 348) |
| 4A-225 | QVQLKESGPGLVAPSQSLSITCTVSGFSLTSFG VNWFRQPPGKGLEWLGIIWGDGSTNFHSALM SRLSISKDNSKSQVFLKLNRLQTDDTATYYCA KRDYDGRDDVMGYWGQGTSVTVSS (SEQ ID NO: 343) | DIVMTQSQKIMSTSVGDRVSITCKASQ TVRTAVAWYQQKPGQSPKALIYLASN RHTGVPDRFTGSGSGTDFTLTISNVQSE DLADYFCLQHWSYPLTFGAGTKLEMK (SEQ ID NO: 349) |
| 4A-214 | EVKLEESGGGLVQPGRSMKLSCVASGFTFSN YWMNWVRQSPEKGLEWVAEIRLKSNNYATH YAESVKGRFTISRDDSKSSVYLQMNNLRAED TGIYYCSSMIIVDYWGQGTTVTVSS (SEQ ID NO: 344) | DIVLTQSPASLTVSLGQRATISCRASQS VSSSTYSYLHWYQQRPGQPPKLLIYA SNLESGVPARFSGSGSGTVFTLNIHPVE EEDTATYYCQHSWEIPLTFGAGTKLE MK (SEQ ID NO: 350) |
| 4A-220 | EVQLQQSGPDLVKPGASVKISCKASGYSFNG YFMNWVMQSHGESLEWIGRINPYNGDTLYN QKFKGKATLTVDKSSSTGHMELRSLASEDSA VYYCARVKGYDYDGAMDYWGQGTSVTVSS (SEQ ID NO: 345) | DIVMTQSPDSLAVSLGERATINCRSSQS LLQSGNQKSSLAWYQQKPGQPPKLLIF WARTRQSGVPDRFSGSGSGTDFTLTIS SVQAEDVAVYYCQQYSDTPFTFGQGT KLEIK (SEQ ID NO: 351) |

Example 27: Generation of Purified Anti-MS4A4A Chimera Antibodies

Amino acid sequences for the VH and VL regions were optimized for expression in HEK cells as follows. The nucleotide sequences encoding the VH and VL of the anti-MS4A4A antibodies were amended electronically by addition of sequences encoding antibody signal peptides at the 5' end and the human Kappa constant region or a human IgG1 Fc region for the light chain and heavy chain respectively. SapI restriction enzyme sites were added at each end to enable cloning into the vector. The HC and LC DNA sequences comprising the inserts were synthesized by Atum Bio (Newark, Calif.) and inserted into the pM269 shuttle vector. The HC and LC DNA inserts were cloned using the Electra cloning kit into the pD2610-V6 vector for expression. Competent DH10B *E. coli* (Max Efficiency DH10B catalog #18297010) were thawed on ice and 2 µl of the ligation mix (~20 ng of plasmid DNA) was added to 30 ul of competent cells and allowed to incubate on ice for 30-45 minutes. The cells were then heat-shocked at 39° C. for 45 seconds and replaced on ice. 0.5 ml of SOC Medium was added and the cells incubated for a further 30-45 min at 37° C. 5 ul of the transformation mix was plated onto LB agar plates with kanamycin (TEKNOVA) and allowed to grow overnight at 37° C. Individual colonies picked and were grown up in LB+Kan overnight. The resulting minipreps were purified using a Qiagen mini-prep kit and sequence-confirmed. To generate sufficient DNA for stable cell line construction, 60 mL *E. coli* cultures of the correct colonies were grown for two days and then purified using Qigen Plasmid Maxi Prep Kits.

Transfections into HEK 293 cells were performed at the 250 ml scale in 1 L shake flasks using the EXPI-293 transfection kit (Invitrogen). 150 µg of light chain expression vector and 100 µg of heavy chain expression vector were mixed together with the Fectin reagent, allowed to sit for 20 minutes, and then added to the cells with gently mixing. The cells were returned to the shaker incubator for 6 hours whereupon the enhancer media was added per the manufacturer's instructions. Cells were harvested 5-6 days post-transfection by spinning out the cells in a clinical centrifuge, sterile-filtering the cell-free supernatant using a Nalgene 0.2 µm filter, and stringing the conditioned media at 4° C. until purified.

Protein was purified using a protein A matrix (Mab Select Sure) packed into glass or polypropylene columns (GE Healthcare). The conditioned media was loaded onto the column, washed extensively, and then eluted with an elution buffer gradient containing arginine or glycine at a pH of 3.0-3.5. The eluted antibody was neutralized and formulated into storage buffer (citrate or histidine depending on the antibody's solubility), concentrated to >1 mg/ml, and then sterile filtered. The antibodies were tested by nanodrop, SDS-PAGE, and SEC prior to shipment. Preparative SEC was performed if the % monomer content was less than 95%. Yields typically ranged from 15-50 mgs of antibody depending on the antibody pair being expressed.

Example 28: Binding of Purified Anti-MS4A4A Antibodies to Cells Expressing MS4A4A Purified huIgG1 chimeric anti-MS4A4A antibodies were screened for their ability to differentially bind MS4A4A on U937 cells stably overexpressing human MS4A4A, U937 cells with human MS4A4A knocked out, and parental U937 cells. Differential binding to MS4A4A expressed on these cells was assessed by FACS analysis using 5 µg/ml of purified anti-MS4A4A chimeric antibodies, as described above. The APC MFI for each antibody was determined; the ratio of that MFI value over the MFI value observed with secondary antibody binding alone is shown in Table 10 below. These results indicated that anti-MS4A4A antibodies of the present disclosure bound specifically to human MS4A4A and did not bind to cells with human MS4A4A knocked out.

TABLE 10

| Antibody ID | U937-human MS4A4A | U937-human MS4A4A (knock out) | U937 parental |
| --- | --- | --- | --- |
| 4A-201 | 8.9 | 1.1 | 1.1 |
| 4A-202 | 219.6 | 1.1 | 3.4 |
| 4A-203 | 8.0 | 12.1 | 7.0 |
| 4A-205 | 25.3 | 1.1 | 1.0 |
| 4A-206 | 18.5 | 1.1 | 1.1 |
| 4A-207 | 10.0 | 1.0 | 1.1 |
| 4A-208 | 19.9 | 1.2 | 1.1 |
| 4A-209 | 19.8 | 1.1 | 1.1 |
| 4A-210 | 4.0 | 1.1 | 1.1 |
| 4A-213 | 13.0 | 1.1 | 1.1 |
| 4A-216 | 3.3 | 1.0 | 1.1 |
| 4A-217 | 23.6 | 1.1 | 1.1 |
| 4A-219 | 102.7 | 52.6 | 47.3 |
| 4A-18 | 649.2 | 1.1 | 2.9 |
| 4A-21 | 368.9 | 1.1 | 2.4 |
| huIgG1 isotype ctrl | 1.1 | 1.1 | 1.1 |

Example 29: MS4A4A Structural Predictions, Variant Peptide Design for Epitope Mapping, and Epitope Determination of Anti-MS4A4A Antibodies The primary amino acid sequence of MS4A4A provides important information about its secondary and tertiary structure. The MS4A4A protein has four transmembrane domains (TMDs) and each TMD is composed of 21 amino acids. A typical TMD is composed of a phosphodiester lipid bilayer with approximately 40 Å in thickness. The phosphate head moiety creates a hydrophilic layer that interacts with the hydrophilic environment either in the extracellular or cytosolic space and the lipid tail creates an internal lipid bilayer that interacts with the lipophilic residues of the TMDs. The thickness of the TMD lipid bilayer is approximately 32 to 34 Å. Predicted from the amino acid composition, residue numbers, and the thickness of the lipid bilayer, MS4A4A is predicted to comprise a four-helix bundle (4HB) with two extra cellular loops (ECLs), connecting TMD1 and TMD2, and TMD3 and TMD4 from the N-terminus to the C-terminus, respectively. The 4-helix bundle stabilizes the MS4A4A in the membrane by a significant enthalpy gain obtained from the helix-lipid bilayer interactions and helix-helix interactions.

The primary amino acid sequence and composition of the MS4A4A ECLs indicate important features associated with epitopes and dynamic properties. ECL1 is composed of 13 amino acids including one cysteine, one methionine, one alanine, three serine, one threonine, two asparagine, one tyrosine, one proline, one isoleucine, and only one glycine residue(s). ECL2 is composed of 21 amino acids including two cysteine residues which are separated by 8 amino acids, three serine, one threonine, one phenylalanine, three histidine, one proline, three tyrosine, four asparagine, one methionine, and only two glycine residues. Very few glycine residues but several large beta-branched amino acid residues and a proline residue are found in ECL1 and ECL2. Moreover, ECL2 contains two cysteine residues that are predicted to create an intra-loop disulfide bond, which further reduces conformational entropy. As a result, ECL1 and ECL2 tend to employ a significantly reduced number of conformational isomers interacting with each other in rigid-body type internal movements.

An expression plasmid encoding human MS4A4A (NM_024021) containing a C-terminal GFP tag was purchased from Origene (cat #RG223557) and used as template to generate single alanine scanning mutations in the coding region of extracellular loop 1 (ECL1) of human MS4A4A (4A.Ala1-Ala13 in Table 11 below; C67 to S79 of SEQ ID NO:1 corresponding to ECL1; CMASNTYGSNPIS (SEQ ID NO:289); in the coding region of extracellular loop 2 (ECL2) of human MS4A4A (4A.Ala14-Ala34 in Table 11 below; 5140 to 5160 of SEQ ID NO:1 corresponding to ECL2; SFHHPYCNYYGNSNNCHGTMS (SEQ ID NO:290); and ECL2 deletion mutations (4A.Ala35 (deletion of amino acid residues 150-152 of SEQ ID NO:1 within ECL2) and 4A.Ala36 (deletion of amino acid residues 148-152 of SEQ ID NO:1 within ECL2) in Table 12 below). The mutations were performed using overlap polymerase chain reaction techniques standard in the art. Each polymerase chain reaction polynucleic acid fragment was purified and subcloned back into the expression vector using MluI and AsiSI restriction sites.

Prior to performing epitope determination using alanine-scanning techniques, relative EC50s of the anti-MS4A4A antibodies were determined as follows using transient transfections of the above-described expression constructs in HEK293T cells. HEK293T cells were seeded in 6 well plates and grown overnight. The next day, cells were transfected with Fugene HD (Promega) or Lipofectamine 3000 (Thermo Fisher Scientific) with a 4:1 ratio of Fugene to DNA or a 3:1 ratio of Lipofectamine to DNA, following the manufacturer's protocols. Approximately 24 hours after transfection, cells were harvested using Trypsin-EDTA and processed for FACS staining.

For FACS staining, 150,000 cells were added to each well of 96 well plates and a titration of anti-MS4A4A antibodies was added in FACS buffer (PBS+2% FBS) and incubated on ice for 60 minutes. Plates were centrifuged (1,400 rpm, 3 minutes), supernatant decanted, and the cells were washed thrice with 200 µl FACS buffer, each followed by a spin and decant step. Antibodies were tested as msIgG1 or huIgG1 chimera and either goat anti-human PE (Southern Biotech, Cat #2040-09, 1:200) or goat anti-mouse APC (BD Biosciences, Cat #550826, 1:100) were added in FACS buffer on ice for 30 minutes. Cells were subsequently washed twice with 200 µl FACS buffer and imaged on an iQue cytometer. Median fluorescence intensity (MFI) was measured on the GFP positive population, representing cells expressing MS4A4A.

Six of the initially tested anti-MS4A4A antibodies bind to HEK293T cells expressing wild-type (WT) MS4A4A-GFP: these included anti-MS4A4A antibodies 4A-18, 4A-21, 4A-202, as well as published murine monoclonal anti-MS4A4A antibodies 4H2 (Kerafast), 5C12 (Biolegend), 3F2 (Millipore). Titration curves for each antibody were determined to establish the optimal anti-MS4A4A antibody concentrations for subsequent epitope mapping studies.

For epitope mapping experiments, HEK293T cells were transfected with the different human MS4A4A expression constructs (as described above; see Table 11 below), and antibody binding was determined using six different anti-MS4A4A antibodies: 4A-21, 4A-18, 4A-202, 4H2, 5C12, and 3F5. Anti-MS4A4A antibody binding was calculated as the % of the MFI from binding to cells transfected with wildtype human MS4A4A expression construct. If an amino acid mutation in the MS4A4A polypeptide resulted in decreased antibody binding to below 20% of that of binding to wildtype MS4A4A, the mutated amino acid was considered a critical amino acid necessary for anti-MS4A4A antibody binding to the MS4A4A protein. Some amino acid mutations in the MS4A4A protein resulted in a decrease in anti-MS4A4A antibody binding to below 51% but above 20% (compared to the binding to wildtype MS4A4A); such amino acids were defined as amino acids contributing to binding of the anti-MS4A4A antibody to the MS4A4A protein.

Some amino acids in MS4A4A affected binding of all tested antibodies, such as the two cysteines, C165 and C174, that are thought to form a cysteine bridge in MS4-type proteins. Such amino acids were considered structural amino acids.

The results of these experiments are provided in Table 11 below. As stated above, Ala.1 to Ala.13 refer to MS4A4A mutations in ECL1; Ala.14 to Ala.36 refer to MS4A4A mutations in ECL2. Data is shown as % binding of the anti-MS4A4A antibodies to the various alanine-scanning mutations compared to the binding of the anti-MS4A4A antibodies to wildtype MS4A4A protein. The mapping experiments were independently repeated twice with very similar results. One difference was that anti-MS4A4A antibodies 4A-21 and 4A-18 were tested once as huIgG1 and second as msIgG1 at two concentrations. Table 12 below shows results from the msIgG1 test for these antibodies. For all other antibodies, Table 11 shows average antibody binding across both experiments. Values showing anti-MS4A4A antibody binding to MS4A4A protein below 20% of that measured for binding to wildtype MS4A4A are in bold in Table 11 below.

All mutations showed equivalent transfection efficiencies of between approximately 22-33% (data not shown). No correlation between average antibody binding and GFP levels in the cells was observed, suggesting that GFP levels cannot be used as a predictor for MS4A4A cell surface expression.

TABLE 11

| Construct | Loop sequence | 4A-21 | 4A-18 | 4A-202* | 4H2 | 5C12 | 3F2 |
|---|---|---|---|---|---|---|---|
| WT ECL1 | CMASNTYGSNPIS (SEQ ID NO: 289) | | | 100 | | | |
| 4A.Ala.1 | <u>S</u>MASNTYGSNPIS (SEQ ID NO: 255) | 84.1 | 96.6 | 86.99 | 72.80 | 82.36 | 79.58 |
| 4A.Ala.2 | C<u>A</u>ASNTYGSNPIS (SEQ ID NO: 256) | 12.5 | 19.1 | 9.93 | 7.42 | 11.04 | 7.33 |
| 4A.Ala.3 | CM<u>S</u>SNTYGSNPIS (SEQ ID NO: 257) | 90.7 | 116.6 | 99.12 | 87.76 | 94.47 | 87.46 |
| 4A.Ala.4 | CMA<u>A</u>NTYGSNPIS (SEQ ID NO: 258) | 91.2 | 85.8 | 92.48 | 77.90 | 88.62 | 82.49 |
| 4A.Ala.5 | CMAS<u>A</u>TYGSNPIS (SEQ ID NO: 259) | 93.1 | 65.6 | 81.64 | 75.95 | 80.92 | 83.89 |
| 4A.Ala.6 | CMASN<u>A</u>YGSNPIS (SEQ ID NO: 260) | 100.4 | 87.5 | 83.22 | 77.29 | 78.57 | 78.38 |
| 4A.Ala.7 | CMASNT<u>A</u>GSNPIS (SEQ ID NO: 261) | 114.5 | 15.8 | 98.41 | 93.36 | 94.96 | 92.91 |
| 4A.Ala.8 | CMASNTY<u>A</u>SNPIS (SEQ ID NO: 262) | 94.6 | 70.4 | 83.82 | 74.41 | 17.39 | 84.41 |
| 4A.Ala.9 | CMASNTYG<u>A</u>NPIS (SEQ ID NO: 263) | 99.6 | 106.0 | 102.06 | 85.83 | 89.83 | 94.67 |

TABLE 11-continued

| Construct | Loop sequence | 4A-21 | 4A-18 | 4A-202* | 4H2 | 5C12 | 3F2 |
|---|---|---|---|---|---|---|---|
| 4A.Ala.10 | CMASNTYGSAPIS (SEQ ID NO: 264) | 102.3 | 103.2 | 124.27 | 91.27 | 93.95 | 89.57 |
| 4A.Ala.11 | CMASNTYGSNAIS (SEQ ID NO: 265) | 28.7 | 14.8 | 35.06 | 20.53 | 32.79 | 25.29 |
| 4A.Ala.12 | CMASNTYGSNPAS (SEQ ID NO: 266) | 66.4 | 91.4 | 57.21 | 48.93 | 56.33 | 49.19 |
| 4A.Ala.13 | CMASNTYGSNPIA (SEQ ID NO: 267) | 38.4 | 41.8 | 32.34 | 27.38 | 36.36 | 28.92 |
| WT ECL2 | SFHHPYCNYYGNSNNCHGTMS (SEQ ID NO: 290) | | | 100 | | | |
| 4A.Ala.14 | AFHHPYCNYYGNSNNCHGTMS (SEQ ID NO: 268) | 94.3 | 87.8 | 78.14 | 83.99 | 81.28 | 85.27 |
| 4A.Ala.15 | SAHHPYCNYYGNSNNCHGTMS (SEQ ID NO: 269) | 118.7 | 116.9 | 111.77 | 84.71 | 98.51 | 87.20 |
| 4A.Ala.16 | SFAHPYCNYYGNSNNCHGTMS (SEQ ID NO: 270) | 71.0 | 48.1 | 76.87 | 58.00 | 71.46 | 64.58 |
| 4A.Ala.17 | SFHAPYCNYYGNSNNCHGTMS (SEQ ID NO: 271) | 102.8 | 99.4 | 125.37 | 77.01 | 82.95 | 85.21 |
| 4A.Ala.18 | SFHHAYCNYYGNSNNCHGTMS (SEQ ID NO: 353) | 101.4 | 103.7 | 89.39 | 36.92 | 46.13 | 42.33 |
| 4A.Ala.19 | SFHHPACNYYGNSNNCHGTMS (SEQ ID NO: 272) | 83.8 | 16.3 | 26.68 | 1.66 | 42.27 | 1.08 |
| 4A.Ala.20 | SFHHPYSNYYGNSNNCHGTMS (SEQ ID NO: 273) | 5.0 | 2.8 | 8.66 | 1.94 | 1.74 | 1.60 |
| 4A.Ala.21 | SFHHPYCAYYGNSNNCHGTMS (SEQ ID NO: 274) | 1.8 | 73.3 | 93.33 | 70.08 | 73.76 | 80.30 |
| 4A.Ala.22 | SFHHPYCNAYGNSNNCHGTMS (SEQ ID NO: 275) | 1.8 | 3.0 | 31.23 | 1.10 | 0.99 | 0.88 |
| 4A.Ala.23 | SFHHPYCNYAGNSNNCHGTMS (SEQ ID NO: 276) | 1.4 | 2.7 | 50.05 | 1.19 | 0.96 | 0.95 |
| 4A.Ala.24 | SFHHPYCNYYANSNNCHGTMS (SEQ ID NO: 277) | 57.5 | 63.0 | 75.76 | 27.67 | 18.20 | 33.76 |
| 4A.Ala.25 | SFHHPYCNYYGASNNCHGTMS (SEQ ID NO: 278) | 69.2 | 40.0 | 100.54 | 37.09 | 25.55 | 45.60 |
| 4A.Ala.26 | SFHHPYCNYYGNANCHGTMS (SEQ ID NO: 279) | 89.3 | 96.5 | 90.84 | 68.48 | 81.73 | 68.38 |
| 4A.Ala.27 | SFHHPYCNYYGNSANCHGTMS (SEQ ID NO: 354) | 98.3 | 118.6 | 98.39 | 99.46 | 91.60 | 94.25 |
| 4A.Ala.28 | SFHHPYCNYYGNSNACHGTMS (SEQ ID NO: 280) | 87.3 | 116.4 | 98.61 | 86.22 | 85.94 | 83.37 |
| 4A.Ala.29 | SFHHPYCNYYGNSNNSHGTMS (SEQ ID NO: 281) | 8.4 | 2.7 | 4.54 | 1.09 | 1.01 | 0.91 |
| 4A.Ala.30 | SFHHPYCNYYGNSNNCAGTMS (SEQ ID NO: 282) | 87.5 | 62.6 | 92.83 | 72.87 | 80.56 | 82.45 |
| 4A.Ala.31 | SFHHPYCNYYGNSNNCHATMS (SEQ ID NO: 283) | 147.8 | 158.6 | 142.81 | 123.13 | 124.19 | 135.58 |
| 4A.Ala.32 | SFHHPYCNYYGNSNNCHGAMS (SEQ ID NO: 284) | 61.6 | 42.9 | 63.28 | 44.61 | 56.19 | 45.14 |
| 4A.Ala.33 | SFHHPYCNYYGNSNNCHGTAS (SEQ ID NO: 285) | 81.8 | 36.1 | 73.09 | 62.83 | 59.85 | 60.45 |
| 4A.Ala.34 | SFHHPYCNYYGNSNNCHGTMA (SEQ ID NO: 286) | 113.4 | 91.0 | 117.02 | 102.44 | 99.15 | 103.80 |

TABLE 11-continued

| Construct | Loop sequence | 4A-21 | 4A-18 | 4A-202* | 4H2 | 5C12 | 3F2 |
|---|---|---|---|---|---|---|---|
| 4A.Ala.35 | SFHHPYCNYY---NNCHGTMS (SEQ ID NO: 287) | 107.3 | 2.7 | 73.14 | 1.08 | 1.00 | 0.88 |
| 4A.Ala.36 | SFHHPYCN-----NNCHGTMS (SEQ ID NO: 288) | 1.3 | 2.6 | 0.07 | 0.99 | 0.93 | 0.83 |

*antibody tested as huIgG1 chimera

Results shown above suggest that anti-MS4A4A antibodies of the present disclosure recognize distinct linear and/or 3D structural epitopes within MS4A4A.

Based on the anti-MS4A4A antibody binding data obtained from these experiments, the following loop amino acid residues within human MS4A4A were considered structural amino acids within the MS4A4A protein as mutating each of them affected binding of all anti-MS4A4A antibodies tested: M87, C165, Y167, Y168, C174 (Based on human MS4A4A protein; SEQ ID NO:1). Amino acid residues C165 and C174 are predicted to establish a cysteine bridge forming a loop in ECL2. In the absence of this cysteine bridge, anti-MS4A4A antibodies did not bind MS4A4A protein, suggesting that the loop structure within ECL2 of MS4A4A is important for antibody binding. More evidence for loop structure being important comes from the two loop deletion mutants (Ala.35 and Ala.36) which also strongly affect binding of the antibodies.

The results further showed that amino acid residues Y167 and Y168 strongly affected binding of anti-MS4A4A antibodies 4A-21, 4A-18, 4H2, 5C12, and 3F2. These amino acid residues also affected binding of anti-MS4A4A antibody 4A-202 to a lesser degree. Additionally, amino acid residues P96, I97, and S98 in ECL1 reduced binding to some degree of all anti-MS4A4A antibodies tested. These results suggested either that mutations in any of these five amino acid residues altered the structure of the extracellular domains important for antibody recognition and binding, or that these amino acid residues are important for the interaction and binding of each of the six anti-MS4A4A listed. Proline is the most restrained amino acid residue, which is critical to the secondary and tertiary structure of a polypeptide. For example, proline acts as a disrupter in the middle of regular secondary structure elements, including that of alpha helices and beta sheets; however, proline is commonly found as the first amino acid residue of an alpha helix and in the edge stands of beta sheets. Tyrosine, isoleucine, and serine residues provide multiple antigen-antibody interactions, including, for example, Van der Waals interaction(s), pi-pi stacking and pi-facial hydrogen bonding interactions, and/or hydrogen bonds. Accordingly, either tyrosine, proline, isoleucine, or serine residues can create well-defined structural epitopes. Any subtle changes in these four amino acid residues have the potential to significantly disrupt antibody binding affinity.

The mutation at amino acid residue M87A in MS4A4A greatly reduced or abolished binding of all anti-MS4A4A antibodies tested. Based on the prediction that ECL1 and ECL2 employ well-defined rigid body structures and may interact with each other, the M87A binding result shown indicated that the M87 amino acid residue is predicted to be one of the most critical residues in maintaining the rigid loop structure of MS4A4A, as the side chain of M87 can interact with one or more beta-branched amino acids in ECL1 and/or ECL2 by Van de Waals contacts and hydrogen bonds through backbone-side chain and/or backbone-backbone interactions.

Table 12 below lists the unique binding amino acid residues for the anti-MS4A4A antibodies disclosed herein. Anti-MS4A4A antibody 4A-21 requires N166 in ECL2 for binding to human MS4A4A. The data showed that anti-MS4A4A antibodies 4A-18 and 5C12 bind ECL1 as well as ECL2 of human MS4A4A. Anti-MS4A4A antibody 4A-202 had some binding contribution by amino acid residue Y164.

All three commercial anti-MS4A4A antibodies bind P163, whereas none of the anti-MS4A4A antibodies disclosed herein and tested in this study did. This proline P163 of human MS4A4A is replaced by arginine in the cynomolgous MS4A4A protein. Such observation suggests that this proline to arginine change is important for determining cyno cross-reactivity, or the lack thereof, as displayed by the binding characteristics of the commercial MS4A4A antibodies. Proline is the most structurally-restrained amino acid residue and arginine (in cyno MS4A4A) is a positively-charged amino acid at physiological pH. The proline to arginine difference in human vs cyno MS4A4A may profoundly affect the conformation of the MS4A4A protein, therefore preventing the commercial MS4A4A antibodies from binding. Anti-MS4A4A antibodies 4A-18, 4A-21, and 4A-202 appeared not to be dependent on this amino acid for binding, and thus their binding to the cynomolgous protein was not affected.

In summary, anti-MS4A4A antibodies 4A-21, 4A-18, and 4A-202 bound epitopes on MS4A4A which are distinct from that of commercially-available anti-MS4A4A antibodies (Table 12 below). The commercial anti-MS4A4A antibodies 4H2 and 3F2 exhibited identical epitopes, which overlapped significantly with that of anti-MS4A4A antibody 5C12. In contrast, anti-MS4A4A antibodies 4A-18, 4A-21, and 4A-202 each exhibited unique epitope binding characteristics distinct from each other and distinct from that of the commercial ant-MS4A4A antibodies. These differences in binding properties are shown in Table 11. Additionally, the results showed that no two anti-MS4A4A antibodies tested bound identical epitopes within human MS4A4A; however, there are shared amino acid binding residues across some or all antibodies (e.g., amino acid residues Y167 and Y168, Y164, N170, T177).

TABLE 12

| Antibody | ECL1 residues | ECL2 residues |
|---|---|---|
| 4A-21 | | N166 (critical) |
| 4A-18 | Y92 (critical) | Y164 (critical) |
| | | H161, N170, T177, M178 (contribute) |
| 4A-202 | | Y164 (contributes) |
| 4H2 | | Y164 (critical) |
| | | P163, G169, N170, T177 (contribute) |

TABLE 12-continued

| Antibody | ECL1 residues | ECL2 residues |
|---|---|---|
| 5C12 | G93 (critical) | G169 (critical) |
|  |  | P163, Y164, N170 (contribute) |
| 3F2 |  | Y164 (critical) |
|  |  | P163, G169, N170, T177 (contribute) |

Example 30: Effect of Anti-MS4A4A Antibodies on TREM2 Expression

Data from human genetics studies have suggested strong genetic links between MS4A4A and TREM2 and susceptibility to Alzheimer's disease (Piccio et al., 2016, Acta Neuropathol, 131:925-9330. MS4A4A alleles protective for Alzheimer's disease are linked to increased sTREM2 levels in the cerebrospinal fluid. To examine the effect of anti-MS4A4A antibodies of the present disclosure modulating sTREM2 and plasma-membrane/cell surface TREM2 (mTREM2) levels in macrophages, the following studies were performed.

Primary human macrophages were generated as described above in Example 24. The isolated cells were then plated in 96-well plates and treated with the panel of anti-MS4A4A antibodies (10 µg/ml) in complete RPMI. After 48 hours of incubation, supernatants were collected and sTREM2 levels determined using Meso Scale Discovery (MSD). Briefly, wells of an MSD plate (Cat #L15XA-3) were incubated with capture antibody at 1 µg/ml, overnight on orbital shaker at 500 RPM at 4° C. The wells were washed and then blocked in binding buffer (1% heat-inactivated high-grade BSA) in PBS) for an hour on an orbital shaker at 500 RPM at 20° C. Standards (Recombinant Human Trem2 Fc 1828-T2 (R&D Systems)) and unknown samples at proper concentrations were prepared in binding buffer, added to the wells, then incubated for 1 hour on orbital shaker at 500 RPM at 20° C. The wells were washed and then incubated with secondary antibody (Biotinylated goat anti-human TREM2 (R&D Systems Cat #BAF1828)) at 100 ng/ml for 1 hour on an orbital shaker at 500 RPM at 20° C. The wells were washed and then incubated with a detection reagent (Sulfo Tag-Streptavidin; MSD Cat #R32AD) at 0.2 µg/ml in binding buffer. The wells were then washed, 150 µl read buffer (1×, MSD) was added to each well, and the plates read on a Sector Imager.

Separately, anti-MS4A4A antibody treated cells (above) were collected and subjected to flow cytometry to determine mTREM2 levels using an anti-TREM2 antibody (Alector) conjugated to allophycocyanin or similar fluorophores.

As shown in Table 13, anti-MS4A4A antibodies increased the level of sTREM2 in the supernatants of cultured human primary macrophages obtained from various donors. The results described herein showed that the anti-MS4A4A antibodies of the present disclosure increase or upregulate sTREM2 levels in the supernatants of human primary macrophages. Numbers reported in Table 13 are relative to those obtained using an isotype control antibody, which was set at 100.

TABLE 13

| Antibody | Donor | | |
|---|---|---|---|
|  | 686 | 687 | 688 |
| 4A-201 | 138.6 | 129.3 | 119.8 |
| 4A-202 | 249.7 | 208.9 | 431.2 |
| 4A-203 | 113.9 | 119.9 | 130.2 |
| 4A-204 | 101.6 | 104.8 | 123.2 |
| 4A-205 | 113.3 | 114.5 | 126.2 |

TABLE 13-continued

| Antibody | Donor | | |
|---|---|---|---|
|  | 686 | 687 | 688 |
| 4A-206 | 132.2 | 131.3 | 141.2 |
| 4A-207 | 126.5 | 135.7 | 133.9 |
| 4A-208 | 174.1 | 195.0 | 157.4 |
| 4A-209 | 120.0 | 115.4 | 83.4 |
| 4A-210 | 114.7 | 127.0 | 140.2 |
| 4A-214 | 142.8 | 168.3 | 137.7 |
| 4A-217 | 158.3 | 153.4 | 120.2 |
| 4A-219 | 102.6 | 92.3 | 85.3 |
| 4A-18 | 151.2 | 152.4 | 181.0 |
| 4A-21 | 340.0 | 230.4 | 489.7 |
| huIgG1 | 100 | 100 | 100 |

As shown below in Table 14, anti-MS4A4A antibodies increased the level of plasma-membrane/cell surface TREM2 (mTREM2) on cultured human primary macrophages obtained from various donors. These results were consistent with the corresponding increase in sTREM2 observed in the supernatants of these cells, as shown above in Table 13. Numbers reported in Table 14 are relative to those obtained using an isotype control antibody, which was set at 100.

TABLE 14

| Antibody | Donor | | |
|---|---|---|---|
|  | 695 | 696 | 697 |
| 4A-201 | 107.1 | 117.7 | 90.8 |
| 4A-202 | 319.2 | 374.5 | 373.2 |
| 4A-203 | 89.4 | 111.9 | 92.9 |
| 4A-204 | 83.3 | 98.6 | 90.2 |
| 4A-205 | 129.8 | 128.4 | 100.7 |
| 4A-206 | 116.5 | 111.9 | 86.7 |
| 4A-207 | 112.3 | 112.5 | 90.2 |
| 4A-208 | 63.7 | 114.0 | 107.2 |
| 4A-209 | 109.7 | 109.9 | 116.0 |
| 4A-210 | 102.0 | 116.1 | 111.6 |
| 4A-214 | 178.3 | 124.6 | 65.7 |
| 4A-217 | 116.5 | 85.6 | 97.9 |
| 4A-219 | 82.0 | 96.6 | 104.3 |
| 4A-18 | 273.0 | 286.1 | 313.6 |
| 4A-21 | 209.1 | 356.4 | 546.1 |
| hIgG1 | 100.0 | 100.0 | 100.0 |

These data showed that treatment of human primary macrophages with anti-MS4A4A antibodies of the present disclosure increased both sTREM2 and mTREM2 levels in these cells of myeloid lineage. These results are in contrast to a prior report showing that the commercially-available anti-MS4A4A antibody 5C12 reduced sTREM2 levels in supernatants of cultured human macrophages (Deming et al, supra). As genetic studies have linked the Alzheimer's disease protective MS4A4A allele with increased levels of sTREM2 in Alzheimer's disease patients, these results suggested that anti-MS4A4A antibodies are an effective treatment for Alzheimer's disease and other neurodegenerative disorders by modulating (i.e., increasing) TREM2 activity and function.

Example 31: Effect of Anti-MS4A4A Antibodies on Cellular ATP Levels

Intracellular ATP levels correlate with and reflect cell health and viability. As impaired myeloid cell health and viability contribute to neurodegenerative disease and disorders, therapies that enhance myeloid cell viability and function may affect the severity and progression of neurodegenerative diseases and disorders. In order to examine the effect of anti-MS4A4A antibodies on ATP levels within cells, the following experiments were performed. Human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate). For dendritic cell derivation, 100 ng/ml human GM-CSF (hu-GMCSF) and human IL-4 (hu-IL-4) were added to the monocytes for 6-7 days. For macrophages, 100 ng/ml human M-CSF and 8% v/v human serum were added to the cells for 5-7 days.

The cells were then plated at 50,000 cells/well in complete RPMI-1640 and cultured for 2 days in the presence or absence of anti-MS4A4A antibodies or isotype control antibody at various concentrations (10 µg/ml, 1.0 µg/ml, and 0.1 µg/ml) in solution. ATP content within the cells was then quantified using the CellTiter-Glo Luminescent cell viability kit (Promega, Cat #G7571) following the manufacturer's protocol. Data presented in Tables 15A and 15B indicates ATP content (as arbitrary units) within the primary human macrophages following anti-MS4A4A antibodies treatment for 48 hours; values are corrected by subtracting the values obtained using an isotype control antibody (huIgG1) from the values obtained with each anti-MS4A4A antibody. As shown Tables 15A and 15B, anti-MS4A4A antibodies modulated ATP levels in human macrophages; the effect was generally dose-dependent manner, with varying potencies observed among the panel of anti-MS4A4A antibodies tested.

TABLE 15A

| | Donor 692 | | | Donor 693 (µg/ml) | | | Donor 694 | | |
|---|---|---|---|---|---|---|---|---|---|
| Antibody | 10 | 1 | 0.1 | 10 | 1 | 0.1 | 10 | 1 | 0.1 |
| 4A-201 | 49425 | 35731 | 18234 | 6814 | 6540 | 2728 | 8218 | 5311 | 15 |
| 4A-202 | 53645 | 52252 | 20337 | 18635 | 11433 | 12879 | 6532 | 4094 | −258 |
| 4A-203 | 23033 | 14071 | 9150 | 10116 | 1028 | −4644 | 7343 | −4123 | −4488 |
| 4A-204 | 12224 | 8552 | 16694 | 5258 | −2516 | −2021 | −1868 | −9069 | −3626 |
| 4A-205 | 33653 | 20814 | 7474 | 2596 | −1856 | −6620 | 9926 | 6398 | −7654 |
| 4A-206 | 8009 | 20172 | 3322 | 11120 | 2924 | 438 | 2653 | 3352 | −3334 |
| 4A-207 | 53997 | 47379 | 21604 | 7695 | 1351 | −2673 | 10137 | 5106 | −3300 |
| 4A-208 | 11465 | 3324 | 4134 | 5465 | 6010 | 5803 | 7814 | 5048 | −803 |
| 4A-209 | 34882 | 14342 | 14762 | 12525 | 1906 | 1850 | 12259 | 3837 | 1383 |
| 4A-210 | 14016 | 12484 | 6372 | 12374 | 5899 | 2757 | 10753 | 9923 | 7296 |
| 4A-214 | 51168 | 31853 | 2293 | 9143 | 6207 | 3794 | 6557 | 14513 | 4019 |
| 4A-217 | 13140 | 5564 | −3842 | 26765 | 17646 | 3053 | 9635 | 13291 | 1299 |
| 4A-219 | 13668 | −2090 | −11510 | 5150 | −2535 | −2986 | 3649 | 6722 | 1039 |
| 4A-18 | 23160 | 6906 | −5787 | 23204 | 16769 | 6236 | 11566 | 13304 | 3069 |
| 4A-21 | 26760 | 12833 | −8816 | 4388 | 6502 | 3899 | 3142 | 1396 | 4351 |

TABLE 15B

| | Donor 696 | | | Donor 697 | | |
|---|---|---|---|---|---|---|
| | | (µg/ml) | | | | |
| Antibody | 10 | 1 | 0.1 | 10 | 1 | 0.1 |
| 4A-201 | 8959 | 10765 | 2909 | 14547 | 10624 | 661 |
| 4A-202 | 32860 | 29424 | 27628 | 45490 | 34016 | 6018 |
| 4A-203 | 5255 | 6276 | 1275 | 6163 | 4854 | 210 |
| 4A-204 | 7832 | 4853 | 10947 | 16656 | 11747 | 2388 |
| 4A-205 | 13612 | 9057 | −1090 | 18833 | 16104 | 1714 |
| 4A-206 | 12654 | 9994 | 5316 | 27686 | 16893 | 416 |
| 4A-207 | 25143 | 11329 | 1513 | 26671 | 14010 | 4525 |
| 4A-208 | 9970 | 10807 | 7426 | 22796 | 19978 | 2325 |

TABLE 15B-continued

| | Donor 696 | | | Donor 697 | | |
|---|---|---|---|---|---|---|
| | | (µg/ml) | | | | |
| Antibody | 10 | 1 | 0.1 | 10 | 1 | 0.1 |
| 4A-209 | 14315 | −13997 | −19916 | 21512 | 8414 | 424 |
| 4A-210 | −16039 | −14851 | −14616 | 14956 | 12118 | −5297 |
| 4A-214 | 10700 | 5928 | −644 | 21341 | 9816 | −8711 |
| 4A-217 | 12476 | 7934 | 788 | 31035 | 11827 | −2760 |
| 4A-219 | 647 | −4091 | −4813 | −2805 | −2977 | −6445 |
| 4A-18 | 19762 | 14761 | 25364 | 18360 | 17007 | −3374 |
| 4A-21 | 12401 | 14058 | 8868 | 6130 | 5652 | −2946 |

As shown above, treatment of human primary macrophages with anti-MS4A4A antibodies of the present disclosure induced an increase in intracellular ATP levels above that observed with an isotype antibody. These results suggested that anti-MS4A4A antibodies of the present disclosure are effective at enhancing the health and viability of myeloid cells, and therefore able to reverse or reduce the loss of CNS myeloid cell function associated with various neurodegenerative diseases and disorders.

Additionally, as shown above in Example 30, anti-MS4A4A antibodies of the present disclosure increased soluble TREM2 and membrane TREM2 levels. The increase in TREM2 together with the increased viability and ATP levels in response to anti-MS4A4A antibody addition indicated that the observed increase in TREM2 is of functional consequence of the cells.

Example 32: Effect of Anti-MS4A4A Antibodies on Macrophage Cell Surface Markers

The effect of anti-MS4A4A antibodies on various M1 and M2 macrophage cell surface markers was examined as follows. Human primary macrophages were treated with various anti-MS4A4A antibodies (10 µg/ml) in complete RPMI1640 for 48 hours. The cells were then harvested and subjected to flow cytometry, using antibodies specific for M1 markers (CD16, MHC Class II, CD86), M2 markers (CD200R, Dectin-1, CD163), and a pan-macrophage marker CD14.

The results of these studies are shown in Table 16A and Table 16B below. Cell surface marker expression levels were assayed by flow cytometry and were normalized to that obtained in cells treated with an isotype control antibody, which was set at 100%. The data was averaged across three donors for each marker. The cell surface expression of certain M1 markers, including CD86 and MHC-II, were unaltered or only modestly affected by anti-MS4A4A antibody treatment. By contrast, the cell surface expression of certain M2 markers, including CD200R, CD163, and Dectin-1 was significantly reduced by anti-MS4A4A antibody treatment. In addition, the cell surface expression levels of SIRPα and of the pan-macrophage marker CD14 were reduced by anti-MS4A4A antibody treatment. Certain anti-MS4A4A antibodies reduced the cell surface expression of CD14 and SIRPα and of M1 markers CD200R and CD163 more significantly compared to commercially available antibodies 3F2, 4H2, and 5C12.

TABLE 16A

| Antibody | CD200R (M2) | CD14 (Pan) | Dectin-1 (M2) | CD16 (M1) | CD163 (M2) | MHC-II (M1) | CD86 (M1) |
|---|---|---|---|---|---|---|---|
| huIgG1 | 100.0 | 100.0 | 100.0 | 100.0 | 100.0 | 100.0 | 100.0 |
| 4A-201 | 95.5 | 102.5 | 89.1 | 115.1 | 118.6 | 119.4 | 111.4 |
| 4A-202 | 35.2 | 60.2 | 47.3 | 171.0 | 39.1 | 73.6 | 121.8 |
| 4A-203 | 84.0 | 86.8 | 65.7 | 105.3 | 100.0 | 94.5 | 90.6 |
| 4A-204 | 92.7 | 99.2 | 96.2 | 104.4 | 103.8 | 98.3 | 97.4 |
| 4A-205 | 86.8 | 113.4 | 120.8 | 113.6 | 104.6 | 107.6 | 119.5 |
| 4A-206 | 95.5 | 87.8 | 69.8 | 142.3 | 120.4 | 98.6 | 140.9 |
| 4A-207 | 92.2 | 77.4 | 56.5 | 99.5 | 109.6 | 89.8 | 123.9 |
| 4A-208 | 92.5 | 82.7 | 54.3 | 131.4 | 119.0 | 95.3 | 108.8 |
| 4A-209 | 85.3 | 63.3 | 45.9 | 64.7 | 131.1 | 110.5 | 109.8 |
| 4A-210 | 88.4 | 77.2 | 48.2 | 84.6 | 99.2 | 100.8 | 97.0 |
| 4A-214 | 89.5 | 98.1 | 108.3 | 106.5 | 112.8 | 144.2 | 131.6 |
| 4A-217 | 93.0 | 94.8 | 87.6 | 118.3 | 108.3 | 113.6 | 120.3 |
| 4A-219 | 101.1 | 102.5 | 117.2 | 109.3 | 106.7 | 110.2 | 100.2 |
| 4A-18 | 29.0 | 56.6 | 46.6 | 239.3 | 33.6 | 45.6 | 112.3 |
| 4A-21 | 67.9 | 39.4 | 22.9 | 75.5 | 65.0 | 81.3 | 177.0 |

TABLE 16B

| Antibody | CD16 | CD163 | CD86 | CD200R | CD14 | CD11b | SIRPα |
|---|---|---|---|---|---|---|---|
| 4A-201 | 117.33 | 102.19 | 91.60 | 68.60 | 96.87 | 143.11 | 90.38 |
| 4A-202 | 354.77 | 77.83 | 88.29 | 34.64 | 69.20 | 162.31 | 64.55 |
| 4A-205 | 118.53 | 98.14 | 99.49 | 69.43 | 96.21 | 121.98 | 92.92 |
| 4A-206 | 116.56 | 96.61 | 91.85 | 76.07 | 84.85 | 114.54 | 87.03 |
| 4A-207 | 128.40 | 101.51 | 91.19 | 75.05 | 89.45 | 108.50 | 89.96 |
| 4A-208 | 100.79 | 90.27 | 100.28 | 71.05 | 81.89 | 116.79 | 84.77 |
| 4A-209 | 47.49 | 85.62 | 98.87 | 70.23 | 45.96 | 63.96 | 76.88 |
| 4A-210 | 86.79 | 101.56 | 91.52 | 80.17 | 80.11 | 98.76 | 94.35 |
| 4A-216 | 93.18 | 95.75 | 89.07 | 50.22 | 83.50 | 107.44 | 79.14 |
| 4A-219 | 112.17 | 104.82 | 92.42 | 83.67 | 94.09 | 111.82 | 84.98 |
| 4A-18 | 352.24 | 58.38 | 90.82 | 22.63 | 70.74 | 194.20 | 53.26 |
| 4A-21 | 113.76 | 56.87 | 102.46 | 13.08 | 41.40 | 102.00 | 60.76 |
| 4A-25 | 84.61 | 84.27 | 121.07 | 80.73 | 49.03 | 70.22 | 100.87 |
| 4A-225 | 88.73 | 96.48 | 107.80 | 86.01 | 72.87 | 69.23 | 100.16 |
| 4A-213 | 110.57 | 97.45 | 113.31 | 84.55 | 109.83 | 110.87 | 99.25 |
| 4A-204 | 216.17 | 80.64 | 86.06 | 85.11 | 81.87 | 126.45 | 90.03 |
| 4A-214 | 293.86 | 64.01 | 103.66 | 26.93 | 78.81 | 163.63 | 67.94 |
| 4A-220 | 362.61 | 77.15 | 72.60 | 39.41 | 84.42 | 160.95 | 70.07 |
| 3F2 | 252.36 | 65.13 | 79.88 | 59.75 | 70.95 | 142.34 | 75.92 |
| 4H2 | 264.43 | 71.42 | 79.63 | 39.25 | 72.90 | 140.97 | 77.59 |
| 5C12 | 136.32 | 80.24 | 112.48 | 84.58 | 87.71 | 132.90 | 101.67 |

Together, these results indicated that anti-MS4A4A antibodies of the present disclosure affect macrophage polarization, affecting cells away from an M2 phenotype. These results suggested that within the CNS, anti-MS4A4A antibody treatment may provide a beneficial enhancement of microglial activity by potentiating, increasing, or restoring their neuroprotective function in the context of neurodegenerative diseases and disorders. As homeostatic microglia in healthy conditions express more M2 markers, such as CD200R, CD163 and CD115, these results suggested that anti-MS4A4A antibodies of the present disclosure are affective at altering the physiological state of microglial cells to that of a more protective phenotype, including to a more proinflammatory or activated state. As disease associated microglia (DAM) in Alzheimer's disease mouse models and in human Alzheimer's disease are in a proinflammatory or activated state, which is considered beneficial in Alzheimer's disease, anti-MS4A4A antibodies of the present disclosure are useful in treating Alzheimer's disease and other neurodegenerative disorders.

Example 33: Antibody Humanization

Antibody humanization is used to transform antibodies generated in a different species to best resemble a human antibody through sequence and structural relationships in order to prevent immunogenicity in human administration. Antibodies from different species share characteristic sequence and structural features that allow the grafting of the specificity-determining regions (SDRs) of the non-human antibody onto a human antibody framework. This results in retention of the specificity of the non-human antibody. The humanization process involves identification of the non-human antibody sequence and features, including the framework regions and SDRs. The following criteria are used to humanize an antibody: 1) percent similarity in framework regions between non-human and known human antibodies, 2) length similarity in SDRs between non-human and known human antibodies, 3) genes used to generate the framework regions of the human antibody, and 4) pervious use of human antibody frameworks in humanizations and as therapeutics. Similarly, in framework regions and SDR lengths are important because differences can generate structural differences in the antibody that can alter the specificity of the antibody. Specific genes used to generate the framework of human antibodies are known to be beneficial or detrimental to the stability or specificity of the antibody and are selectively used or avoided, accordingly. Lastly, previously successful humanization frameworks, including those used in human therapeutics, which are well-tolerated with good half-lives, are likely candidates for future successful humanizations.

Various methods can be used for antibody humanization. For example, the heavy chain variable region (VH) and the light chain variable region (VL) sequences of an anti-TMWM106B antibody of the present disclosure is used as input to the IgBLAST program on the NCBI website (Ye et al, Nucleic Acids Res, 2013, 41:W34-W40). IgBLAST takes a murine VH or VL sequence and compares it to a library of known human germline sequences. The databases to use are IMGT human VH genes (F+ORF, 273 germline sequences) and IMGT human LVkappa genes (F+ORF, 74 germline sequences). An appropriate VH germline and joining region (J gene) and an appropriate VL germline and joining region (J gene) are chosen as good acceptor sequences. Complementary determining regions (CDRs) for the antibody VH and VH are defined according to AbM definition (AbM antibody modeling software). Alteration of human germline framework (i.e., non-CDR residues in the VH and VL) positions to corresponding parental murine sequences may be required to optimize binding to the humanized antibody.

Example 34: Effect of Anti-MS4A4A Antibodies on TREM2 Transcription and mRNA

The effect of anti-MS4A4A antibodies on TREM2 transcriptional level and mRNA is evaluated as follows. Cultured cells are treated with various concentration of an anti-MS4A4A antibody of the present disclosure for various periods of time. Afterward, changes in TREM2 mRNA levels within the cells are then determined using standard methodologies for measuring and/or quantitating mRNA levels known to one of skill in the art.

Example 35: Effect of Anti-MS4A4A Antibodies on TREM2 Recycling and Degradation

In order to better understand the effect of anti-MS4A4A antibodies on increased levels of sTREM2 and mTREM2, the following studies to examine TREM2 recycling and/or degradation are performed. In these studies, cycloheximide treatment of cells is used in order to prevent further new TREM2 synthesis in association with anti-MS4A4A antibody treatment. Various methods known in the are available to examine the recycling and degradation of TRME2 in control cells compared to cells treated with anti-MS4A4A antibodies.

Example 36: Effect of Anti-MS4A4A Antibodies on DAP12 Associated TREM2 Phosphorylation TREM2 signals through its binding partner DAP12 leading to downstream activation of PI3 kinase and other intracellular signals. The ability of anti-MS4A4A antibodies to induce DAP12/TREM2 activation is examined in cultured macrophages by measuring the phosphorylation state of DAP12/TREM2 in protein cell extracts. Before stimulation with anti-MS4A4A antibodies, mouse or human macrophages are starved in media containing 1% serum. The cells are then incubated on ice with anti-MS4A4A antibodies or isotype control antibodies. The cells are then washed and incubated at 37° C. in the presence of goat anti-mouse IgG or goat anti-human IgG. After stimulation, the cells are lysed with lysis buffer followed by centrifugation at 4° C. to remove insoluble materials. Cell lysates are immunoprecipitated with an anti-TREM2 antibody. Precipitated proteins are fractionated by SDS-PAGE, transferred to PVDF membranes, and probed with anti-phosphotyrosine antibody (4G10, Millipore). The membrane is then stripped and re-probed with an anti-DAP12 antibody (Cells Signaling, D7G1X). Each cell lysate used for these immunoprecipitations contains an equal amount of proteins as indicated by a control anti-actin antibody.

Changes to and the extent of TREM2 and/or DAP12 phosphorylation in response to anti-MS4A4A antibody treatment is compared to that observed in cells treated with an isotype control antibody.

Example 37: Effect of Anti-MS4A4A Antibodies on Trafficking of TREM2

The effect of anti-MS4A4A antibodies on trafficking of TREM2 in cells is evaluated as follows. Cells are stimulated cells with an anti-TREM2 antibody in order to activate TREM2. The cell/TREM2 bound anti-TREM2 antibody is labeled in order to track endocytosis of TREM2 by tracking the endocytosis of the labeled anti-TREM2 antibody bound to TREM2 on the cells. Anti-MS4A4A antibodies are added to the cells. Changes in TREM2 endocytosis and internalization in cells treated with anti-MS4A4A antibody compared to that observed in non-treated cells is determined. These studies test whether anti-MS4A4A antibodies of the present disclosure are capable of changing or altering the dynamics of TREM2 internalization in cells.

Example 38: Effect of Anti-MS4A4A Antibodies on Myelin Degradation and Myelin Phagocytosis The effect of anti-MS4A4A antibodies on myelin degradation and phagocytosis is evaluated as follows. Macrophages and microglia are isolated using standard methods. The cells are plated in 12-well plates. Myelin is incubated with a pH-sensitive dye (pH-Rodamine, Invitrogen) for 1 hour in PBS (pH 8.0). Dyed myelin is pelleted, resuspended in PBS (pH 8.0), and added to the macrophages or myeloid cells. Anti-MS4A4A antibodies and isotype control antibodies are added to the cells either before or after the addition of labeled myelin. Myelin uptake is then monitored. Following incubation of the cells with dyed myelin, the cells are washed, detached, pelleted, and passed through a flow cytometer in which internalized myelin is quantified.

Example 39: Functional Affinity of Anti-MS4A4A Antibodies on Cells Stably-Transfected with MS4A4A Expression Constructs Equilibrium dissociation constant ($K_D$) between monoclonal antibodies and their antigenic target are typically determined with purified protein reagents. For MS4A4A, a transmembrane receptor with short extracellular loops, such soluble protein reagents are not available. To address this, binding characteristics of anti-MS4A4A antibodies to cells stably-transfected with human and cynomolgous MS4A4A expression constructs were determined by flow cytometry. The $K_D$ values obtained by this procedure is known as "functional affinity" to reflect the fact that the interaction between an antibody and its cell surface-bound antigen is not a 1:1 interaction (Drake and Klakamp 2007, DOI: 10.1016/j.jim.2006.08.015).

Determination of functional affinity/$K_D$ was carried out as follows. A constant number of 300.19 cells stably transfected with constructs expressing MS4A4A were blocked against non-specific binding, and then incubated with anti-MS4A4A antibodies at various concentrations predetermined to span from saturation-binding to no antibodies present for three hours on ice so the reaction is allowed to achieve near equilibrium. The cells were then washed and incubated with fluorophore-conjugated secondary antibodies, washed again, and signal determined by FACS Cantos (Becton Dickinson, Franklin Lake, N.J.). To determine functional/$K_D$, the four-parameter dose response curve with variable slope was fitted onto the data by Prism (Graphpad, San Diego, Calif.), based on the multiple independent binding site model described by Drake and Klakamp, supra.

Functional affinity/$K_D$ measurements as determined by Prism are listed in Table 17 below (determined by four-parameter dose response curve fitting; all values in nanomolar; ND, not determined). Anti-MS4A4A antibodies 4A-18 and 4A-202 displayed functional avidities that were considerably stronger than those of commercially-available anti-MS4A4A antibodies 5C12, 3F2, and 4H2. There results indicated that anti-MS4A4A antibodies of the present disclosure have improved binding characteristics compared to the commercially-available anti-MS4A4A antibodies 5C12, 3F2, and 4H2.

TABLE 17

|  | 4A-18 (hIgG1) | 4A-18 (msIgG1) | 4A-21 (hIgG1) | 4A-21 (msIgG1) | 4A-202 (hIgG1) | 5C12 (msIgG1) | 3F2 (msIgG1) | 4H2 (msIgG1) |
|---|---|---|---|---|---|---|---|---|
| Human MS4A4A | 0.84 | 1.6 | 8.7 | 14.0 | 3.5 | 27.0 | 9.5 | 10.0 |
| Cyno MS4A4A | 3.1 | ND | 7.6 | ND | 1.8 | Does not bind | Does not bind | Does not bind |

Example 40: Potency of Anti-MS4A4A Antibodies in Inducing Viability in Primary Human Macrophages Treatment of human primary macrophages with anti-MS4A4A antibodies induced an increase in intracellular ATP levels, indicating a change in the metabolic status and increased viability in cells treated with anti-MS4A4A antibodies of the present disclosure. To determine the potency of some of the anti-MS4A4A antibodies in the present disclosure, a dose titration was performed. Commercially-available anti-MS4A4A antibodies were also tested for their potency in this assay Primary human macrophages were plated at 50,000 cells/well in complete RPMI-1640 and cultured for 2 days in the presence or absence of anti-MS4A4A antibodies or isotype control antibody at pre-determined concentrations in solution. The doses spanned ATP contents within cells were then quantified using the CellTiter-Glo Luminescent cell viability kit (Promega, Cat. No. G7571) per manufacturer's protocol and luminescence was determined as a measure of cell viability. Values obtained were fitted to a four-parameter dose response curve with variable slope in Prism (Graphpad, San Diego, Calif.) to determine the EC50, concentration of antibody that gives half maximal response—a lower value corresponds to greater antibody potency.

The results of these experiments are shown below in Table 18. Two of the three anti-MS4A4A antibodies of the present disclosure tested, anti-MS4A4A antibodies 4A-18 and 4A-202, showed a considerably lower EC50 (therefore higher potency) compared to that of any one of the three commercially-available anti-MS4A4A antibodies. The third anti-MS4A4A antibody of the present disclosure (4A-21) showed results comparable to anti-MS4A4A antibody 5C12, and more potent than anti-MS4A34A antibodies 3F2 and 4H2.

TABLE 18

| | Anti-MS4A4A antibody | | | | | |
|---|---|---|---|---|---|---|
| | 4A-18 | 4A-21 | 4A-202 | 5C12 | 3F2 | 4H2 |
| EC50 (M) | 4.843e−011 | 4.511e−010 | 8.497e−011 | 7.371e−010 | 1.689e−009 | 1.016e−008 |

Example 41: Modulation of TREM2 by Anti-MS4A4A Antibodies

It has been reported that SNPs in the MS4A locus affect soluble TREM2 (sTREM2) levels in humans, and treatment of human macrophages in culture with commercially-available anti-MS4A4A antibodies reduces sTREM2 levels (Piccio et. al. Acta Neuropathol 2016, 131:925-933). The effect of anti-MS4A4A antibodies of the present disclosure on sTREM2 and membrane-bound TREM2 (mTREM2) were determined.

Human primary macrophages were plated in 96-well plates and treated with the panel of anti-MS4A4A antibodies diluted at 10 µg/ml in complete RPMI media. After 48 hours of incubation, supernatants were collected and sTREM2 levels determined using an MSD assay. Separately treated cells were collected and subjected to flow cytometry to determine mTREM2 levels using an in-house anti-TREM2 antibody conjugated to allophycocyanin or similar fluorophores. The anti-MS4A4A antibodies were prepared to have low endotoxin levels.

For the generation of purified chimera antibodies for functional studies, the following protocol was used. Amino acid sequences for the VH and VL regions were optimized for expression in HEK cells. The nucleotide sequences encoding the VH and VL of the AL101 antibody were amended electronically by addition of sequences encoding antibody signal peptides at the 5' end and the human Kappa constant region or a human IgG1 Fc region for the light chain and heavy chain respectively. SapI restriction enzyme sites were added at each end to enable cloning into the vector. The HC and LC DNA sequences comprising the inserts were synthesized by Atum Bio (Newark, Calif.) and inserted into the pM269 shuttle vector. The HC and LC DNA inserts were cloned using the Electra cloning kit into the pD2610-V6 vector for expression. Competent DH10B *E. coli* (Max Efficiency DH10B catalog #18297010) thawed on ice. 2 ul of the ligation mix (~20 ng of plasmid DNA) was added to 30 ul of competent cells and allowed to incubate on ice for 30-45 minutes. The cells were then heat-shocked at 39° C. for 45 seconds and replaced on ice. 0.5 ml of SOC Medium was added and the cells incubated for a further 30-45 min at 37° C. 5 ul of the transformation mix was plated onto LB agar plates with kanamycin (TEKNOVA) and allowed to grow overnight at 37° C. Individual colonies picked and were grown up in LB+Kan overnight. The resulting minipreps were purified using a Qiagen mini-prep kit and sequence-confirmed. To generate sufficient DNA for stable cell line construction, 60 mL *E. coli* cultures of the correct colonies were grown for two days and then purified using Qigen Plasmid Maxi Prep Kits.

Transfections into HEK 293 cells were performed at the 250 ml scale in 1 L shake flasks using the EXPI-293 transfection kit (Invitrogen). 150 ug of light chain vector and 100 ug of heavy chain vector were mixed together with the Fectin reagent, allowed to sit for 20 minutes, and then added to the cells with gently mixing. The cells were returned to the shaker incubator for 6 hours whereupon the enhancer media was added per the manufacturer's instructions. Cells were harvested 5-6 days post-transfection by spinning out the cells in a clinical centrifuge, sterile-filtering the cell-free supernatant using a Nalgene 0.2 um filter, and string the conditioned media at 4° C. until purified.

Protein was purified using a protein A matrix (Mab Select Sure) packed into glass or polypropylene columns (GE Healthcare). The conditioned media was loaded onto the column, washed extensively, and then eluted with an elution buffer gradient containing arginine or glycine at a pH of 3.0-3.5. The eluted antibody was neutralized and formulated into storage buffer (citrate or histidine depending on the antibody's solubility), concentrated to >1 mg/ml, and then sterile filtered. The antibodies were tested by nanodrop, SDS-PAGE, and SEC prior to shipment. Preparative SEC was performed if the % monomer content was less than 95%. Yields typically range from 15-50 mgs of antibody depending on the antibody pair being expressed.

Levels of sTREM2 as measured in culture supernatants are shown in Table 19 below. Most of the anti-MS4A4A antibodies of the present disclosure, when highly purified and free of endotoxin, induced increased sTREM2 levels to varying degrees. Commercially available anti-MS4A4A antibodies 3F2, 4H2, and 5C12 also increased sTREM2 levels, but to a lesser degree. These results are in contrast to previously-published data, which showed that these commercially-available anti-MS4A4A antibodies reduced sTREM2 levels in culture; this is likely due to contaminating endotoxin, impurities, and aggregates present in commercial preparations. Data in Table 19 shows levels of sTREM2 expressed in ng/ml as a mean percent change across three donors compared to isotype control antibody (delta from isotype control).

The increase in sTREM2 observed was paralleled by an increase in membrane-bound TREM2 (mTREM2) levels after anti-MS4A4A antibody treatment (Table 20 below). Variation among donors' responsiveness notwithstanding, most of the anti-MS4A4A antibodies increased the level of mTREM2 in 2 or 3 of the three donors tested. When compared to commercially available anti-MS4A4A antibodies (3F2, 4H2 and 5C12), a number of antibodies in the present disclosure display equivalent or superior activity. Levels shown in Table 20 below are expressed as mean percent change across three donors as determined by flow cytometry, and are normalized to that observed using isotype control antibody (isotype control antibody set at 100%).

TABLE 19

| Antibody | Mean Change (%) | SEM |
| --- | --- | --- |
| 4A-201 | 12.30 | 4.55 |
| 4A-202 | 27.22 | 11.62 |
| 4A-205 | 21.49 | 11.38 |
| 4A-206 | 21.90 | 16.54 |
| 4A-207 | 10.55 | 5.51 |
| 4A-208 | 16.46 | 12.65 |
| 4A-209 | -4.49 | 2.44 |
| 4A-210 | 6.26 | 4.13 |
| 4A-213 | 22.21 | 19.17 |
| 4A-216 | 16.82 | 14.26 |
| 4A-219 | 9.92 | 13.13 |
| 4A-18 | 17.39 | 18.77 |
| 4A-21 | 70.12 | 20.85 |
| 4A-25 | 22.44 | 6.32 |
| 4A-225 | 3.35 | 6.90 |
| 4A-204 | 19.59 | 8.75 |
| 4A-214 | 29.17 | 8.32 |
| 4A-220 | 4.66 | 11.06 |
| 3F2 | 12.14 | 3.70 |
| 4H2 | 0.45 | 3.71 |
| 5C12 | 13.44 | 11.01 |

TABLE 20

| Antibody | Mean change (%) | SEM |
| --- | --- | --- |
| 4A-201 | 105.57 | 21.34 |
| 4A-202 | 238.08 | 55.06 |
| 4A-205 | 110.84 | 25.87 |
| 4A-206 | 100.01 | 19.40 |
| 4A-207 | 100.70 | 17.80 |
| 4A-208 | 111.92 | 31.23 |
| 4A-209 | 105.63 | 16.52 |
| 4A-210 | 101.07 | 9.81 |
| 4A-216 | 94.26 | 16.25 |
| 4A-219 | 91.27 | 13.10 |
| 4A-18 | 179.54 | 45.61 |
| 4A-21 | 250.09 | 41.94 |
| 4A-25 | 159.46 | 28.74 |
| 4A-225 | 104.24 | 16.59 |
| 4A-213 | 114.59 | 15.39 |
| 4A-204 | 144.13 | 32.11 |
| 4A-214 | 281.29 | 55.61 |
| 4A-220 | 176.33 | 63.39 |
| 3F2 | 161.01 | 30.80 |
| 4H2 | 157.27 | 29.73 |
| 5C12 | 144.81 | 18.93 |

What is claimed is:

1. An isolated antibody that binds to human MS4A4A, wherein the antibody comprises a heavy chain variable region and a light chain variable region,
wherein the heavy chain variable region and the light chain variable region comprise an HVR-H1, HVR-H2, HVR-H3, HVR-L1, HVR-L2, and HVR-L3 comprising the amino acid sequences selected from the group consisting of SEQ ID NOs:4, 20, 38, 56, 75, and 86, respectively; SEQ ID NOs:5, 21, 39, 57, 76, and 87, respectively; SEQ ID NOs:6, 22, 40, 58, 76, and 88, respectively; SEQ ID NOs:7, 23, 41, 59, 77, and 89, respectively; SEQ ID NOs:8, 24, 42, 60, 78, and 90, respectively; SEQ ID NOs:9, 25, 43, 61, 76, and 91, respectively; SEQ ID NOs:10, 26, 44, 62, 79, and 93, respectively; SEQ ID NOs:7, 27, 45, 63, 77, and 89, respectively; SEQ ID NOs:7, 28, 46, 64, 77, and 89, respectively; SEQ ID NOs:11, 29, 47, 65, 80, and 93, respectively; SEQ ID NOs:7, 27, 45, 63, 77, and 89, respectively; SEQ ID NOs:12, 27, 45, 66, 77, and 89, respectively; SEQ ID NOs:13, 30, 48, 67, 76, and 94, respectively; SEQ ID NOs:14, 31, 49, 68, 81, and 95, respectively; SEQ ID NOs:16, 33, 51, 70, 77, and 97, respectively; SEQ ID NOs:17, 34, 52, 71, 83, and 98, respectively; SEQ ID NOs:19, 36, 54, 73, 84, and 100, respectively; SEQ ID NOs:7, 37, 55, 74, 85, and 89, respectively; SEQ ID NOs:142, 154, 168, 183, 197, and 210, respectively; SEQ ID NOs:144, 156, 170, 185, 199, and 212, respectively; SEQ ID NOs:144, 157, 171, 186, 81, and 213, respectively; SEQ ID NOs:145, 158, 172, 186, 81, and 214, respectively; SEQ ID NOs:146, 159, 173, 187, 200, and 215, respectively; SEQ ID NOs:147, 160, 174, 188, 201, and 216, respectively; SEQ ID NOs:148, 161, 175, 189, 202, and 217, respectively; SEQ ID NOs:149, 162, 176, 190, 203, and 218, respectively; SEQ ID NOs:150, 163, 177, 191, 204, and 219, respectively; SEQ ID NOs:151, 164, 178, 192, 205, and 220, respectively; SEQ ID NOs:147, 160, 179, 193, 206, and 221, respectively; SEQ ID NOs:152, 165, 180, 194, 207, and 222, respectively; SEQ ID NOs:153, 166, 181, 195, 208, and 223, respectively; SEQ ID NOs:151, 167, 182, 196, 209, and 224, respectively; SEQ ID NOs:304, 310, 316, 322, 328, and 334, respectively; SEQ ID NOs:305, 311, 317, 323, 329, and 335, respectively; SEQ ID NOs:306, 312, 318, 324, 330, and 336, respectively; SEQ ID NOs:307, 313, 319, 325, 331, and 337, respectively; SEQ ID NOs:308, 314, 320, 326, 332, and 338, respectively; SEQ ID NOs:309, 315, 321, 327, 333, and 339, respectively; SEQ ID NOs:15, 32, 50, 69, 82, and 86, respectively; SEQ ID NOs:18, 35, 53, 72, 77, and 99, respectively; and SEQ ID NOs:143, 155, 169, 184, 198, and 211.

2. The antibody of claim 1, wherein the heavy chain variable region and the light chain variable region comprise amino acid sequences selected from the group consisting of SEQ ID NOs:101 and 121, respectively; SEQ ID NOs: 102 and 122, respectively; SEQ ID NOs: 103 and 123, respectively; SEQ ID NOs: 104 and 124, respectively; SEQ ID NOs: 105 and 125, respectively; SEQ ID NOs: 106 and 126, respectively; SEQ ID NOs: 107 and 127, respectively; SEQ ID NOs: 108 and 128, respectively; SEQ ID NOs: 109 and 129, respectively; SEQ ID NOs: 110 and 130, respectively; SEQ ID NOs: 108 and 128, respectively; SEQ ID NOs: 111 and 131, respectively; SEQ ID NOs: 112 and 132, respectively; SEQ ID NOs: 113 and 128, respectively; SEQ ID NOs: 114 and 133, respectively; SEQ ID NOs: 115 and 134, respectively; SEQ ID NOs: 116 and 135, respectively; SEQ ID NOs: 117 and 136, respectively; SEQ ID NOs: 118 and 137, respectively; SEQ ID NOs: 119 and 138, respectively; SEQ ID NOs: 120 and 139, respectively; SEQ ID NOs: 225 and 240, respectively; SEQ ID NOs: 226 and 241, respectively; SEQ ID NOs: 227 and 242, respectively; SEQ ID NOs: 228 and 243, respectively; SEQ ID NOs: 229 and 244, respectively; SEQ ID NOs: 230 and 245, respectively; SEQ ID NOs: 231 and 246, respectively; SEQ ID NOs: 232 and 247, respectively; SEQ ID NOs: 233 and 248, respectively; SEQ ID NOs: 234 and 249, respectively; SEQ ID NOs: 235 and 250, respectively; SEQ ID NOs: 236 and 251, respectively; SEQ ID NOs: 237 and 252, respectively; SEQ ID NOs: 238 and 253, respectively; SEQ ID NOs: 239 and 254, respectively; SEQ ID NOs: 340 and 346, respectively; SEQ ID NOs: 341 and 347, respectively; SEQ ID NOs: 342 and 348, respectively; SEQ ID NOs: 343 and 349, respectively; SEQ ID NOs: 344 and 350, respectively; and SEQ ID NOs: 345 and 351, respectively.

3. The antibody of claim 1, wherein the antibody is a murine antibody, a humanized antibody, a bispecific antibody, a monoclonal antibody, a multivalent antibody, a conjugated antibody, or a chimeric antibody.

4. The antibody of claim 1, wherein the antibody is of the IgG class, the IgM class, or the IgA class.

5. The antibody of claim 4, wherein the antibody is of the IgG class and has an IgG1, IgG2, or IgG4 isotype.

6. The antibody of claim 1, wherein the antibody is an antibody fragment.

7. The antibody of claim 6, wherein the fragment is a Fab, Fab', Fab'-SH, F(ab')2, Fv or scFv fragment.

8. The antibody of claim 1, wherein the antibody further comprises:
(a) an antigen facilitating transport across the blood brain barrier, wherein the antigen facilitating transport across the blood brain selected is from the group consisting of transferrin receptor (TR), insulin receptor (HIR), insulin-like growth factor receptor (IGFR), lowdensity lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005;
(b) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine(PA) repeat peptides, ubiquitin, and proline-arginine (PR) repeat peptides;

(c) ligands and/or proteins expressed on immune cells, wherein the ligands and/or proteins selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (d) a protein, lipid, polysaccharide, or glycolipid expressed on one or more tumor cells.

9. A pharmaceutical composition comprising the antibody of claim 1 and a pharmaceutically acceptable carrier.

10. An isolated antibody that binds to human MS4A4A, wherein the antibody comprises a heavy chain variable region and a light chain variable region, wherein:
the heavy chain variable region comprises an HVR-H1 comprising the amino acid sequence of SEQ ID NO: 18, an HVR-H2 comprising the amino acid sequence of SEQ ID NO: 35, and HVR-H3 comprising the amino acid sequence of SEQ ID NO: 53, and the light chain variable region comprises an HVR-L1 comprising the amino acid sequence of SEQ ID NO: 72, an HVR-L2 comprising the amino acid sequence of SEQ ID NO: 77, and an HVR-L3 comprising the amino acid sequence of SEQ ID NO: 99.

11. The isolated antibody of claim 10, wherein the antibody increases soluble TREM2 levels, increases plasma-membrane or cell surface TREM2 levels, or increases soluble TREM2 and increases plasma-membrane or cell surface TREM2 levels in myeloid cells.

12. The isolated antibody of claim 11, wherein the antibody increases soluble TREM2 levels by at least 15% compared to a control antibody of the same isotype.

13. The isolated antibody of claim 11, wherein the antibody increases plasma-membrane or cell surface TREM2 levels by at least 65% compared to a control antibody of the same isotype.

14. The isolated antibody of claim 11, wherein the antibody reduces expression of M2 cell surface receptors/markers on myeloid cells.

15. The isolated antibody of claim 14, wherein the antibody reduces expression of one or more of CD200R, Dectin-1, CD163, CD14, and SIRPα on myeloid cells.

16. The isolated antibody of claim 11, wherein the antibody increases the viability of macrophages.

17. The isolated antibody of claim 11, wherein the antibody binds to cynomolgus MS4A4A.

18. The antibody of claim 10, wherein the antibody reduces decline in cognitive and behavioral function and improves cognitive and behavioral function.

19. The antibody of claim 10, wherein the heavy chain variable region and the light chain variable region comprises the amino acid sequences of SEQ ID NOs:118 and 137, respectively.

20. A pharmaceutical composition comprising the antibody of claim 10 and a pharmaceutically acceptable carrier.

21. The antibody of claim 10, wherein the antibody is of the IgG class, the IgM class, or the IgA class.

22. The antibody of claim 10, wherein the antibody is of the IgG class and has an IgG1 isotype.

23. A pharmaceutical composition comprising the antibody of claim 22 and a pharmaceutically acceptable carrier.

24. An isolated antibody that binds to human MS4A4A, wherein the antibody comprises a heavy chain variable region and a light chain variable region, wherein the heavy chain variable region comprises an HVR-H1 comprising the amino acid sequence of SEQ ID NO:15, an HVR-H2 comprising the amino acid sequence of SEQ ID NO:32, and an HVR-H3 comprising the amino acid sequence of SEQ ID NO:50, and the light chain variable region comprises an HVR-L1 comprising the amino acid sequence of SEQ ID NO:69, an HVR-L2 comprising the amino acid sequence of SEQ ID NO:82, and an HVR-L3 comprising the amino acid sequence of SEQ ID NO:96.

25. The antibody of claim 24, wherein the heavy chain variable region and the light chain variable region comprises the amino acid sequences of SEQ ID NOs:115 and 134, respectively.

26. A pharmaceutical composition comprising the antibody of claim 24 and a pharmaceutically acceptable carrier.

27. An isolated antibody that binds to human MS4A4A, wherein the antibody comprises a heavy chain variable region and a light chain variable region, wherein the heavy chain variable region comprises an HVR-H1 comprising the amino acid sequence of SEQ ID NO:143, an HVR-H2 comprising the amino acid sequence of SEQ ID NO:155, and an HVR-H3 comprising the amino acid sequence of SEQ ID NO:169, and the light chain variable region comprises an HVR-L1 comprising the amino acid sequence of SEQ ID NO:184, an HVR-L2 comprising the amino acid sequence of SEQ ID NO:198, and an HVR-L3 comprising the amino acid sequence of SEQ ID NO:211.

28. The antibody of claim 27, wherein the heavy chain variable region and the light chain variable region comprises the amino acid sequences of SEQ ID NOs:226 and 241, respectively.

29. A pharmaceutical composition comprising the antibody of claim 27 and a pharmaceutically acceptable carrier.

* * * * *

UNITED STATES PATENT AND TRADEMARK OFFICE
CERTIFICATE OF CORRECTION

| | |
|---|---|
| PATENT NO. | : 11,472,874 B2 |
| APPLICATION NO. | : 16/965676 |
| DATED | : October 18, 2022 |
| INVENTOR(S) | : Philip Kong et al. |

It is certified that error appears in the above-identified patent and that said Letters Patent is hereby corrected as shown below:

In the Specification

In Column 30, Line 36, Change "dichlormethane," to "dichloromethane,"

In Column 30, Lines 38-39, Change "dichlormethane," to "dichloromethane,"

In Column 30, Line 47, Change "librariescan" to "libraries can"

In Column 38, Line 52, Change "zogamicin," to "ozogamicin,"

In Column 73, Line 26, Change "N-aceylgalactosamine," to "N-acetylgalactosamine,"

In Column 84, Line 39, Change "taupathy" to "tauopathy"

In Column 85, Line 8, Change "taupathy" to "tauopathy"

In Column 85, Line 49, Change "taupathy" to "tauopathy"

In Column 90, Line 37, Change "taupathy" to "tauopathy"

In Column 92, Line 20, Change "500" to "50 µl"

In Column 95, Line 31, Change "504," to "50 µL"

In Column 95, Line 33, Change "504," to "50 µL"

In Column 96, Line 21, Change "500" to "50 µl"

In Column 105, Line 56, Change "504," to "50 µL"

Signed and Sealed this
Fourteenth Day of March, 2023

Katherine Kelly Vidal
*Director of the United States Patent and Trademark Office*

CERTIFICATE OF CORRECTION (continued) Page 2 of 2
U.S. Pat. No. 11,472,874 B2

In Column 113, Line 15, Change "500" to "50 µl"

In Column 114, Line 42, Change "504," to "50 µL"

In Column 114, Line 44, Change "504," to "50 µL"

In the Claims

In Claim 1, Column 307, Line 29, Delete "SEQ ID NOs: 7, 27, 45, 63, 77, and 89, respectively;"

In Claim 1, Column 307, Line 62, Change "211 ." to "211."

In Claim 2, Column 308, Line 16, Delete "SEQ ID NOs: 108 and 128, respectively;"

In Claim 10, Column 309, Line 43, Change "99 ." to "99."